United States Patent
Mohan et al.

(10) Patent No.: US 11,242,350 B2
(45) Date of Patent: Feb. 8, 2022

(54) SPIROCYCLIC ROR-GAMMA MODULATORS

(71) Applicant: Escalier Biosciences B.V., Encinitas, CA (US)

(72) Inventors: Raju Mohan, Encinitas, CA (US); John Nuss, Encinitas, CA (US); Jason Harris, Encinitas, CA (US); Shendong Yuan, Encinitas, CA (US)

(73) Assignee: ESCALIER BIOSCIENCES B.V., Encinitas, CA (US)

( * ) Notice: Subject to any disclaimer, the term of this patent is extended or adjusted under 35 U.S.C. 154(b) by 0 days.

(21) Appl. No.: 16/979,833

(22) PCT Filed: Mar. 11, 2019

(86) PCT No.: PCT/US2019/021671
§ 371 (c)(1),
(2) Date: Sep. 10, 2020

(87) PCT Pub. No.: WO2019/177997
PCT Pub. Date: Sep. 19, 2019

(65) Prior Publication Data
US 2021/0053976 A1    Feb. 25, 2021

Related U.S. Application Data

(60) Provisional application No. 62/641,949, filed on Mar. 12, 2018.

(51) Int. Cl.
| | | |
|---|---|---|
| *C07D 487/10* | (2006.01) | |
| *C07D 205/04* | (2006.01) | |
| *C07D 211/24* | (2006.01) | |
| *C07D 471/10* | (2006.01) | |
| *C07D 495/10* | (2006.01) | |
| *C07D 211/54* | (2006.01) | |
| *A61P 17/06* | (2006.01) | |
| *A61P 37/06* | (2006.01) | |
| *A61P 19/02* | (2006.01) | |
| *A61P 1/00* | (2006.01) | |

(52) U.S. Cl.
CPC .............. *C07D 487/10* (2013.01); *A61P 1/00* (2018.01); *A61P 17/06* (2018.01); *A61P 19/02* (2018.01); *A61P 37/06* (2018.01); *C07D 205/04* (2013.01); *C07D 211/24* (2013.01); *C07D 471/10* (2013.01); *C07D 495/10* (2013.01)

(58) Field of Classification Search
CPC .. C07D 487/10; C07D 205/04; C07D 211/24; C07D 471/10; C07D 495/10; C07D 211/54; A61P 17/06; A61P 37/06; A61P 19/02; A61P 1/00
See application file for complete search history.

(56) References Cited

U.S. PATENT DOCUMENTS

| | | |
|---|---|---|
| 6,432,957 B1 | 8/2002 | Kodoma et al. |
| 9,586,928 B2 | 3/2017 | Kamenecka et al. |
| 2010/0029621 A1 | 2/2010 | Cooke et al. |
| 2014/0031330 A1 | 1/2014 | Bodil Van Niel et al. |
| 2014/0187554 A1 | 7/2014 | Kamenecka et al. |
| 2016/0120850 A1 | 5/2016 | Goldberg et al. |
| 2016/0122335 A1 | 5/2016 | Goldberg et al. |
| 2016/0122336 A1 | 5/2016 | Goldberg et al. |
| 2016/0318870 A1 | 11/2016 | Dhar et al. |
| 2017/0313691 A1 | 11/2017 | Goldberg et al. |
| 2019/0269674 A1 | 9/2019 | Mohan et al. |

FOREIGN PATENT DOCUMENTS

| | | |
|---|---|---|
| WO | WO-2004032933 A1 | 4/2004 |
| WO | WO-2011115892 A1 | 9/2011 |
| WO | WO-2012158784 A2 | 11/2012 |
| WO | WO-2016014910 A1 | 1/2016 |
| WO | WO-2017127442 A1 | 7/2017 |
| WO | WO-2017131156 A1 | 8/2017 |
| WO | WO-2018081558 A1 | 5/2018 |
| WO | WO-2019177996 A1 | 9/2019 |
| WO | WO-2019177997 A1 | 9/2019 |

OTHER PUBLICATIONS

Amselem et al.: In vitro tests to predict in vivo performance of liposomal dosage forms. Chem Phys Lipids 64: 219-237 (1993).
Burnham et al.: Polymers for delivering peptides and proteins. Am J Hosp Pharm 51: 210-218 (1994).
Co-pending U.S. Appl. No. 202016979834, inventors Mohan; Raju et al., filed Sep. 10, 2020.
Co-pending U.S. Appl. No. 202017102105, inventors Mohan; Raju et al., filed Nov. 23, 2020.
Davis et al.: Enzyme polyethylene glycol adducts: modified enzymes with unique properties. Enzyme Eng 4:169-173 (1978).
Hackam et al., Translation of research evidence from animals to humans. JAMA, 296(14):1731-1732, 2006.
International Application No. PCT/US2017/058755 International Preliminary Report on Patentability dated Apr. 30, 2019.
International Application No. PCT/US2017/058755 International Search Report and Written Opinion dated Feb. 23, 2018.
Jordan, V. C., "Tamoxifen: a most unlikely pioneering medicine" Nature Reviews: Drug Discovery, 2, 2003, 205.
PCT/US2019/021668 International Search Report and Written Opinion dated May 30, 2019.
PCT/US2019/021671 International Search Report and Written Opinion dated Jul. 10, 2019.
PubChem CID 3233343, https://pubchem.ncbi.nlm.nih.gov/compound/3233343 (2005).
Science IP Search Results (2016) 93 pages.

(Continued)

*Primary Examiner* — Laura L Stockton
(74) *Attorney, Agent, or Firm* — Wilson Sonsini Goodrich & Rosati

(57) ABSTRACT

Described herein are retinoic acid related-related orphan nuclear receptor (ROR) modulators and methods of utilizing ROR-gamma modulators in the treatment of diseases, disorders or conditions. Also described herein are pharmaceutical compositions containing such compounds.

20 Claims, No Drawings

(56) References Cited

OTHER PUBLICATIONS

U.S. Appl. No. 16/344,919 Office Action dated May 1, 2020.
Vippagunta et al. Crystalline Solids. Advanced Drug Delivery Reviews 48:3-26 (2001).
Wu et al., Discovery and structural optimization of 4-(4-(benzyloxy)phenyl)-3,4-dihydropyrimidin-2(1H)-ones as RORc inverse agonists. Acta Pharmacologica Sinica. 37(11):1516-1524 (2016).
European Application No. 19/768,383 Search Report dated Oct. 13, 2021.

SPIROCYCLIC ROR-GAMMA MODULATORS

CROSS-REFERENCE

This application is a U.S. National Phase of International Application No.: PCT/US2019/021671, filed Mar. 11, 2019, which claims benefit of U.S. Provisional Application No. 62/641,949, filed on Mar. 12, 2018, which are herein incorporated by reference in their entirety.

BACKGROUND OF THE INVENTION

The retinoic acid related orphan nuclear receptors (RORs) have three members: RORα, RORβ and RORγ. RORβ expression is mostly restricted to the brain and retina, while RORα and RORγ expressions are widespread. RORγ also has a shorter isoform, RORγt, which is mostly expressed in the immune system.

RORγt is essential for the development of secondary lymphoid tissues, in particular lymph nodes and Peyer's patches. Recent studies identified a critical role for RORγt in lineage specification of uncommitted CD4+ T helper cells into Th17 cells as well as the development of Tc17 (cytotoxic) T cells. Th17 response has been implicated in a myriad of autoimmune diseases such as psoriasis, inflammatory bowel disease, arthritis and multiple scoliosis. Inhibition of Th17 and Tc17 response has also been shown to a mechanism for cancer cells to evade anti-tumor immunity in several experimental tumor models. These findings implicate both RORγ agonists and inverse agonists as potential therapeutics for a variety of diseases.

SUMMARY OF THE INVENTION

In one aspect, provided herein are compounds having the Formula (I), or a pharmaceutically acceptable salt, solvate, or stereoisomer thereof:

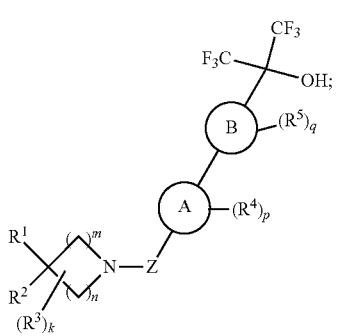

Formula (I)

wherein:

is phenyl, or a 5-membered or 6-membered heteroaryl ring;

is phenyl, or a 5-membered or 6-membered heteroaryl ring;

Z is $-(C(R^6)(R^7))_t-$;

$R^1$ and $R^2$ are selected from (i) and (ii):
(i) $R^1$ and $R^2$, together with the carbon atom to which they are attached, form a 4-, 5-, or 6-membered heterocyclyl ring wherein the 4-, 5-, or 6-membered heterocyclyl ring is optionally substituted with 1 to 4 $R^{3a}$ groups; and
(ii) $R^1$ is hydrogen and $R^2$ is $-S(O)_2R^{10}$, $-C_1$-$C_6$alkyl-$S(O)_2R^{10}$, $-N(R^{11})S(O)_2R^{10}$, or $-C_1$-$C_6$alkyl-$N(R^{11})S(O)_2R^{10}$;

each $R^3$ is independently selected from halo and $C_1$-$C_6$alkyl;

each $R^{3a}$ is independently selected from $C_1$-$C_6$alkyl, $C_1$-$C_6$haloalkyl, $C_2$-$C_9$heteroaryl, $(C_2$-$C_9$heteroaryl)-$C_1$-$C_6$alkylene-, oxo, $-S(O)_2R^{10}$, $-C(O)R^{10}$, $-C(O)OR^{11}$, and $-C(O)N(R^{11})_2$, wherein $C_2$-$C_9$heteroaryl and $(C_2$-$C_9$heteroaryl)-$C_1$-$C_6$alkylene- are optionally substituted with 1 to 3 groups independently selected from halo, $C_1$-$C_6$alkyl, $C_1$-$C_6$haloalkyl, and hydroxyl;

each $R^4$ and each $R^5$ are each independently selected from halo, cyano, $-OH$, $C_1$-$C_6$alkyl, $C_1$-$C_6$alkenyl, $C_1$-$C_6$haloalkyl, $C_1$-$C_6$alkoxy, $C_3$-$C_8$cycloalkyl, $-N(R^9)_2$, $-C(O)R^8$, $-C(O)OR^9$, $-C(O)N(R^9)_2$, $-N(R^9)C(O)R^8$, $-N(R^9)SO_2R^8$, $-SO_2R^8$, and $-SO_2N(R^8)_2$;

each $R^6$ and each $R^7$ are each independently hydrogen, halo, or $C_1$-$C_6$alkyl;

each $R^8$ is independently $C_1$-$C_6$alkyl or $C_1$-$C_6$haloalkyl;

each $R^9$ is independently hydrogen, $C_1$-$C_6$alkyl, or $C_1$-$C_6$haloalkyl;

each $R^{10}$ is independently $C_1$-$C_6$alkyl, $C_1$-$C_6$haloalkyl, $C_1$-$C_6$alkyl-$O$-$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or $(C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or $(C_2$-$C_9$heteroaryl)-$C_1$-$C_6$alkylene- is optionally substituted with 1 to 3 groups selected from halo, $C_1$-$C_6$alkyl, $C_1$-$C_6$haloalkyl, and hydroxyl;

each $R^{11}$ is independently hydrogen, $C_1$-$C_6$alkyl, or $C_1$-$C_6$haloalkyl;

m is 1, 2, or 3;
n is 1, 2, or 3;
k is 0, 1, 2, 3, or 4;
p is 0, 1, 2, 3, or 4;
q is 0, 1, 2, 3 or 4; and
t is 0, 1, 2, or 3.

In some embodiments is a compound of Formula (I), or a pharmaceutically acceptable salt, solvate, or stereoisomer thereof, wherein

is phenyl or a 6-membered heteroaryl ring. In some embodiments is a compound of Formula (I), or a pharmaceutically acceptable salt, solvate, or stereoisomer thereof, wherein

is phenyl. In some embodiments is a compound of Formula (I), or a pharmaceutically acceptable salt, solvate, or stereoisomer thereof, wherein

B is a 6-membered heteroaryl ring. In some embodiments is a compound of Formula (I), or a pharmaceutically acceptable salt, solvate, or stereoisomer thereof, wherein

B is pyridyl. In some embodiments is a compound of Formula (I), or a pharmaceutically acceptable salt, solvate, or stereoisomer thereof, wherein

A is phenyl or a 6-membered heteroaryl ring. In some embodiments is a compound of Formula (I), or a pharmaceutically acceptable salt, solvate, or stereoisomer thereof, wherein

A is phenyl. In some embodiments is a compound of Formula (I), or a pharmaceutically acceptable salt, solvate, or stereoisomer thereof, wherein

A is a 6-membered heteroaryl ring. In some embodiments is a compound of Formula I), or a pharmaceutically acceptable salt, solvate, or stereoisomer thereof, wherein

A is pyridyl. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 to 4 $R^{3a}$ groups. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 to 2 $R^{3a}$ groups. In some embodiments is a compound of Formula (I), or a pharmaceutically acceptable salt, solvate, or stereoisomer thereof, having the Formula (II):

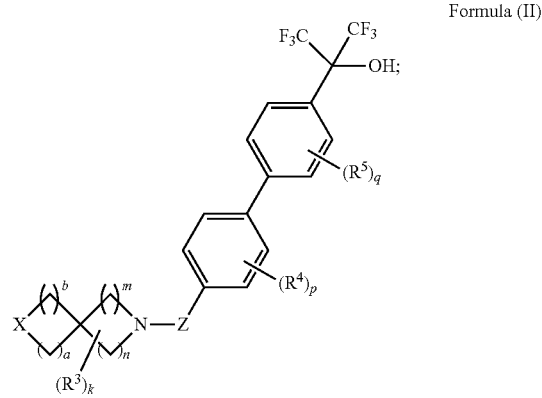

Formula (II)

wherein X is —O—, —NH—, —N($R^{3a}$)—, —S—, —S(O)—, or —S(O)$_2$—; a is 1 or 2; and b is 1 or 2. In some embodiments is a compound of Formula (II), or a pharmaceutically acceptable salt, solvate, or stereoisomer thereof, wherein a is 1, b is 1, m is 2, and n is 2. In some embodiments is a compound of Formula (II), or a pharmaceutically acceptable salt, solvate, or stereoisomer thereof, wherein a is 1, b is 2, m is 1, and n is 2. In some embodiments is a compound of Formula (II), or a pharmaceutically acceptable salt, solvate, or stereoisomer thereof, wherein a is 1, b is 1, m is 1, and n is 2. In some embodiments is a compound of Formula (II), or a pharmaceutically acceptable salt, solvate, or stereoisomer thereof, wherein a is 2, b is 2, m is 1, and n is 1. In some embodiments is a compound of Formula (II), or a pharmaceutically acceptable salt, solvate, or stereoisomer thereof, wherein a is 2, b is 1, m is 1, and n is 1. In some embodiments is a compound of Formula (II), or a pharmaceutically acceptable salt, solvate, or stereoisomer thereof, wherein a is 1, b is 1, m is 1, and n is 1. In some embodiments is a compound of Formula (II), or a pharmaceutically acceptable salt, solvate, or stereoisomer thereof, having the Formula (IIa):

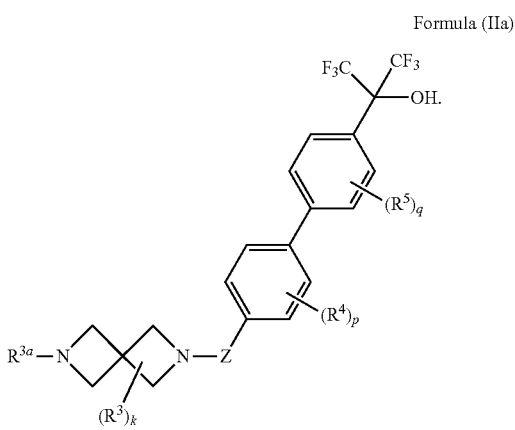

Formula (IIa)

In some embodiments is a compound of Formula (I), (II), or (IIa), or a pharmaceutically acceptable salt, solvate, or stereoisomer thereof, wherein $R^{3a}$ is —S(O)$_2R^{10}$, —C(O)$R^{10}$, or —C(O)O$R^{11}$. In some embodiments is a compound of Formula (I), (II), or (IIa), or a pharmaceutically acceptable salt, solvate, or stereoisomer thereof, wherein $R^{3a}$ is —S(O)$_2$R$^{10}$. In some embodiments is a compound of Formula (I), (II), or (IIa), or a pharmaceutically acceptable salt, solvate, or stereoisomer thereof, wherein $R^{10}$ is $C_1$-$C_6$alkyl or $C_3$-$C_8$cycloalkyl. In some embodiments is a compound of Formula (I), (II), or (IIa), or a pharmaceutically acceptable salt, solvate, or stereoisomer thereof, wherein $R^{10}$ is $C_1$-$C_6$alkyl. In some embodiments is a compound of Formula (I), (II), or (IIa), or a pharmaceutically acceptable salt, solvate, or stereoisomer thereof, wherein $R^{3a}$ is —S(O)$_2$CH$_3$. In some embodiments is a compound of Formula (I), or a pharmaceutically acceptable salt, solvate, or stereoisomer thereof, wherein $R^1$ is hydrogen and $R^2$ is —S(O)$_2$R$^{10}$, —C$_1$-C$_6$alkyl-S(O)$_2$R$^{10}$, —N(R$^{11}$)S(O)$_2$R$^{10}$, or —C$_1$-C$_6$alkyl-N(R$^{11}$)S(O)$_2$R$^{10}$. In some embodiments is a compound of Formula (I), or a pharmaceutically acceptable salt, solvate, or stereoisomer thereof, wherein $R^2$ is —S(O)$_2$R$^{10}$, —CH$_2$S(O)$_2$R$^{10}$, —N(R$^{11}$)S(O)$_2$R$^{10}$, or —CH$_2$N(R$^{11}$)S(O)$_2$R$^{10}$. In some embodiments is a compound of Formula (I), or a pharmaceutically acceptable salt, solvate, or stereoisomer thereof, wherein $R^{10}$ is $C_1$-$C_6$alkyl. In some embodiments is a compound of Formula (I), or a pharmaceutically acceptable salt, solvate, or stereoisomer thereof, wherein $R^2$ is —S(O)$_2$CH$_3$, —CH$_2$S(O)$_2$CH$_3$, —CH$_2$N(H)S(O)$_2$CH$_3$, or —CH$_2$N(CH$_3$)S(O)$_2$CH$_3$. In some embodiments is a compound of Formula (I), or a pharmaceutically acceptable salt, solvate, or stereoisomer thereof, wherein m is 1 and n is 1. In some embodiments is a compound of Formula (I), or a pharmaceutically acceptable salt, solvate, or stereoisomer thereof, wherein m is 2 and n is 1. In some embodiments is a compound of Formula (I), or a pharmaceutically acceptable salt, solvate, or stereoisomer thereof, wherein m is 2 and n is 2. In some embodiments is a compound of Formula (I), (II), or (IIa), or a pharmaceutically acceptable salt, solvate, or stereoisomer thereof, wherein each $R^6$ and each $R^7$ are hydrogen. In some embodiments is a compound of Formula (I), (II), or (IIa), or a pharmaceutically acceptable salt, solvate, or stereoisomer thereof, wherein t is 1, 2, or 3. In some embodiments is a compound of Formula (I), (II), or (IIa), or a pharmaceutically acceptable salt, solvate, or stereoisomer thereof, wherein t is 1. In some embodiments is a compound of Formula (I), (II), or (IIa), or a pharmaceutically acceptable salt, solvate, or stereoisomer thereof, wherein p is 0, 1, 2, or 3. In some embodiments is a compound of Formula (I), (II), or (IIa), or a pharmaceutically acceptable salt, solvate, or stereoisomer thereof, wherein each $R^4$ is independently halo, $C_1$-$C_6$alkyl, $C_1$-$C_6$alkenyl, $C_1$-$C_6$haloalkyl, $C_1$-$C_6$alkoxy, or $C_3$-$C_8$cycloalkyl. In some embodiments is a compound of Formula (I), (II), or (IIa), or a pharmaceutically acceptable salt, solvate, or stereoisomer thereof, wherein each $R^4$ is independently halo, $C_1$-$C_6$alkyl, or $C_3$-$C_8$cycloalkyl. In some embodiments is a compound of Formula (I), (II), or (IIa), or a pharmaceutically acceptable salt, solvate, or stereoisomer thereof, wherein p is 1. In some embodiments is a compound of Formula (I), (II), or (IIa), or a pharmaceutically acceptable salt, solvate, or stereoisomer thereof, wherein p is 2. In some embodiments is a compound of Formula (I), (II), or (Ia), or a pharmaceutically acceptable salt, solvate, or stereoisomer thereof, wherein p is 3. In some embodiments is a compound of Formula (I), (II), or (IIa), or a pharmaceutically acceptable salt, solvate, or stereoisomer thereof, wherein p is 0. In some embodiments is a compound of Formula (I), (II), or (IIa), or a pharmaceutically acceptable salt, solvate, or stereoisomer thereof, wherein q is 0, 1, or 2. In some embodiments is a compound of Formula (I), (II), or (IIa), or a pharmaceutically acceptable salt, solvate, or stereoisomer thereof, wherein each $R^5$ is independently halo, cyano, $C_1$-$C_6$alkyl, $C_1$-$C_6$haloalkyl, or $C_1$-$C_6$alkoxy. In some embodiments is a compound of Formula (I), (II), or (IIa), or a pharmaceutically acceptable salt, solvate, or stereoisomer thereof, wherein each $R^5$ is independently halo or $C_1$-$C_6$alkyl. In some embodiments is a compound of Formula (I), (II), or (IIa), or a pharmaceutically acceptable salt, solvate, or stereoisomer thereof, wherein q is 1. In some embodiments is a compound of Formula (I), (II), or (IIa), or a pharmaceutically acceptable salt, solvate, or stereoisomer thereof, wherein q is 2. In some embodiments is a compound of Formula (I), (II), or (IIa), or a pharmaceutically acceptable salt, solvate, or stereoisomer thereof, wherein q is 0. In some embodiments is a compound of Formula (I), (II), or (IIa), or a pharmaceutically acceptable salt, solvate, or stereoisomer thereof, wherein k is 0.

In another aspect is a pharmaceutical composition comprising a compound of Formula (I), or a pharmaceutically acceptable salt, solvate, or stereoisomer thereof, and a pharmaceutically acceptable carrier. In some embodiments is a pharmaceutical composition comprising a compound of Formula (II), or a pharmaceutically acceptable salt, solvate, or stereoisomer thereof, and a pharmaceutically acceptable carrier. In some embodiments is a pharmaceutical composition comprising a compound of Formula (IIa), or a pharmaceutically acceptable salt, solvate, or stereoisomer thereof, and a pharmaceutically acceptable carrier.

In another aspect is a method of treating a disease, disorder or condition in an individual in need thereof comprising administering to the individual a therapeutically effective amount of a compound of Formula (I), (II), or (IIa), or a pharmaceutically acceptable salt, solvate, or stereoisomer thereof, wherein the disease, disorder or condition is selected from psoriasis, psoriatic arthritis, uveitis, ulcerative colitis, asthma, allergic rhinitis, chronic obstructive pulmonary disease (COPD), atopic dermatitis, vitiligo, vesiculobullous dermatosis, rheumatoid arthritis, ankylosing spondylitis, reactive arthritis, arthritis associated with inflammatory bowel disease, juvenile rheumatoid arthritis, Crohn's disease, inflammatory bowel disease, lupus, lupus nephritis, multiple sclerosis, axial spodyloarthritides, hidraenitis suppurativa, Sjögren's syndrome, regional enteritis, Tolosa-Hunt syndrome, undifferentiated connective tissue disease, obesity, obesity-induced insulin resistance, atherosclerosis, and type II diabetes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the context of this disclosure, a number of terms shall be utilized.

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field.

Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ . . . $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

"Alkylene" and "alkylene chain" as used herein and unless otherwise indicated, refer to a straight or branched divalent hydrocarbon chain consisting solely of carbon and hydrogen, containing no unsaturation and having from one to eight or one to six carbon atoms, examples of which include methylene, ethylene, propylene, n-butylene and the like. The alkylene chain may be attached to the rest of the molecule through the replacement of any two hydrogen atoms within the chain.

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)=$CR_2$, wherein R refers to the remaining portions of the alkenyl group, which may be the same or different. Non-limiting examples of an alkenyl group include —CH=$CH_2$, —C($CH_3$)=$CH_2$, —CH=$CHCH_3$, —CH=C($CH_3)_2$ and —C($CH_3$)=$CHCH_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

"Alkenylene" or "alkenylene chain" as used herein and unless otherwise indicated, refers to a straight or branched chain unsaturated divalent group consisting solely of carbon and hydrogen atoms, having from two to eight carbon atoms, wherein the unsaturation is present only as double bonds and wherein the double bond can exist between any two carbon atoms in the chain, examples of which include ethenylene, prop-1-enylene, but-2-enylene and the like. The alkenylene chain may be attached to the rest of the molecule through the replacement of any two hydrogen atoms within the chain.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡$CCH_3$, —C≡$CCH_2CH_3$ and —C≡$CCH_2CH_2CH_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Alkynylene" or "alkynylene chain" as used herein and unless otherwise indicated, refers to a straight or branched chain unsaturated divalent group consisting solely of carbon and hydrogen atoms, having from two to eight carbon atoms, wherein the unsaturation is present only as triple bonds and wherein the triple bond can exist between any two carbon atoms in the chain, examples of which include ethynylene, prop-1-ynylene, but-2-ynylene, pent-1-ynylene, pent-3-ynylene and the like. The alkynylene chain may be attached to the rest of the molecule through the replacement of any two hydrogen atoms within the chain.

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

"Aralkyl" as used herein and unless otherwise indicated, refers to a monovalent alkyl group substituted with aryl. In certain embodiments, both alkyl and aryl may be optionally substituted with one or more substituents.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl). "Aryl" as used herein and unless otherwise indicated, refers to a group of carbocylic ring system, including monocyclic, bicyclic, tricyclic, tetracyclic C$_6$-C$_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphthene, indene, and fluorene.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

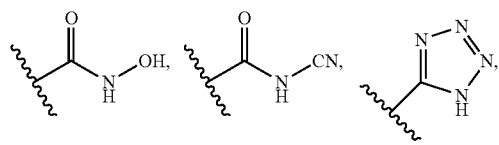

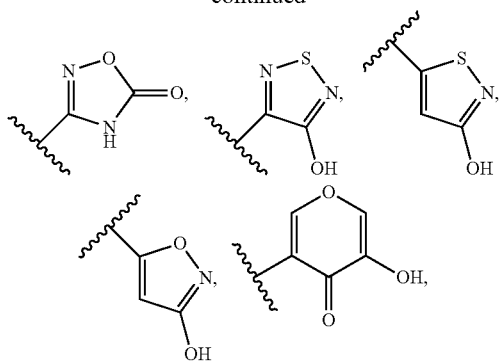

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms.

"Cycloalkylalkyl" as used herein and unless otherwise indicated, refers to a monovalent alkyl group substituted with cycloalkyl. In certain embodiments, both alkyl and cycloalkyl may be optionally substituted with one or more substituents.

"Deuterium" as used herein and unless otherwise indicated, refers to the heavy isotope of hydrogen represented by the symbol D or $^2$H. As used herein, when a particular position in a compound is designated as having deuterium, it is understood that the compound is an isotopically enriched compound and the abundance of deuterium at that position in the compound is substantially greater than its natural abundance of 0.0156%.

"Deuterated" as applied to a chemical group and unless otherwise indicated, refers to a chemical group that is isotopically enriched with deuterium in an amount substantially greater than its natural abundance.

"Heteroaralkyl" as used herein and unless otherwise indicated, refers to a monovalent alkyl group substituted with heteroaryl. In certain embodiments, both alkyl and heteroaryl may be optionally substituted with one or more substituents.

"Heteroaryl" as used herein and unless otherwise indicated, refers to a 5- to 15-membered monocyclic aromatic ring or a multicyclic aromatic ring system wherein the ring or at least one ring of the multicyclic system contains one to five heteroatoms each independently selected from O, S, or N, with the remaining ring atoms being carbon atoms. Each ring of a heteroaryl group can contain up to two O atoms, up to two S atoms, and/or up to four N atoms, provided that the total number of heteroatoms in each ring is four or less and each ring contains at least one carbon atom.

Examples of such heteroaryl groups include, but are not limited to, furanyl, pyrrolyl, thienyl, imidazolyl, pyrazolyl, oxazolyl, isoxazolyl, thiazolyl, isothiazolyl, triazolyl, oxadiazolyl, thiadiazolyl, tetrazolyl, pyrimidinyl, pyridinyl, pyridazinyl, pyrazinyl, benzimidazolyl, benzoisoxazolyl, benzopyranyl, benzothiadiazolyl, benzothiazolyl, pyridopyridyl, pyrrolopyridyl, quinolinyl, quinoxalinyl, quinazolinyl, naphthridinyl, 1,5-naphthyridinyl, 1,6-naphthyridinyl, thieno[3,2-b]pyridinyl, thieno[2,3-b]pyridinyl, 1H-pyrazolo[4,3-b]pyridinyl, 1H-pyrrolo[2,3-b]pyridinyl, 5H-pyrrolo[2,3-b]pyrazinyl, 1H-imidazo[4,5-b]pyrazinyl, 1H-pyrazolo[3,4-b]pyridinyl, thiadiazolopyrimidyl, and thienopyridyl.

"Heterocyclyl", as used herein and unless otherwise indicated, refers to a 3- to 15-membered monocyclic non-aromatic ring or a multicyclic ring system that contains at least one non-aromatic ring, wherein the ring or at least one ring contains one to five heteroatoms each independently selected from O, S, or N; and the remaining ring atoms being carbon atoms. In certain embodiments, the heterocyclyl is a monocyclic, bicyclic, tricyclic, or tetracyclic ring system, which may include a fused or bridged ring system, and in which the nitrogen or sulfur atoms may be optionally substituted with an oxo group or additionally with a second oxo group or an imino group, the nitrogen atoms may be optionally quaternized or substituted, and some rings may be partially or fully saturated, or aromatic. In certain embodiments, the heterocyclyl is monocyclic, which may include a fused or bridged ring system, and in which the nitrogen or sulfur atoms may be optionally substituted with an oxo group or additionally with a second oxo group or an imino group, the nitrogen atoms may be optionally quaternized or substituted with, and some rings may be partially or fully saturated, or aromatic. The heterocyclyl may be attached to the main structure at any heteroatom or carbon atom which results in the creation of a stable compound. The heterocyclyl, when substituted, may be substituted at the carbon atom or the heteroatom. Exemplary heterocylic radicals include, but are not limited to homopiperazinyl, morpholinyl, piperidinyl, piperazinyl, pyranyl, pyrrolidinyl, tetrahydrofuranyl, tetrahydropyranyl, ethylene oxide, oxetanyl, azetidinyl, quinuclidinyl, octahydroquinolizinyl, decahydroquinolizinyl, azabicyclo[3.2.1]octanyl, azabicyclo[2.2.2]octanyl, 6,7,8,9-tetrahydro-5H-pyrazino[2,3-b]indolyl.

"Heterocyclylalkyl" as used herein and unless otherwise indicated, refers to a monovalent alkyl group substituted with heterocyclyl. In certain embodiments, both alkyl and heterocyclyl may be optionally substituted with one or more substituents.

The term "halo" or, alternatively, "halogen" means fluoro, chloro, bromo and iodo.

The term "haloalkyl" refers to an alkyl group that is substituted with one or more halogens. The halogens may be the same or they may be different. Non-limiting examples of haloalkyls include —CH$_2$Cl, —CF$_3$, —CHF$_2$, —CH$_2$CF$_3$, —CF$_2$CF$_3$, and the like.

The terms "fluoroalkyl" and "fluoroalkoxy" include alkyl and alkoxy groups, respectively, that are substituted with one or more fluorine atoms. Non-limiting examples of fluoroalkyls include —CF$_3$, —CHF$_2$, —CH$_2$F, —CH$_2$CF$_3$, —CF$_2$CF$_3$, —CF$_2$CF$_2$CF$_3$, —CF(CH$_3$)$_3$, and the like. Non-limiting examples of fluoroalkoxy groups, include —OCF$_3$, —OCHF$_2$, —OCH$_2$F, —OCH$_2$CF$_3$, —OCF$_2$CF$_3$, —OCF$_2$CF$_2$CF$_3$, —OCF(CH$_3$)$_2$, and the like.

"Imino" as used herein and unless otherwise indicated, refers to the group =NH or =NR attached to a carbon or sulfur atom.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, alkenyl, cycloalkyl, aryl, heteroaryl (bonded through a ring carbon), and heterocyclyl.

The term "optionally substituted" or "substituted" means that the referenced group may be substituted with one or more additional group(s) individually and independently selected from alkyl, cycloalkyl, aryl, heteroaryl, heterocyclyl, —OH, alkoxy, aryloxy, alkylthio, arylthio, alkylsulfoxide, arylsulfoxide, alkylsulfone, arylsulfone, —CN, alkyne, C$_1$-C$_6$alkylalkyne, halo, acyl, acyloxy, —CO$_2$H, —CO$_2$-alkyl, nitro, haloalkyl, fluoroalkyl, and amino, including mono- and di-substituted amino groups (e.g. —NH$_2$, —NHR, —N(R)$_2$), and the protected derivatives thereof. By way of example, an optional substituents may be L$^S$R$^S$, wherein each L$^S$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —(C$_1$-C$_6$alkyl)-, or —(C$_2$-C$_6$alkenyl)-; and each R$^S$ is independently selected from among H, (C$_1$-C$_6$alkyl), (C$_3$-C$_8$cycloalkyl), aryl, heteroaryl, and heterocyclyl. The protecting groups that may form the protective derivatives of the above substituents are found in sources such as Greene and Wuts, above.

"Oxo" as used herein refers to the group =O attached to a carbon or sulfur atom.

As used herein, the term "about" or "approximately" means within 20%, preferably within 10%, and more preferably within 5% of a given value or range.

The term a "therapeutically effective amount" as used herein refers to the amount of an RORγ modulator that, when administered to a mammal in need, is effective to at least partially ameliorate or to at least partially prevent conditions related to skin aging.

As used herein, the term "expression" includes the process by which polynucleotides are transcribed into mRNA and translated into peptides, polypeptides, or proteins.

The term "modulate" encompasses either a decrease or an increase in activity or expression depending on the target molecule.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The term "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

The term "skin aging" includes conditions derived from intrinsic chronological aging (for example, deepened expression lines, reduction of skin thickness, inelasticity, and/or unblemished smooth surface), those derived from photoaging (for example, deep wrinkles, yellow and leathery surface, hardening of the skin, elastosis, roughness, dyspigmentations (age spots) and/or blotchy skin), and those derived from steroid-induced skin thinning.

In the description herein, if there is any discrepancy between a chemical name and chemical structure, the structure preferably controls.

RORγ Modulators

RORγ modulators contemplated for use in the compositions and methods described herein are compounds with RORγ modulator activities. The term "RORγ modulator" includes RORγ and/or RORγt agonists and inverse agonists.

In some embodiments, provided herein is a compound of Formula (I), or a pharmaceutically acceptable salt, solvate, or stereoisomer thereof:

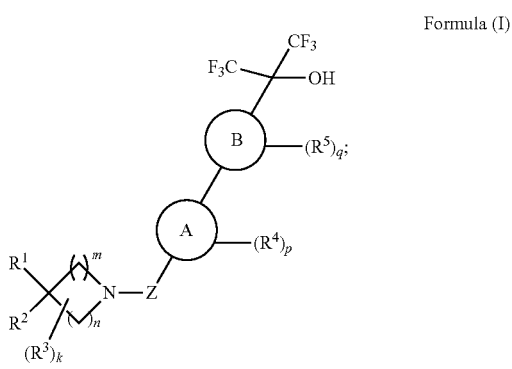

Formula (I)

wherein:

is phenyl, or a 5-membered or 6-membered heteroaryl ring;

is phenyl, or a 5-membered or 6-membered heteroaryl ring;

Z is $-(C(R^6)(R^7))_t-$;

$R^1$ and $R^2$ are selected from (i) and (ii):

(i) $R^1$ and $R^2$, together with the carbon atom to which they are attached, form a 4-, 5-, or 6-membered heterocyclyl ring wherein the 4-, 5-, or 6-membered heterocyclyl ring is optionally substituted with 1 to 4 $R^{3a}$ groups; and (ii) $R^1$ is hydrogen and $R^2$ is $-S(O)_2R^{10}$, $-C_1-C_6$alkyl-$S(O)_2R^{10}$, $-N(R^{11})S(O)_2R^{10}$, or $-C_1-C_6$alkyl-$N(R^{11})S(O)_2R^{10}$;

each $R^3$ is independently selected from halo and $C_1-C_6$alkyl;

each $R^{3a}$ is independently selected from $C_1-C_6$alkyl, $C_1-C_6$haloalkyl, $C_2-C_9$heteroaryl, $(C_2-C_9$heteroaryl)-$C_1-C_6$alkylene-, oxo, $-S(O)_2R^{10}$, $-C(O)R^{10}$, $-C(O)OR^{11}$, and $-C(O)N(R^{11})_2$, wherein $C_2-C_9$heteroaryl and $(C_2-C_9$heteroaryl)-$C_1-C_6$alkylene- are optionally substituted with 1 to 3 groups independently selected from halo, $C_1-C_6$alkyl, $C_1-C_6$haloalkyl, and hydroxyl;

each $R^4$ and each $R^5$ are each independently selected from halo, cyano, $-OH$, $C_1-C_6$alkyl, $C_1-C_6$alkenyl, $C_1-C_6$haloalkyl, $C_1-C_6$alkoxy, $C_3-C_8$cycloalkyl, $-N(R^9)_2$, $-C(O)R^8$, $-C(O)OR^9$, $-C(O)N(R^9)_2$, $-N(R^9)C(O)R^8$, $-N(R^9)SO_2R^8$, $-SO_2R^8$, and $-SO_2N(R^8)_2$;

each $R^6$ and each $R^7$ are each independently hydrogen, halo, or $C_1-C_6$alkyl;

each $R^8$ is independently $C_1-C_6$alkyl or $C_1-C_6$haloalkyl;

each $R^9$ is independently hydrogen, $C_1-C_6$alkyl, or $C_1-C_6$haloalkyl;

each $R^{10}$ is independently $C_1-C_6$alkyl, $C_1-C_6$haloalkyl, $C_1-C_6$alkyl-O-$C_1-C_6$alkyl-, $C_3-C_8$cycloalkyl, $C_2-C_9$heterocyclyl, phenyl, (phenyl)-$C_1-C_6$alkylene-, $C_2-C_9$heteroaryl, or $(C_2-C_9$heteroaryl)-$C_1-C_6$alkylene-, wherein the $C_3-C_8$cycloalkyl, $C_2-C_9$heterocyclyl, phenyl, (phenyl)-$C_1-C_6$alkylene-, $C_2-C_9$heteroaryl, or $(C_2-C_9$heteroaryl)-$C_1-C_6$alkylene- is optionally substituted with 1 to 3 groups selected from halo, $C_1-C_6$alkyl, $C_1-C_6$haloalkyl, and hydroxyl;

each $R^{11}$ is independently hydrogen, $C_1-C_6$alkyl, or $C_1-C_6$haloalkyl;

m is 1, 2, or 3;

n is 1, 2, or 3;

k is 0, 1, 2, 3, or 4;

p is 0, 1, 2, 3, or 4;

q is 0, 1, 2, 3 or 4; and t is 0, 1, 2, or 3.

In some embodiments is a compound of Formula (I), or a pharmaceutically acceptable salt, solvate, or stereoisomer thereof, wherein

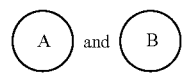

are each independently phenyl or a 6-membered heteroaryl. In some embodiments is a compound of Formula (I), or a pharmaceutically acceptable salt, solvate, or stereoisomer thereof, wherein

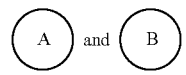

are each independently phenyl or a 5-membered heteroaryl. In some embodiments is a compound of Formula (I), or a pharmaceutically acceptable salt, solvate, or stereoisomer thereof, wherein

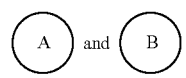

are each independently selected from phenyl, pyridine, pyrimidine, pyrazine, pyridazine, pyrrole, imidazole, pyrazole, thiazole, isothiazole, oxazole, isoxazole, thiadiazole, triazole, oxadiazole, thiophene and furan. In some embodiments is a compound of Formula (I), or a pharmaceutically acceptable salt, solvate, or stereoisomer thereof, wherein

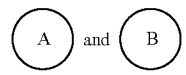

are each independently selected from phenyl, pyridine, pyrimidine, pyrazine and pyridazine. In some embodiments is a compound of Formula (I), or a pharmaceutically acceptable salt, solvate, or stereoisomer thereof, wherein

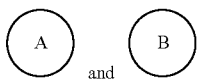

are both pyridine. In some embodiments is a compound of Formula (I), or a pharmaceutically acceptable salt, solvate, or stereoisomer thereof, wherein

is selected from phenyl, pyridine, pyrimidine, pyrazine, and pyridazine and

is phenyl or pyridine. In some embodiments is a compound of Formula (I), or a pharmaceutically acceptable salt, solvate, or stereoisomer thereof, wherein

is selected from phenyl, pyridine, pyrimidine, pyrazine, and pyridazine and

is phenyl. In some embodiments is a compound of Formula (I), or a pharmaceutically acceptable salt, solvate, or stereoisomer thereof, wherein

is phenyl or pyridine and

is phenyl. In some embodiments is a compound of Formula (I), or a pharmaceutically acceptable salt, solvate, or stereoisomer thereof, wherein

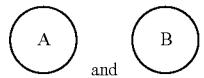

are both phenyl. In some embodiments is a compound of Formula (I), or a pharmaceutically acceptable salt, solvate, or stereoisomer thereof, wherein

is pyridine and

is phenyl. In some embodiments is a compound of Formula (I), or a pharmaceutically acceptable salt, solvate, or stereoisomer thereof, wherein

is phenyl and

is pyridine.

In some embodiments, provided herein is a compound of Formula (I), or a pharmaceutically acceptable salt, solvate, or stereoisomer thereof, wherein each $R^6$ and each $R^7$ are each independently hydrogen or $C_1$-$C_6$alkyl. In some embodiments, provided herein is a compound of Formula (I), or a pharmaceutically acceptable salt, solvate, or stereoisomer thereof, wherein each $R^6$ and each $R^7$ are hydrogen. In some embodiments, provided herein is a compound of Formula (I), or a pharmaceutically acceptable salt, solvate, or stereoisomer thereof, wherein each $R^6$ and each $R^7$ are each independently $C_1$-$C_6$alkyl. In some embodiments, provided herein is a compound of Formula (I), or a pharmaceutically acceptable salt, solvate, or stereoisomer thereof, wherein each $R^6$ and each $R^7$ are —$CH_3$. In some embodiments, provided herein is a compound of Formula (I), or a pharmaceutically acceptable salt, solvate, or stereoisomer thereof, wherein each $R^6$ and each $R^7$ are each independently halo.

In some embodiments, provided herein is a compound of Formula (I), or a pharmaceutically acceptable salt, solvate, or stereoisomer thereof, wherein t is 0. In some embodiments, provided herein is a compound of Formula (I), or a pharmaceutically acceptable salt, solvate, or stereoisomer thereof, wherein t is 1, 2, or 3. In some embodiments, provided herein is a compound of Formula (I), or a pharmaceutically acceptable salt, solvate, or stereoisomer thereof, wherein t is 1. In some embodiments, provided herein is a compound of Formula (I), or a pharmaceutically acceptable salt, solvate, or stereoisomer thereof, wherein t is 2. In some embodiments, provided herein is a compound of Formula (I), or a pharmaceutically acceptable salt, solvate, or stereoisomer thereof, wherein t is 3.

In some embodiments, provided herein is a compound of Formula (I), or a pharmaceutically acceptable salt, solvate, or stereoisomer thereof, wherein Z is —CH$_2$—. In some embodiments, provided herein is a compound of Formula (I), or a pharmaceutically acceptable salt, solvate, or stereoisomer thereof, wherein Z is —CH$_2$CH$_2$—. In some embodiments, provided herein is a compound of Formula (I), or a pharmaceutically acceptable salt, solvate, or stereoisomer thereof, wherein Z is —CH$_2$CH$_2$CH$_2$—.

In some embodiments is a compound of Formula (I), or a pharmaceutically acceptable salt, solvate, or stereoisomer thereof, wherein m is 1 and n is 1. In some embodiments is a compound of Formula (I), or a pharmaceutically acceptable salt, solvate, or stereoisomer thereof, wherein m is 2 and n is 1. In some embodiments is a compound of Formula (I), or a pharmaceutically acceptable salt, solvate, or stereoisomer thereof, wherein m is 2 and n is 2. In some embodiments is a compound of Formula (I), or a pharmaceutically acceptable salt, solvate, or stereoisomer thereof, wherein m is 3 and n is 1. In some embodiments is a compound of Formula (I), or a pharmaceutically acceptable salt, solvate, or stereoisomer thereof, wherein m is 3 and n is 2. In some embodiments is a compound of Formula (I), or a pharmaceutically acceptable salt, solvate, or stereoisomer thereof, wherein m is 3 and n is 3.

In some embodiments is a compound of Formula (I), or a pharmaceutically acceptable salt, solvate, or stereoisomer thereof, wherein R$^1$ and R$^2$, together with the carbon atom to which they are attached, form a 4-, 5-, or 6-membered heterocyclyl ring, wherein the 4-, 5-, or 6-membered heterocyclyl ring is optionally substituted with 1 to 4 R$^{3a}$ groups. In some embodiments is a compound of Formula (I), or a pharmaceutically acceptable salt, solvate, or stereoisomer thereof, wherein R$^1$ and R$^2$, together with the carbon atom to which they are attached, form a 4-membered heterocyclyl ring, wherein the 4-membered heterocyclyl ring is optionally substituted with 1 to 4 R$^{3a}$ groups. In some embodiments is a compound of Formula (I), or a pharmaceutically acceptable salt, solvate, or stereoisomer thereof, wherein R$^1$ and R$^2$, together with the carbon atom to which they are attached, form a 5-membered heterocyclyl ring, wherein the 5-membered heterocyclyl ring is optionally substituted with 1 to 4 R$^{3a}$ groups. In some embodiments is a compound of Formula (I), or a pharmaceutically acceptable salt, solvate, or stereoisomer thereof, wherein R$^1$ and R$^2$, together with the carbon atom to which they are attached, form a 6-membered heterocyclyl ring, wherein the 6-membered heterocyclyl ring is optionally substituted with 1 to 4 R$^{3a}$ groups. In some embodiments is a compound of Formula (I), or a pharmaceutically acceptable salt, solvate, or stereoisomer thereof, wherein R$^1$ and R$^2$, together with the carbon atom to which they are attached, form a 4-, 5-, or 6-membered heterocyclyl ring, wherein the 4-, 5-, or 6-membered heterocyclyl ring is optionally substituted with 1 or 2 R$^{3a}$ groups. In some embodiments is a compound of Formula (I), or a pharmaceutically acceptable salt, solvate, or stereoisomer thereof, wherein R$^1$ and R$^2$, together with the carbon atom to which they are attached, form a 4-membered heterocyclyl ring, wherein the 4-membered heterocyclyl ring is optionally substituted with 1 or 2 R$^{3a}$ groups. In some embodiments is a compound of Formula (I), or a pharmaceutically acceptable salt, solvate, or stereoisomer thereof, wherein R$^1$ and R$^2$, together with the carbon atom to which they are attached, form a 5-membered heterocyclyl ring, wherein the 5-membered heterocyclyl ring is optionally substituted with 1 or 2 R$^{3a}$ groups. In some embodiments is a compound of Formula (I), or a pharmaceutically acceptable salt, solvate, or stereoisomer thereof, wherein R$^1$ and R$^2$, together with the carbon atom to which they are attached, form a 6-membered heterocyclyl ring, wherein the 6-membered heterocyclyl ring is optionally substituted with 1 or 2 R$^{3a}$ groups. In some embodiments is a compound of Formula (I), or a pharmaceutically acceptable salt, solvate, or stereoisomer thereof, wherein R$^1$ and R$^2$, together with the carbon atom to which they are attached, form a 4-, 5-, or 6-membered heterocyclyl ring, wherein the 4-, 5-, or 6-membered heterocyclyl ring is optionally substituted with 1 R$^{3a}$ group. In some embodiments is a compound of Formula (I), or a pharmaceutically acceptable salt, solvate, or stereoisomer thereof, wherein R$^1$ and R$^2$, together with the carbon atom to which they are attached, form a 4-membered heterocyclyl ring, wherein the 4-membered heterocyclyl ring is optionally substituted with 1 R$^{3a}$ group. In some embodiments is a compound of Formula (I), or a pharmaceutically acceptable salt, solvate, or stereoisomer thereof, wherein R$^1$ and R$^2$, together with the carbon atom to which they are attached, form a 5-membered heterocyclyl ring, wherein the 5-membered heterocyclyl ring is optionally substituted with 1 R$^{3a}$ group. In some embodiments is a compound of Formula (I), or a pharmaceutically acceptable salt, solvate, or stereoisomer thereof, wherein R$^1$ and R$^2$, together with the carbon atom to which they are attached, form a 6-membered heterocyclyl ring, wherein the 6-membered heterocyclyl ring is optionally substituted with 1 R$^{3a}$ group.

In some embodiments is a compound of Formula (I), or a pharmaceutically acceptable salt, solvate, or stereoisomer thereof, wherein R$^1$ and R$^2$, together with the carbon atom to which they are attached, form a 4-, 5-, or 6-membered heterocyclyl ring, wherein the 4-, 5-, or 6-membered heterocyclyl ring is optionally substituted with 1 or 2 R$^{3a}$ groups and each R$^{3a}$ is selected from C$_1$-C$_6$alkyl, C$_1$-C$_6$haloalkyl, C$_2$-C$_9$heteroaryl, (C$_2$-C$_9$heteroaryl)-C$_1$-C$_6$alkylene-, oxo, —S(O)$_2$R$^{10}$, —C(O)R$^{10}$, —C(O)OR$^{11}$, and —C(O)N(R$^1$)$_2$, wherein C$_2$-C$_9$heteroaryl and (C$_2$-C$_9$heteroaryl)-C$_1$-C$_6$alkylene- are optionally substituted with 1 to 3 groups independently selected from halo, C$_1$-C$_6$alkyl, C$_1$-C$_6$haloalkyl, and hydroxyl. In some embodiments is a compound of Formula (I), or a pharmaceutically acceptable salt, solvate, or stereoisomer thereof, wherein R$^1$ and R$^2$, together with the carbon atom to which they are attached, form a 4-, 5-, or 6-membered heterocyclyl ring, wherein the 4-, 5-, or 6-membered heterocyclyl ring is optionally substituted with 1 or 2 R$^{3a}$ groups and each R$^{3a}$ is selected from C$_1$-C$_6$alkyl, oxo, —S(O)$_2$R$^{10}$, —C(O)R$^{10}$, and —C(O)OR$^{11}$. In some embodiments is a compound of Formula (I), or a pharmaceutically acceptable salt, solvate, or stereoisomer thereof, wherein R$^1$ and R$^2$, together with the carbon atom to which they are attached, form a 4-, 5-, or 6-membered heterocyclyl ring, wherein the 4-, 5-, or 6-membered heterocyclyl ring is optionally substituted with 1 or 2 R$^{3a}$ groups and each R$^{3a}$ is selected from C$_1$-C$_6$alkyl, oxo, —S(O)$_2$R$^{10}$, —C(O)R$^{10}$, and —C(O)OR$^{11}$. In some embodiments is a compound of Formula (I), or a pharmaceutically acceptable salt, solvate, or stereoisomer thereof, wherein R$^1$ and R$^2$, together with the carbon atom to which they are attached, form a 4-membered heterocyclyl ring, wherein the 4-membered heterocyclyl ring is optionally substituted with 1 or 2 R$^{3a}$ groups and each R$^{3a}$ is selected from C$_1$-C$_6$alkyl, oxo, —S(O)$_2$R$^{10}$, —C(O)R$^{10}$, and —C(O)OR$^{11}$. In some embodiments is a compound of Formula (I), or a pharmaceutically acceptable salt, solvate, or stereoisomer thereof, wherein R$^1$ and R$^2$, together with the carbon atom to which they are attached, form a 5-membered heterocyclyl ring, wherein the 5-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$. In some embodiments is a compound of Formula (I), or a pharmaceutically acceptable salt, solvate, or stereoisomer thereof, wherein $R^1$ and $R^2$, together with the carbon atom to which they are attached, form a 6-membered heterocyclyl ring, wherein the 6-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$.

In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group and $R^{3a}$ is —$S(O)_2R^{10}$. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, $C_6$-$C_{10}$aryl, or ($C_6$-$C_{10}$aryl)-$C_1$-$C_6$alkylene-. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is $C_1$-$C_6$alkyl or $C_3$-$C_8$cycloalkyl. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is $C_1$-$C_6$alkyl. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is —$CH_3$. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is —$CH_2CH_3$. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is —$CH_2CH_2CH_3$. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is $C_3$-$C_8$cycloalkyl. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is cyclopropyl.

In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group and $R^{3a}$ is —$C(O)R^{10}$. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$C(O)R^{10}$, and $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, $C_6$-$C_{10}$aryl, or ($C_6$-$C_{10}$aryl)-$C_1$-$C_6$alkylene-. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$C(O)R^{10}$, and $R^{10}$ is $C_1$-$C_6$alkyl. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$C(O)R^{10}$, and $R^{10}$ is —$CH_3$. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$C(O)R^{10}$, and $R^{10}$ is —$CH_2CH_3$. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$C(O)R^{10}$, and $R^{10}$ is —$CH_2CH_2CH_3$.

In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group and $R^{3a}$ is —$C(O)OR^{11}$. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$C(O)OR^{11}$, and $R^{11}$ is $C_1$-$C_6$alkyl. In some embodiments is a compound of Formula (I), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)OR$^{11}$, and R$^{11}$ is —CH$_3$. In some embodiments is a compound of Formula (I), or a pharmaceutically acceptable salt, solvate, or stereoisomer thereof, wherein R$^1$ and R$^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)OR$^{11}$, and R$^{11}$ is —CH$_2$CH$_3$. In some embodiments is a compound of Formula (I), or a pharmaceutically acceptable salt, solvate, or stereoisomer thereof, wherein R$^1$ and R$^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)OR$^{11}$, and R$^{11}$ is —CH$_2$CH$_2$CH$_3$.

In some embodiments is a compound of Formula (I), or a pharmaceutically acceptable salt, solvate, or stereoisomer thereof, wherein p is 0, 1, 2, or 3. In some embodiments is a compound of Formula (I), or a pharmaceutically acceptable salt, solvate, or stereoisomer thereof, wherein p is 0.

In some embodiments is a compound of Formula (I), or a pharmaceutically acceptable salt, solvate, or stereoisomer thereof, wherein p is 1. In some embodiments is a compound of Formula (I), or a pharmaceutically acceptable salt, solvate, or stereoisomer thereof, wherein p is 2. In some embodiments is a compound of Formula (I), or a pharmaceutically acceptable salt, solvate, or stereoisomer thereof, wherein p is 3. In some embodiments is a compound of Formula (I), or a pharmaceutically acceptable salt, solvate, or stereoisomer thereof, wherein p is 1, 2, or 3. In some embodiments is a compound of Formula (I), or a pharmaceutically acceptable salt, solvate, or stereoisomer thereof, wherein p is 1, 2, or 3 and each R$^4$ is independently halo, $C_1$-$C_6$alkyl, $C_1$-$C_6$alkenyl, $C_1$-$C_6$haloalkyl, $C_1$-$C_6$alkoxy, or $C_3$-$C_8$cycloalkyl. In some embodiments is a compound of Formula (I), or a pharmaceutically acceptable salt, solvate, or stereoisomer thereof, wherein p is 1, 2, or 3 and each R$^4$ is independently halo, $C_1$-$C_6$alkyl, or $C_3$-$C_8$cycloalkyl. In some embodiments is a compound of Formula (I), or a pharmaceutically acceptable salt, solvate, or stereoisomer thereof, wherein p is 1 and R$^4$ is halo, $C_1$-$C_6$alkyl, or $C_3$-$C_8$cycloalkyl. In some embodiments is a compound of Formula (I), or a pharmaceutically acceptable salt, solvate, or stereoisomer thereof, wherein p is 2 and each R$^4$ is independently halo, $C_1$-$C_6$alkyl, or $C_3$-$C_8$cycloalkyl. In some embodiments is a compound of Formula (I), or a pharmaceutically acceptable salt, solvate, or stereoisomer thereof, wherein p is 3 and each R$^4$ is independently halo, $C_1$-$C_6$alkyl, or $C_3$-$C_8$cycloalkyl.

In some embodiments is a compound of Formula (I), or a pharmaceutically acceptable salt, solvate, or stereoisomer thereof, wherein q is 0, 1, 2, or 3. In some embodiments is a compound of Formula (I), or a pharmaceutically acceptable salt, solvate, or stereoisomer thereof, wherein q is 0. In some embodiments is a compound of Formula (I), or a pharmaceutically acceptable salt, solvate, or stereoisomer thereof, wherein q is 1. In some embodiments is a compound of Formula (I), or a pharmaceutically acceptable salt, solvate, or stereoisomer thereof, wherein q is 2. In some embodiments is a compound of Formula (I), or a pharmaceutically acceptable salt, solvate, or stereoisomer thereof, wherein q is 3. In some embodiments is a compound of Formula (I), or a pharmaceutically acceptable salt, solvate, or stereoisomer thereof, wherein q is 1, 2, or 3. In some embodiments is a compound of Formula (I), or a pharmaceutically acceptable salt, solvate, or stereoisomer thereof, wherein q is 1, 2, or 3 and each R$^5$ is independently halo, cyano, $C_1$-$C_6$alkyl, $C_1$-$C_6$haloalkyl, $C_1$-$C_6$alkoxy, or $C_3$-$C_8$cycloalkyl. In some embodiments is a compound of Formula (I), or a pharmaceutically acceptable salt, solvate, or stereoisomer thereof, wherein q is 1, 2, or 3 and each R$^5$ is independently halo, cyano, $C_1$-$C_6$alkyl, $C_1$-$C_6$haloalkyl, or $C_1$-$C_6$alkoxy. In some embodiments is a compound of Formula (I), or a pharmaceutically acceptable salt, solvate, or stereoisomer thereof, wherein q is 1, 2, or 3 and each R$^5$ is independently halo or $C_1$-$C_6$alkyl. In some embodiments is a compound of Formula (I), or a pharmaceutically acceptable salt, solvate, or stereoisomer thereof, wherein q is 1 and R$^5$ is halo or $C_1$-$C_6$alkyl. In some embodiments is a compound of Formula (I), or a pharmaceutically acceptable salt, solvate, or stereoisomer thereof, wherein q is 2 and each R$^5$ is independently halo or $C_1$-$C_6$alkyl. In some embodiments is a compound of Formula (I), or a pharmaceutically acceptable salt, solvate, or stereoisomer thereof, wherein q is 3 and each R$^5$ is independently halo or $C_1$-$C_6$alkyl.

In some embodiments is a compound of Formula (I), or a pharmaceutically acceptable salt, solvate, or stereoisomer thereof, wherein k is 0, 1, 2, 3, or 4. In some embodiments is a compound of Formula (I), or a pharmaceutically acceptable salt, solvate, or stereoisomer thereof, wherein k is 0, 1, 2, or 3. In some embodiments is a compound of Formula (I), or a pharmaceutically acceptable salt, solvate, or stereoisomer thereof, wherein k is 0, 1, or 2. In some embodiments is a compound of Formula (I), or a pharmaceutically acceptable salt, solvate, or stereoisomer thereof, wherein k is 0 or 1. In some embodiments is a compound of Formula (I), or a pharmaceutically acceptable salt, solvate, or stereoisomer thereof, wherein k is 0. In some embodiments is a compound of Formula (I), or a pharmaceutically acceptable salt, solvate, or stereoisomer thereof, wherein k is 1. In some embodiments is a compound of Formula (I), or a pharmaceutically acceptable salt, solvate, or stereoisomer thereof, wherein k is 1 and R$^3$ is halo, $C_1$-$C_6$alkyl, or $C_1$-$C_6$haloalkyl. In some embodiments is a compound of Formula (I), or a pharmaceutically acceptable salt, solvate, or stereoisomer thereof, wherein k is 2. In some embodiments is a compound of Formula (I), or a pharmaceutically acceptable salt, solvate, or stereoisomer thereof, wherein k is 2 and each R$^3$ is independently halo, $C_1$-$C_6$alkyl, or $C_1$-$C_6$haloalkyl.

In some embodiments, provided herein is a compound of Formula (Ia), or a pharmaceutically acceptable salt, solvate, or stereoisomer thereof:

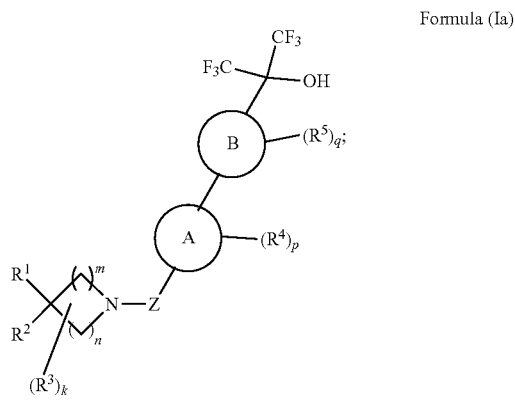

Formula (Ia)

wherein:

is phenyl;

is a pyridyl ring;
Z is —(C(R$^6$)(R$^7$))$_t$—;
R$^1$ and R$^2$ are selected from (i) and (ii):
(i) R$^1$ and R$^2$, together with the carbon atom to which they are attached, form a 4-, 5-, or 6-membered heterocyclyl ring wherein the 4-, 5-, or 6-membered heterocyclyl ring is optionally substituted with 1 to 4 R$^{3a}$ groups; and
(ii) R$^1$ is hydrogen and R$^2$ is —S(O)$_2$R$^{10}$, —C$_1$-C$_6$alkyl-S(O)$_2$R$^{10}$, —N(R$^{11}$)S(O)$_2$R$^{10}$, or —C$_1$-C$_6$alkyl-N(R$^{11}$)S(O)$_2$R$^{10}$;
each R$^3$ is independently selected from halo and C$_1$-C$_6$alkyl;
each R$^{3a}$ is independently selected from C$_1$-C$_6$alkyl, C$_1$-C$_6$haloalkyl, C$_2$-C$_9$heteroaryl, (C$_2$-C$_9$heteroaryl)-C$_1$-C$_6$alkylene-, oxo, —S(O)$_2$R$^{10}$, —C(O)R$^{10}$, —C(O)OR$^{11}$, and —C(O)N(R$^{11}$)$_2$, wherein C$_2$-C$_9$heteroaryl and (C$_2$-C$_9$heteroaryl)-C$_1$-C$_6$alkylene- are optionally substituted with 1 to 3 groups independently selected from halo, C$_1$-C$_6$alkyl, C$_1$-C$_6$haloalkyl, and hydroxyl;
each R$^4$ and each R$^5$ are each independently selected from halo, cyano, —OH, C$_1$-C$_6$alkyl, C$_1$-C$_6$alkenyl, C$_1$-C$_6$haloalkyl, C$_1$-C$_6$alkoxy, C$_3$-C$_8$cycloalkyl, —N(R$^9$)$_2$, —C(O)R$^8$, —C(O)OR$^9$, —C(O)N(R$^9$)$_2$, —N(R$^9$)C(O)R$^8$, —N(R$^9$)SO$_2$R$^8$, —SO$_2$R$^8$, and —SO$_2$N(R$^8$)$_2$;
each R$^6$ and each R$^7$ are each independently hydrogen, halo, or C$_1$-C$_6$alkyl;
each R$^8$ is independently C$_1$-C$_6$alkyl or C$_1$-C$_6$haloalkyl;
each R$^9$ is independently hydrogen, C$_1$-C$_6$alkyl, or C$_1$-C$_6$haloalkyl;
each R$^{10}$ is independently C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 to 3 groups selected from halo, C$_1$-C$_6$alkyl, C$_1$-C$_6$haloalkyl, and hydroxyl;
each R$^{11}$ is independently hydrogen, C$_1$-C$_6$alkyl, or C$_1$-C$_6$haloalkyl;
m is 1, 2, or 3;
n is 1, 2, or 3;
k is 0, 1, 2, 3, or 4;
p is 0, 1, 2, 3, or 4;
q is 0, 1, 2, or 3; and
t is 0, 1, 2, or 3.

In some embodiments, provided herein is a compound of Formula (Ia), or a pharmaceutically acceptable salt, solvate, or stereoisomer thereof, wherein each R$^6$ and each R$^7$ are each independently hydrogen or C$_1$-C$_6$alkyl. In some embodiments, provided herein is a compound of Formula (Ia), or a pharmaceutically acceptable salt, solvate, or stereoisomer thereof, wherein each R$^6$ and each R$^7$ are hydrogen. In some embodiments, provided herein is a compound of Formula (Ia), or a pharmaceutically acceptable salt, solvate, or stereoisomer thereof, wherein each R$^6$ and each R$^7$ are each independently C$_1$-C$_6$alkyl. In some embodiments, provided herein is a compound of Formula (Ia), or a pharmaceutically acceptable salt, solvate, or stereoisomer thereof, wherein each R$^6$ and each R$^7$ are —CH$_3$. In some embodiments, provided herein is a compound of Formula (Ia), or a pharmaceutically acceptable salt, solvate, or stereoisomer thereof, wherein each R$^6$ and each R$^7$ are each independently halo.

In some embodiments, provided herein is a compound of Formula (Ia), or a pharmaceutically acceptable salt, solvate, or stereoisomer thereof, wherein t is 0. In some embodiments, provided herein is a compound of Formula (Ia), or a pharmaceutically acceptable salt, solvate, or stereoisomer thereof, wherein t is 1, 2, or 3. In some embodiments, provided herein is a compound of Formula (Ia), or a pharmaceutically acceptable salt, solvate, or stereoisomer thereof, wherein t is 1. In some embodiments, provided herein is a compound of Formula (Ia), or a pharmaceutically acceptable salt, solvate, or stereoisomer thereof, wherein t is 2. In some embodiments, provided herein is a compound of Formula (Ia), or a pharmaceutically acceptable salt, solvate, or stereoisomer thereof, wherein t is 3.

In some embodiments, provided herein is a compound of Formula (Ia), or a pharmaceutically acceptable salt, solvate, or stereoisomer thereof, wherein Z is —CH$_2$—. In some embodiments, provided herein is a compound of Formula (Ia), or a pharmaceutically acceptable salt, solvate, or stereoisomer thereof, wherein Z is —CH$_2$CH$_2$—. In some embodiments, provided herein is a compound of Formula (Ia), or a pharmaceutically acceptable salt, solvate, or stereoisomer thereof, wherein Z is —CH$_2$CH$_2$CH$_2$—.

In some embodiments is a compound of Formula (Ia), or a pharmaceutically acceptable salt, solvate, or stereoisomer thereof, wherein m is 1 and n is 1. In some embodiments is a compound of Formula (Ia), or a pharmaceutically acceptable salt, solvate, or stereoisomer thereof, wherein m is 2 and n is 1. In some embodiments is a compound of Formula (Ia), or a pharmaceutically acceptable salt, solvate, or stereoisomer thereof, wherein m is 2 and n is 2. In some embodiments is a compound of Formula (Ia), or a pharmaceutically acceptable salt, solvate, or stereoisomer thereof, wherein m is 3 and n is 1. In some embodiments is a compound of Formula (Ia), or a pharmaceutically acceptable salt, solvate, or stereoisomer thereof, wherein m is 3 and n is 2. In some embodiments is a compound of Formula (Ia), or a pharmaceutically acceptable salt, solvate, or stereoisomer thereof, wherein m is 3 and n is 3.

In some embodiments is a compound of Formula (Ia), or a pharmaceutically acceptable salt, solvate, or stereoisomer thereof, wherein R$^1$ and R$^2$, together with the carbon atom to which they are attached, form a 4-, 5-, or 6-membered heterocyclyl ring, wherein the 4-, 5-, or 6-membered heterocyclyl ring is optionally substituted with 1 to 4 R$^{3a}$ groups. In some embodiments is a compound of Formula (Ia), or a pharmaceutically acceptable salt, solvate, or stereoisomer thereof, wherein R$^1$ and R$^2$, together with the carbon atom to which they are attached, form a 4-membered heterocyclyl ring, wherein the 4-membered heterocyclyl ring is optionally substituted with 1 to 4 R$^{3a}$ groups. In some embodiments is a compound of Formula (Ia), or a pharmaceutically acceptable salt, solvate, or stereoisomer thereof, wherein $R^1$ and $R^2$, together with the carbon atom to which they are attached, form a 5-membered heterocyclyl ring, wherein the 5-membered heterocyclyl ring is optionally substituted with 1 to 4 $R^{3a}$ groups. In some embodiments is a compound of Formula (Ia), or a pharmaceutically acceptable salt, solvate, or stereoisomer thereof, wherein $R^1$ and $R^2$, together with the carbon atom to which they are attached, form a 6-membered heterocyclyl ring, wherein the 6-membered heterocyclyl ring is optionally substituted with 1 to 4 $R^{3a}$ groups. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 or 2 $R^{3a}$ groups. In some embodiments is a compound of Formula (Ia), or a pharmaceutically acceptable salt, solvate, or stereoisomer thereof, wherein $R^1$ and $R^2$, together with the carbon atom to which they are attached, form a 4-membered heterocyclyl ring, wherein the 4-membered heterocyclyl ring is optionally substituted with 1 or 2 $R^{3a}$ groups. In some embodiments is a compound of Formula (Ia), or a pharmaceutically acceptable salt, solvate, or stereoisomer thereof, wherein $R^1$ and $R^2$, together with the carbon atom to which they are attached, form a 5-membered heterocyclyl ring, wherein the 5-membered heterocyclyl ring is optionally substituted with 1 or 2 $R^{3a}$ groups. In some embodiments is a compound of Formula (Ia), or a pharmaceutically acceptable salt, solvate, or stereoisomer thereof, wherein $R^1$ and $R^2$, together with the carbon atom to which they are attached, form a 6-membered heterocyclyl ring, wherein the 6-membered heterocyclyl ring is optionally substituted with 1 or 2 $R^{3a}$ groups. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group. In some embodiments is a compound of Formula (Ia), or a pharmaceutically acceptable salt, solvate, or stereoisomer thereof, wherein $R^1$ and $R^2$, together with the carbon atom to which they are attached, form a 4-membered heterocyclyl ring, wherein the 4-membered heterocyclyl ring is optionally substituted with 1 $R^{3a}$ group. In some embodiments is a compound of Formula (Ia), or a pharmaceutically acceptable salt, solvate, or stereoisomer thereof, wherein $R^1$ and $R^2$, together with the carbon atom to which they are attached, form a 5-membered heterocyclyl ring, wherein the 5-membered heterocyclyl ring is optionally substituted with 1 $R^{3a}$ group. In some embodiments is a compound of Formula (Ia), or a pharmaceutically acceptable salt, solvate, or stereoisomer thereof, wherein $R^1$ and $R^2$, together with the carbon atom to which they are attached, form a 6-membered heterocyclyl ring, wherein the 6-membered heterocyclyl ring is optionally substituted with 1 $R^{3a}$ group.

In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 or 2 $R^{3a}$ groups and each $R^{3a}$ is selected from $C_1$-$C_6$alkyl, $C_1$-$C_6$haloalkyl, $C_2$-$C_9$heteroaryl, ($C_2$-$C_9$heteroaryl)-$C_1$-$C_6$alkylene-, oxo, —$S(O)_2R^{10}$, —$C(O)R^{10}$, —$C(O)OR^{11}$, and —$C(O)N(R^{11})_2$, wherein $C_2$-$C_9$heteroaryl and ($C_2$-$C_9$heteroaryl)-$C_1$-$C_6$alkylene- are optionally substituted with 1 to 3 groups independently selected from halo, $C_1$-$C_6$alkyl, $C_1$-$C_6$haloalkyl, and hydroxyl. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$. In some embodiments is a compound of Formula (Ia), or a pharmaceutically acceptable salt, solvate, or stereoisomer thereof, wherein $R^1$ and $R^2$, together with the carbon atom to which they are attached, form a 4-membered heterocyclyl ring, wherein the 4-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$. In some embodiments is a compound of Formula (Ia), or a pharmaceutically acceptable salt, solvate, or stereoisomer thereof, wherein R and $R^2$, together with the carbon atom to which they are attached, form a 5-membered heterocyclyl ring, wherein the 5-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$. In some embodiments is a compound of Formula (Ia), or a pharmaceutically acceptable salt, solvate, or stereoisomer thereof, wherein $R^1$ and $R^2$, together with the carbon atom to which they are attached, form a 6-membered heterocyclyl ring, wherein the 6-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$.

In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group and $R^{3a}$ is —$S(O)_2R^{10}$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, $C_6$-$C_{10}$aryl, or ($C_6$-$C_{10}$aryl)-$C_1$-$C_6$alkylene-. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is $C_1$-$C_6$alkyl or $C_3$-$C_8$cycloalkyl. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —S(O)$_2$R$^{10}$, and $R^{10}$ is $C_1$-$C_6$alkyl. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —S(O)$_2$R$^{10}$, and $R^{10}$ is —CH$_3$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —S(O)$_2$R$^{10}$, and $R^{10}$ is —CH$_2$CH$_3$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —S(O)$_2$R$^{10}$, and $R^{10}$ is —CH$_2$CH$_2$CH$_3$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —S(O)$_2$R$^{10}$, and $R^{10}$ is $C_3$-$C_8$cycloalkyl. In some embodiments is a compound of Formula (Ia), or a pharmaceutically acceptable salt, solvate, or stereoisomer thereof, wherein R and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —S(O)$_2$R$^{10}$, and $R^{10}$ is cyclopropyl.

In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group and $R^{3a}$ is —C(O)R$^{10}$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)R$^{10}$, and $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, $C_6$-$C_{10}$aryl, or ($C_6$-$C_{10}$aryl)-$C_1$-$C_6$alkylene-. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)R$^{10}$, and $R^{10}$ is $C_1$-$C_6$alkyl. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)R$^{10}$, and $R^{10}$ is —CH$_3$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)R$^{10}$, and $R^{10}$ is —CH$_2$CH$_3$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)R$^{10}$, and $R^{10}$ is —CH$_2$CH$_2$CH$_3$.

In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group and $R^{3a}$ is —C(O)OR$^{11}$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)OR$^{11}$, and $R^{11}$ is $C_1$-$C_6$alkyl. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)OR$^{11}$, and $R^{11}$ is —CH$_3$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)OR$^{11}$, and $R^{11}$ is —CH$_2$CH$_3$. In some embodiments is a compound of Formula (Ia), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)OR$^{11}$, and $R^{11}$ is —CH$_2$CH$_2$CH$_3$.

In some embodiments is a compound of Formula (Ia), or a pharmaceutically acceptable salt, solvate, or stereoisomer thereof, wherein p is 0, 1, 2, or 3. In some embodiments is a compound of Formula (Ia), or a pharmaceutically acceptable salt, solvate, or stereoisomer thereof, wherein p is 0. In some embodiments is a compound of Formula (Ia), or a pharmaceutically acceptable salt, solvate, or stereoisomer thereof, wherein p is 1. In some embodiments is a compound of Formula (Ia), or a pharmaceutically acceptable salt, solvate, or stereoisomer thereof, wherein p is 2. In some embodiments is a compound of Formula (Ia), or a pharmaceutically acceptable salt, solvate, or stereoisomer thereof, wherein p is 3. In some embodiments is a compound of Formula (Ia), or a pharmaceutically acceptable salt, solvate, or stereoisomer thereof, wherein p is 1, 2, or 3. In some embodiments is a compound of Formula (Ia), or a pharmaceutically acceptable salt, solvate, or stereoisomer thereof, wherein p is 1, 2, or 3 and each $R^4$ is independently halo, $C_1$-$C_6$alkyl, $C_1$-$C_6$alkenyl, $C_1$-$C_6$haloalkyl, $C_1$-$C_6$alkoxy, or $C_3$-$C_8$cycloalkyl. In some embodiments is a compound of Formula (Ia), or a pharmaceutically acceptable salt, solvate, or stereoisomer thereof, wherein p is 1, 2, or 3 and each $R^4$ is independently halo, $C_1$-$C_6$alkyl, or $C_3$-$C_8$cycloalkyl. In some embodiments is a compound of Formula (Ia), or a pharmaceutically acceptable salt, solvate, or stereoisomer thereof, wherein p is 1 and $R^4$ is halo, $C_1$-$C_6$alkyl, or $C_3$-$C_8$cycloalkyl. In some embodiments is a compound of Formula (Ia), or a pharmaceutically acceptable salt, solvate, or stereoisomer thereof, wherein p is 2 and each $R^4$ is independently halo, $C_1$-$C_6$alkyl, or $C_3$-$C_8$cycloalkyl. In some embodiments is a compound of Formula (Ia), or a pharmaceutically acceptable salt, solvate, or stereoisomer thereof, wherein p is 3 and each $R^4$ is independently halo, $C_1$-$C_6$alkyl, or $C_3$-$C_8$cycloalkyl.

In some embodiments is a compound of Formula (Ia), or a pharmaceutically acceptable salt, solvate, or stereoisomer thereof, wherein q is 0, 1, or 2. In some embodiments is a compound of Formula (Ia), or a pharmaceutically acceptable salt, solvate, or stereoisomer thereof, wherein q is 0. In some embodiments is a compound of Formula (Ia), or a pharmaceutically acceptable salt, solvate, or stereoisomer thereof, wherein q is 1. In some embodiments is a compound of Formula (Ia), or a pharmaceutically acceptable salt, solvate, or stereoisomer thereof, wherein q is 2. In some embodiments is a compound of Formula (Ia), or a pharmaceutically acceptable salt, solvate, or stereoisomer thereof, wherein q is 3. In some embodiments is a compound of Formula (Ia), or a pharmaceutically acceptable salt, solvate, or stereoisomer thereof, wherein q is 1, 2, or 3 and each $R^5$ is independently halo, cyano, $C_1$-$C_6$alkyl, $C_1$-$C_6$haloalkyl, $C_1$-$C_6$alkoxy, or $C_3$-$C_8$cycloalkyl. In some embodiments is a compound of Formula (Ia), or a pharmaceutically acceptable salt, solvate, or stereoisomer thereof, wherein q is 1, 2, or 3 and each $R^5$ is independently halo, cyano, $C_1$-$C_6$alkyl, $C_1$-$C_6$haloalkyl, or $C_1$-$C_6$alkoxy. In some embodiments is a compound of Formula (Ia), or a pharmaceutically acceptable salt, solvate, or stereoisomer thereof, wherein q is 1, 2, or 3 and each $R^5$ is independently halo or $C_1$-$C_6$alkyl. In some embodiments is a compound of Formula (Ia), or a pharmaceutically acceptable salt, solvate, or stereoisomer thereof, wherein q is 1 and $R^5$ is halo or $C_1$-$C_6$alkyl. In some embodiments is a compound of Formula (Ia), or a pharmaceutically acceptable salt, solvate, or stereoisomer thereof, wherein q is 2 and each $R^5$ is independently halo or $C_1$-$C_6$alkyl. In some embodiments is a compound of Formula (Ia), or a pharmaceutically acceptable salt, solvate, or stereoisomer thereof, wherein q is 3 and each $R^5$ is independently halo or $C_1$-$C_6$alkyl.

In some embodiments is a compound of Formula (Ia), or a pharmaceutically acceptable salt, solvate, or stereoisomer thereof, wherein k is 0, 1, 2, 3, or 4. In some embodiments is a compound of Formula (Ia), or a pharmaceutically acceptable salt, solvate, or stereoisomer thereof, wherein k is 0, 1, 2, or 3. In some embodiments is a compound of Formula (Ia), or a pharmaceutically acceptable salt, solvate, or stereoisomer thereof, wherein k is 0, 1, or 2. In some embodiments is a compound of Formula (Ia), or a pharmaceutically acceptable salt, solvate, or stereoisomer thereof, wherein k is 0 or 1. In some embodiments is a compound of Formula (Ia), or a pharmaceutically acceptable salt, solvate, or stereoisomer thereof, wherein k is 0. In some embodiments is a compound of Formula (Ia), or a pharmaceutically acceptable salt, solvate, or stereoisomer thereof, wherein k is 1. In some embodiments is a compound of Formula (Ia), or a pharmaceutically acceptable salt, solvate, or stereoisomer thereof, wherein k is 1 and $R^3$ is halo, $C_1$-$C_6$alkyl, or $C_1$-$C_6$haloalkyl. In some embodiments is a compound of Formula (Ia), or a pharmaceutically acceptable salt, solvate, or stereoisomer thereof, wherein k is 2. In some embodiments is a compound of Formula (Ia), or a pharmaceutically acceptable salt, solvate, or stereoisomer thereof, wherein k is 2 and each $R^3$ is independently halo, $C_1$-$C_6$alkyl, or $C_1$-$C_6$haloalkyl.

In some embodiments, provided herein is a compound of Formula (Ib), or a pharmaceutically acceptable salt, solvate, or stereoisomer thereof:

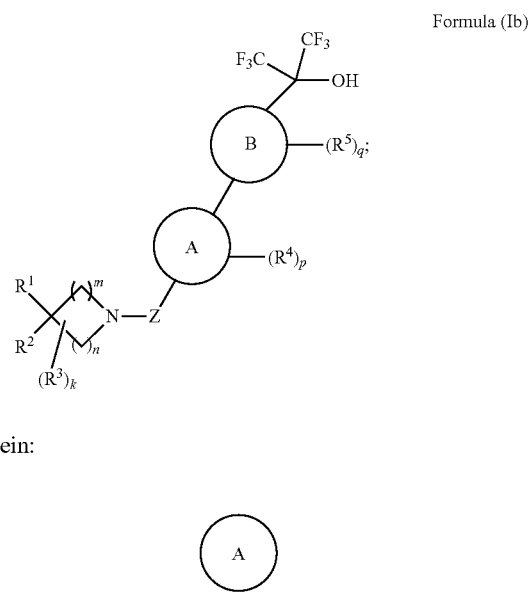

Formula (Ib)

wherein:

a is a pyridyl ring;

is phenyl;
Z is $-(C(R^6)(R^7))_t-$;
$R^1$ and $R^2$ are selected from (i) and (ii):
(i) $R^1$ and $R^2$, together with the carbon atom to which they are attached, form a 4-, 5-, or 6-membered heterocyclyl ring wherein the 4-, 5-, or 6-membered heterocyclyl ring is optionally substituted with 1 to 4 $R^{3a}$ groups; and
(ii) $R^1$ is hydrogen and $R^2$ is $-S(O)_2R^{10}$, $-C_1$-$C_6$alkyl-$S(O)_2R^{10}$, $-N(R^{11})S(O)_2R^{10}$, or $-C_1$-$C_6$alkyl-$N(R^{11})S(O)_2R^{10}$;
each $R^3$ is independently selected from halo and $C_1$-$C_6$alkyl;
each $R^{3a}$ is independently selected from $C_1$-$C_6$alkyl, $C_1$-$C_6$haloalkyl, $C_2$-$C_9$heteroaryl, $(C_2$-$C_9$heteroaryl)-$C_1$-$C_6$alkylene-, oxo, $-S(O)_2R^{10}$, $-C(O)R^{10}$, $-C(O)OR^{11}$, and $-C(O)N(R^{11})_2$, wherein $C_2$-$C_9$heteroaryl and $(C_2$-$C_9$heteroaryl)-$C_1$-$C_6$alkylene- are optionally substituted with 1 to 3 groups independently selected from halo, $C_1$-$C_6$alkyl, $C_1$-$C_6$haloalkyl, and hydroxyl;
each $R^4$ and each $R^5$ are each independently selected from halo, cyano, $-OH$, $C_1$-$C_6$alkyl, $C_1$-$C_6$alkenyl, $C_1$-$C_6$haloalkyl, $C_1$-$C_6$alkoxy, $C_3$-$C_8$cycloalkyl, $-N(R^9)_2$, $-C(O)R^8$, $-C(O)OR^9$, $-C(O)N(R^9)_2$, $-N(R^9)C(O)R^8$, $-N(R^9)SO_2R^8$, $-SO_2R^8$, and $-SO_2N(R^8)_2$;
each $R^6$ and each $R^7$ are each independently hydrogen, halo, or $C_1$-$C_6$alkyl;

each $R^8$ is independently $C_1$-$C_6$alkyl or $C_1$-$C_6$haloalkyl;
each $R^9$ is independently hydrogen, $C_1$-$C_6$alkyl, or $C_1$-$C_6$haloalkyl;
each $R^{10}$ is independently $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene- is optionally substituted with 1 to 3 groups selected from halo, $C_1$-$C_6$alkyl, $C_1$-$C_6$haloalkyl, and hydroxyl;
each $R^{11}$ is independently hydrogen, $C_1$-$C_6$alkyl, or $C_1$-$C_6$haloalkyl;
m is 1, 2, or 3;
n is 1, 2, or 3;
k is 0, 1, 2, 3, or 4;
p is 0, 1, 2, or 3;
q is 0, 1, 2, 3, or 4; and
t is 0, 1, 2, or 3.

In some embodiments, provided herein is a compound of Formula (Ib), or a pharmaceutically acceptable salt, solvate, or stereoisomer thereof, wherein each $R^6$ and each $R^7$ are each independently hydrogen or $C_1$-$C_6$alkyl. In some embodiments, provided herein is a compound of Formula (Ib), or a pharmaceutically acceptable salt, solvate, or stereoisomer thereof, wherein each $R^6$ and each $R^7$ are hydrogen. In some embodiments, provided herein is a compound of Formula (Ib), or a pharmaceutically acceptable salt, solvate, or stereoisomer thereof, wherein each $R^6$ and each $R^7$ are each independently $C_1$-$C_6$alkyl. In some embodiments, provided herein is a compound of Formula (Ib), or a pharmaceutically acceptable salt, solvate, or stereoisomer thereof, wherein each $R^6$ and each $R^7$ are —$CH_3$. In some embodiments, provided herein is a compound of Formula (Ib), or a pharmaceutically acceptable salt, solvate, or stereoisomer thereof, wherein each $R^6$ and each $R^7$ are each independently halo.

In some embodiments, provided herein is a compound of Formula (Ib), or a pharmaceutically acceptable salt, solvate, or stereoisomer thereof, wherein t is 0. In some embodiments, provided herein is a compound of Formula (Ib), or a pharmaceutically acceptable salt, solvate, or stereoisomer thereof, wherein t is 1, 2, or 3. In some embodiments, provided herein is a compound of Formula (Ib), or a pharmaceutically acceptable salt, solvate, or stereoisomer thereof, wherein t is 1. In some embodiments, provided herein is a compound of Formula (Ib), or a pharmaceutically acceptable salt, solvate, or stereoisomer thereof, wherein t is 2. In some embodiments, provided herein is a compound of Formula (Ib), or a pharmaceutically acceptable salt, solvate, or stereoisomer thereof, wherein t is 3.

In some embodiments, provided herein is a compound of Formula (Ib), or a pharmaceutically acceptable salt, solvate, or stereoisomer thereof, wherein Z is —$CH_2$—. In some embodiments, provided herein is a compound of Formula (Ib), or a pharmaceutically acceptable salt, solvate, or stereoisomer thereof, wherein Z is —$CH_2CH_2$—. In some embodiments, provided herein is a compound of Formula (Ib), or a pharmaceutically acceptable salt, solvate, or stereoisomer thereof, wherein Z is —$CH_2CH_2CH_2$—.

In some embodiments is a compound of Formula (Ib), or a pharmaceutically acceptable salt, solvate, or stereoisomer thereof, wherein m is 1 and n is 1. In some embodiments is a compound of Formula (Ib), or a pharmaceutically acceptable salt, solvate, or stereoisomer thereof, wherein m is 2 and n is 1. In some embodiments is a compound of Formula (Ib), or a pharmaceutically acceptable salt, solvate, or stereoisomer thereof, wherein m is 2 and n is 2. In some embodiments is a compound of Formula (Ib), or a pharmaceutically acceptable salt, solvate, or stereoisomer thereof, wherein m is 3 and n is 1. In some embodiments is a compound of Formula (Ib), or a pharmaceutically acceptable salt, solvate, or stereoisomer thereof, wherein m is 3 and n is 2. In some embodiments is a compound of Formula (Ib), or a pharmaceutically acceptable salt, solvate, or stereoisomer thereof, wherein m is 3 and n is 3.

In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 to 4 $R^{3a}$ groups. In some embodiments is a compound of Formula (Ib), or a pharmaceutically acceptable salt, solvate, or stereoisomer thereof, wherein $R^1$ and $R^2$, together with the carbon atom to which they are attached, form a 4-membered heterocyclyl ring, wherein the 4-membered heterocyclyl ring is optionally substituted with 1 to 4 $R^{3a}$ groups. In some embodiments is a compound of Formula (Ib), or a pharmaceutically acceptable salt, solvate, or stereoisomer thereof, wherein $R^1$ and $R^2$, together with the carbon atom to which they are attached, form a 5-membered heterocyclyl ring, wherein the 5-membered heterocyclyl ring is optionally substituted with 1 to 4 $R^{3a}$ groups. In some embodiments is a compound of Formula (Ib), or a pharmaceutically acceptable salt, solvate, or stereoisomer thereof, wherein $R^1$ and $R^2$, together with the carbon atom to which they are attached, form a 6-membered heterocyclyl ring, wherein the 6-membered heterocyclyl ring is optionally substituted with 1 to 4 $R^{3a}$ groups. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 or 2 $R^{3a}$ groups. In some embodiments is a compound of Formula (Ib), or a pharmaceutically acceptable salt, solvate, or stereoisomer thereof, wherein R and $R^2$, together with the carbon atom to which they are attached, form a 4-membered heterocyclyl ring, wherein the 4-membered heterocyclyl ring is optionally substituted with 1 or 2 $R^{3a}$ groups. In some embodiments is a compound of Formula (Ib), or a pharmaceutically acceptable salt, solvate, or stereoisomer thereof, wherein $R^1$ and $R^2$, together with the carbon atom to which they are attached, form a 5-membered heterocyclyl ring, wherein the 5-membered heterocyclyl ring is optionally substituted with 1 or 2 $R^{3a}$ groups. In some embodiments is a compound of Formula (Ib), or a pharmaceutically acceptable salt, solvate, or stereoisomer thereof, wherein $R^1$ and $R^2$, together with the carbon atom to which they are attached, form a 6-membered heterocyclyl ring, wherein the 6-membered heterocyclyl ring is optionally substituted with 1 or 2 $R^{3a}$ groups. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group. In some embodiments is a compound of Formula (Ib), or a pharmaceutically acceptable salt, solvate, or stereoisomer thereof, wherein $R^1$ and $R^2$, together with the carbon atom to which they are attached, form a 4-membered heterocyclyl ring, wherein the 4-membered heterocyclyl ring is optionally substituted with 1 $R^{3a}$ group. In some embodiments is a compound of Formula (Ib), or a pharmaceutically acceptable salt, solvate, or stereoisomer thereof, wherein $R^1$ and $R^2$, together with the carbon atom to which they are attached, form a 5-membered heterocyclyl ring, wherein the 5-membered heterocyclyl ring is optionally substituted with 1 $R^{3a}$ group. In some embodiments is a compound of Formula (Ib), or a pharmaceutically acceptable salt, solvate, or stereoisomer thereof, wherein $R^1$ and $R^2$, together with the carbon atom to which they are attached, form a 6-membered heterocyclyl ring, wherein the 6-membered heterocyclyl ring is optionally substituted with 1 $R^{3a}$ group.

In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 or 2 $R^{3a}$ groups and each $R^{3a}$ is selected from $C_1$-$C_6$alkyl, $C_1$-$C_6$haloalkyl, $C_2$-$C_9$heteroaryl, ($C_2$-$C_9$heteroaryl)-$C_1$-$C_6$alkylene-, oxo, —$S(O)_2R^{10}$, —$C(O)R^{10}$, —$C(O)OR^{11}$, and —$C(O)N(R^{11})_2$, wherein $C_2$-$C_9$heteroaryl and ($C_2$-$C_9$heteroaryl)-$C_1$-$C_6$alkylene- are optionally substituted with 1 to 3 groups independently selected from halo, $C_1$-$C_6$alkyl, $C_1$-$C_6$haloalkyl, and hydroxyl. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$. In some embodiments is a compound of Formula (Ib), or a pharmaceutically acceptable salt, solvate, or stereoisomer thereof, wherein $R^1$ and $R^2$, together with the carbon atom to which they are attached, form a 4-membered heterocyclyl ring, wherein the 4-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$. In some embodiments is a compound of Formula (Ib), or a pharmaceutically acceptable salt, solvate, or stereoisomer thereof, wherein $R^1$ and $R^2$, together with the carbon atom to which they are attached, form a 5-membered heterocyclyl ring, wherein the 5-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$. In some embodiments is a compound of Formula (Ib), or a pharmaceutically acceptable salt, solvate, or stereoisomer thereof, wherein $R^1$ and $R^2$, together with the carbon atom to which they are attached, form a 6-membered heterocyclyl ring, wherein the 6-membered heterocyclyl ring is optionally substituted with 1 or 2 $R^{3a}$ groups and each $R^{3a}$ is selected from $C_1$-$C_6$alkyl, oxo, —$S(O)_2R^{10}$, —$C(O)R^{10}$, and —$C(O)OR^{11}$.

In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group and $R^{3a}$ is —$S(O)_2R^{10}$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, $C_6$-$C_{10}$aryl, or ($C_6$-$C_{10}$aryl)-$C_1$-$C_6$alkylene-. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is $C_1$-$C_6$alkyl or $C_3$-$C_8$cycloalkyl. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is $C_1$-$C_6$alkyl. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is —$CH_3$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is —$CH_2CH_3$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is —$CH_2CH_2CH_3$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is $C_3$-$C_8$cycloalkyl. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —$S(O)_2R^{10}$, and $R^{10}$ is cyclopropyl.

In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group and $R^{3a}$ is —$C(O)R^{10}$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)$R^{10}$, and $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, $C_6$-$C_{10}$aryl, or ($C_6$-$C_{10}$aryl)-$C_1$-$C_6$alkylene-. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)$R^{10}$, and $R^{10}$ is $C_1$-$C_6$alkyl. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)$R^{10}$, and $R^{10}$ is —$CH_3$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)$R^{10}$, and $R^{10}$ is —$CH_2CH_3$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)$R^{10}$, and $R^{10}$ is —$CH_2CH_2CH_3$.

In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group and $R^{3a}$ is —C(O)O$R^{11}$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)O$R^{11}$, and $R^{11}$ is $C_1$-$C_6$alkyl. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)O$R^{11}$, and $R^{11}$ is —$CH_3$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)O$R^{11}$, and $R^{11}$ is —$CH_2CH_3$. In some embodiments is a compound of Formula (Ib), or a pharmaceutically acceptable salt, solvate, or stereoisomer thereof, wherein $R^1$ and $R^2$, together with the carbon atom to which they are attached, form a 4-, 5-, or 6-membered heterocyclyl ring, wherein the 4-, 5-, or 6-membered heterocyclyl ring is optionally substituted with 1 $R^{3a}$ group, $R^{3a}$ is —C(O)O$R^{11}$, and $R^{11}$ is —$CH_2CH_2CH_3$.

In some embodiments is a compound of Formula (Ib), or a pharmaceutically acceptable salt, solvate, or stereoisomer thereof, wherein p is 0, 1, or 2. In some embodiments is a compound of Formula (Ib), or a pharmaceutically acceptable salt, solvate, or stereoisomer thereof, wherein p is 0. In some embodiments is a compound of Formula (Ib), or a pharmaceutically acceptable salt, solvate, or stereoisomer thereof, wherein p is 1. In some embodiments is a compound of Formula (Ib), or a pharmaceutically acceptable salt, solvate, or stereoisomer thereof, wherein p is 2. In some embodiments is a compound of Formula (Ib), or a pharmaceutically acceptable salt, solvate, or stereoisomer thereof, wherein p is 3. In some embodiments is a compound of Formula (Ib), or a pharmaceutically acceptable salt, solvate, or stereoisomer thereof, wherein p is 1, 2, or 3. In some embodiments is a compound of Formula (Ib), or a pharmaceutically acceptable salt, solvate, or stereoisomer thereof, wherein p is 1, 2, or 3 and each $R^4$ is independently halo, $C_1$-$C_6$alkyl, $C_1$-$C_6$alkenyl, $C_1$-$C_6$haloalkyl, $C_1$-$C_6$alkoxy, or $C_3$-$C_8$cycloalkyl. In some embodiments is a compound of Formula (Ib), or a pharmaceutically acceptable salt, solvate, or stereoisomer thereof, wherein p is 1, 2, or 3 and each $R^4$ is independently halo, $C_1$-$C_6$alkyl, or $C_3$-$C_8$cycloalkyl. In some embodiments is a compound of Formula (Ib), or a pharmaceutically acceptable salt, solvate, or stereoisomer thereof, wherein p is 1 and $R^4$ is halo, $C_1$-$C_6$alkyl, or $C_3$-$C_8$cycloalkyl. In some embodiments is a compound of Formula (Ib), or a pharmaceutically acceptable salt, solvate, or stereoisomer thereof, wherein p is 2 and each $R^4$ is independently halo, $C_1$-$C_6$alkyl, or $C_3$-$C_8$cycloalkyl. In some embodiments is a compound of Formula (Ib), or a pharmaceutically acceptable salt, solvate, or stereoisomer thereof, wherein p is 3 and each $R^4$ is independently halo, $C_1$-$C_6$alkyl, or $C_3$-$C_8$cycloalkyl.

In some embodiments is a compound of Formula (Ib), or a pharmaceutically acceptable salt, solvate, or stereoisomer thereof, wherein q is 0, 1, 2, or 3. In some embodiments is a compound of Formula (Ib), or a pharmaceutically acceptable salt, solvate, or stereoisomer thereof, wherein q is 0. In some embodiments is a compound of Formula (Ib), or a pharmaceutically acceptable salt, solvate, or stereoisomer thereof, wherein q is 1. In some embodiments is a compound of Formula (Ib), or a pharmaceutically acceptable salt, solvate, or stereoisomer thereof, wherein q is 2. In some embodiments is a compound of Formula (Ib), or a pharmaceutically acceptable salt, solvate, or stereoisomer thereof, wherein q is 3. In some embodiments is a compound of Formula (Ib), or a pharmaceutically acceptable salt, solvate, or stereoisomer thereof, wherein q is 1, 2, or 3. In some embodiments is a compound of Formula (Ib), or a pharmaceutically acceptable salt, solvate, or stereoisomer thereof, wherein q is 1, 2, or 3 and each $R^5$ is independently halo, cyano, $C_1$-$C_6$alkyl, $C_1$-$C_6$haloalkyl, $C_1$-$C_6$alkoxy, or $C_3$-$C_8$cycloalkyl. In some embodiments is a compound of Formula (Ib), or a pharmaceutically acceptable salt, solvate, or stereoisomer thereof, wherein q is 1, 2, or 3 and each $R^5$ is independently halo, cyano, $C_1$-$C_6$alkyl, $C_1$-$C_6$haloalkyl, or $C_1$-$C_6$alkoxy. In some embodiments is a compound of Formula (Ib), or a pharmaceutically acceptable salt, solvate, or stereoisomer thereof, wherein q is 1, 2, or 3 and each $R^5$ is independently halo or $C_1$-$C_6$alkyl. In some embodiments is a compound of Formula (Ib), or a pharmaceutically acceptable salt, solvate, or stereoisomer thereof, wherein q is 1 and $R^5$ is halo or $C_1$-$C_6$alkyl. In some embodiments is a compound of Formula (Ib), or a pharmaceutically acceptable salt, solvate, or stereoisomer thereof, wherein q is 2 and each $R^5$ is independently halo or $C_1$-$C_6$alkyl. In some embodiments is a compound of Formula (Ib), or a pharmaceutically acceptable salt, solvate, or stereoisomer thereof, wherein q is 3 and each $R^5$ is independently halo or $C_1$-$C_6$alkyl.

In some embodiments is a compound of Formula (Ib), or a pharmaceutically acceptable salt, solvate, or stereoisomer thereof, wherein k is 0, 1, 2, 3, or 4. In some embodiments is a compound of Formula (Ib), or a pharmaceutically acceptable salt, solvate, or stereoisomer thereof, wherein k is 0, 1, 2, or 3. In some embodiments is a compound of Formula (Ib), or a pharmaceutically acceptable salt, solvate, or stereoisomer thereof, wherein k is 0, 1, or 2. In some embodiments is a compound of Formula (Ib), or a pharmaceutically acceptable salt, solvate, or stereoisomer thereof, wherein k is 0 or 1. In some embodiments is a compound of Formula (Ib), or a pharmaceutically acceptable salt, solvate, or stereoisomer thereof, wherein k is 0. In some embodiments is a compound of Formula (Ib), or a pharmaceutically acceptable salt, solvate, or stereoisomer thereof, wherein k is 1. In some embodiments is a compound of Formula (Ib), or a pharmaceutically acceptable salt, solvate, or stereoisomer thereof, wherein k is 1 and $R^3$ is halo, $C_1$-$C_6$alkyl, or $C_1$-$C_6$haloalkyl. In some embodiments is a compound of Formula (Ib), or a pharmaceutically acceptable salt, solvate, or stereoisomer thereof, wherein k is 2. In some embodiments is a compound of Formula (Ib), or a pharmaceutically acceptable salt, solvate, or stereoisomer thereof, wherein k is 2 and each $R^3$ is independently halo, $C_1$-$C_6$alkyl, or $C_1$-$C_6$haloalkyl.

In some embodiments, provided herein is a compound of Formula (II), or a pharmaceutically acceptable salt, solvate, or stereoisomer thereof:

Formula (II)

wherein:
X is —O—, —NH—, —N($R^{3a}$)—, —S—, —S(O)—, or —S(O)$_2$—
Z is —(C($R^6$)($R^7$))$_t$—;
each $R^3$ is independently selected from halo and $C_1$-$C_6$alkyl;
$R^{3a}$ is selected from $C_1$-$C_6$alkyl, $C_1$-$C_6$haloalkyl, $C_2$-$C_9$heteroaryl, ($C_2$-$C_9$heteroaryl)-$C_1$-$C_6$alkylene-, oxo, —S(O)$_2$$R^{10}$, —C(O)$R^{10}$, —C(O)O$R^{11}$, and —C(O)N($R^{11}$)$_2$, wherein $C_2$-$C_9$heteroaryl and ($C_2$-$C_9$heteroaryl)-$C_1$-$C_6$alkylene- are optionally substituted with 1 to 3 groups independently selected from halo, $C_1$-$C_6$alkyl, $C_1$-$C_6$haloalkyl, and hydroxyl;
each $R^4$ and each $R^5$ are each independently selected from halo, cyano, —OH, $C_1$-$C_6$alkyl, $C_1$-$C_6$alkenyl, $C_1$-$C_6$haloalkyl, $C_1$-$C_6$alkoxy, $C_3$-$C_8$cycloalkyl, —N($R^9$)$_2$, —C(O)$R^8$, —C(O)O$R^9$, —C(O)N($R^9$)$_2$, —N($R^9$)C(O)$R^8$, —N($R^9$)SO$_2$$R^8$, —SO$_2$$R^8$, and —SO$_2$N($R^8$)$_2$;
each $R^6$ and each $R^7$ are each independently hydrogen, halo, or $C_1$-$C_6$alkyl;
each $R^8$ is independently $C_1$-$C_6$alkyl or $C_1$-$C_6$haloalkyl;
each $R^9$ is independently hydrogen, $C_1$-$C_6$alkyl, or $C_1$-$C_6$haloalkyl;
$R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene- is optionally substituted with 1 to 3 groups selected from halo, $C_1$-$C_6$alkyl, $C_1$-$C_6$haloalkyl, and hydroxyl;
$R^{11}$ is independently hydrogen, $C_1$-$C_6$alkyl, or $C_1$-$C_6$haloalkyl;
a is 1 or 2;
b is 1 or 2;
m is 1, 2, or 3;
n is 1, 2, or 3;
k is 0, 1, 2, 3, or 4;
p is 0, 1, 2, 3, or 4;
q is 0, 1, 2, 3 or 4; and
t is 0, 1, 2, or 3.

In some embodiments, provided herein is a compound of Formula (II), or a pharmaceutically acceptable salt, solvate, or stereoisomer thereof, wherein each $R^6$ and each $R^7$ are each independently hydrogen or $C_1$-$C_6$alkyl. In some embodiments, provided herein is a compound of Formula (II), or a pharmaceutically acceptable salt, solvate, or stereoisomer thereof, wherein each $R^6$ and each $R^7$ are hydrogen. In some embodiments, provided herein is a compound of Formula (II), or a pharmaceutically acceptable salt, solvate, or stereoisomer thereof, wherein each $R^6$ and each $R^7$ are each independently $C_1$-$C_6$alkyl. In some embodiments, provided herein is a compound of Formula (II), or a pharmaceutically acceptable salt, solvate, or stereoisomer thereof, wherein each $R^6$ and each $R^7$ are —CH$_3$. In some embodiments, provided herein is a compound of Formula (II), or a pharmaceutically acceptable salt, solvate, or stereoisomer thereof, wherein each $R^6$ and each $R^7$ are each independently halo.

In some embodiments, provided herein is a compound of Formula (II), or a pharmaceutically acceptable salt, solvate, or stereoisomer thereof, wherein t is 0. In some embodiments, provided herein is a compound of Formula (II), or a pharmaceutically acceptable salt, solvate, or stereoisomer thereof, wherein t is 1, 2, or 3. In some embodiments, provided herein is a compound of Formula (II), or a pharmaceutically acceptable salt, solvate, or stereoisomer thereof, wherein t is 1. In some embodiments, provided herein is a compound of Formula (II), or a pharmaceutically acceptable salt, solvate, or stereoisomer thereof, wherein t is 2. In some embodiments, provided herein is a compound of Formula (II), or a pharmaceutically acceptable salt, solvate, or stereoisomer thereof, wherein t is 3.

In some embodiments, provided herein is a compound of Formula (II), or a pharmaceutically acceptable salt, solvate, or stereoisomer thereof, wherein Z is —CH$_2$—. In some embodiments, provided herein is a compound of Formula (II), or a pharmaceutically acceptable salt, solvate, or stereoisomer thereof, wherein Z is —CH$_2$CH$_2$—. In some embodiments, provided herein is a compound of Formula (II), or a pharmaceutically acceptable salt, solvate, or stereoisomer thereof, wherein Z is —CH$_2$CH$_2$CH$_2$—.

In some embodiments is a compound of Formula (II), or a pharmaceutically acceptable salt, solvate, or stereoisomer thereof, wherein m is 1 and n is 1. In some embodiments is a compound of Formula (II), or a pharmaceutically acceptable salt, solvate, or stereoisomer thereof, wherein m is 2 and n is 1. In some embodiments is a compound of Formula (II), or a pharmaceutically acceptable salt, solvate, or stereoisomer thereof, wherein m is 2 and n is 2. In some embodiments is a compound of Formula (II), or a pharmaceutically acceptable salt, solvate, or stereoisomer thereof, wherein m is 3 and n is 1. In some embodiments is a compound of Formula (II), or a pharmaceutically acceptable salt, solvate, or stereoisomer thereof, wherein m is 3 and n is 2. In some embodiments is a compound of Formula (II), or a pharmaceutically acceptable salt, solvate, or stereoisomer thereof, wherein m is 3 and n is 3.

In some embodiments is a compound of Formula (II), or a pharmaceutically acceptable salt, solvate, or stereoisomer thereof, wherein a is 1, b is 1, m is 2, and n is 2. In some embodiments is a compound of Formula (II), or a pharmaceutically acceptable salt, solvate, or stereoisomer thereof, wherein a is 1, b is 2, m is 2, and n is 2. In some embodiments is a compound of Formula (II), or a pharmaceutically acceptable salt, solvate, or stereoisomer thereof, wherein a is 1, b is 2, m is 1, and n is 2. In some embodiments is a compound of Formula (II), or a pharmaceutically acceptable salt, solvate, or stereoisomer thereof, wherein a is 1, b is 1, m is 1, and n is 2. In some embodiments is a compound of Formula (II), or a pharmaceutically acceptable salt, solvate, or stereoisomer thereof, wherein a is 2, b is 2, m is 1, and n is 2. In some embodiments is a compound of Formula (II), or a pharmaceutically acceptable salt, solvate, or stereoisomer thereof, wherein a is 2, b is 2, m is 1, and n is 1. In some embodiments is a compound of Formula (II), or a pharmaceutically acceptable salt, solvate, or stereoisomer thereof, wherein a is 2, b is 1, m is 1, and n is 1. In some embodiments is a compound of Formula (II), or a pharmaceutically acceptable salt, solvate, or stereoisomer thereof, wherein a is 1, b is 1, m is 1, and n is 1.

In some embodiments, provided herein is a compound of Formula (II), or a pharmaceutically acceptable salt, solvate, or stereoisomer thereof, wherein X is —O—. In some embodiments, provided herein is a compound of Formula (II), or a pharmaceutically acceptable salt, solvate, or stereoisomer thereof, wherein X is —NH—. In some embodiments, provided herein is a compound of Formula (II), or a pharmaceutically acceptable salt, solvate, or stereoisomer thereof, wherein X is —N(R$^{3a}$)—. In some embodiments, provided herein is a compound of Formula (II), or a pharmaceutically acceptable salt, solvate, or stereoisomer thereof, wherein X is —S—. In some embodiments, provided herein is a compound of Formula (II), or a pharmaceutically acceptable salt, solvate, or stereoisomer thereof, wherein X is —S(O)—. In some embodiments, provided herein is a compound of Formula (II), or a pharmaceutically acceptable salt, solvate, or stereoisomer thereof, wherein X is —S(O)$_2$—.

In some embodiments is a compound of Formula (II), or a pharmaceutically acceptable salt, solvate, or stereoisomer thereof, wherein X is —N(R$^{3a}$)— and R$^{3a}$ is selected from C$_1$-C$_6$alkyl, —S(O)$_2$R$^{10}$, —C(O)R$^{10}$, and —C(O)OR$^{11}$. In some embodiments is a compound of Formula (II), or a pharmaceutically acceptable salt, solvate, or stereoisomer thereof, wherein X is —N(R$^{3a}$)— and R$^{3a}$ is selected from —S(O)$_2$R$^{10}$, —C(O)R$^{10}$, and —C(O)OR$^{11}$.

In some embodiments is a compound of Formula (II), or a pharmaceutically acceptable salt, solvate, or stereoisomer thereof, wherein X is —N(R$^{3a}$)— and R$^{3a}$ is —S(O)$_2$R$^{10}$. In some embodiments is a compound of Formula (II), or a pharmaceutically acceptable salt, solvate, or stereoisomer thereof, wherein X is —N(R$^{3a}$), R$^{3a}$ is —S(O)$_2$R$^{10}$, and R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, or (phenyl)-C$_1$-C$_6$alkylene-. In some embodiments is a compound of Formula (II), or a pharmaceutically acceptable salt, solvate, or stereoisomer thereof, wherein X is —N(R$^{3a}$)— R$^{3a}$ is —S(O)$_2$R$^{10}$, and R$^{10}$ is C$_1$-C$_6$alkyl. In some embodiments is a compound of Formula (II), or a pharmaceutically acceptable salt, solvate, or stereoisomer thereof, wherein X is —N(R$^{3a}$), R$^{3a}$ is —S(O)$_2$R$^{10}$, and R$^{10}$ is —CH$_3$. In some embodiments is a compound of Formula (II), or a pharmaceutically acceptable salt, solvate, or stereoisomer thereof, wherein X is —N(R$^{3a}$), R$^{3a}$ is —S(O)$_2$R$^{10}$, and R$^{10}$ is —CH$_2$CH$_3$. In some embodiments is a compound of Formula (II), or a pharmaceutically acceptable salt, solvate, or stereoisomer thereof, wherein X is —N(R$^{3a}$), R$^{3a}$ is —S(O)$_2$R$^{10}$, and R$^{10}$ is —CH$_2$CH$_2$CH$_3$. In some embodiments is a compound of Formula (II), or a pharmaceutically acceptable salt, solvate, or stereoisomer thereof, wherein X is —N(R$^{3a}$), R$^{3a}$ is —S(O)$_2$R$^{10}$, and R$^{10}$ is C$_1$-C$_6$haloalkyl. In some embodiments is a compound of Formula (II), or a pharmaceutically acceptable salt, solvate, or stereoisomer thereof, wherein X is —N(R$^{3a}$), R$^{3a}$ is —S(O)$_2$R$^{10}$, and R$^{10}$ is —CF$_3$. In some embodiments is a compound of Formula (II), or a pharmaceutically acceptable salt, solvate, or stereoisomer thereof, wherein X is —N(R$^{3a}$), R$^{3a}$ is —S(O)$_2$R$^{10}$, and R$^{10}$ is C$_3$-C$_8$cycloalkyl. In some embodiments is a compound of Formula (II), or a pharmaceutically acceptable salt, solvate, or stereoisomer thereof, wherein X is —N(R$^{3a}$), R$^{3a}$ is —S(O)$_2$R$^{10}$, and R$^{10}$ is cyclopropyl.

In some embodiments is a compound of Formula (II), or a pharmaceutically acceptable salt, solvate, or stereoisomer thereof, wherein X is —N(R$^{3a}$)— and R$^{3a}$ is —C(O)R$^{10}$. In some embodiments is a compound of Formula (II), or a pharmaceutically acceptable salt, solvate, or stereoisomer thereof, wherein X is —N(R$^{3a}$), R$^{3a}$ is —C(O)R$^{10}$, and R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, or (phenyl)-C$_1$-C$_6$alkylene-. In some embodiments is a compound of Formula (II), or a pharmaceutically acceptable salt, solvate, or stereoisomer thereof, wherein X is —N(R$^{3a}$), R$^{3a}$ is —C(O)R$^{10}$, and R$^{10}$ is C$_1$-C$_6$alkyl. In some embodiments is a compound of Formula (II), or a pharmaceutically acceptable salt, solvate, or stereoisomer thereof, wherein X is —N(R$^{3a}$), R$^{3a}$ is —C(O)R$^{10}$, and R$^{10}$ is —CH$_3$. In some embodiments is a compound of Formula (II), or a pharmaceutically acceptable salt, solvate, or stereoisomer thereof, wherein X is —N(R$^{3a}$), R$^{3a}$ is —C(O)R$^{10}$, and R$^{10}$ is —CH$_2$CH$_3$. In some embodiments is a compound of Formula (II), or a pharmaceutically acceptable salt, solvate, or stereoisomer thereof, wherein X is —N(R$^{3a}$), R$^{3a}$ is —C(O)R$^{10}$, and R$^{10}$ is —CH$_2$CH$_2$CH$_3$. In some embodiments is a compound of Formula (II), or a pharmaceutically acceptable salt, solvate, or stereoisomer thereof, wherein X is —N(R$^{3a}$), R$^{3a}$ is —C(O)R$^{10}$, and R$^{10}$ is C$_1$-C$_6$alkyl-O—C$_1$-C$_6$alkyl-. In some embodiments is a compound of Formula (II), or a pharmaceutically acceptable salt, solvate, or stereoisomer thereof, wherein X is —N(R$^{3a}$), R$^{3a}$ is —C(O)R$^{10}$, and R$^{10}$ is C$_3$-C$_8$cycloalkyl. In some embodiments is a compound of Formula (II), or a pharmaceutically acceptable salt, solvate, or stereoisomer thereof, wherein X is —N(R$^{3a}$), R$^{3a}$ is —C(O)R$^{10}$, and R$^{10}$ is C$_2$-C$_9$heterocyclyl.

In some embodiments is a compound of Formula (II), or a pharmaceutically acceptable salt, solvate, or stereoisomer thereof, wherein X is —N(R$^{3a}$)— and R$^{3a}$ is —C(O)OR$^{11}$. In some embodiments is a compound of Formula (II), or a pharmaceutically acceptable salt, solvate, or stereoisomer thereof, wherein X is —N(R$^{3a}$), R$^{3a}$ is —C(O)OR$^{11}$, and R$^{11}$ is C$_1$-C$_6$alkyl. In some embodiments is a compound of Formula (II), or a pharmaceutically acceptable salt, solvate, or stereoisomer thereof, wherein X is —N(R$^{3a}$), R$^{3a}$ is —C(O)OR$^{11}$, and R$^{11}$ is —CH$_3$. In some embodiments is a compound of Formula (II), or a pharmaceutically acceptable salt, solvate, or stereoisomer thereof, wherein X is —N(R$^{3a}$), R$^{3a}$ is —C(O)OR$^{11}$, and R$^{11}$ is —CH$_2$CH$_3$. In some embodiments is a compound of Formula (II), or a pharmaceutically acceptable salt, solvate, or stereoisomer thereof, wherein X is —N(R$^{3a}$), R$^{3a}$ is —C(O)OR$^{11}$, and R$^{11}$ is —CH$_2$CH$_2$CH$_3$.

In some embodiments is a compound of Formula (II), or a pharmaceutically acceptable salt, solvate, or stereoisomer thereof, wherein p is 0, 1, 2, or 3. In some embodiments is a compound of Formula (II), or a pharmaceutically acceptable salt, solvate, or stereoisomer thereof, wherein p is 0. In some embodiments is a compound of Formula (II), or a pharmaceutically acceptable salt, solvate, or stereoisomer thereof, wherein p is 1. In some embodiments is a compound of Formula (II), or a pharmaceutically acceptable salt, solvate, or stereoisomer thereof, wherein p is 2. In some embodiments is a compound of Formula (II), or a pharmaceutically acceptable salt, solvate, or stereoisomer thereof, wherein p is 3. In some embodiments is a compound of Formula (II), or a pharmaceutically acceptable salt, solvate, or stereoisomer thereof, wherein p is 1, 2, or 3. In some embodiments is a compound of Formula (II), or a pharmaceutically acceptable salt, solvate, or stereoisomer thereof, wherein p is 1, 2, or 3 and each R$^4$ is independently halo, C$_1$-C$_6$alkyl, C$_1$-C$_6$alkenyl, C$_1$-C$_6$haloalkyl, C$_1$-C$_6$alkoxy, or C$_3$-C$_8$cycloalkyl. In some embodiments is a compound of Formula (II), or a pharmaceutically acceptable salt, solvate, or stereoisomer thereof, wherein p is 1, 2, or 3 and each R$^4$ is independently halo, C$_1$-C$_6$alkyl, or C$_3$-C$_8$cycloalkyl. In some embodiments is a compound of Formula (II), or a pharmaceutically acceptable salt, solvate, or stereoisomer thereof, wherein p is 1 and R$^4$ is halo, C$_1$-C$_6$alkyl, or C$_3$-C$_8$cycloalkyl. In some embodiments is a compound of Formula (II), or a pharmaceutically acceptable salt, solvate, or stereoisomer thereof, wherein p is 2 and each R$^4$ is independently halo, C$_1$-C$_6$alkyl, or C$_3$-C$_8$cycloalkyl. In some embodiments is a compound of Formula (II), or a pharmaceutically acceptable salt, solvate, or stereoisomer thereof, wherein p is 3 and each R$^4$ is independently halo, C$_1$-C$_6$alkyl, or C$_3$-C$_8$cycloalkyl.

In some embodiments is a compound of Formula (II), or a pharmaceutically acceptable salt, solvate, or stereoisomer thereof, wherein q is 0, 1, 2, or 3. In some embodiments is a compound of Formula (II), or a pharmaceutically acceptable salt, solvate, or stereoisomer thereof, wherein q is 0. In some embodiments is a compound of Formula (II), or a pharmaceutically acceptable salt, solvate, or stereoisomer thereof, wherein q is 1. In some embodiments is a compound of Formula (II), or a pharmaceutically acceptable salt, solvate, or stereoisomer thereof, wherein q is 2. In some embodiments is a compound of Formula (II), or a pharmaceutically acceptable salt, solvate, or stereoisomer thereof, wherein q is 3. In some embodiments is a compound of Formula (II), or a pharmaceutically acceptable salt, solvate, or stereoisomer thereof, wherein q is 1, 2, or 3. In some embodiments is a compound of Formula (II), or a pharmaceutically acceptable salt, solvate, or stereoisomer thereof, wherein q is 1, 2, or 3 and each R$^5$ is independently halo, cyano, C$_1$-C$_6$alkyl, C$_1$-C$_6$haloalkyl, C$_1$-C$_6$alkoxy, or C$_3$-C$_8$cycloalkyl. In some embodiments is a compound of Formula (II), or a pharmaceutically acceptable salt, solvate, or stereoisomer thereof, wherein q is 1, 2, or 3 and each R$^5$ is independently halo, cyano, C$_1$-C$_6$alkyl, C$_1$-C$_6$haloalkyl, or C$_1$-C$_6$alkoxy. In some embodiments is a compound of Formula (II), or a pharmaceutically acceptable salt, solvate, or stereoisomer thereof, wherein q is 1, 2, or 3 and each R$^5$ is independently halo or C$_1$-C$_6$alkyl. In some embodiments is a compound of Formula (II), or a pharmaceutically acceptable salt, solvate, or stereoisomer thereof, wherein q is 1 and R$^5$ is halo or C$_1$-C$_6$alkyl. In some embodiments is a compound of Formula (II), or a pharmaceutically acceptable salt, solvate, or stereoisomer thereof, wherein q is 2 and each R$^5$ is independently halo or C$_1$-C$_6$alkyl. In some embodiments is a compound of Formula (II), or a pharmaceutically acceptable salt, solvate, or stereoisomer thereof, wherein q is 3 and each R$^5$ is independently halo or C$_1$-C$_6$alkyl.

In some embodiments is a compound of Formula (II), or a pharmaceutically acceptable salt, solvate, or stereoisomer thereof, wherein k is 0, 1, 2, 3, or 4. In some embodiments is a compound of Formula (II), or a pharmaceutically acceptable salt, solvate, or stereoisomer thereof, wherein k is 0, 1, 2, or 3. In some embodiments is a compound of Formula (II), or a pharmaceutically acceptable salt, solvate, or stereoisomer thereof, wherein k is 0, 1, or 2. In some embodiments is a compound of Formula (II), or a pharmaceutically acceptable salt, solvate, or stereoisomer thereof, wherein k is 0 or 1. In some embodiments is a compound of Formula (II), or a pharmaceutically acceptable salt, solvate, or stereoisomer thereof, wherein k is 0. In some embodiments is a compound of Formula (II), or a pharmaceutically acceptable salt, solvate, or stereoisomer thereof, wherein k is 1. In some embodiments is a compound of Formula (II), or a pharmaceutically acceptable salt, solvate, or stereoisomer thereof, wherein k is 1 and R$^3$ is halo, C$_1$-C$_6$alkyl, or C$_1$-C$_6$haloalkyl. In some embodiments is a compound of Formula (II), or a pharmaceutically acceptable salt, solvate, or stereoisomer thereof, wherein k is 2. In some embodiments is a compound of Formula (II), or a pharmaceutically acceptable salt, solvate, or stereoisomer thereof, wherein k is 2 and each R$^3$ is independently halo, C$_1$-C$_6$alkyl, or C$_1$-C$_6$haloalkyl.

In some embodiments, provided herein is a compound of Formula (IIa), or a pharmaceutically acceptable salt, solvate, or stereoisomer thereof:

Formula (IIa)

wherein:

Z is —(C(R$^6$)(R$^7$))$_t$—;

each R$^3$ is independently selected from halo and C$_1$-C$_6$alkyl;

R$^{3a}$ is selected from C$_1$-C$_6$alkyl, C$_1$-C$_6$haloalkyl, C$_2$-C$_9$heteroaryl, (C$_2$-C$_9$heteroaryl)-C$_1$-C$_6$alkylene-, oxo, —S(O)$_2$R$^{10}$, —C(O)R$^{10}$, —C(O)OR$^{11}$, and —C(O)N(R$^{11}$)$_2$, wherein C$_2$-C$_9$heteroaryl and (C$_2$-C$_9$heteroaryl)-C$_1$-C$_6$alkylene- are optionally substituted with 1 to 3 groups independently selected from halo, C$_1$-C$_6$alkyl, C$_1$-C$_6$haloalkyl, and hydroxyl;

each R$^4$ and each R$^5$ are each independently selected from halo, cyano, —OH, C$_1$-C$_6$alkyl, C$_1$-C$_6$alkenyl, C$_1$-C$_6$haloalkyl, C$_1$-C$_6$alkoxy, C$_3$-C$_8$cycloalkyl, —N(R$^9$)$_2$, —C(O)R$^8$, —C(O)OR$^9$, —C(O)N(R$^9$)$_2$, —N(R$^9$)C(O)R$^8$, —N(R$^9$)SO$_2$R$^8$, —SO$_2$R$^8$, and —SO$_2$N(R$^8$)$_2$;

each R$^6$ and each R$^7$ are each independently hydrogen, halo, or C$_1$-C$_6$alkyl;

each R$^8$ is independently C$_1$-C$_6$alkyl or C$_1$-C$_6$haloalkyl;

each R$^9$ is independently hydrogen, C$_1$-C$_6$alkyl, or C$_1$-C$_6$haloalkyl;

R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 to 3 groups selected from halo, C$_1$-C$_6$alkyl, C$_1$-C$_6$haloalkyl, and hydroxyl;

R$^{11}$ is independently hydrogen, C$_1$-C$_6$alkyl, or C$_1$-C$_6$haloalkyl;

k is 0, 1, 2, 3, or 4;

p is 0, 1, 2, 3, or 4;

q is 0, 1, 2, 3 or 4; and t is 0, 1, 2, or 3.

In some embodiments, provided herein is a compound of Formula (IIa), or a pharmaceutically acceptable salt, solvate, or stereoisomer thereof, wherein each R$^6$ and each R$^7$ are each independently hydrogen or C$_1$-C$_6$alkyl. In some embodiments, provided herein is a compound of Formula (IIa), or a pharmaceutically acceptable salt, solvate, or stereoisomer thereof, wherein each R$^6$ and each R$^7$ are hydrogen. In some embodiments, provided herein is a compound of Formula (IIa), or a pharmaceutically acceptable salt, solvate, or stereoisomer thereof, wherein each R$^6$ and each R$^7$ are each independently C$_1$-C$_6$alkyl. In some embodiments, provided herein is a compound of Formula (IIa), or a pharmaceutically acceptable salt, solvate, or stereoisomer thereof, wherein each R$^6$ and each R$^7$ are —CH$_3$. In some embodiments, provided herein is a compound of Formula (Ia), or a pharmaceutically acceptable salt, solvate, or stereoisomer thereof, wherein each R$^6$ and each R$^7$ are each independently halo.

In some embodiments, provided herein is a compound of Formula (IIa), or a pharmaceutically acceptable salt, solvate, or stereoisomer thereof, wherein t is 0. In some embodiments, provided herein is a compound of Formula (IIa), or a pharmaceutically acceptable salt, solvate, or stereoisomer thereof, wherein t is 1, 2, or 3. In some embodiments, provided herein is a compound of Formula (IIa), or a pharmaceutically acceptable salt, solvate, or stereoisomer thereof, wherein t is 1. In some embodiments, provided herein is a compound of Formula (IIa), or a pharmaceutically acceptable salt, solvate, or stereoisomer thereof, wherein t is 2. In some embodiments, provided herein is a compound of Formula (IIa), or a pharmaceutically acceptable salt, solvate, or stereoisomer thereof, wherein t is 3.

In some embodiments, provided herein is a compound of Formula (IIa), or a pharmaceutically acceptable salt, solvate, or stereoisomer thereof, wherein Z is —CH$_2$—. In some embodiments, provided herein is a compound of Formula (IIa), or a pharmaceutically acceptable salt, solvate, or stereoisomer thereof, wherein Z is —CH$_2$CH$_2$—. In some embodiments, provided herein is a compound of Formula (IIa), or a pharmaceutically acceptable salt, solvate, or stereoisomer thereof, wherein Z is —CH$_2$CH$_2$CH$_2$—.

In some embodiments is a compound of Formula (IIa), or a pharmaceutically acceptable salt, solvate, or stereoisomer thereof, wherein R$^{3a}$ is selected from C$_1$-C$_6$alkyl, C$_2$-C$_9$heteroaryl, (C$_2$-C$_9$heteroaryl)-C$_1$-C$_6$alkylene-, —S(O)$_2$R$^{10}$, —C(O)R$^{10}$, and —C(O)OR$^{11}$. In some embodiments is a compound of Formula (IIa), or a pharmaceutically acceptable salt, solvate, or stereoisomer thereof, wherein R$^{3a}$ is selected from C$_1$-C$_6$alkyl, —S(O)$_2$R$^{10}$, —C(O)R$^{10}$, and —C(O)OR$^{11}$. In some embodiments is a compound of Formula (IIa), or a pharmaceutically acceptable salt, solvate, or stereoisomer thereof, wherein R$^{3a}$ is selected from —S(O)$_2$R$^{10}$, —C(O)R$^{10}$, and —C(O)OR$^{11}$.

In some embodiments is a compound of Formula (IIa), or a pharmaceutically acceptable salt, solvate, or stereoisomer thereof, wherein R$^{3a}$ is —S(O)$_2$R$^{10}$. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, or (phenyl)-C$_1$-C$_6$alkylene-. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is C$_1$-C$_6$alkyl. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is —CH$_3$. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is —CH$_2$CH$_3$. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is —CH$_2$CH$_2$CH$_3$. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is C$_1$-C$_6$haloalkyl. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is —CF$_3$. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is C$_3$-C$_8$cycloalkyl.

In some embodiments is a compound of Formula (IIa), or a pharmaceutically acceptable salt, solvate, or stereoisomer thereof, wherein R$^{3a}$ is —C(O)R$^{10}$. In some embodiments is a compound of Formula (IIa), or a pharmaceutically acceptable salt, solvate, or stereoisomer thereof, wherein R$^{3a}$ is —C(O)R$^{10}$ and R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, or (phenyl)-C$_1$-C$_6$alkylene-. In some embodiments is a compound of Formula (IIa), or a pharmaceutically acceptable salt, solvate, or stereoisomer thereof, wherein R$^{3a}$ is —C(O)R$^{10}$ and R$^{10}$ is C$_1$-C$_6$alkyl. In some embodiments is a compound of Formula (IIa), or a pharmaceutically acceptable salt, solvate, or stereoisomer thereof, wherein R$^{3a}$ is —C(O)R$^{10}$, and R$^{10}$ is —CH$_3$. In some embodiments is a compound of Formula (IIa), or a pharmaceutically acceptable salt, solvate, or stereoisomer thereof, wherein $R^{3a}$ is —C(O)$R^{10}$ and $R^{10}$ is —$CH_2CH_3$. In some embodiments is a compound of Formula (IIa), or a pharmaceutically acceptable salt, solvate, or stereoisomer thereof, wherein $R^{3a}$ is —C(O)$R^{10}$ and $R^{10}$ is —$CH_2CH_2CH_3$. In some embodiments is a compound of Formula (IIa), or a pharmaceutically acceptable salt, solvate, or stereoisomer thereof, wherein $R^{3a}$ is —C(O)$R^{10}$ and $R^{10}$ is $C_1$-$C_6$alkyl-O—$C_1$-$C_6$alkyl-. In some embodiments is a compound of Formula (IIa), or a pharmaceutically acceptable salt, solvate, or stereoisomer thereof, wherein $R^{3a}$ is —C(O)$R^{10}$ and $R^{10}$ is $C_3$-$C_8$cycloalkyl. In some embodiments is a compound of Formula (IIa), or a pharmaceutically acceptable salt, solvate, or stereoisomer thereof, wherein $R^{3a}$ is —C(O)$R^{10}$ and $R^{10}$ is $C_2$-$C_9$heterocyclyl.

In some embodiments is a compound of Formula (IIa), or a pharmaceutically acceptable salt, solvate, or stereoisomer thereof, wherein $R^{3a}$ is —C(O)O$R^{11}$. In some embodiments is a compound of Formula (IIa), or a pharmaceutically acceptable salt, solvate, or stereoisomer thereof, wherein $R^{3a}$ is —C(O)O$R^{11}$ and $R^{11}$ is $C_1$-$C_6$alkyl. In some embodiments is a compound of Formula (IIa), or a pharmaceutically acceptable salt, solvate, or stereoisomer thereof, wherein $R^{3a}$ is —C(O)O$R^{11}$ and $R^{11}$ is —$CH_3$. In some embodiments is a compound of Formula (IIa), or a pharmaceutically acceptable salt, solvate, or stereoisomer thereof, wherein $R^{3a}$ is —C(O)O$R^{11}$ and $R^{11}$ is —$CH_2CH_3$. In some embodiments is a compound of Formula (IIa), or a pharmaceutically acceptable salt, solvate, or stereoisomer thereof, wherein $R^{3a}$ is —C(O)O$R^{11}$ and $R^{11}$ is —$CH_2CH_2CH_3$.

In some embodiments is a compound of Formula (IIa), or a pharmaceutically acceptable salt, solvate, or stereoisomer thereof, wherein p is 0, 1, 2, or 3. In some embodiments is a compound of Formula (IIa), or a pharmaceutically acceptable salt, solvate, or stereoisomer thereof, wherein p is 0. In some embodiments is a compound of Formula (IIa), or a pharmaceutically acceptable salt, solvate, or stereoisomer thereof, wherein p is 1. In some embodiments is a compound of Formula (IIa), or a pharmaceutically acceptable salt, solvate, or stereoisomer thereof, wherein p is 2. In some embodiments is a compound of Formula (IIa), or a pharmaceutically acceptable salt, solvate, or stereoisomer thereof, wherein p is 3. In some embodiments is a compound of Formula (IIa), or a pharmaceutically acceptable salt, solvate, or stereoisomer thereof, wherein p is 1, 2, or 3. In some embodiments is a compound of Formula (IIa), or a pharmaceutically acceptable salt, solvate, or stereoisomer thereof, wherein p is 1, 2, or 3 and each $R^4$ is independently halo, $C_1$-$C_6$alkyl, $C_1$-$C_6$alkenyl, $C_1$-$C_6$haloalkyl, $C_1$-$C_6$alkoxy, or $C_3$-$C_8$cycloalkyl. In some embodiments is a compound of Formula (IIa), or a pharmaceutically acceptable salt, solvate, or stereoisomer thereof, wherein p is 1, 2, or 3 and each $R^4$ is independently halo, $C_1$-$C_6$alkyl, or $C_3$-$C_8$cycloalkyl. In some embodiments is a compound of Formula (IIa), or a pharmaceutically acceptable salt, solvate, or stereoisomer thereof, wherein p is 1 and $R^4$ is halo, $C_1$-$C_6$alkyl, or $C_3$-$C_8$cycloalkyl. In some embodiments is a compound of Formula (IIa), or a pharmaceutically acceptable salt, solvate, or stereoisomer thereof, wherein p is 2 and each $R^4$ is independently halo, $C_1$-$C_6$alkyl, or $C_3$-$C_8$cycloalkyl. In some embodiments is a compound of Formula (IIa), or a pharmaceutically acceptable salt, solvate, or stereoisomer thereof, wherein p is 3 and each $R^4$ is independently halo, $C_1$-$C_6$alkyl, or $C_3$-$C_8$cycloalkyl.

In some embodiments is a compound of Formula (IIa), or a pharmaceutically acceptable salt, solvate, or stereoisomer thereof, wherein q is 0, 1, 2, or 3. In some embodiments is a compound of Formula (IIa), or a pharmaceutically acceptable salt, solvate, or stereoisomer thereof, wherein q is 0. In some embodiments is a compound of Formula (IIa), or a pharmaceutically acceptable salt, solvate, or stereoisomer thereof, wherein q is 1. In some embodiments is a compound of Formula (IIa), or a pharmaceutically acceptable salt, solvate, or stereoisomer thereof, wherein q is 2. In some embodiments is a compound of Formula (IIa), or a pharmaceutically acceptable salt, solvate, or stereoisomer thereof, wherein q is 3. In some embodiments is a compound of Formula (IIa), or a pharmaceutically acceptable salt, solvate, or stereoisomer thereof, wherein q is 1, 2, or 3. In some embodiments is a compound of Formula (IIa), or a pharmaceutically acceptable salt, solvate, or stereoisomer thereof, wherein q is 1, 2, or 3 and each $R^5$ is independently halo, cyano, $C_1$-$C_6$alkyl, $C_1$-$C_6$haloalkyl, $C_1$-$C_6$alkoxy, or $C_3$-$C_8$cycloalkyl. In some embodiments is a compound of Formula (IIa), or a pharmaceutically acceptable salt, solvate, or stereoisomer thereof, wherein q is 1, 2, or 3 and each $R^5$ is independently halo, cyano, $C_1$-$C_6$alkyl, $C_1$-$C_6$haloalkyl, or $C_1$-$C_6$alkoxy. In some embodiments is a compound of Formula (IIa), or a pharmaceutically acceptable salt, solvate, or stereoisomer thereof, wherein q is 1, 2, or 3 and each $R^5$ is independently halo or $C_1$-$C_6$alkyl. In some embodiments is a compound of Formula (IIa), or a pharmaceutically acceptable salt, solvate, or stereoisomer thereof, wherein q is 1 and $R^5$ is halo or $C_1$-$C_6$alkyl. In some embodiments is a compound of Formula (IIa), or a pharmaceutically acceptable salt, solvate, or stereoisomer thereof, wherein q is 2 and each $R^5$ is independently halo or $C_1$-$C_6$alkyl. In some embodiments is a compound of Formula (IIa), or a pharmaceutically acceptable salt, solvate, or stereoisomer thereof, wherein q is 3 and each $R^5$ is independently halo or $C_1$-$C_6$alkyl.

In some embodiments is a compound of Formula (IIa), or a pharmaceutically acceptable salt, solvate, or stereoisomer thereof, wherein k is 0, 1, 2, 3, or 4. In some embodiments is a compound of Formula (IIa), or a pharmaceutically acceptable salt, solvate, or stereoisomer thereof, wherein k is 0, 1, 2, or 3. In some embodiments is a compound of Formula (IIa), or a pharmaceutically acceptable salt, solvate, or stereoisomer thereof, wherein k is 0, 1, or 2. In some embodiments is a compound of Formula (IIa), or a pharmaceutically acceptable salt, solvate, or stereoisomer thereof, wherein k is 0 or 1. In some embodiments is a compound of Formula (IIa), or a pharmaceutically acceptable salt, solvate, or stereoisomer thereof, wherein k is 0. In some embodiments is a compound of Formula (IIa), or a pharmaceutically acceptable salt, solvate, or stereoisomer thereof, wherein k is 1. In some embodiments is a compound of Formula (IIa), or a pharmaceutically acceptable salt, solvate, or stereoisomer thereof, wherein k is 1 and $R^3$ is halo, $C_1$-$C_6$alkyl, or $C_1$-$C_6$haloalkyl. In some embodiments is a compound of Formula (IIa), or a pharmaceutically acceptable salt, solvate, or stereoisomer thereof, wherein k is 2. In some embodiments is a compound of Formula (IIa), or a pharmaceutically acceptable salt, solvate, or stereoisomer thereof, wherein k is 2 and each $R^3$ is independently halo, $C_1$-$C_6$alkyl, or $C_1$-$C_6$haloalkyl.

In some embodiments, provided herein is a compound of Formula I selected from:

2-(3',6'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(3',5'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-4'-((4-((methylsulfonyl)methyl)piperidin-1-yl)methyl)-[1,1'-biphenyl]-4-yl)-1,1,1,3,3,3-hexafluoropropan-2-ol;

2-(2'-ethyl-4'-((4-(methylsulfonyl)piperidin-1-yl)methyl)-[1,1'-biphenyl]-4-yl)-1,1,1,3,3,3-hexafluoropropan-2-ol;

6-((4'-(1,1,1,3,3,3-hexafluoro-2-hydroxypropan-2-yl)-2-isopropyl-2'-methyl-[1,1'-biphenyl]-4-yl)methyl)-2-thia-6-azaspiro[3.4]octane 2,2-dioxide;

6-((4'-(1,1,1,3,3,3-hexafluoro-2-hydroxypropan-2-yl)-2-isopropyl-2'-methyl-[1,1'-biphenyl]-4-yl)methyl)-2-thia-6-azaspiro[3.3]heptane 2,2-dioxide;

2-(2'-ethyl-4'-((6-(methylsulfonyl)-2-azaspiro[3.3]heptan-2-yl)methyl)-[1,1'-biphenyl]-4-yl)-1,1,1,3,3,3-hexafluoropropan-2-ol;

2-(2'-(sec-butyl)-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2',3'-difluoro-6'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(2'-fluoro-6'-isopropyl-4'-((6-(methylsulfonyl)-2,6-diazaspiro[3.3]heptan-2-yl)methyl)-[1,1'-biphenyl]-4-yl)propan-2-ol;

6-((2-ethyl-4'-(1,1,1,3,3,3-hexafluoro-2-hydroxypropan-2-yl)-2'-methyl-[1,1'-biphenyl]-4-yl)methyl)-2-thia-6-azaspiro[3.4]octane 2,2-dioxide;

6-((2-ethyl-4'-(1,1,1,3,3,3-hexafluoro-2-hydroxypropan-2-yl)-[1,1'-biphenyl]-4-yl)methyl)-2-thia-6-azaspiro[3.4]octane 2,2-dioxide;

6-((2-ethyl-4'-(1,1,1,3,3,3-hexafluoro-2-hydroxypropan-2-yl)-2'-methyl-[1,1'-biphenyl]-4-yl)methyl)-2-thia-6-azaspiro[3.3]heptane 2,2-dioxide;

2-(2'-ethyl-4'-((6-(methylsulfonyl)-2,6-diazaspiro[3.5]nonan-2-yl)methyl)-[1,1'-biphenyl]-4-yl)-1,1,1,3,3,3-hexafluoropropan-2-ol;

2-(2'-ethyl-4'-((2-(methylsulfonyl)-2,6-diazaspiro[3.5]nonan-6-yl)methyl)-[1,1'-biphenyl]-4-yl)-1,1,1,3,3,3-hexafluoropropan-2-ol;

2-(2'-ethyl-4'-((6-(isobutylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-4'-((6-(propylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-4'-((6-(ethylsulfonyl)-2,6-diazaspiro[3.3]heptan-2-yl)methyl)-[1,1'-biphenyl]-4-yl)-1,1,1,3,3,3-hexafluoropropan-2-ol;

2-((2-ethyl-4'-(1,1,1,3,3,3-hexafluoro-2-hydroxypropan-2-yl)-[1,1'-biphenyl]-4-yl)methyl)-7-thia-2-azaspiro[3.5]nonane 7,7-dioxide;

2-(2'-(tert-butyl)-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-((2-ethyl-4'-(1,1,1,3,3,3-hexafluoro-2-hydroxypropan-2-yl)-[1,1'-biphenyl]-4-yl)methyl)-6-thia-2-azaspiro[3.4]octane 6,6-dioxide;

2-((2-ethyl-4'-(1,1,1,3,3,3-hexafluoro-2-hydroxypropan-2-yl)-[1,1'-biphenyl]-4-yl)methyl)-6-thia-2-azaspiro[3.4]octane 6-oxide;

6-((2-ethyl-4'-(1,1,1,3,3,3-hexafluoro-2-hydroxypropan-2-yl)-[1,1'-biphenyl]-4-yl)methyl)-2-thia-6-azaspiro[3.3]heptane 2,2-dioxide;

6-((2-ethyl-4'-(1,1,1,3,3,3-hexafluoro-2-hydroxypropan-2-yl)-[1,1'-biphenyl]-4-yl)methyl)-2-thia-6-azaspiro[3.3]heptane 2-oxide;

2-(4'-((2-thia-6-azaspiro[3.3]heptan-6-yl)methyl)-2'-ethyl-[1,1'-biphenyl]-4-yl)-1,1,1,3,3,3-hexafluoropropan-2-ol;

N-((1-((2-ethyl-4'-(1,1,1,3,3,3-hexafluoro-2-hydroxypropan-2-yl)-[1,1'-biphenyl]-4-yl)methyl)azetidin-3-yl)methyl)-N-methylmethanesulfonamide;

2-(2'-ethyl-4'-((2-(methylsulfonyl)-2,6-diazaspiro[3.4]octan-6-yl)methyl)-[1,1'-biphenyl]-4-yl)-1,1,1,3,3,3-hexafluoropropan-2-ol;

2-(2'-ethyl-4'-((7-(methylsulfonyl)-2,7-diazaspiro[4.4]nonan-2-yl)methyl)-[1,1'-biphenyl]-4-yl)-1,1,1,3,3,3-hexafluoropropan-2-ol;

N-((1-((2-ethyl-4'-(1,1,1,3,3,3-hexafluoro-2-hydroxypropan-2-yl)-[1,1'-biphenyl]-4-yl)methyl)azetidin-3-yl)methyl)methanesulfonamide;

2-(2'-ethyl-4'-((7-(methylsulfonyl)-2,7-diazaspiro[3.5]nonan-2-yl)methyl)-[1,1'-biphenyl]-4-yl)-1,1,1,3,3,3-hexafluoropropan-2-ol;

2-(2'-ethyl-4'-((2-(methylsulfonyl)-2,7-diazaspiro[3.5]nonan-7-yl)methyl)-[1,1'-biphenyl]-4-yl)-1,1,1,3,3,3-hexafluoropropan-2-ol;

2-(2'-ethyl-2-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-4'-((6-(methylsulfonyl)-2,6-diazaspiro[3.4]octan-2-yl)methyl)-[1,1'-biphenyl]-4-yl)-1,1,1,3,3,3-hexafluoropropan-2-ol;

2-(2'-ethyl-6'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-5'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-3'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

tert-butyl 2-((2-ethyl-4'-(1,1,1,3,3,3-hexafluoro-2-hydroxypropan-2-yl)-[1,1'-biphenyl]-4-yl)methyl)-2,6-diazaspiro[3.4]octane-6-carboxylate;

2-(2'-ethyl-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

methyl 6-((2-ethyl-4'-(1,1,1,3,3,3-hexafluoro-2-hydroxypropan-2-yl)-[1,1'-biphenyl]-4-yl)methyl)-2,6-diazaspiro[3.3]heptane-2-carboxylate;

2-(4'-((6-(cyclopropylsulfonyl)-2,6-diazaspiro[3.3]heptan-2-yl)methyl)-2'-ethyl-[1,1'-biphenyl]-4-yl)-1,1,1,3,3,3-hexafluoropropan-2-ol;

2-(2'-cyclopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(2'-isopropyl-4'-((6-(methylsulfonyl)-2,6-diazaspiro[3.3]heptan-2-yl)methyl)-[1,1'-biphenyl]-4-yl)propan-2-ol;

tert-butyl 6-((2-ethyl-4'-(1,1,1,3,3,3-hexafluoro-2-hydroxypropan-2-yl)-[1,1'-biphenyl]-4-yl)methyl)-2,6-diazaspiro[3.3]heptane-2-carboxylate;

1,1,1,3,3,3-hexafluoro-2-(4'-((6-(methylsulfonyl)-2,6-diazaspiro[3.3]heptan-2-yl)methyl)-2'-(prop-1-en-2-yl)-[1,1'-biphenyl]-4-yl)propan-2-ol;

2-(2'-bromo-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(4'-((6-(methylsulfonyl)-2,6-diazaspiro[3.3]heptan-2-yl)methyl)-2'-(trifluoromethyl)-[1,1'-biphenyl]-4-yl)propan-2-ol;

2-(2'-chloro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1-(6-((2-ethyl-4'-(1,1,1,3,3,3-hexafluoro-2-hydroxypropan-2-yl)-[1,1'-biphenyl]-4-yl)methyl)-2,6-diazaspiro[3.3]heptan-2-yl)ethan-1-one;

2-(2'-ethyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1-(6-((4'-(1,1,1,3,3,3-hexafluoro-2-hydroxypropan-2-yl)-2-methyl-[1,1'-biphenyl]-4-yl)methyl)-2,6-diazaspiro[3.3]heptan-2-yl)ethan-1-one;

1,1,1,3,3,3-hexafluoro-2-(2'-methyl-4'-((6-(methylsulfonyl)-2,6-diazaspiro[3.3]heptan-2-yl)methyl)-[1,1'-biphenyl]-4-yl)propan-2-ol;

1,1,1,3,3,3-hexafluoro-2-(2'-methyl-4'-((6-(pyridin-4-ylmethyl)-2,6-diazaspiro[3.3]heptan-2-yl)methyl)-[1,1'-biphenyl]-4-yl)propan-2-ol;

2-(4-(3-ethyl-5-((6-(methylsulfonyl)-2,6-diazaspiro[3.3]heptan-2-yl)methyl)pyridin-2-yl)phenyl)-1,1,1,3,3,3-hexafluoropropan-2-ol;

7-((2-ethyl-4'-(1,1,1,3,3,3-hexafluoro-2-hydroxypropan-2-yl)-[1,1'-biphenyl]-4-yl)methyl)-2,7-diazaspiro[4.4]nonan-1-one;

7-((2-ethyl-4'-(1,1,1,3,3,3-hexafluoro-2-hydroxypropan-2-yl)-[1,1'-biphenyl]-4-yl)methyl)-2,7-diazaspiro[4.4]nonan-3-one;

4'-(1,1,1,3,3,3-hexafluoro-2-hydroxypropan-2-yl)-N,N-dimethyl-4-((6-(methylsulfonyl)-2,6-diazaspiro[3.3]heptan-2-yl)methyl)-[1,1'-biphenyl]-2-carboxamide;

2-(2'-ethyl-2-methoxy-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(2'-methoxy-2-methyl-4'-((6-(methylsulfonyl)-2,6-diazaspiro[3.3]heptan-2-yl)methyl)-[1,1'-biphenyl]-4-yl)propan-2-ol;

7-((2-ethyl-4'-(1,1,1,3,3,3-hexafluoro-2-hydroxypropan-2-yl)-[1,1'-biphenyl]-4-yl)methyl)-2-thia-7-azaspiro[4.4]nonane 2,2-dioxide;

2-(5-(2-ethyl-4-((6-(methylsulfonyl)-2,6-diazaspiro[3.3]heptan-2-yl)methyl)phenyl)pyridin-2-yl)-1,1,1,3,3,3-hexafluoropropan-2-ol;

2-(4-(4-ethyl-6-((6-(methylsulfonyl)-2,6-diazaspiro[3.3]heptan-2-yl)methyl)pyridin-3-yl)phenyl)-1,1,1,3,3,3-hexafluoropropan-2-ol;

4'-(1,1,1,3,3,3-hexafluoro-2-hydroxypropan-2-yl)-4-((6-(methylsulfonyl)-2,6-diazaspiro[3.3]heptan-2-yl)methyl)-[1,1'-biphenyl]-3-ol;

2-(2'-cyclopropyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-cyclopropyl-2,3',6'-trifluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-2'-cyclopropyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(2,3',6'-trifluoro-2'-isopropyl-4'-((6-(methylsulfonyl)-2,6-diazaspiro[3.3]heptan-2-yl)methyl)-[1,1'-biphenyl]-4-yl)propan-2-ol;

2-(2'-cyclopropyl-2-ethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-cyclopropyl-3',6'-difluoro-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-5'-fluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(5'-fluoro-2'-isopropyl-2-methyl-4'-((6-(methylsulfonyl)-2,6-diazaspiro[3.3]heptan-2-yl)methyl)-[1,1'-biphenyl]-4-yl)propan-2-ol;

2-(2,5'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-3',6'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-ethyl-3',6'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(3',6'-difluoro-2'-isopropyl-2-methyl-4'-((6-(methylsulfonyl 2-(2'-ethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2,2'-diethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-2'-ethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-2'-ethyl-5'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-2,5'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(5'-fluoro-2'-isopropyl-4'-((6-(methylsulfonyl)-2,6-diazaspiro[3.3]heptan-2-yl)methyl)-[1,1'-biphenyl]-4-yl)propan-2-ol;

2-(2,2'-diethyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-2,3',6'-trifluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-ethyl-2'-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-2'-ethyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(3',6'-difluoro-2'-isopropyl-4'-((2-(methylsulfonyl)-2,6-diazaspiro[3.4]octan-6-yl)methyl)-[1,1'-biphenyl]-4-yl)-1,1,1,3,3,3-hexafluoropropan-2-ol;

2-(4-(2-ethyl-6-((6-(methylsulfonyl)-2,6-diazaspiro[3.3]heptan-2-yl)methyl)pyridin-3-yl)-3-methylphenyl)-1,1,1,3,3,3-hexafluoropropan-2-ol;

2-(2'-ethyl-3',6'-difluoro-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2'-ethyl-4-(1,1,1,3,3,3-hexafluoro-2-hydroxypropan-2-yl)-4'-((6-(methylsulfonyl)-2,6-diazaspiro[3.3]heptan-2-yl)methyl)-[1,1'-biphenyl]-2-carbonitrile;

2-(4-(4-ethyl-6-((6-(methylsulfonyl)-2,6-diazaspiro[3.3]heptan-2-yl)methyl)pyridin-3-yl)-3-methylphenyl)-1,1,1,3,3,3-hexafluoropropan-2-ol;

2-(6-(2-ethyl-4-((6-(methylsulfonyl)-2,6-diazaspiro[3.3]heptan-2-yl)methyl)phenyl)pyridin-3-yl)-1,1,1,3,3,3-hexafluoropropan-2-ol;

2-(4-(3-ethyl-5-((6-(methylsulfonyl)-2,6-diazaspiro[3.3]heptan-2-yl)methyl)pyridin-2-yl)-3-methylphenyl)-1,1,1,3,3,3-hexafluoropropan-2-ol;

1,1,1,3,3,3-hexafluoro-2-(3-methyl-4-(6-(6-(methylsulfonyl)-2,6-diazaspiro[3.3]heptan-2-yl)pyridin-2-yl)phenyl)propan-2-ol; and 2-(2,2'-dimethyl-3'-(6-(methylsulfonyl)-2,6-diazaspiro[3.3]heptan-2-yl)-[1,1'-biphenyl]-4-yl)-1,1,1,3,3,3-hexafluoropropan-2-ol; or a pharmaceutically acceptable salt or solvate thereof.

In some embodiments, the compounds provided herein were found to have $IC_{50}$s of about or less than 50 nM in the RORγ Gal4ligand binding assay. In some embodiments, the compounds provided herein were found to have $IC_{50}$s of about or less than 100 nM in the RORγ Gal4ligand binding assay. In some embodiments, the compounds provided herein have $IC_{50}$s of about 10 nM or less, about 20 nM or less, about 25 nM or less, about 50 nM or less, about 100 nM or less, about 250 nM or less, or about 500 nM or less in the RORγ Gal4 ligand binding assay. In another embodiment, the compounds provided herein modulate RORγ selectively over RORalpha.

Any combination of the groups described above for the various variables is contemplated herein. Throughout the specification, groups and substituents thereof can be chosen by one skilled in the field to provide stable moieties and compounds.

In some embodiments, the compound described herein is present in the pharmaceutical composition as a pharmaceutically acceptable salt. In some embodiments, any compound described above is suitable for any method or composition described herein.

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns. In some embodiments, a compound of Formula (I), (Ia), (Ib), (II), or (IIa) is used as a single enantiomer. In some embodiments, a compound of Formula (I), (Ia), (Ib), (II), or (IIa) is used as a racemic mixture.

The methods and formulations described herein include the use of N-oxides (if appropriate), or pharmaceutically acceptable salts of compounds having the structures presented herein, as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

In some embodiments, the compounds of Formula (I), (Ia), (Ib), (II), or (IIa) described herein include solvent addition forms thereof. Solvates contain either stoichiometric or non-stoichiometric amounts of a solvent with pharmaceutically acceptable solvents such as water, ethanol, and the like. Hydrates are formed when the solvent is water, or alcoholates are formed when the solvent is alcohol.

In some embodiments, sites on the compounds of Formula (I), (Ia), (Ib), (II), or (IIa) disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the compounds of Formula (I), (Ia), (Ib), (II), or (IIa) disclosed herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements and thus decreasing toxicity or lowering the probability of drug-drug interactions.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

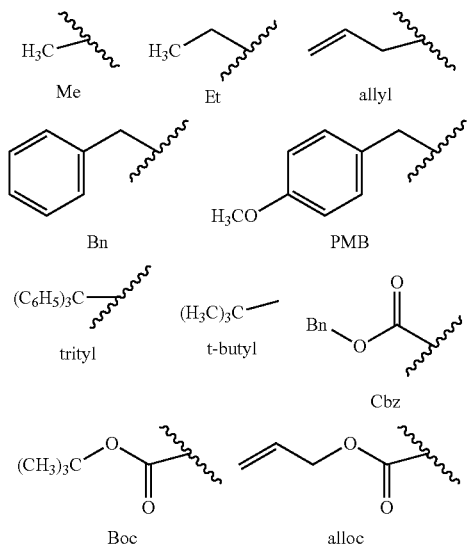

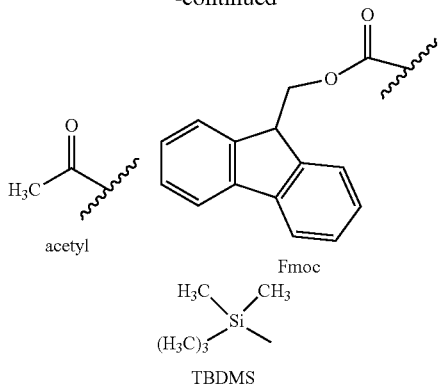

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Methods of Treatment and Prevention

In one embodiment, provided herein are methods for modulating of RORγ activity in a cell by contacting the cell with an RORγ modulator. Examples of such ROR modulators are described above.

In some embodiments is a method of treating a disease, disorder, or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is selected from psoriasis, psoriatic arthritis, uveitis, ulcerative colitis, asthma, allergic rhinitis, chronic obstructive pulmonary disease (COPD), atopic dermatitis, vitiligo, vesiculobullous dermatosis, rheumatoid arthritis, ankylosing spondylitis, reactive arthritis, arthritis associated with inflammatory bowel disease, juvenile rheumatoid arthritis, Crohn's disease, inflammatory bowel disease, lupus, lupus nephritis, multiple sclerosis, axial spodyloarthritides, hidraenitis suppurativa, Sjögren's syndrome, regional enteritis, Tolosa-Hunt syndrome, undifferentiated connective tissue disease, obesity, obesity-induced insulin resistance, atherosclerosis, and type II diabetes. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is psoriasis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is psoriatic arthritis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is uveitis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is ulcerative colitis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is asthma. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is allergic rhinitis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is chronic obstructive pulmonary disease (COPD). In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is atopic dermatitis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is vitiligo. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is vesiculobullous dermatosis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is rheumatoid arthritis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is ankylosing spondylitis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is reactive arthritis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is arthritis associated with inflammatory bowel disease. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is juvenile rheumatoid arthritis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is Crohn's disease. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is inflammatory bowel disease. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is lupus. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is lupus nephritis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is multiple sclerosis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is axial spodyloarthritides. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is hidraenitis suppurativa. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is Sjögren's syndrome. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is regional enteritis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is Tolosa-Hunt syndrome. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is undifferentiated connective tissue disease. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is obesity. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is obesity-induced insulin resistance. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is atherosclerosis. In some embodiments is a method of treating a disease, disorder or condition in an individual in need thereof comprising administering to the individual a therapeutically effective amount of a compound of Formula (I), (Ia), (Ib), (II), or (IIa), or a pharmaceutically acceptable salt or solvate thereof, wherein the disease, disorder, or condition is type II diabetes.

Pharmaceutical Compositions and Methods of Administration of RORγ Modulators

RORγ modulators described herein are administered to subjects in a biologically compatible form suitable for administration to treat or prevent diseases, disorders or conditions. Administration of RORγ modulators as described herein can be in any pharmacological form including a therapeutically effective amount of an RORγ modulator alone or in combination with a pharmaceutically acceptable carrier.

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)).

Accordingly, provided herein is a pharmaceutical composition comprising at least one compound described herein, or a pharmaceutically acceptable salt, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

In some embodiments is a pharmaceutical composition comprising a pharmaceutically acceptable carrier and a compound of Formula (I), (Ia), (Ib), (II), or (IIa), or a pharmaceutically acceptable salt or solvate thereof. In some embodiments is a pharmaceutical composition comprising a pharmaceutically acceptable carrier and a compound of Formula (I), or a pharmaceutically acceptable salt or solvate thereof. In some embodiments is a pharmaceutical composition comprising a pharmaceutically acceptable carrier and a compound of Formula (Ia), or a pharmaceutically acceptable salt or solvate thereof. In some embodiments is a pharmaceutical composition comprising a pharmaceutically acceptable carrier and a compound of Formula (Ib), or a pharmaceutically acceptable salt or solvate thereof. In some embodiments is a pharmaceutical composition comprising a pharmaceutically acceptable carrier and a compound of Formula (II), or a pharmaceutically acceptable salt or solvate thereof. In some embodiments is a pharmaceutical composition comprising a pharmaceutically acceptable carrier and a compound of Formula (IIa), or a pharmaceutically acceptable salt or solvate thereof.

In some embodiments is a pharmaceutical composition consisting essentially of a pharmaceutically acceptable carrier and a compound of Formula (I), (Ia), (Ib), (II), or (IIa), or a pharmaceutically acceptable salt thereof. In some embodiments is a pharmaceutical composition consisting essentially of a pharmaceutically acceptable carrier and a compound of Formula (I), or a pharmaceutically acceptable salt or solvate thereof. In some embodiments is a pharmaceutical composition consisting essentially of a pharmaceutically acceptable carrier and a compound of Formula (Ia), or a pharmaceutically acceptable salt or solvate thereof. In some embodiments is a pharmaceutical composition consisting essentially of a pharmaceutically acceptable carrier and a compound of Formula (Ib), or a pharmaceutically acceptable salt or solvate thereof. In some embodiments is a pharmaceutical composition consisting essentially of a pharmaceutically acceptable carrier and a compound of Formula (II), or a pharmaceutically acceptable salt or solvate thereof. In some embodiments is a pharmaceutical composition consisting essentially of a pharmaceutically acceptable carrier and a compound of Formula (IIa), or a pharmaceutically acceptable salt or solvate thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, topical, buccal, parenteral (e.g., subcutaneous, intramuscular, intradermal, or intravenous), or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants The dose of the composition comprising at least one compound described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the RORγ modulator and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the RORγ modulator activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such RORγ modulators can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. RORγ modulators that exhibit large therapeutic indices are preferred. While ROR, modulators that exhibit toxic side effects may be used, care should be taken to design a delivery system that targets such modulators to the site of affected tissue in order to minimize potential damage to uninfected cells and, thereby, reduce side effects.

The data obtained from the cell culture assays and animal studies can be used in formulating a range of dosage for use in humans. The dosage of such RORγ modulators lies preferably within a range of circulating concentrations that include the $ED_{50}$ with little or no toxicity. The dosage may vary within this range depending upon the dosage form employed and the route of administration utilized. For any RORγ modulator used in a method described herein, the therapeutically effective dose can be estimated initially from cell culture assays. A dose may be formulated in animal models to achieve a circulating plasma concentration range that includes the $IC_{50}$ (i.e., the concentration of RORγ modulator that achieves a half-maximal inhibition of symptoms) as determined in cell culture. Such information can be used to more accurately determine useful doses in humans. Levels in plasma may be measured, for example, by high performance liquid chromatography.

EXAMPLES

The following examples are offered for purposes of illustration, and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

Standard abbreviations and acronyms as defined in *J. Org. Chem.* 2007 72(1): 23A-24A are used herein. Other abbreviations and acronyms used herein are as follows:

| | |
|---|---|
| AcOH | acetic acid |
| DCM | dichloromethane |
| DMP | Dess-Martin periodinane |
| dppf | (diphenylphosphino)ferrocene |
| EtOAc | ethyl acetate |
| HBTU | N,N,N',N'-tetramethyl-O-(1H-benzotriazol-1-yl)uronium hexafluorophosphate |
| LC-MS | liquid chromatography-mass spectrometry |
| MeOH | methanol |
| TEA | triethylamine |
| rt | room temperature |

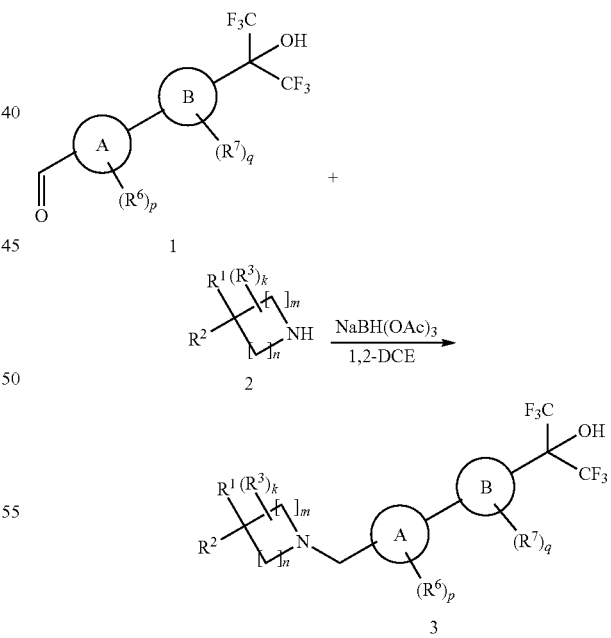

General Synthetic Scheme:

General Procedure

Aldehyde (1) (1.0 equiv) and secondary amine (2) (1.2 equiv) were combined in 1,2-DCE with catalytic amount of acid such as acetic acid or TFA. The mixture was stirred at rt for 1 h to 3 h. NaBH(OAc)$_3$ (3.0 equiv) was added to the solution. The resulting mixture was stirred at room temperature overnight. The reaction was quenched with MeOH and extracted with ethyl acetate (2×20 mL). The crude mixture was purified on a silica gel column to afford clean product (3).

Example A: Synthesis of Aldehyde Intermediate
Synthesis of Intermediate 1, Intermediate 2 and Intermediates 2A-2D

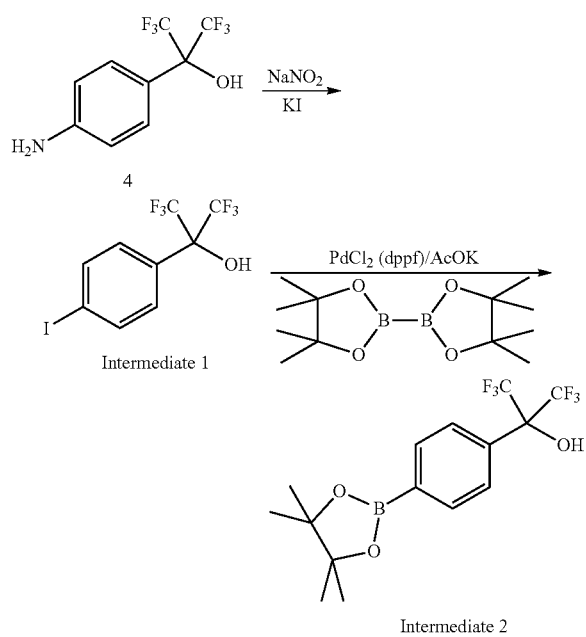

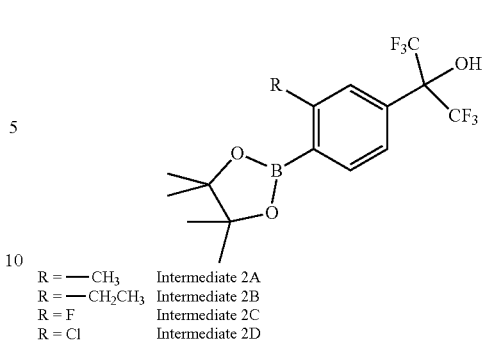

R = —CH₃     Intermediate 2A
R = —CH₂CH₃  Intermediate 2B
R = F         Intermediate 2C
R = Cl        Intermediate 2D 1,1,1,3,3,3-Hexafluoro-2-(3-methyl-4-(4,4,5,5-tetramethyl-1,3,2-dioxaborolan-2-yl)phenyl)propan-2-ol (Intermediate 2A) was prepared as described in Step B substituting 2-(4-bromo-3-methylphenyl)-1,1,1,3,3,3-hexafluoropropan-2-ol for Intermediate 1.

2-(3-ethyl-4-(4,4,5,5-tetramethyl-1,3,2-dioxaborolan-2-yl)phenyl)-1,1,1,3,3,3-hexafluoropropan-2-ol (Intermediate 2B) was prepared as described in Step B substituting 2-(4-bromo-3-ethylphenyl)-1,1,1,3,3,3-hexafluoropropan-2-ol for Intermediate 1.

1,1,1,3,3,3-hexafluoro-2-(3-fluoro-4-(4,4,5,5-tetramethyl-1,3,2-dioxaborolan-2-yl)phenyl)propan-2-ol (Intermediate 2C) was prepared as described in Step B substituting 2-(4-bromo-3-fluorophenyl)-1,1,1,3,3,3-hexafluoropropan-2-ol for Intermediate 1.

2-(3-chloro-4-(4,4,5,5-tetramethyl-1,3,2-dioxaborolan-2-yl)phenyl)-1,1,1,3,3,3-hexafluoropropan-2-ol (Intermediate 2D) was prepared as described in Step B substituting 2-(4-bromo-3-chlorophenyl)-1,1,1,3,3,3-hexafluoropropan-2-ol for Intermediate 1.

Step A. To a solution of 2-(4-aminophenyl)-1,1,1,3,3,3-hexafluoropropan-2-ol (4) (15.0 g, 1.0 equiv) in DMF (120 mL) was added a solution of NaNO₂ (4.4 g, 1.1 equiv) in 30 mL water. The mixture was cooled to 0° C. for 15 min. 6 N HCl (29 mL, 3.0 equiv) was added dropwise to the reaction mixture over 15 min at 0° C. The resulting mixture was stirred at 0° C. for 1 h. KI (10.1 g, 1.05 equiv) was added with portions (over 15 mins). The reaction mixture was stirred at 0° C. for 1 h, and then at room temperature overnight. The reaction was diluted with water (~500 mL) and extracted with EtOAc/hexane (2:1, 3×150 mL). The combined organic phase was washed with NaHSO₃, water, and brine. The crude mixture was purified on a silica gel column to afford 1,1,1,3,3,3-hexafluoro-2-(4-iodophenyl)propan-2-ol (Intermediate 1) (18.9 g, yield 88%) as a pale yellow oil.

Procedure 1, Step B. To a solution of compound Intermediate 1 (1.0 g, 1.0 equiv) in anhydrous 1,4-dioxane (20 mL) was added bis(pinacolato)diboron (0.89 g, 1.3 equiv), potassium acetate (0.265 g, 3.0 equiv), and Pd(dppf)₂Cl₂ (100 mg, 0.05 equiv). The mixture was degassed and then bubbled with N₂ for 5 min, and then stirred at 90° C. overnight. Upon cooling to room temperature, the mixture was poured into NH₄Cl solution and extracted with DCM. The organic phase was dried over MgSO₄, concentrated, and purified with silica gel column chromatography to afford 1,1,1,3,3,3-hexafluoro-2-(4-(4,4,5,5-tetramethyl-1,3,2-dioxaborolan-2-yl)phenyl)propan-2-ol (Intermediate 2) (450 mg, yield 45%) as a white solid.

Example B: Synthesis of 2-(4-bromo-3-fluorophenyl)-1,1,1,3,3,3-hexafluoropropan-2-ol (Intermediate 3) and 2-(4-bromo-3-methylphenyl)-1,1,1,3,3,3-hexafluoropropan-2-ol Intermediate 4

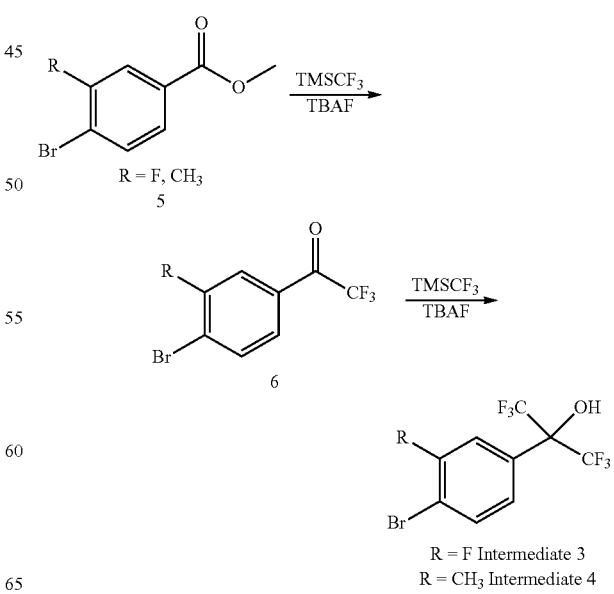

R = F Intermediate 3
R = CH₃ Intermediate 4

Methyl 4-bromo-3-methylbenzoate (5) (1.0 g, 1.0 equiv) was dissolved in 20 mL THF and TMSCF$_3$ (3.1 g, 5.0 equiv) was added. The mixture was cooled at −15° C. To the mixture was added 1 M TBAF (13 mL, 3.0 equiv) dropwise over 20 min. After addition of TMSCF$_3$, 1N HCl (80 mL) was added slowly. The mixture was stirred at rt for 15 min and then extracted with 2×40 mL hexane. The organic phase was dried over MgSO$_4$ and concentrated in vacuum to afford (6) (0.98 g) that was used for the next reaction without purification. The intermediate (6) and TMSCF$_3$ (3.0 g) was dissolved in anhydride THF (20 mL) and cooled with ice-water. TBAF (1 M, 5 mL) was added dropwise. The resulting mixture was stirred at 0° C. for 2 h. The reaction was quenched with 1N HCl (80 mL). The mixture was extracted with 2×40 mL hexane. The crude mixture was purified on a silica gel column to afford 2-(4-bromo-3-methylphenyl)-1,1,1,3,3,3-hexafluoropropan-2-ol (Intermediate 4) (420 mg, yield 29% in two-steps) as a white solid.

2-(4-bromo-3-fluorophenyl)-1,1,1,3,3,3-hexafluoropropan-2-ol (Intermediate 3) was synthesized as described in this Example B, by replacing methyl 4-bromo-3-methylbenzoate with 4-bromo-3-fluorobenzoate.

Example C: Synthesis of 2-ethyl-4'-(1,1,1,3,3,3-hexafluoro-2-hydroxypropan-2-yl)-[1,1'-biphenyl]-4-carbaldehyde (Aldehyde Intermediate 5)

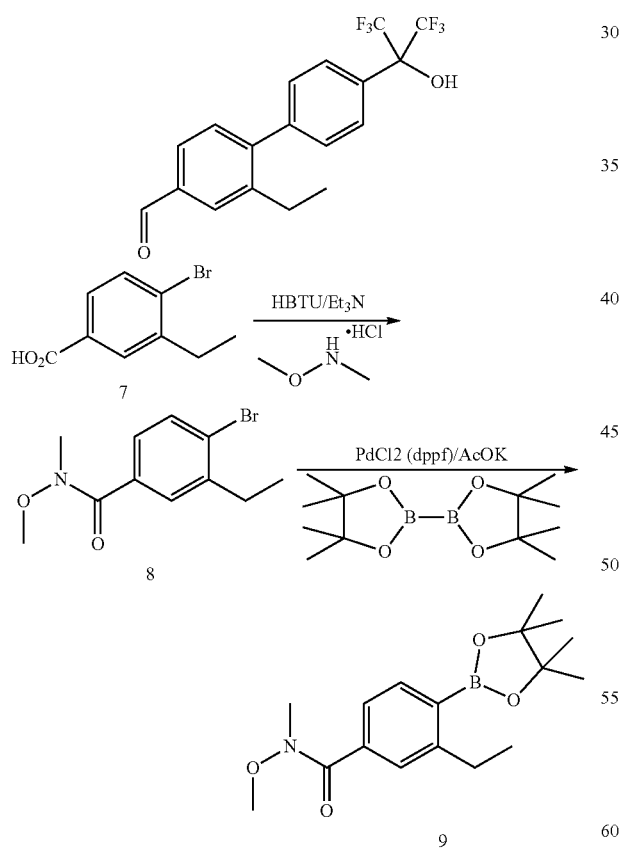

Step A. 4-bromo-3-ethylbenzoic acid (7) (5.0 g, 1.0 equiv), N,O-dimethylhydroxylamine hydrochloride (3.2 g, 1.5 equiv) and HBTU (9.6 g, 1.15 equiv) were combined in 80 mL DMF at room temperature. To the reaction mixture was added Et$_3$N (11.2 g, 4.0 equiv) dropwise. The resulting mixture was stirred at rt overnight. The reaction was diluted with 200 mL of ethyl acetate and 100 mL of hexane, then washed with 2×150 mL water, 2×100 mL 1N HCl, 2×100 mL saturated NaHCO$_3$, and brine. The organic phase was dried over MgSO$_4$ and concentrated in vacuum to provide 4-bromo-3-ethyl-N-methoxy-N-methylbenzamide (8) (5.8 g, yield 98%) as a pale yellow oil which was used without further purification.

Step B. 4-Bromo-3-ethyl-N-methoxy-N-methylbenzamide (8) (3.0 g, 1.0 equiv) and 4,4,4',4',5,5,5',5'-octamethyl-2,2'-bi(1,3,2-dioxaborolane) (3.2 g, 1.15 equiv) were dissolved in dry dioxane (25 mL). The mixture was degassed by bubbling N$_2$ for 5 min. PdCl$_2$ (dppf) (0.81 g, 0.1 equiv) and potassium acetate (1.6 g, 1.5 equiv) were added to the reaction mixture. The resulting mixture was heated at 100° C. in a sealed-tube for 15 h. The reaction mixture was diluted with 80 mL acetate and 80 mL hexane, washed with 3×80 mL water and 50 mL brine. The crude mixture was purified on a silica gel column to afford 3-ethyl-N-methoxy-N-methyl-4-(4,4,5,5-tetramethyl-1,3,2-dioxaborolan-2-yl)benzamide (9) (3.3 g, yield 95%) as a pale yellow oil.

Step C. 3-ethyl-N-methoxy-N-methyl-4-(4,4,5,5-tetramethyl-1,3,2-dioxaborolan-2-yl)benzamide (9) (2.24 g, 1.0 equiv), 1,1,1,3,3,3-hexafluoro-2-(4-iodophenyl)propan-2-ol (2.85 g, 1.1 equiv), Pd(PPh$_3$)$_4$ (0.81 g, 0.1 equiv) and K$_2$CO$_3$ (2.9 g, 3.0 equiv) were combined in 35 mL dioxane and 10 mL water. The mixture was flushed with N$_2$ for 5 min, and then heated at 95° C. for 14 h under N$_2$. The reaction was extracted with EtOAc (2×200 mL). The combined organic phase was washed with 1N HCl and brine. The crude mixture was purified on a silica gel column to afford 2-ethyl-4'-(1,1,1,3,3,3-hexafluoro-2-hydroxypropan-2-yl)-N-methoxy-N-methyl-[1,1'-biphenyl]-4-carboxamide (2.28 g, yield 75%) as a white solid.

2-ethyl-4'-(1,1,1,3,3,3-hexafluoro-2-hydroxypropan-2-yl)-N-methoxy-N-methyl-[1,1'-biphenyl]-4-carboxamide (2.0 g, 1.0 equiv) was dissolved in dry THF (20 mL) and the solution was cooled to −50° C. under N$_2$. LAH (4.6 mL, 1.0 equiv) was added dropwise. The mixture was stirred at −30° C. to −10° C. for an additional 40 min. The reaction was quenched with 1 mL water at −10° C. and then diluted with 50 mL 2N HCl. The mixture was extracted with 2×50 mL of ethyl acetate. The crude mixture was purified on a silica gel column to provide 2-ethyl-4'-(1,1,1,3,3,3-hexafluoro-2-hydroxypropan-2-yl)-[1,1'-biphenyl]-4-carbaldehyde (Aldehyde Intermediate 5) (1.41 g, yield 82%) as a white solid.

Example D: Synthesis of 2-ethyl-6-fluoro-4'-(1,1,1,3,3,3-hexafluoro-2-hydroxypropan-2-yl)-[1,1'-biphenyl]-4-carbaldehyde (Aldehyde Intermediate 6)

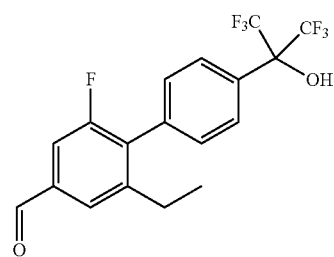 [SMILES: CCc1cc(C=O)cc(F)c1-c1ccc(C(O)(C(F)(F)F)C(F)(F)F)cc1]

To a solution of 3-fluoro-2-hydroxybenzaldehyde (1.4 g, 10 mmol) in THF (20 mL) was added MeMgCl (8 mL, 24 mmol) at 0° C. The reaction mixture was stirred at 0° C. to rt for 1 h, diluted with EtOAc, and quenched with saturated NH₄Cl. The organic layer was dried and evaporated to afford crude 2-fluoro-6-(1-hydroxyethyl)phenol (1.4 g).

To a solution of 2-fluoro-6-(1-hydroxyethyl)phenol (1.4 g) in MeOH (20 mL) was added 10% Pd/C (100 mg) and hydrogenated under hydrogen (50 PSI) overnight. The mixture was filtered through Celite and the filtration was concentrated to give 2-ethyl-6-fluorophenol (1.0 g).

To a solution of 2-ethyl-6-fluorophenol (1 g, 7.1 mmol) in AcOH (10 mL) was added NBS (1.3 g) at 0° C. The reaction mixture was stirred at 0° C. to rt for 1 h, diluted with EtOAc, and washed with water. The organic layer was concentrated and purified on a silica gel column to give 4-bromo-2-ethyl-6-fluorophenol (0.9 g).

The mixture of 4-bromo-2-ethyl-6-fluorophenol (0.88 g, 4 mmol), Zn(CN)₂ (0.93 g, 8 mmol) and Pd(PPh₃)₄ (100 mg, 0.09 mmol) in toluene (10 mL) was heated at 90° C. under N₂ overnight. The mixture was cooled to rt and washed with water and brine. The organic layer was concentrated and purified on a silica gel column to give 3-ethyl-5-fluoro-4-hydroxybenzonitrile (0.35 g).

To a solution of 3-ethyl-5-fluoro-4-hydroxybenzonitrile (0.34 g, 2.0 mmol) in CH₂Cl₂ (10 mL) was added DIBAL (4.5 mL, 4.5 mmol) at −78° C. under N₂. The reaction mixture was stirred at −78° C. to 0° C. for 2 h and then quenched with 1N HCl. The organic layer was concentrated and purified on a silica gel column to give 3-ethyl-5-fluoro-4-hydroxybenzaldehyde (0.17 g).

To a solution of 3-ethyl-5-fluoro-4-hydroxybenzaldehyde (0.17 g, 1 mmol) in CH₂Cl₂ (10 mL) was added N(Et)₃ (0.2 g, 2 mmol) at 0° C. followed by addition of (Tf)₂O (0.28 g, 1 mmol) under N₂. The reaction mixture was stirred at 0° C. to 2 h and quenched with water. The organic layer was concentrated and purified on a silica gel column to give 2-ethyl-6-fluoro-4-formylphenyl trifluoromethanesulfonate (0.15 g).

A mixture of 2-ethyl-6-fluoro-4-formylphenyl trifluoromethanesulfonate (0.15 g, 0.5 mmol), 1,1,1,3,3,3-hexafluoro-2-(4-(4,4,5,5-tetramethyl-1,3,2-dioxaborolan-2-yl)phenyl)propan-2-ol (Intermediate 2) (0.15 g), Pd(PPh₃)₄ (55 mg), and Na₂CO₃ (2N solution, 0.5 mL) in dioxane (10 mL) was heated at 90° C. under N₂ overnight. The mixture was cooled to rt and washed with water and brine. The organic layer was concentrated and purified on a silica gel column to afford 2-ethyl-6-fluoro-4'-(1,1,1,3,3,3-hexafluoro-2-hydroxypropan-2-yl)-[1,1'-biphenyl]-4-carbaldehyde (Aldehyde Intermediate 6) (85 mg).

Example E: Synthesis of 2-ethyl-5-fluoro-4'-(1,1,1,3,3,3-hexafluoro-2-hydroxypropan-2-yl)-[1,1'-biphenyl]-4-carbaldehyde (Aldehyde Intermediate 7)

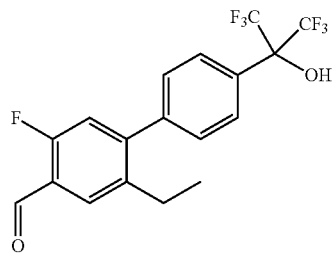 [SMILES: CCc1cc(C=O)c(F)cc1-c1ccc(C(O)(C(F)(F)F)C(F)(F)F)cc1]

To a solution of 1-(4-fluoro-3-nitrophenyl)ethan-1-one (1.8 g, 10 mmol) in THF (20 mL) was added NaBH₄ (0.38 g, 10 mmol) at 0° C. The reaction mixture was stirred at 0° C. to rt for 1 h, diluted with EtOAc, and quenched with saturated NH₄Cl. The organic layer was dried and evaporated to afford 1-(4-fluoro-3-nitrophenyl)ethan-1-ol (1.5 g).

To a solution of 1-(4-fluoro-3-nitrophenyl)ethan-1-ol (1.5 g) in MeOH (20 mL) was added 10% Pd/C (100 mg) and hydrogenated under hydrogen (50 PSI) overnight. The mixture was filtered through Celite and the filtration was concentrated to give 5-ethyl-2-fluoroaniline (1.0 g).

To a solution of 5-ethyl-2-fluoroaniline (0.62 g, 4.4 mmol) in DMF (10 mL) was added NBS (0.83 g) at 0° C. The reaction mixture was stirred at 0° C. to rt for 1 h, diluted with EtOAc, and washed with water. The organic layer was concentrated and purified by flash cartridge (ISCO) to give 4-bromo-5-ethyl-2-fluoroaniline (0.92 g).

To a solution of 4-bromo-5-ethyl-2-fluoroaniline (0.88 g, 4 mmol) in H₂O (15 mL) was added H₂SO₄ (4 mL, 2N solution). The mixture was sonicated for 30 mins and cooled to 0° C. NaNO₂ (0.3 g, 4.4 mmol) in water (10 mL) was added dropwise. After stirring at 0° C. for 1 h, Na₂CO₃ was added to adjust pH to 7. The aqueous mixture was added to KCN (0.52 g. 8 mmol) and CuCN (0.36 g, 4 mmol) in water at 70° C. and the mixture was stirred at 70° C. for 2 h and extracted with EtOAc. The organic layer was washed with water, brine and concentrated, the residue was purified by flash cartridge (ISCO) to give 4-bromo-5-ethyl-2-fluorobenzonitrile (0.35 g).

To a solution of 4-bromo-5-ethyl-2-fluorobenzonitrile compound (0.34 g, 2 mmol) in CH₂Cl₂ (10 mL) was added DIBAL (2.2 mL, 2.2 mmol) at −78° C. under N₂. The reaction mixture was stirred at −78° C. to 0° C. for 2 h and quenched with 1N HCl. The organic layer was concentrated and purified by flash cartridge (ISCO) to afford 4-bromo-5-ethyl-2-fluorobenzaldehyde (0.15 g).

A mixture of 4-bromo-5-ethyl-2-fluorobenzaldehyde (0.11 g, 0.5 mmol), 1,1,1,3,3,3-hexafluoro-2-(4-(4,4,5,5-tetramethyl-1,3,2-dioxaborolan-2-yl)phenyl)propan-2-ol (0.15 g), Pd(PPh₃)₄ (55 mg), and Na₂CO₃ (2N solution, 0.5 mL) in dioxane (10 mL) was heated at 90° C. under N₂ overnight. The mixture was cooled to rt and washed with water and brine. The organic layer was concentrated and purified by flash cartridge (ISCO) to give compound 2-ethyl-5-fluoro-4'-(1,1,1,3,3,3-hexafluoro-2-hydroxypropan-2-yl)-[1,1'-biphenyl]-4-carbaldehyde (52 mg).

Example F: Synthesis of 2-ethyl-3-fluoro-4'-(1,1,1,3,3,3-hexafluoro-2-hydroxypropan-2-yl)-[1,1'-biphenyl]-4-carbaldehyde (Aldehyde Intermediate 8)

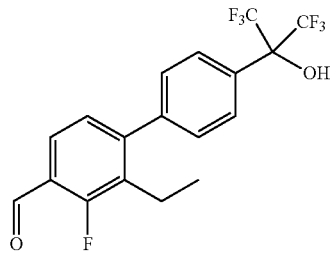 [SMILES: CCc1c(-c2ccc(C(O)(C(F)(F)F)C(F)(F)F)cc2)ccc(C=O)c1F]

To a solution of 4-bromo-2-fluoro-1-iodobenzene (3.0 g, 10 mmol) in THF (20 mL) was added LDA (12 mL, 12 mmol) at −78° C. under N₂. The reaction was slowly warmed to −20° C. and then cooled to −78° C. EtI (4.7 g, 30 mmol) was added. The mixture was stirred at −78° C. to rt overnight, diluted with EtOAc, and washed with water. The organic layer was concentrated and purified by flash cartridge (ISCO) to give 1-bromo-2-ethyl-3-fluoro-4-iodobenzene (1.2 g).

The mixture of 1-bromo-2-ethyl-3-fluoro-4-iodobenzene (1.0 g, 3.0 mmol), Zn(CN)$_2$ (0.19 g, 1.6 mmol) and Pd(PPh$_3$)$_4$ (0.17 g, 0.15 mmol) in toluene (10 mL) was heated at 70° C. under N$_2$ overnight. The mixture was cooled to r.t. and washed with water and brine. The organic layer was concentrated and purified by flash cartridge (ISCO) to give 4-bromo-3-ethyl-2-fluorobenzonitrile (0.25 g).

To a solution of 4-bromo-3-ethyl-2-fluorobenzonitrile (0.17 g, 1.0 mmol) in CH$_2$Cl$_2$ (10 mL) was added DIBAL (1.1 mL, 1.1 mmol) at −78° C. under N$_2$. The reaction mixture was stirred at −78° C. to 0° C. for 2 h and quenched with 1N HCl. The organic layer was concentrated and purified by flash cartridge (ISCO) to 4-bromo-3-ethyl-2-fluorobenzaldehyde (0.12 g).

A mixture of 4-bromo-3-ethyl-2-fluorobenzaldehyde (0.11 g, 0.5 mmol), 1,1,1,3,3,3-hexafluoro-2-(4-(4,4,5,5-tetramethyl-1,3,2-dioxaborolan-2-yl)phenyl)propan-2-ol (Intermediate 2) (0.15 g), Pd(PPh$_3$)$_4$ (55 mg), and Na$_2$CO$_3$ (2N solution, 0.5 mL) in dioxane (10 mL) was heated at 90° C. under N$_2$ overnight. The mixture was cooled to rt and washed with water followed by brine. The organic layer was concentrated and purified by flash cartridge (ISCO) to give 2-ethyl-3-fluoro-4'-(1,1,1,3,3,3-hexafluoro-2-hydroxypropan-2-yl)-[1,1'-biphenyl]-4-carbaldehyde (48 mg).

Example G: Synthesis of 4'-(1,1,1,3,3,3-hexafluoro-2-hydroxypropan-2-yl)-2-isopropyl-[1,1'-biphenyl]-4-carbaldehyde (Aldehyde Intermediate 9) and 2-(sec-butyl)-4'-(1,1,1,3,3,3-hexafluoro-2-hydroxypropan-2-yl)-[1,1'-biphenyl]-4-carbaldehyde (Aldehyde Intermediate 10)

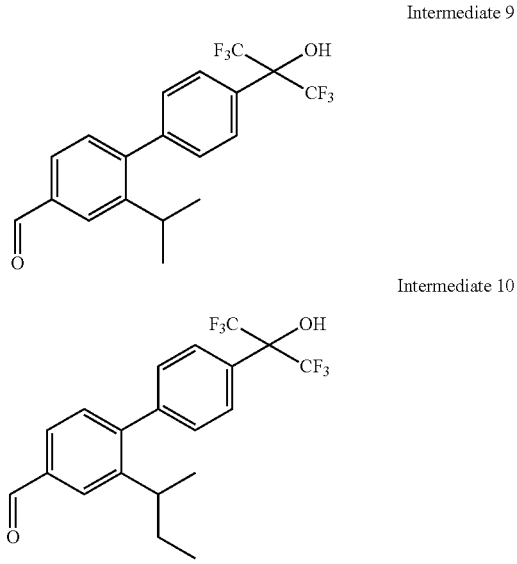

Intermediate 9

Intermediate 10

Step A. To a solution of 2-isopropylphenol (6.5 g, 48 mmol, 1.0 equiv) in 50% aqueous NaOH (30 mL) was added Cu powder (240 mg) and carbon tetrachloride (6.7 mL, 62 mmol, 1.3 equiv). The mixture was heated at reflux for 16 h. Upon cooling, the mixture was acidified to pH 2 by addition of concentrated HCl and was extracted with EtOAc. The organic phase was then extracted with saturated NaHCO$_3$ solution and the aqueous layer was acidified to pH 2 by careful titration with concentrated HCl. The solution was extracted with EtOAc. The organic layer was washed with water, separated and concentrated to dryness to afford 4-hydroxy-3-isopropylbenzoic acid (4 g) as a bright red solid which was used without further purification.

Step B. To a mixture of 4-hydroxy-3-isopropylbenzoic acid (2.0 g, 11 mmol, 1 equiv), triethylamine (3.30 g, 33 mmol, 3 equiv), and N,O-dimethylhydroxylamine hydrochloride (1.08 g, 110 mmol, 10 equiv) in DCM (100 mL) was added HBTU (6.25 g, 1.65 mmol, 1.5 equiv). The mixture was stirred at room temperature overnight. The mixture was washed with saturated NaHCO$_3$ solution, 2N HCl, and water. The organic phase was dried over MgSO$_4$ and concentrated in vacuo to afford 4-hydroxy-3-isopropyl-N-methoxy-N-methylbenzamide (4.5 g) as a pale red solid which was used without further purification.

Step C. To a mixture of 4-hydroxy-3-isopropyl-N-methoxy-N-methylbenzamide (500 mg, 2.2 mmol, 1 equiv) and pyridine (525 µL, 6.6 mmol, 3 equiv) in DCM (30 ml) was added trifluoromethanesulfonic anhydride (0.93 g, 3.3 mmol, 1.5 equiv) dropwise at 0° C. The mixture was stirred at 0° C. for 1 h, and washed with saturated NaHCO$_3$ solution and water. The organic phase was dried over MgSO$_4$, concentrated, and purified on a silica gel column to afford 2-isopropyl-4-(methoxy(methyl)carbamoyl)phenyl trifluoromethanesulfonate (680 mg) as a white solid.

Step D. To a solution of 2-isopropyl-4-(methoxy(methyl)carbamoyl)phenyl trifluoromethanesulfonate (680 mg, 1.9 mmol, 1 equiv) in anhydrous 1,4-dioxane (20 mL) was added bis(pinacolato)diboron (0.63 g, 2.5 mmol, 1.3 equiv), potassium acetate (0.56 g, 5.7 mmol, 3 equiv), and Pd(dppf)$_2$Cl$_2$ (70 mg, 0.095 mmol, 0.05 equiv). The mixture was degassed and then bubbled with N$_2$ for 5 min, and then stirred at 90° C. for 3 h. Upon cooling to room temperature, the mixture was poured into NH$_4$Cl solution and extracted with DCM. The organic phase was dried over MgSO$_4$, concentrated, and purified on a silica gel column to afford 3-isopropyl-N-methoxy-N-methyl-4-(4,4,5,5-tetramethyl-1,3,2-dioxaborolan-2-yl)benzamide (500 mg) as a white solid.

Step E. To a solution of 3-isopropyl-N-methoxy-N-methyl-4-(4,4,5,5-tetramethyl-1,3,2-dioxaborolan-2-yl)benzamide (100 mg, 0.3 mmol, 1 equiv) in anhydrous 1,4-dioxane (2 mL) was added 1,1,1,3,3,3-hexafluoro-2-(4-iodophenyl)propan-2-ol (Intermediate 1) (145 mg, 0.39 mmol, 1.3 equiv), 2 M potassium carbonate solution (0.45 ml, 0.9 mmol, 3 equiv), and Pd(PPh$_3$)$_4$ (17 mg, 0.015 mmol, 0.05 equiv). The mixture was degassed and then bubbled with N$_2$ for 5 min, and then stirred at 90° C. for 3 h. Upon cooling to room temperature, the mixture was poured into NH$_4$Cl solution and extracted with DCM. The organic phase was dried over MgSO$_4$, concentrated, and purified on a silica gel column to afford 3-isopropyl-N-methoxy-N-methyl-4-(4,4,5,5-tetramethyl-1,3,2-dioxaborolan-2-yl)benzamide (100 mg) as a white solid.

Step F. To a solution of 3-isopropyl-N-methoxy-N-methyl-4-(4,4,5,5-tetramethyl-1,3,2-dioxaborolan-2-yl)benzamide (100 mg, 0.22 mmol, 1.0 equiv) in anhydrous THF (2 mL) was added 1.0 M LAH solution in THF (220 µL, 1.0 equiv) at −78° C. The reaction was stirred at −78° C. for 1 h and quenched by adding EtOAc before being warmed to room temperature. The mixture was poured into NH$_4$Cl solution and extracted with DCM. The organic phase was dried over MgSO$_4$, concentrated, and purified on a silica gel column to afford 4'-(1,1,1,3,3,3-hexafluoro-2-hydroxypropan-2-yl)-2-isopropyl-[1,1'-biphenyl]-4-carbaldehyde (Aldehyde Intermediate 9) (90 mg) as a white solid.

Aldehyde Intermediate 10 was prepared using the same method but substituting 2-(sec-butyl)phenol for 2-isopropanol phenol.

Example H: Synthesis of 3,6-difluoro-4'-(1,1,1,3,3,3-hexafluoro-2-hydroxypropan-2-yl)-2-isopropyl-[1,1'-biphenyl]-4-carbaldehyde (Aldehyde Intermediate 11)

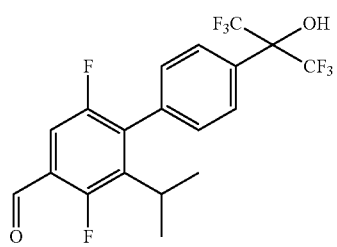 [SMILES: CC(C)c1c(F)c(C=O)cc(F)c1-c1ccc(C(O)(C(F)(F)F)C(F)(F)F)cc1]

Step A. 2,5-difluoro-4-methoxybenzoic acid (500 mg) was treated with BBr$_3$ at room temperature for 24 h. The reaction was worked up with 2N HCl, and purified on a silica gel column to give 2,5-difluoro-4-hydroxybenzoic acid.

Step B. To a mixture of 2,5-difluoro-4-hydroxybenzoic acid (380 mg, 2.18 mmol, 1 equiv), triethylamine (660 mg, 6.6 mmol, 3 equiv) and N,O-dimethylhydroxylamine hydrochloride (2.14 g, 21.8 mmol, 10 equiv) in DCM (20 mL) was added HBTU (1.25 g, 3.27 mmol, 1.5 equiv). The mixture was stirred at room temperature overnight, then washed with saturated NaHCO$_3$ solution, 2N HCl, and water. The organic phase was dried over MgSO$_4$, concentrated, and purified on a silica gel column to afford 2,5-difluoro-4-hydroxy-N-methoxy-N-methylbenzamide (190 mg) as a colorless oil.

Step C. To a solution of 2,5-difluoro-4-hydroxy-N-methoxy-N-methylbenzamide (190 mg, 0.87 mmol, 1 equiv) in acetic acid (4 mL) was added NBS (190 mg, 1.05 mmol, 1.2 equiv) at 0° C. The reaction was warmed to rt and stirred for 2 h. The solvent was removed in high vacuo, the residue was dissolved in EtOAc, washed with water, concentrated, and purified on a silica gel column to afford 3-bromo-2,5-difluoro-4-hydroxy-N-methoxy-N-methylbenzamide (240 mg) as a white solid.

Step D. To a solution of 3-bromo-2,5-difluoro-4-hydroxy-N-methoxy-N-methylbenzamide (240 mg, 0.81 mmol, 1 equiv) in anhydrous 1,4-dioxane (9 mL) was added isopropenylboronic acid pinacol ester (204 mg, 1.22 mmol, 1.5 equiv), 2 M potassium carbonate solution (1.2 mL, 2.4 mmol, 3 equiv), and Pd(PPh$_3$)$_4$ (45 mg, 0.04 mmol, 0.05 equiv). The mixture was degassed and then bubbled with N$_2$ for 5 min, and then stirred at 90° C. overnight. Upon cooling to room temperature, the mixture was poured into NH$_4$Cl solution and extracted with DCM. The organic phase was dried over MgSO$_4$, concentrated, and purified on a silica gel column to afford 2,5-difluoro-4-hydroxy-N-methoxy-N-methyl-3-(prop-1-en-2-yl)benzamide (180 mg) as a white solid.

Step E. To a mixture of 2,5-difluoro-4-hydroxy-N-methoxy-N-methyl-3-(prop-1-en-2-yl)benzamide (180 mg, 0.7 mmol, 1 equiv) and pyridine (0.5 mL) in DCM (50 mL) was added trifluoromethanesulfonic anhydride (0.33 g, 1.05 mmol, 1.5 equiv) dropwise at 0° C. The mixture was stirred at 0° C. for 1 h and washed with saturated NaHCO$_3$ solution and water. The organic phase was dried over MgSO$_4$, concentrated, and purified on a silica gel column to afford 3,6-difluoro-4-(methoxy(methyl)carbamoyl)-2-(prop-1-en-2-yl)phenyl trifluoromethanesulfonate (240 mg) as a pale yellow oil.

Step F. To a solution of 3,6-difluoro-4-(methoxy(methyl)carbamoyl)-2-(prop-1-en-2-yl)phenyl trifluoromethanesulfonate (240 mg, 0.61 mmol, 1 equiv) in anhydrous 1,4-dioxane (10 mL) was added 1,1,1,3,3,3-hexafluoro-2-(4-(4,4,5,5-tetramethyl-1,3,2-dioxaborolan-2-yl)phenyl)propan-2-ol (340 mg, 0.93 mmol, 1.5 equiv), 2 M potassium carbonate solution (1.0 mL, 1.8 mmol, 3 equiv), and Pd(PPh$_3$)$_4$ (35 mg, 0.03 mmol, 0.05 equiv). The mixture was degassed and then bubbled with N$_2$ for 5 min, and then stirred at 90° C. overnight. Upon cooling to room temperature, the mixture was poured into NH$_4$Cl solution and extracted with DCM. The organic phase was dried over MgSO$_4$, concentrated, and purified on a silica gel column to afford 3,6-difluoro-4'-(1,1,1,3,3,3-hexafluoro-2-hydroxypropan-2-yl)-N-methoxy-N-methyl-2-(prop-1-en-2-yl)-[1,1'-biphenyl]-4-carboxamide (140 mg) as a white solid.

Step G. To a solution of 3,6-difluoro-4'-(1,1,1,3,3,3-hexafluoro-2-hydroxypropan-2-yl)-N-methoxy-N-methyl-2-(prop-1-en-2-yl)-[1,1'-biphenyl]-4-carboxamide (140 mg, 0.29 mmol, 1 equiv) in MeOH (10 mL) was added Pd/C (10% wt., 14 mg). The reaction was shaken under H$_2$ (50 psi) environment for 4 h. The mixture was filtered to remove catalyst and concentrated to afford 3,6-difluoro-4'-(1,1,1,3,3,3-hexafluoro-2-hydroxypropan-2-yl)-2-isopropyl-N-methoxy-N-methyl-[1,1'-biphenyl]-4-carboxamide (120 mg) as a white solid.

Step H. To a solution of 3,6-difluoro-4'-(1,1,1,3,3,3-hexafluoro-2-hydroxypropan-2-yl)-2-isopropyl-N-methoxy-N-methyl-[1,1'-biphenyl]-4-carboxamide (120 mg, 0.25 mmol, 1 equiv) in anhydrous THF (2 mL) was added 1.0 M LAH solution in THF (250 µL, 1.0 equiv) at −78° C. The reaction was stirred at −78° C. for 1 h and quenched by adding EtOAc before being warmed to room temperature. The mixture was poured into NH$_4$Cl solution and extracted with DCM. The organic phase was dried over MgSO$_4$, concentrated, and purified on a silica gel column to afford 3,6-difluoro-4'-(1,1,1,3,3,3-hexafluoro-2-hydroxypropan-2-yl)-2-isopropyl-[1,1'-biphenyl]-4-carbaldehyde (Aldehyde Intermediate 11) (100 mg) as a white solid.

Synthesis of 3,5-difluoro-4'-(1,1,1,3,3,3-hexafluoro-2-hydroxypropan-2-yl)-2-isopropyl-[1,1'-biphenyl]-4-carbaldehyde (Aldehyde Intermediate 12)

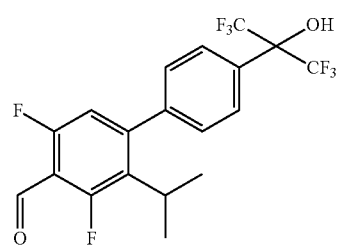 [SMILES: CC(C)c1c(-c2ccc(C(O)(C(F)(F)F)C(F)(F)F)cc2)cc(F)c(C=O)c1F]

Aldehyde Intermediate 12 was prepared using the above methods by substituting 2,6-difluoro-4-hydroxybenzoic acid for 2,5-difluoro-4-hydroxybenzoic acid.

Example I: Synthesis of 2-(tert-butyl)-4'-(1,1,1,3,3,3-hexafluoro-2-hydroxypropan-2-yl)-[1,1'-biphenyl]-4-carbaldehyde (Aldehyde Intermediate 13)

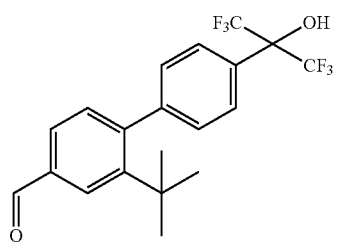 [SMILES: CC(C)(C)c1cc(C=O)ccc1-c1ccc(C(O)(C(F)(F)F)C(F)(F)F)cc1]

Step A. To a mixture of 3-(tert-butyl)-4-hydroxybenzoic acid (300 mg, 1 equiv), TEA (470 mg, 3 equiv) and N,O-dimethylhydroxylamine hydrochloride (1.51 g, 10 equiv) in DCM (20 mL) was added HBTU (0.88 g, 1.5 equiv). The mixture was stirred at room temperature overnight. The mixture was washed with saturated NaHCO$_3$ solution, 2N HCl, and water. The organic phase was dried over MgSO$_4$, concentrated, and purified on a silica gel column to afford 3-(tert-butyl)-4-hydroxy-N-methoxy-N-methylbenzamide (202 mg, yield 55%) as a colorless oil.

Step B. To a mixture of 3-(tert-butyl)-4-hydroxy-N-methoxy-N-methylbenzamide (202 mg, 1 equiv) and pyridine (0.6 mL) in DCM (50 mL) was added trifluoromethanesulfonic anhydride (0.36 g, 1.5 equiv) dropwise at 0° C. The mixture was stirred at 0° C. for 1 h, and washed with saturated NaHCO$_3$ solution and water. The organic phase was dried over MgSO$_4$, concentrated, and purified on a silica gel column to afford 2-(tert-butyl)-4-(methoxy(methyl)carbamoyl)phenyl trifluoromethanesulfonate (220 mg) as a pale yellow oil.

Step C. To a solution of 2-(tert-butyl)-4-(methoxy(methyl)carbamoyl)phenyl trifluoromethanesulfonate (240 mg, 1 equiv) in anhydrous 1,4-dioxane (10 mL) was added 1,1,1,3,3,3-hexafluoro-2-(4-(4,4,5,5-tetramethyl-1,3,2-dioxaborolan-2-yl)phenyl)propan-2-ol (330 mg, 1.5 equiv), 2 M potassium carbonate solution (1.1 mL, 3 equiv), and Pd(PPh$_3$)$_4$ (38 mg, 0.05 equiv). The mixture was degassed and then bubbled with N$_2$ for 5 min, and then stirred at 90° C. overnight. Upon cooling to room temperature, the mixture was poured into NH$_4$Cl solution and extracted with DCM. The organic phase was dried over MgSO$_4$, concentrated, and purified on a silica gel column to afford 2-(tert-butyl)-4'-(1,1,1,3,3,3-hexafluoro-2-hydroxypropan-2-yl)-N-methoxy-N-methyl-[1,1'-biphenyl]-4-carboxamide (183 mg, yield 75%) as a white solid.

Step D. To a solution of 2-(tert-butyl)-4'-(1,1,1,3,3,3-hexafluoro-2-hydroxypropan-2-yl)-N-methoxy-N-methyl-[1,1'-biphenyl]-4-carboxamide (183 mg, 1.0 equiv) in anhydrous THF (2 mL) was added 1.0 M LAH solution in THF (450 μL, 1.0 equiv) at −78° C. The reaction was stirred at −78° C. for 1 h and quenched by adding EtOAc before being warmed to room temperature. The mixture was poured into NH$_4$Cl solution and extracted with DCM. The organic phase was dried over MgSO$_4$, concentrated, and purified on a silica gel column to afford 2-(tert-butyl)-4'-(1,1,1,3,3,3-hexafluoro-2-hydroxypropan-2-yl)-[1,1'-biphenyl]-4-carbaldehyde (120 mg) as a white solid.

Example J: Synthesis of 4'-(1,1,1,3,3,3-hexafluoro-2-hydroxypropan-2-yl)-2-methyl-[1,1'-biphenyl]-4-carbaldehyde (Aldehyde Intermediate 14), 2-chloro-4'-(1,1,1,3,3,3-hexafluoro-2-hydroxypropan-2-yl)-[1,1'-biphenyl]-4-carbaldehyde (Aldehyde Intermediate 15) and 4'-(1,1,1,3,3,3-hexafluoro-2-hydroxypropan-2-yl)-2-(trifluoromethyl)-[1,1'-biphenyl]-4-carbaldehyde (Aldehyde Intermediate 16)

Intermediate 14

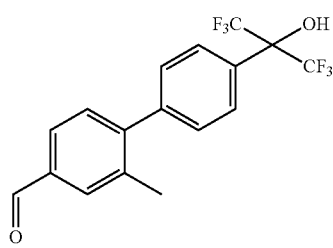

Intermediate 15

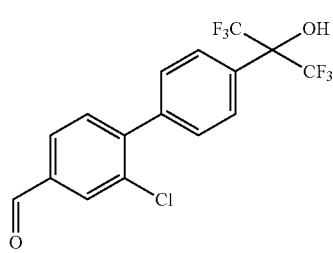

Intermediate 16

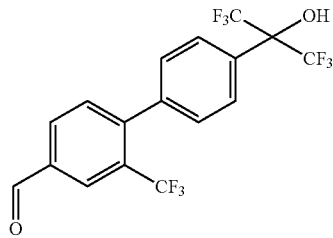

(4-Formyl-2-methylphenyl)boronic acid (6.65 g, 1.0 equiv), 1,1,1,3,3,3-hexafluoro-2-(4-iodophenyl)propan-2-ol (3.2 g, 1.2 equiv), Pd(PPh$_3$)$_4$ (2.05 g, 0.1 equiv) and K$_2$CO$_3$ (7.4 g, 3.0 equiv) were combined in dioxane (150 mL) and water (40 mL). The mixture was flushed with N$_2$ for 5 min, and then heated at 80° C. for 8 h under N$_2$. The reaction was extracted with EtOAc (2×200 mL). The combined organic phase was washed with 1N HCl and brine. The crude mixture was purified on a silica gel column to afford 4'-(1,1,1,3,3,3-hexafluoro-2-hydroxypropan-2-yl)-2-methyl-[1,1'-biphenyl]-4-carbaldehyde (4.6 g, yield 73%) as a white solid.

Aldehyde Intermediate 15 was prepared using the same method, but substituting (2-chloro-4-formylphenyl)boronic acid for (4-formyl-2-methylphenyl)boronic acid.

Aldehyde Intermediate 16 was prepared using the same method, but substituting (4-formyl-2-(trifluoromethyl)phenyl)boronic acid for (4-formyl-2-methylphenyl)boronic acid.

Example K: Synthesis of 2-bromo-4'-(1,1,1,3,3,3-hexafluoro-2-hydroxypropan-2-yl)-[1,1'-biphenyl]-4-carbaldehyde (Aldehyde Intermediate 17)

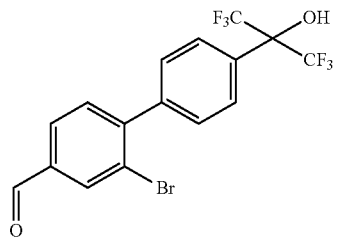 [SMILES: O=Cc1ccc(-c2ccc(C(O)(C(F)(F)F)C(F)(F)F)cc2)c(Br)c1]

Step A: Methyl 3-amino-4-(4,4,5,5-tetramethyl-1,3,2-dioxaborolan-2-yl)benzoate (1.0 g, 1.0 equiv), 1,1,1,3,3,3-hexafluoro-2-(4-iodophenyl)propan-2-ol (1.6 g, 1.2 equiv), Pd(PPh$_3$)$_4$ (0.42 g, 0.1 equiv) and K$_2$CO$_3$ (1.5 g, 3.0 equiv) were combined in dioxane (30 mL) and water (10 mL). The mixture was flushed with N$_2$ for 5 mins, and then heated at 80° C. for 8 h under N$_2$. The reaction was extracted with EtOAc (2×60 mL). The combined organic phase was washed with 1N HCl and brine. The crude mixture was purified on a silica gel column to afford methyl 2-amino-4'-(1,1,1,3,3,3-hexafluoro-2-hydroxypropan-2-yl)-[1,1'-biphenyl]-4-carboxylate (1.16 g, yield 82%).

Step B: To a solution of methyl 2-amino-4'-(1,1,1,3,3,3-hexafluoro-2-hydroxypropan-2-yl)-[1,1'-biphenyl]-4-carboxylate aniline (1.16 g, 1.0 equiv) in DMF (15 mL) was added a solution of NaNO$_2$ (0.23 g, 1.1 equiv) in water (10 mL). The mixture was cooled to 0° C. for 15 mins. 6 N H$_2$SO$_4$ (9 mL, 3.0 equiv) was added dropwise to the reaction mixture for over 15 min at 0° C. The resulting mixture was stirred at 0° C. for 1 h. CuBr (0.64 g, 1.5 equiv) was added. The reaction mixture was stirred at 0° C. for 1 h and then rt overnight. The reaction was diluted with water (~500 mL) and extracted with EtOAc/Hexane (2:1, 3×150 mL). The combined organic phase was washed with NaHSO$_3$, water, and brine. The crude mixture was purified on a silica gel column to afford methyl 2-bromo-4'-(1,1,1,3,3,3-hexafluoro-2-hydroxypropan-2-yl)-[1,1'-biphenyl]-4-carboxylate (650 mg, yield 48%).

Step C: Methyl 2-bromo-4'-(1,1,1,3,3,3-hexafluoro-2-hydroxypropan-2-yl)-[1,1'-biphenyl]-4-carboxylate was converted to corresponding acid by treating with 2N LiOH in MeOH. The acid was coupled with N,O-dimethylhydroxylamine hydrochloride to afford 2-bromo-4'-(1,1,1,3,3,3-hexafluoro-2-hydroxypropan-2-yl)-N-methoxy-N-methyl-[1,1'-biphenyl]-4-carboxamide. 2-Bromo-4'-(1,1,1,3,3,3-hexafluoro-2-hydroxypropan-2-yl)-N-methoxy-N-methyl-[1,1'-biphenyl]-4-carboxamide was converted to 2-bromo-4'-(1,1,1,3,3,3-hexafluoro-2-hydroxypropan-2-yl)-[1,1'-biphenyl]-4-carbaldehyde with LAH reduction at −70° C.

Example L: Synthesis of 4'-(1,1,1,3,3,3-hexafluoro-2-hydroxypropan-2-yl)-2-(prop-1-en-2-yl)-[1,1'-biphenyl]-4-carbaldehyde (Aldehyde Intermediate 18)

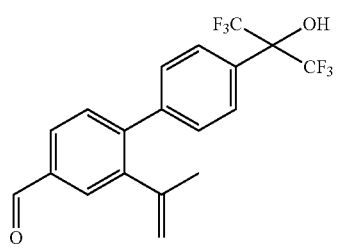 [SMILES: C=C(C)c1cc(C=O)ccc1-c1ccc(C(O)(C(F)(F)F)C(F)(F)F)cc1]

Suzuki coupling between 2-bromo-4'-(1,1,1,3,3,3-hexafluoro-2-hydroxypropan-2-yl)-N-methoxy-N-methyl-[1,1'-biphenyl]-4-carboxamide intermediate from Step C of Example K and 4,4,5,5-tetramethyl-2-(prop-1-en-2-yl)-1,3,2-dioxaborolane under reactions conditions described in Step A of Example K (except with heating to 90° C. overnight) afforded 4'-(1,1,1,3,3,3-hexafluoro-2-hydroxypropan-2-yl)-N-methoxy-N-methyl-2-(prop-1-en-2-yl)-[1,1'-biphenyl]-4-carboxamide which was converted to the corresponding aldehyde, 4'-(1,1,1,3,3,3-hexafluoro-2-hydroxypropan-2-yl)-2-(prop-1-en-2-yl)-[1,1'-biphenyl]-4-carbaldehyde, with LAH reduction at −70° C.

Example M: Synthesis of 2-cyclopropyl-4'-(1,1,1,3,3,3-hexafluoro-2-hydroxypropan-2-yl)-[1,1'-biphenyl]-4-carbaldehyde (Aldehyde Intermediate 19)

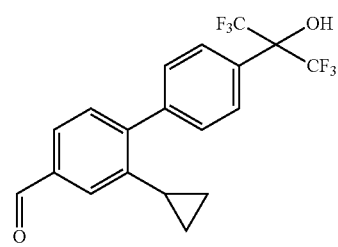 [SMILES: O=Cc1ccc(-c2ccc(C(O)(C(F)(F)F)C(F)(F)F)cc2)c(C2CC2)c1]

Suzuki coupling between 2-bromo-4'-(1,1,1,3,3,3-hexafluoro-2-hydroxypropan-2-yl)-N-methoxy-N-methyl-[1,1'-biphenyl]-4-carboxamide intermediate from Step C of Example K and cyclopropylboronic acid under reactions conditions described in Step A of Example K (except with heating to 90° C. overnight) afforded 2-cyclopropyl-4'-(1,1,1,3,3,3-hexafluoro-2-hydroxypropan-2-yl)-N-methoxy-N-methyl-[1,1'-biphenyl]-4-carboxamide which was converted to the corresponding aldehyde, 2-cyclopropyl-4'-(1,1,1,3,3,3-hexafluoro-2-hydroxypropan-2-yl)-[1,1'-biphenyl]-4-carbaldehyde, with LAH reduction at −70° C.

Example N: Synthesis of 4'-(1,1,1,3,3,3-hexafluoro-2-hydroxypropan-2-yl)-2-isopropyl-2'-methyl-[1,1'-biphenyl]-4-carbaldehyde (Aldehyde Intermediate 20)

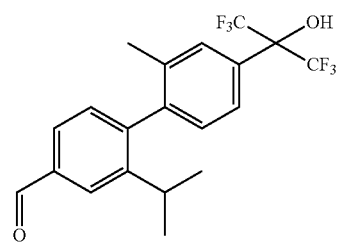 [SMILES: Cc1cc(C(O)(C(F)(F)F)C(F)(F)F)ccc1-c1ccc(C=O)cc1C(C)C]

Standard Suzuki coupling between 3-isopropyl-N-methoxy-N-methyl-4-(4,4,5,5-tetramethyl-1,3,2-dioxaborolan-2-yl)benzamide, the intermediate from Example F Step E, and Intermediate 4 afforded 4'-(1,1,1,3,3,3-hexafluoro-2-hydroxypropan-2-yl)-2-isopropyl-N-methoxy-N,2'-dimethyl-[1,1'-biphenyl]-4-carboxamide which was concerted to corresponding aldehyde with LAH reduction in anhydrous THF at −78° C.

Example O: Synthesis of 2-ethyl-2'-fluoro-4'-(1,1,1,3,3,3-hexafluoro-2-hydroxypropan-2-yl)-[1,1'-biphenyl]-4-carbaldehyde (Aldehyde Intermediate 21) and 2-ethyl-4'-(1,1,1,3,3,3-hexafluoro-2-hydroxypropan-2-yl)-2'-methyl-[1,1'-biphenyl]-4-carbaldehyde (Aldehyde Intermediate 22)

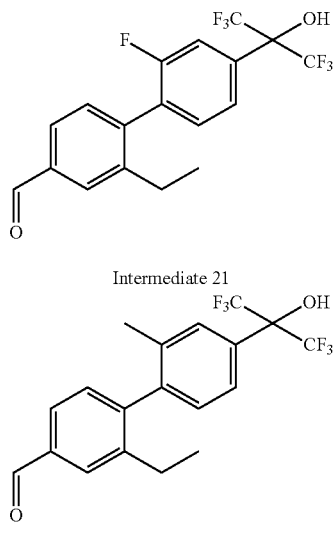

Intermediate 21

Intermediate 22

Standard Suzuki coupling between 3-ethyl-N-methoxy-N-methyl-4-(4,4,5,5-tetramethyl-1,3,2-dioxaborolan-2-yl)benzamide from Step B of Example C and 2-(4-bromo-3-fluorophenyl)-1,1,1,3,3,3-hexafluoropropan-2-ol (Intermediate 3) afforded 2-ethyl-2'-fluoro-4'-(1,1,1,3,3,3-hexafluoro-2-hydroxypropan-2-yl)-N-methoxy-N-methyl-[1,1'-biphenyl]-4-carboxamide which was converted to the corresponding aldehyde 2-ethyl-2'-fluoro-4'-(1,1,1,3,3,3-hexafluoro-2-hydroxypropan-2-yl)-[1,1'-biphenyl]-4-carbaldehyde (Aldehyde Intermediate 21) with LAH reduction in anhydrous THE at −70° C.

Standard Suzuki coupling between 3-ethyl-N-methoxy-N-methyl-4-(4,4,5,5-tetramethyl-1,3,2-dioxaborolan-2-yl)benzamide from Step B of Example C and 2-(4-bromo-3-methylphenyl)-1,1,1,3,3,3-hexafluoropropan-2-ol (Intermediate 4) afforded 2-ethyl-4'-(1,1,1,3,3,3-hexafluoro-2-hydroxypropan-2-yl)-2'-methyl-[1,1'-biphenyl]-4-carbaldehyde which was converted to the corresponding aldehyde 2-ethyl-4'-(1,1,1,3,3,3-hexafluoro-2-hydroxypropan-2-yl)-2'-methyl-[1,1'-biphenyl]-4-carbaldehyde (Aldehyde Intermediate 22) with LAH reduction in anhydrous THE at −70° C.

Example P: Synthesis of 2-(pyridin-4-ylmethyl)-2,6-diazaspiro[3.3]heptane TFA (Amine Intermediate 1)

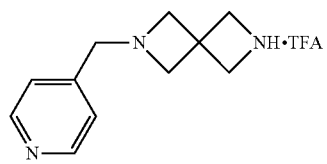 [SMILES: c1cc(CN2CC3(CNC3)C2)ccn1]

Commercially available oxalate (100 mg, 1.2 equiv) and tert-butyl 2,6-diazaspiro[3.3]heptane-2-carboxylate was suspended into 1,2-DCE (15 mL), to which Et₃N (42 mg, 2.0 equiv) was added and stirred at rt for 30 min. Isonicotinaldehyde (40 mg, 1.0 equiv) was added followed by acetic acid (30 μL). The mixture was stirred at rt for 3 h and NaBH(OAc)₃ (240 mg, 3.0 equiv) was added to the solution. The resulting mixture was stirred at rt overnight. The reaction was quenched with MeOH and diluted with saturated NaHCO₃, then extracted with 2×20 mL DCM. The crude mixture was purified on a silica gel column to afford tert-butyl 6-(pyridin-4-ylmethyl)-2,6-diazaspiro[3.3]heptane-2-carboxylate (70 mg, yield 65%). The carboxylate was treated with TFA (3 mL) in DCM (80% v/v) to afford 2-(pyridin-4-ylmethyl)-2,6-diazaspiro[3.3]heptane which was used without purification.

Example Q: Synthesis of 2-(methylsulfonyl)-2,6-diazaspiro[3.3]heptane TFA (Amine Intermediate 2), 2-(ethylsulfonyl)-2,6-diazaspiro[3.3]heptane TFA (Amine Intermediate 3), 2-(cyclopropylsulfonyl)-2,6-diazaspiro[3.3]heptane TFA (Amine Intermediate 4), 2-(propylsulfonyl)-2,6-diazaspiro[3.3]heptane TFA (Amine Intermediate 5) and 2-(isobutylsulfonyl)-2,6-diazaspiro[3.3]heptane TFA (Amine Intermediate 6)

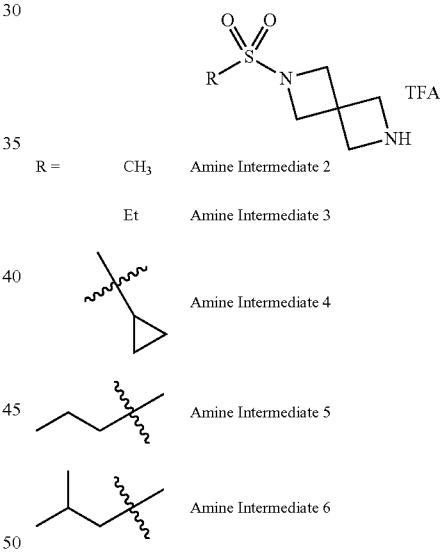

| R = | | |
|---|---|---|
| | CH₃ | Amine Intermediate 2 |
| | Et | Amine Intermediate 3 |
| | cyclopropyl | Amine Intermediate 4 |
| | propyl | Amine Intermediate 5 |
| | isobutyl | Amine Intermediate 6 | tert-Butyl 2,6-diazaspiro[3.3]heptane-2-carboxylate as oxalate salt (5.0 g, 1.0 equiv) was suspended in CH₂Cl₂ (150 mL). To the mixture was added saturated NaHCO₃ (50 mL) at 0° C. The mixture was stirred at 0° C. for 10 min and a solution of MsCl (4.7 g, 2.0 equiv) in CH₂Cl₂ (10 mL) was added dropwise. The resulting mixture was stirred at 0° C. for 1 h and then at rt overnight. The organic phase was separated and washed with brine, then concentrated in vacuum to afford tert-butyl 6-(methylsulfonyl)-2,6-diazaspiro[3.3]heptane-2-carboxylate as a white solid (5.0 g, yield 88%) which was used without further purification.

tert-Butyl 6-(methylsulfonyl)-2,6-diazaspiro[3.3]heptane-2-carboxylate was treated with TFA in DCM (80% v/v) to afford 2-(methylsulfonyl)-2,6-diazaspiro[3.3]heptane (Amine Intermediate 2), which was used without purification.

2-(ethylsulfonyl)-2,6-diazaspiro[3.3]heptane (Amine Intermediate 3) was synthesized using the same methods using ethanesulfonyl chloride in place of MsCl.

2-(cyclopropylsulfonyl)-2,6-diazaspiro[3.3]heptane (Amine Intermediate 4) was synthesized using the same methods using cyclopropanesulfonyl chloride in place of MsCl.

2-(propylsulfonyl)-2,6-diazaspiro[3.3]heptane (Amine Intermediate 5) was synthesized using the same methods using propane-1-sulfonyl chloride in place of MsCl.

2-(isobutylsulfonyl)-2,6-diazaspiro[3.3]heptane (Amine Intermediate 6) was synthesized using the same methods using 2-methylpropane-1-sulfonyl chloride in place of MsCl.

Example R: Synthesis of 1-(2,6-diazaspiro[3.3]heptan-2-yl)ethan-1-one TFA (Amine Intermediate 7) and methyl 2,6-diazaspiro[3.3]heptane-2-carboxylate TFA (Amine Intermediate 8)

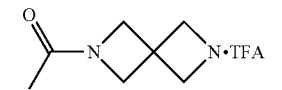

Amine Intermediate 7

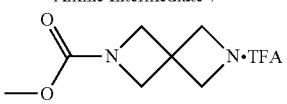

Amine Intermediate 8 tert-Butyl 2,6-diazaspiro[3.3]heptane-2-carboxylate as oxalate salt (100 mg, 1.0 equiv) was suspended in CH$_2$Cl$_2$ (15 mL). To the mixture was added saturated NaHCO$_3$ (5 mL) at 0° C. The mixture was stirred at 0° C. for 10 min, a solution of acetyl chloride (84 mg, 5.0 equiv) in CH$_2$Cl$_2$ (2 mL) was added dropwise. The resulting mixture was stirred at 0° C. for 1 h. The organic phase was separated and washed with brine, then concentrated in vacuum to afford tert-butyl 6-acetyl-2,6-diazaspiro[3.3]heptane-2-carboxylate as a white solid (39 mg, yield 75%) which was used without further purification.

tert-Butyl 6-acetyl-2,6-diazaspiro[3.3]heptane-2-carboxylate was treated with TFA in DCM (80% v/v) to afford 1-(2,6-diazaspiro[3.3]heptan-2-yl)ethan-1-one (Amine Intermediate 7) which was used without purification.

Methyl 2,6-diazaspiro[3.3]heptane-2-carboxylate (Amine Intermediate 8) was synthesized using the same method using methyl chloroformate in place of acetyl chloride.

Example S: Synthesis of 2-thia-6-azaspiro[3.3]heptane 2-oxide (Amine Intermediate 9) and 6-thia-2-azaspiro[3.4]octane 6-oxide (Amine Intermediate 10)

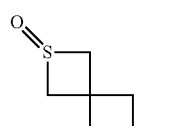

Amine Intermediate 9

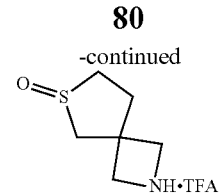

Amine Intermediate 10

To a solution of 2-thia-6-azaspiro[3.3]heptane (100 mg, 1.0 equiv) in DCM (8 mL) was added Et$_3$N (3.0 equiv) and (Boc)$_2$O (1.5 equiv). The resulting mixture was stirred at rt overnight. The mixture was dried in vacuo and purified on a silica gel column to afford tert-butyl 2-thia-6-azaspiro[3.3]heptane-6-carboxylate (170 mg, yield 91%).

tert-Butyl 2-thia-6-azaspiro[3.3]heptane-6-carboxylate (60 mg, 1.0 equiv) was dissolved in DCM (5 mL) and cooled to −30° C. mCPBA (64 mg, 72%, 0.95 equiv) was added. The mixture was stirred at −30° C. for 10 min, then at 0° C. for 1 h. The reaction mixture was diluted with DCM (20 mL) and washed with 3×10 mL saturated NaHCO$_3$. The crude mixture was purified on a silica gel column to afford tert-butyl 2-thia-6-azaspiro[3.3]heptane-6-carboxylate 2-oxide (48 mg, yield 74%). tert-Butyl 2-thia-6-azaspiro[3.3]heptane-6-carboxylate 2-oxide was treated with TFA in DCM (80% v/v) to afford 2-thia-6-azaspiro[3.3]heptane 2-oxide (Amine Intermediate 9) which was used without purification.

Amine Intermediate 10 was synthesized using the same methods, using 6-thia-2-azaspiro[3.4]octane in place of 2-thia-6-azaspiro[3.3]heptane.

Example T: Synthesis of 2-thia-6-azaspiro[3.3]heptane 2,2-dioxide TFA (Amine Intermediate 11) and 6-thia-2-azaspiro[3.4]octane 6,6-dioxide TFA (Amine Intermediate 12)

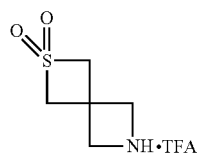

Amine Intermediate 11

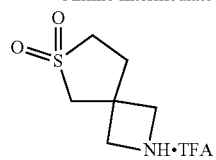

Amine Intermediate 12 tert-Butyl 2-thia-6-azaspiro[3.3]heptane-6-carboxylate (60 mg, 1.0 equiv) was dissolved in DCM (5 mL) and to cooled to 0° C. mCPBA (166 mg, 72%, 2.5 equiv) was added. The mixture was stirred at 0° C. for 10 min, and then at rt for 1 h. The reaction mixture was diluted with DCM (20 mL) and washed with 3×10 mL saturated NaHCO$_3$. The crude mixture was purified on a silica gel column to afford tert-butyl 2-thia-6-azaspiro[3.3]heptane-6-carboxylate 2,2-dioxide (56 mg, yield 80%). tert-Butyl 2-thia-6-azaspiro[3.3]heptane-6-carboxylate 2,2-dioxide was treated with TFA in DCM (80% v/v) to afford 2-thia-6-azaspiro[3.3] heptane 2,2-dioxide TFA salt (Amine Intermediate 11) which was used without purification.

Amine Intermediate 12 was synthesized using the same methods using tert-butyl 6-thia-2-azaspiro[3.4]octane-2-carboxylate in place of tert-butyl 2-thia-6-azaspiro[3.3]heptane-6-carboxylate.

Example U: Synthesis of N-(azetidin-3-ylmethyl)methanesulfonamide TFA (Amine Intermediate 13)

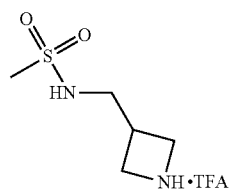

Step A. tert-Butyl 3-(aminomethyl)azetidine-1-carboxylate (300 mg, 1.0 equiv) and pyridine (1 mL) were combined in DCM (20 mL) at 0° C. MsCl (1.1 equiv) was added dropwise. The mixture was stirred at 0° C. for 3 h. The reaction mixture was diluted with DCM (30 mL), washed with 3×30 mL 1N HCl, water, and brine to afford tert-butyl 3-(methylsulfonamidomethyl)azetidine-1-carboxylate (390 mg, yield 91%) which was used without further purification.

Step B. tert-Butyl 3-(methylsulfonamidomethyl)azetidine-1-carboxylate was treated with TFA in DCM (80% v/v) to afford N-(azetidin-3-ylmethyl)methanesulfonamide TFA (Amine Intermediate 13) which was used without purification.

Example V: Synthesis of N-(azetidin-3-ylmethyl)-N-methylmethanesulfonamide TFA (Amine Intermediate 14)

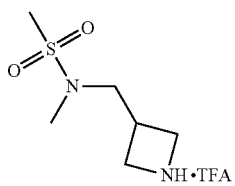

To a solution of tert-butyl 3-(methylsulfonamidomethyl)azetidine-1-carboxylate from Step A of Example U (100 mg, 1.0 equiv) in dry DMF (5 mL) was added NaH (60%, 23 mg, 1.5 equiv). The mixture was stirred at rt for 30 min, and then cooled to 0° C. CH$_3$I (81 mg, 1.5 equiv) was added. The resulting mixture was stirred at rt for 1 h. The reaction mixture was diluted with ethyl acetate (20 mL) and hexane (20 mL). The mixture was washed with 3×30 mL water and brine. The crude mixture was purified on a silica gel column to afford tert-butyl 3-((N-methylmethylsulfonamido)methyl)azetidine-1-carboxylate (72 mg, yield 68%).

tert-Butyl 3-((N-methylmethylsulfonamido)methyl)azetidine-1-carboxylate was treated with TFA in DCM (80% v/v) to afford Amine Intermediate 14 which was used without purification.

Example W: Synthesis of 2-(methylsulfonyl)-2,6-diazaspiro[3.4]octane TFA (Amine Intermediate 15)

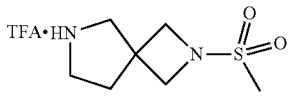

Commercially available tert-butyl 2,6-diazaspiro[3.4]octane-6-carboxylate was treated with MsCl in the presence of TEA to afford tert-butyl 2-(methylsulfonyl)-2,6-diazaspiro[3.4]octane-6-carboxylate which was next treated with TFA in DCM (80% v/v) to afford Amine Intermediate 15 which was used without purification.

Example X: Synthesis of 7-(methylsulfonyl)-2,7-diazaspiro[3.5]nonane TFA (Amine Intermediate 16)

Commercially available tert-butyl 2,7-diazaspiro[3.5]nonane-2-carboxylate was treated with MsCl in the presence of TEA to afford tert-butyl 7-(methylsulfonyl)-2,7-diazaspiro[3.5]nonane-2-carboxylate which was then treated with TFA in DCM (80% v/v) to afford Amine Intermediate 16 as a TFA salt which was used without purification.

Example Y: Synthesis of 6-(methylsulfonyl)-2,6-diazaspiro[3.5]nonane TFA (Amine Intermediate 17)

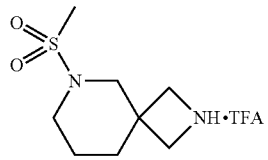

Commercially available tert-butyl 2,6-diazaspiro[3.5]nonane-2-carboxylate was treated with MsCl in the presence of TEA to afford tert-butyl 6-(methylsulfonyl)-2,6-diazaspiro[3.5]nonane-2-carboxylate which was next treated with TFA in DCM (80% v/v) to afford Amine Intermediate 17 as a TFA salt which was used without purification.

Example Z: Synthesis of 2-(methylsulfonyl)-2,7-diazaspiro[4.4]nonane TFA (Amine Intermediate 19)

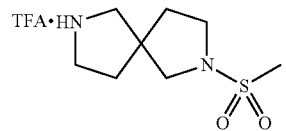

Commercially available tert-buty 2,7-diazaspiro[4.4]nonane-2-carboxylate was treated with MsCl in the presence of TEA to afford tert-butyl 7-(methylsulfonyl)-2,7-diazaspiro[4.4]nonane-2-carboxylate which was next treated with TFA in DCM (80% v/v) to afford Amine Intermediate 19 as a TFA salt which was used without purification.

Example AA: Synthesis of 6-(methylsulfonyl)-2-azaspiro[3.3]heptane TFA (Amine Intermediate 20)

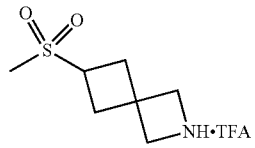

Commercially available tert-butyl 6-hydroxy-2-azaspiro[3.3]heptane-2-carboxylate (250 mg, 1.0 equiv), TEA (360 mg, 3.0 equiv) and DMAP (10 mg) were combined in DCM (25 mL) at 0° C. MsCl (162 mg, 1.2 equiv) was added dropwise. The mixture was stirred at 0° C. for 3 h. The reaction mixture was diluted with DCM (30 mL) and then washed with 1N HCl, water, and brine to afford tert-butyl 6-((methylsulfonyl)oxy)-2-azaspiro[3.3]heptane-2-carboxylate (324 mg, yield 95%) which was used without further purification.

tert-Butyl 6-((methylsulfonyl)oxy)-2-azaspiro[3.3]heptane-2-carboxylate (324 mg, 1.0 equiv) and NaSMe (160 mg, 2.0 equiv) were combined in DMF (15 mL). The mixture was heated at 60° C. for 4 h. The reaction mixture was diluted with ethyl acetate (30 mL) and hexane (30 mL), and then washed with 3×40 mL water and brine. The crude mixture was purified on a silica gel column to afford tert-butyl 6-(methylthio)-2-azaspiro[3.3]heptane-2-carboxylate (144 mg, yield 53%).

tert-Butyl 6-(methylthio)-2-azaspiro[3.3]heptane-2-carboxylate (144 mg, 1.0 equiv) was dissolved in DCM (10 mL) and cooled with ice-water. m-CPBA (355 mg, 2.5 equiv) was added. The resulting mixture was stirred at rt for 1 h. The mixture was diluted with DCM (20 mL) and washed with 3×30 mL saturated $NaHCO_3$. The crude mixture was purified on a silica gel column to afford tert-butyl 6-(methylsulfonyl)-2-azaspiro[3.3]heptane-2-carboxylate (98 mg, yield 60%).

tert-Butyl 6-(methylsulfonyl)-2-azaspiro[3.3]heptane-2-carboxylate was treated with TFA in DCM (80% v/v) to afford 6-(methylsulfonyl)-2-azaspiro[3.3]heptane TFA (Amine Intermediate 20) which was used without purification.

Example BB: Synthesis of 4-((methylsulfonyl)methyl)piperidine TFA (Amine Intermediate 21) and 4-(2-(methylsulfonyl)ethyl)piperidine TFA (Amine Intermediate 22)

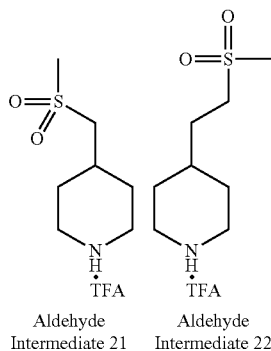

Aldehyde Intermediate 21    Aldehyde Intermediate 22

Amine Intermediate 21 was synthesized using the methods described in Example AA, using commercially available tert-butyl 4-hydroxypiperidine-1-carboxylate in place of tert-butyl 6-hydroxy-2-azaspiro[3.3]heptane-2-carboxylate.

Amine Intermediate 22 was synthesized using the methods described in Example AA, using commercially available tert-butyl 4-(2-hydroxyethyl)piperidine-1-carboxylate in place of tert-butyl 6-hydroxy-2-azaspiro[3.3]heptane-2-carboxylate.

Example CC: Synthesis of 2,3-difluoro-4'-(1,1,1,3,3,3-hexafluoro-2-hydroxypropan-2-yl)-6-isopropyl-[1,1'-biphenyl]-4-carbaldehyde (Aldehyde Intermediate 23) and 2-fluoro-4'-(1,1,1,3,3,3-hexafluoro-2-hydroxypropan-2-yl)-6-isopropyl-[1,1'-biphenyl]-4-carbaldehyde (Aldehyde Intermediate 24)

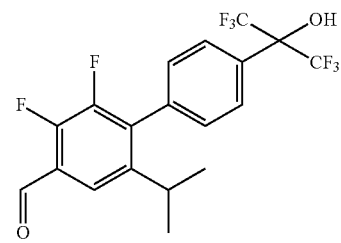

Aldehyde Intermediate 23

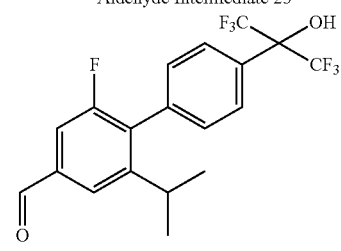

Aldehyde Intermediate 24

Aldehyde Intermediate 23 was prepared using the methods described in Example H, but substituting 2,3-difluoro-4-hydroxybenzoic acid for 2,5-difluoro-4-hydroxybenzoic acid in Step B.

Aldehyde Intermediate 23 was prepared using the methods described in Example H, but substituting 3-fluoro-4-hydroxybenzoic acid for 2,5-difluoro-4-hydroxybenzoic acid in Step B.

Example DD: Synthesis of 4-ethyl-5-(4-(1,1,1,3,3,3-hexafluoro-2-hydroxypropan-2-yl)phenyl)picolinaldehyde (Aldehyde Intermediate 25)

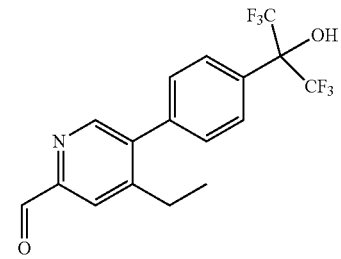 [SMILES: CCc1cc(C=O)ncc1-c1ccc(C(O)(C(F)(F)F)C(F)(F)F)cc1]

Step A. To a solution of 4-ethylpyridin-2-amine (1 g, 8.2 mmol, 1 equiv) in DCM (30 mL) was added NBS (1.45 g, 8.2 mmol, 1 equiv) at −40° C. The reaction was stirring at −40° C. for 30 min. The reaction was quenched with 50 mL water and extracted with DCM. The organic phase was separated and concentrated. The residue was purified on a silica gel column (hexane/ethyl acetate) to afford 5-bromo-4-ethylpyridin-2-amine (1.3 g) as a white solid.

Step B. To solution of 5-bromo-4-ethylpyridin-2-amine (1.0 g, 5.0 mmol, 1.0 equiv), NaNO$_2$ (860 mg, 12.5 mmol, 2.5 equiv) in 40% HBr solution (30 mL) was added Br$_2$ (1.8 g, 2.0 equiv) at 0° C. The mixture was then heated to 70° C. for 2 h. The reaction mixture was poured into DCM (100 mL) and water (100 mL). The organic phase was washed with water and saturated NaHCO$_3$. The crude product was purified on a silica gel column (hexane/ethyl acetate) to afford 2,5-dibromo-4-ethylpyridine (1.1 g) as a white solid.

Step C. To a solution of 2,5-dibromo-4-ethylpyridine (1 g, 3.8 mmol, 1 equiv) in DMF (25 mL) was added CuCN (340 mg, 3.8 mmol, 1 equiv) and NaCN (190 mg, 3.8 mmol, 1 equiv). The mixture was stirred at 150° C. for 5 h. After cooling to rt, the reaction mixture was diluted with EtOAc/hexane (8:1, 100 mL) and washed with water, saturated NaHCO$_3$ solution, and water. The organic phase was dried over MgSO$_4$, concentrated, and purified on a silica gel column to afford 5-bromo-4-ethylpicolinonitrile (580 mg) as a white solid.

Step D. To a solution of 5-bromo-4-ethylpicolinonitrile (300 mg, 1.4 mmol, 1 equiv) in 1,4-dioxane (10 mL) was added Intermediate 2 from Example A (570 mg, 1.54 mmol, 1.1 equiv), 2 M potassium carbonate solution (2.1 mL, 4.2 mmol, 3 equiv), and Pd(PPh$_3$)$_4$ (80 mg, 0.07 mmol, 0.05 equiv). The mixture was degassed and then bubbled with N$_2$ for 5 min. The resulting mixture was stirred at 90° C. for 3 h. Upon cooling to room temperature, the mixture was poured into NH$_4$Cl solution and extracted with DCM. The organic phase was dried over MgSO$_4$, concentrated, and purified on a silica gel column to afford 4-ethyl-5-(4-(1,1,1,3,3,3-hexafluoro-2-hydroxypropan-2-yl)phenyl)picolinonitrile (380 mg) as a white solid.

Step E. 4-Ethyl-5-(4-(1,1,1,3,3,3-hexafluoro-2-hydroxypropan-2-yl)phenyl)picolinonitrile (200 mg, 0.53 mmol, 1 equiv) was dissolved in 6 N HCl solution. The reaction was stirred at 100° C. for 3 h, and then concentrated to give 4-ethyl-5-(4-(1,1,1,3,3,3-hexafluoro-2-hydroxypropan-2-yl)phenyl)picolinic acid which was used without purification.

Step F. To a mixture of 4-ethyl-5-(4-(1,1,1,3,3,3-hexafluoro-2-hydroxypropan-2-yl)phenyl)picolinic acid (200 mg, 0.5 mmol, 1 equiv), triethylamine (150 mg, 1.5 mmol, 3 equiv) and N,O-dimethylhydroxylamine hydrochloride (73 mg, 0.75 mmol, 1.5 equiv) in DCM (10 mL) was added HBTU (285 mg, 0.75 mmol, 1.5 equiv). The mixture was stirred at room temperature overnight. The reaction mixture was diluted with DCM (20 mL) and washed with saturated NaHCO$_3$ solution, 2N HCl, and water. The organic phase was dried over MgSO$_4$ and concentrated in vacuo to afford 4-ethyl-5-(4-(1,1,1,3,3,3-hexafluoro-2-hydroxypropan-2-yl)phenyl)-N-methoxy-N-methylpicolinamide (170 mg) as a pale red solid which was used without further purification.

Step G. To a solution of 4-ethyl-5-(4-(1,1,1,3,3,3-hexafluoro-2-hydroxypropan-2-yl)phenyl)-N-methoxy-N-methylpicolinamide (170 mg, 0.39 mmol, 1 equiv) in anhydrous THF (2 mL) was added 1.0 M LAH solution in THF (0.39 mL, 1.0 equiv) at −78° C. The reaction was stirred at −78° C. for 1 h and quenched by adding EtOAc before being warmed to room temperature. The mixture was poured into NH$_4$Cl solution and extracted with DCM. The organic phase was dried over MgSO$_4$, concentrated, and purified on a silica gel column to afford Aldehyde Intermediate 25 (90 mg) as a white solid.

Example EE: Synthesis of 5-ethyl-6-(4-(1,1,1,3,3,3-hexafluoro-2-hydroxypropan-2-yl)phenyl)nicotinaldehyde (Aldehyde Intermediate 26)

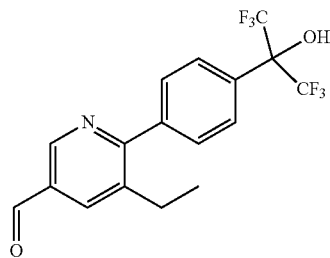 [SMILES: CCc1cc(C=O)cnc1-c1ccc(C(O)(C(F)(F)F)C(F)(F)F)cc1]

To a solution of 3-ethylpyridin-2-amine (1.0 g, 8.2 mmol, 1 equiv) in 1,4-dioxane (10 mL) and water (2 mL) at 0° C. was added NBS (1.45 g, 8.2 mmol, 1 equiv). The resulting mixture was stirring at 0° C. for 2 h. The reaction was diluted with water (50 mL) and extracted with DCM. The organic phase was separated and concentrated. The residue was purified on a silica gel column (hexane/EtOAc) to afford 5-bromo-3-ethylpyridin-2-amine (1.5 g) as a white solid.

5-bromo-3-ethylpyridin-2-amine (1 g, 1 equiv), Zn(CN)$_2$ (1.5 equiv) and PdCl$_2$ (dppf) (10%) were combined in dry DMF (18 mL). The resulting mixture was heated at 120° C. overnight. The reaction mixture was poured into DCM (100 mL) and washed with water and saturated NaHCO$_3$. The organic phase was dried over MgSO$_4$ and concentrated. The residue was purified on a silica gel column (hexane/EtOAc) to afford 6-amino-5-ethylnicotinonitrile (0.7 g) as a white solid.

To a solution of 6-amino-5-ethylnicotinonitrile (0.7 g, 1 equiv) in CH$_3$CN (15 mL) was added CuCl$_2$ (2 equiv) and CuCl (2 equiv). To the mixture was added n-butyl nitrite (1.3 equiv) at rt. The resulting mixture was stirred at rt for 1 h and then heated at reflux overnight. The reaction mixture was diluted with CH$_2$Cl$_2$ and washed with water, saturated NaHCO$_3$ solution, and water. The organic phase was dried over MgSO$_4$, concentrated, and purified on a silica gel column to afford 6-chloro-5-ethylnicotinonitrile (0.42 g) as a white solid.

6-chloro-5-ethylnicotinonitrile (200 mg, 0.53 mmol, 1 equiv) was dissolved in 6 N HCl solution. The reaction was stirred at 100° C. for 3 h, and then concentrated to give 6-chloro-5-ethylnicotinic acid which was used without purification.

To a mixture of 6-chloro-5-ethylnicotinic acid (220 mg, 1 equiv), triethylamine (150 mg, 3 equiv) and N,O-dimethylhydroxylamine hydrochloride (85 mg, 1.5 equiv) in DCM (10 mL) was added HBTU (280 mg, 1.4 equiv). The mixture was stirred at room temperature overnight. The reaction was washed with saturated NaHCO$_3$ solution, 2N HCl, and water. The organic phase was dried over MgSO$_4$ and concentrated in vacuo to afford 6-chloro-5-ethyl-N-methoxy-N-methylnicotinamide (150 mg) which was used without further purification.

6-Chloro-5-ethyl-N-methoxy-N-methylnicotinamide was substituted for 5-bromo-4-ethylpicolinonitrile in the Suzuki coupling reaction described in Step D of Example DD to provide 5-ethyl-6-(4-(1,1,1,3,3,3-hexafluoro-2-hydroxypropan-2-yl)phenyl)-N-methoxy-N-methylnicotinamide.
5-ethyl-6-(4-(1,1,1,3,3,3-hexafluoro-2-hydroxypropan-2-yl)phenyl)-N-methoxy-N-methylnicotinamide was treated with 1 M LAH (1.2 equiv) at −78° C. to afford Aldehyde Intermediate 26.

Example FF: Synthesis of 2-ethyl-4'-(1,1,1,3,3,3-hexafluoro-2-hydroxypropan-2-yl)-2'-methoxy-[1,1'-biphenyl]-4-carbaldehyde (Aldehyde Intermediate 27)

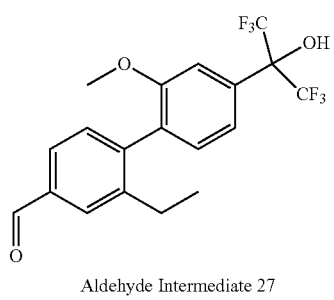 [SMILES: CCc1cc(C=O)ccc1-c1ccc(C(O)(C(F)(F)F)C(F)(F)F)cc1OC]

Aldehyde Intermediate 27

Step A. 4-bromo-3-methoxybenzaldehyde (400 mg, 1.0 equiv) and TMSCF$_3$ (1.5 equiv) was dissolved in dry THF (15 mL), cooled with ice-water under N$_2$. To the mixture was added CsF (1.0 equiv). The mixture was stirred at rt for 2 h. The reaction was quenched with 1 M HCl (30 mL). The mixture was extracted with ethyl acetate and hexane (1:4). The crude mixture was purified on a silica gel column to provide 1-(4-bromo-3-methoxyphenyl)-2,2,2-trifluoroethan-1-ol (280 mg).

Step B. 1-(4-Bromo-3-methoxyphenyl)-2,2,2-trifluoroethan-1-ol (200 mg, 1.0 equiv) was dissolved in dry DCM (10 mL) and cooled to 0° C. DMP (2.0 equiv) was added. The mixture was stirred at rt for 2 h. The crude mixture was purified on a silica gel column to give 1-(4-bromo-3-methoxyphenyl)-2,2,2-trifluoroethan-1-one (190 mg).

Step C. To a solution of 1-(4-bromo-3-methoxyphenyl)-2,2,2-trifluoroethan-1-one (150 mg, 1.0 equiv) and TMSCF$_3$ (1.5 equiv) in dry THE (8 mL) at 0° C. was added TBAF (1 M, 0.1 equiv) dropwise. The mixture was stirred at 0° C. for 20 min, then quenched with 1 M HCl (10 mL). The crude mixture was purified on a silica gel column to give 2-(4-bromo-3-methoxyphenyl)-1,1,1,3,3,3-hexafluoropropan-2-ol (80 mg).

Step D. Preparation of intermediate 3-ethyl-N-methoxy-N-methyl-4-(4,4,5,5-tetramethyl-1,3,2-dioxaborolan-2-yl)benzamide: 4-bromo-3-ethylbenzoic acid (5.0 g, 1.0 equiv), N,O-dimethylhydroxylamine hydrochloride (3.2 g, 1.5 equiv) and HBTU (9.6 g, 1.15 equiv) were combined in DMF (80 mL) at room temperature. To the reaction mixture was added TEA (11.2 g, 4.0 equiv) dropwise. The resulting mixture was stirred at rt overnight. The reaction was diluted with ethyl acetate (200 mL) and hexane (100 mL), then washed with 2×150 mL water, 2×100 mL 1N HCl, 2×100 mL saturated NaHCO$_3$, and brine. The organic phase was dried over MgSO$_4$ and concentrated in vacuum to provide 4-bromo-3-ethyl-N-methoxy-N-methylbenzamide as a pale yellow oil (5.8 g, yield 98%) which was used without further purification. 4-Bromo-3-ethyl-N-methoxy-N-methylbenzamide (3.0 g, 1.0 equiv) and 4,4,4',4',5,5,5',5'-octamethyl-2,2'-bi(1,3,2-dioxaborolane) (3.22 g, 1.15 equiv) was dissolved in dry dioxane (25 mL). The mixture was degassed by bubbling N$_2$ for 5 min. PdCl$_2$(dppf) (0.81 g, 0.1 equiv) and potassium acetate (1.63 g, 1.5 equiv) were added to reaction mixture. The resulting mixture was heated at 100° C. in a sealed-tube for 15 h. The reaction mixture was diluted with ethyl acetate (80 mL) and hexane (80 mL) and washed with 3×80 mL water and 50 mL brine. The crude mixture was purified on a silica gel column to afford 3-ethyl-N-methoxy-N-methyl-4-(4,4,5,5-tetramethyl-1,3,2-dioxaborolan-2-yl)benzamide (3.34 g, yield 95%) as a pale yellow oil.

Step E. 2-(4-bromo-3-methoxyphenyl)-1,1,1,3,3,3-hexafluoropropan-2-ol was substituted for Intermediate 1 in the Suzuki coupling reaction described in Step C of Example C to provide 2-ethyl-4'-(1,1,1,3,3,3-hexafluoro-2-hydroxypropan-2-yl)-N,2'-dimethoxy-N-methyl-[1,1'-biphenyl]-4-. 2-ethyl-4'-(1,1,1,3,3,3-hexafluoro-2-hydroxypropan-2-yl)-N,2'-dimethoxy-N-methyl-[1,1'-biphenyl]-4-carboxamide was treated with 1 M LAH (1.2 equiv) at −78° C. to afford Aldehyde Intermediate 27.

Example GG: Synthesis of 4'-(1,1,1,3,3,3-hexafluoro-2-hydroxypropan-2-yl)-2-methoxy-2'-methyl-[1,1'-biphenyl]-4-carbaldehyde (Aldehyde Intermediate 28)

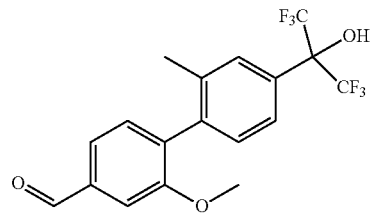 [SMILES: COc1cc(C=O)ccc1-c1ccc(C(O)(C(F)(F)F)C(F)(F)F)cc1C]

Intermediate 4 was substituted for Intermediate 1 in Step B of Example A to yield 1,1,1,3,3,3-hexafluoro-2-(3-methyl-4-(4,4,5,5-tetramethyl-1,3,2-dioxaborolan-2-yl)phenyl)propan-2-ol.
1,1,1,3,3,3-hexafluoro-2-(3-methyl-4-(4,4,5,5-tetramethyl-1,3,2-dioxaborolan-2-yl)phenyl)propan-2-ol was substituted for Intermediate 2 and 4-bromo-3-methoxybenzaldehyde was substituted for 5-bromo-4-ethylpicolinonitrile in the Suzuki coupling reaction described in Step D of Example DD to yield Aldehyde Intermediate 28.

Example HH: Synthesis of 3-ethyl-4-(6-(1,1,1,3,3,3-hexafluoro-2-hydroxypropan-2-yl)pyridin-3-yl)benzaldehyde (Aldehyde Intermediate 29)

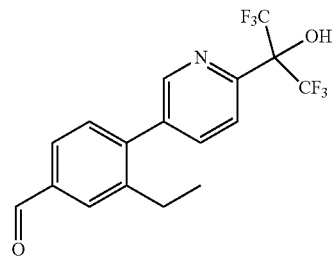 [SMILES: CCc1cc(C=O)ccc1-c1ccc(C(O)(C(F)(F)F)C(F)(F)F)nc1]

Methyl 5-bromopicolinate (1.0 g, 1.0 equiv) and TMSCF$_3$ (6.5 g, 10 equiv) were combined in dry THE (20 mL). The mixture was cooled at 0° C. for 5 min. To the solution was added 1 M TBAF (23 mL) dropwise over 10 min. The mixture was then stirred at 0° C. for 2 h. The reaction was quenched with 1 M HCl (50 mL) at 0° C. The mixture was extracted with 3×30 mL hexane. The crude product was purified on a silica gel column to afford 2-(5-bromopyridin-2-yl)-1,1,1,3,3,3-hexafluoropropan-2-ol (450 mg).

2-(5-bromopyridin-2-yl)-1,1,1,3,3,3-hexafluoropropan-2-ol was substituted for Intermediate 1 in the Suzuki coupling reaction described in Step C of Example C to provide 3-ethyl-4-(6-(1,1,1,3,3,3-hexafluoro-2-hydroxypropan-2-yl)pyridin-3-yl)-N-methoxy-N-methylbenzamide, which was next treated with 1 M LAH (1.2 equiv) at −78° C. to afford Aldehyde Intermediate 29.

Example II: Synthesis of 4-formyl-4'-(1,1,1,3,3,3-hexafluoro-2-hydroxypropan-2-yl)-N,N-dimethyl-[1,1'-biphenyl]-2-carboxamide (Aldehyde Intermediate 30)

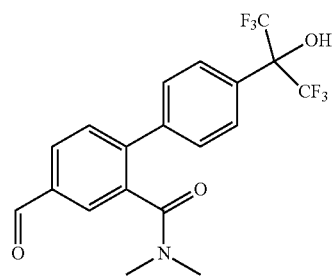 [SMILES: CN(C)C(=O)c1cc(C=O)ccc1-c1ccc(C(O)(C(F)(F)F)C(F)(F)F)cc1]

Methyl 2-bromo-5-formylbenzoate was substituted for 5-bromo-4-ethylpicolinonitrile in the Suzuki coupling reaction described in Step D of Example DD to provide methyl 4-formyl-4'-(1,1,1,3,3,3-hexafluoro-2-hydroxypropan-2-yl)-[1,1'-biphenyl]-2-carboxylate.

Methyl 4-formyl-4'-(1,1,1,3,3,3-hexafluoro-2-hydroxypropan-2-yl)-[1,1'-biphenyl]-2-carboxylate was treated with solution of LiOH in water and MeOH to provide 4-formyl-4'-(1,1,1,3,3,3-hexafluoro-2-hydroxypropan-2-yl)-[1,1'-biphenyl]-2-carboxylic acid. 4-Formyl-4'-(1,1,1,3,3,3-hexafluoro-2-hydroxypropan-2-yl)-[1,1'-biphenyl]-2-carboxylic acid was coupled with N,O-dimethylhydroxylamine hydrochloride in the presence of HBTU to afford Aldehyde Intermediate 30.

Example JJ: Synthesis of 4'-(1,1,1,3,3,3-hexafluoro-2-hydroxypropan-2-yl)-3-hydroxy-[1,1'-biphenyl]-4-carbaldehyde (Aldehyde Intermediate 31)

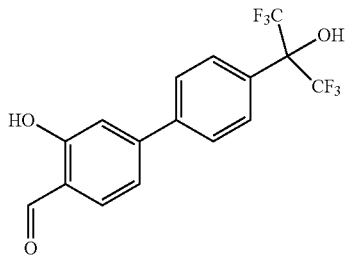 [SMILES: O=Cc1ccc(-c2ccc(C(O)(C(F)(F)F)C(F)(F)F)cc2)cc1O]

4-Bromo-2-hydroxybenzaldehyde was substituted for 5-bromo-4-ethylpicolinonitrile in the Suzuki coupling reaction described in Step D of Example DD to provide Aldehyde Intermediate 31.

Example 1: Synthesis of tert-butyl 6-((2-ethyl-4'-(1,1,1,3,3,3-hexafluoro-2-hydroxypropan-2-yl)-[1,1'-biphenyl]-4-yl)methyl)-2,6-diazaspiro[3.3]heptane-2-carboxylate

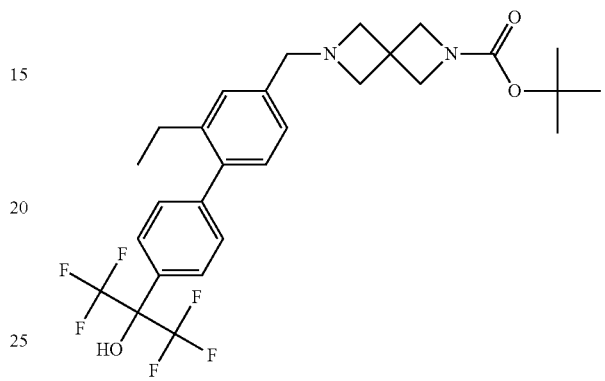

Commercially available tert-butyl 2,6-diazaspiro[3.3]heptane-2-carboxylate as an oxalate salt (62 mg, 1.2 equiv) was suspended into 1,2-DCE (15 mL), added $Et_3N$ (26 mg, 2.0 equiv) and stirred at rt for 30 min. Aldehyde Intermediate 5 (80 mg, 1.0 equiv) was added followed by acetic acid (20 µL). The mixture was stirred at rt for 3 h and $NaBH(OAc)_3$ (136 mg, 3.0 equiv) was added to the solution. The resulting mixture was stirred at rt overnight. The reaction was quenched with MeOH, diluted with 20 mL saturated $NaHCO_3$, and extracted with 2×20 mL ethyl acetate. The crude mixture was purified on a silica gel column to afford the title compound (65 mg, yield 55%) as a white solid. LC-MS (ESI) m/z 559.2 $(M+H)^+$.

Example 2: Synthesis of 2-(2'-ethyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

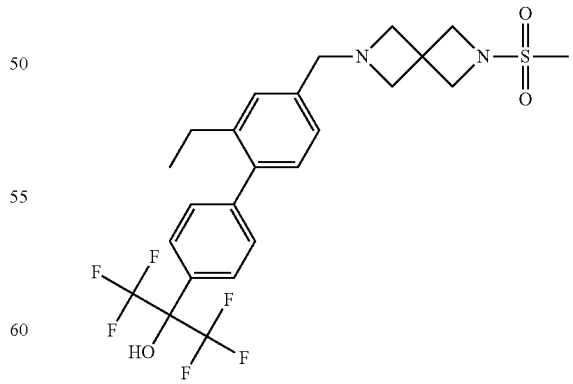

Amine Intermediate 20 (3.7 g, TFA salt, 1.2 equiv) was suspended into 1,2-DCE (50 mL) and to which Aldehyde Intermediate 5 (4.0 g, 1.0 equiv) was added. The mixture was stirred at rt for 3 h. Solid $NaBH(OAc)_3$ (6.76 g, 3.0 equiv) was then added into the reaction. The resulting mixture was stirred at rt overnight. The reaction was quenched with MeOH (10 mL) and washed with saturated NaHCO₃, water, and brine. The crude mixture was purified on a silica gel column to afford the title product (3.5 g, yield 61.4%) as a white solid. LC-MS (ESI) m/z 537.4 (M+H)⁺.

Example 3: Synthesis of 2-((2-ethyl-4'-(1,1,1,3,3,3-hexafluoro-2-hydroxypropan-2-yl)-[1,1'-biphenyl]-4-yl)methyl)-7-thia-2-azaspiro[3.5]nonane 7,7-dioxide

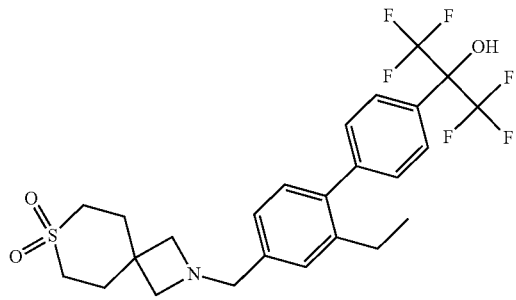 [SMILES: CCc1cc(CN2CC3(CCS(=O)(=O)CC3)C2)ccc1-c1ccc(C(O)(C(F)(F)F)C(F)(F)F)cc1]

7-Thia-2-azaspiro[3.5]nonane 7,7-dioxide (50 mg, 1.2 equiv) and Aldehyde Intermediate 5 (90 mg, 1.0 equiv) were combined in 1,2-DCE (25 mL). To the mixture was added acetic acid (40 µL). The reaction mixture was stirred at rt for 3 h. NaBH(OAc)₃ (155 mg, 3.0 equiv) was added. The resulting mixture was stirred at rt overnight. The reaction was quenched with MeOH, washed with saturated NaHCO₃, and extracted with 2×20 mL DCM. The crude mixture was purified on a silica gel column to afford the title compound (28 mg, yield 22%). LC-MS (ESI) m/z 536.4 (M+H)⁺.

Example 4: Synthesis of 2-(2'-ethyl-4'-((2-(methylsulfonyl)-2,7-diazaspiro[3.5]nonan-7-yl)methyl)-[1,1'-biphenyl]-4-yl)-1,1,1,3,3,3-hexafluoropropan-2-ol

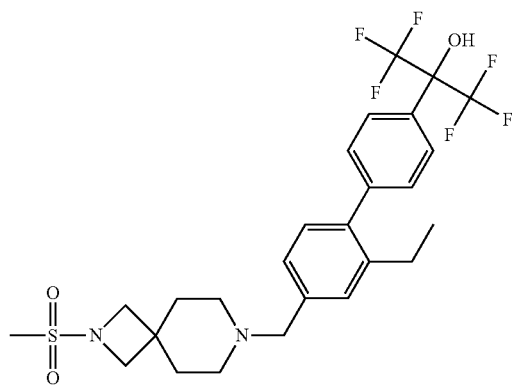 [SMILES: CCc1cc(CN2CCC3(CC2)CN(S(C)(=O)=O)C3)ccc1-c1ccc(C(O)(C(F)(F)F)C(F)(F)F)cc1]

tert-butyl 2,7-diazaspiro[3.5]nonane-2-carboxylate (100 mg, 1.2 equiv) and aldehyde intermediate 5 (85 mg, 1.0 equiv) were combined in 1,2-DCE (15 mL). To the mixture was added acetic acid (20 µL). The reaction mixture was stirred at rt for 3 h. NaBH(OAc)₃ (145 mg, 3.0 equiv) was added. The resulting mixture was stirred at rt overnight. The reaction was quenched with MeOH, washed with saturated NaHCO₃, and extracted with 2×20 mL DCM. The crude mixture was purified on a silica gel column to afford tert-butyl 7-((2-ethyl-4'-(1,1,1,3,3,3-hexafluoro-2-hydroxypropan-2-yl)-[1,1'-biphenyl]-4-yl)methyl)-2,7-diazaspiro[3.5]nonane-2-carboxylate (103 mg, yield 78%).

tert-Butyl 7-((2-ethyl-4'-(1,1,1,3,3,3-hexafluoro-2-hydroxypropan-2-yl)-[1,1'-biphenyl]-4-yl)methyl)-2,7-diazaspiro[3.5]nonane-2-carboxylate (103 mg) was treated with 4 mL (80% TFA in DCM) for 1 h. The solvent was removed in vacuo to afford 2-(4'-((2,7-diazaspiro[3.5]nonan-7-yl)methyl)-2'-ethyl-[1,1'-biphenyl]-4-yl)-1,1,1,3,3,3-hexafluoropropan-2-ol (106 mg) as a TFA salt which was used without purification.

2-(4'-((2,7-Diazaspiro[3.5]nonan-7-yl)methyl)-2'-ethyl-[1,1'-biphenyl]-4-yl)-1,1,1,3,3,3-hexafluoropropan-2-ol TFA salt (53 mg) was suspended in DCM (10 mL) and saturated NaHCO₃ (5 mL) was added. To the mixture was added MsCl (3.0 equiv) in DCM (5 mL) dropwise over 20 min at 0° C. The resulting mixture was stirred at rt for 2 h. The mixture was washed with water and brine. The crude product was purified on a silica gel column to afford the title compound (25 mg, yield 51%). LC-MS (ESI) m/z 565.6 (M+H)⁺.

Example 5: Synthesis of 2-(2'-ethyl-4'-((2-(methylsulfonyl)-2,6-diazaspiro[3.5]nonan-6-yl)methyl)-[1,1'-biphenyl]-4-yl)-1,1,1,3,3,3-hexafluoropropan-2-ol

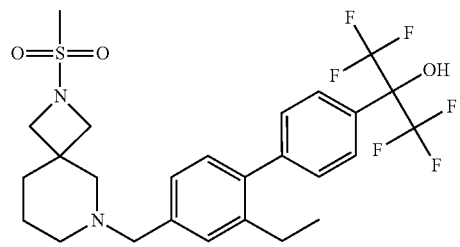 [SMILES: CCc1cc(CN2CCCC3(C2)CN(S(C)(=O)=O)C3)ccc1-c1ccc(C(O)(C(F)(F)F)C(F)(F)F)cc1]

The title compound was made using the method described in Example 4, but substituting tert-butyl 2,6-diazaspiro[3.5]nonane-2-carboxylate for tert-butyl 2,7-diazaspiro[3.5]nonane-2-carboxylate. LC-MS (ESI) m/z 565.5 (M+H)⁺.

Example 6: Synthesis of 2-(2'-ethyl-4'-((6-(methylsulfonyl)-2,6-diazaspiro[3.4]octan-2-yl)methyl)-[1,1'-biphenyl]-4-yl)-1,1,1,3,3,3-hexafluoropropan-2-ol

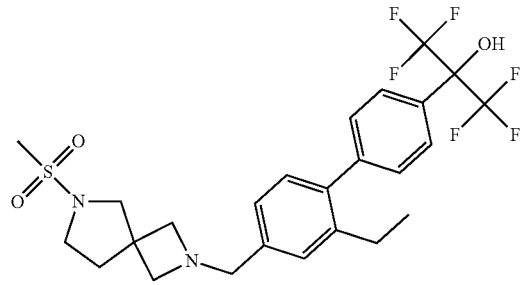 [SMILES: CCc1cc(CN2CC3(CCN(S(C)(=O)=O)C3)C2)ccc1-c1ccc(C(O)(C(F)(F)F)C(F)(F)F)cc1]

The title compound was made using the method described in Example 4, but substituting tert-butyl 2,6-diazaspiro[3.4]octane-2-carboxylate for tert-butyl 2,7-diazaspiro[3.5]nonane-2-carboxylate. LC-MS (ESI) m/z 551.4 (M+H)⁺.

Examples 7-61

The following compounds in Table 1 were synthesized using the procedures described in the preceding examples wherein an aldehyde intermediate (Aldehyde Int.) (1.0 equiv) and an amine intermediate (Amine Int.) (1.2 equiv) were combined to afford the title compounds.

TABLE 1

| Ex. No. | Structure | Chemical Name | Intermediates used | LC-MS (ESI) m/z (M + H)+ |
|---|---|---|---|---|
| 7 | 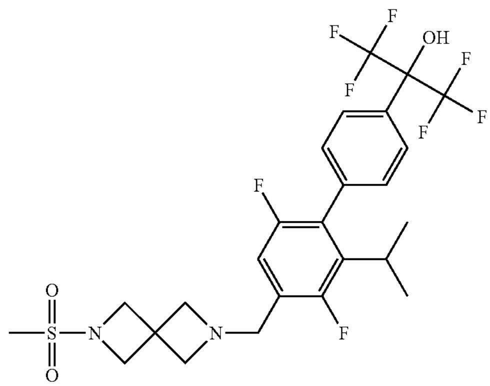 [SMILES: CC(C)c1c(F)c(CN2CC3(C2)CN(S(C)(=O)=O)C3)cc(F)c1-c1ccc(C(O)(C(F)(F)F)C(F)(F)F)cc1] | 2-(3',6'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 11 Amine Int. 2 | 587.2 |
| 8 | 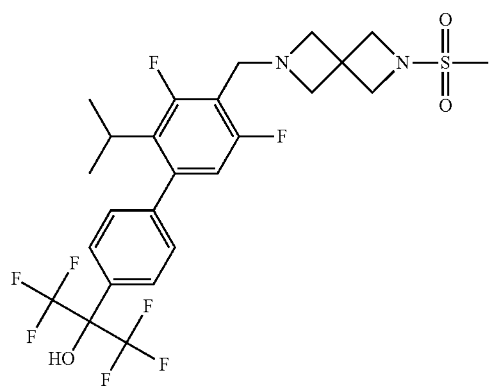 [SMILES: CC(C)c1c(-c2ccc(C(O)(C(F)(F)F)C(F)(F)F)cc2)cc(F)c(CN2CC3(C2)CN(S(C)(=O)=O)C3)c1F] | 2-(3',5'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 12 Amine Int. 2 | 587.4 |
| 9 | 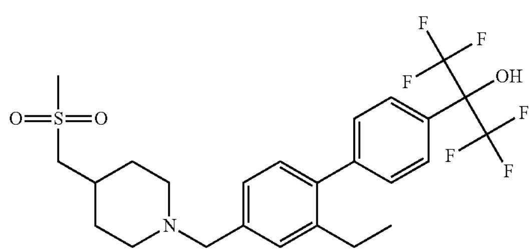 [SMILES: CCc1cc(CN2CCC(CS(C)(=O)=O)CC2)ccc1-c1ccc(C(O)(C(F)(F)F)C(F)(F)F)cc1] | 2-(2'-ethyl-4'-((4-((methylsulfonyl)methyl)piperidin-1-yl)methyl)-[1,1'-biphenyl]-4-yl)-1,1,1,3,3,3-hexafluoropropan-2-ol | Aldehyde Int. 5 Amine Int. 21 | 538.5 |
| 10 | 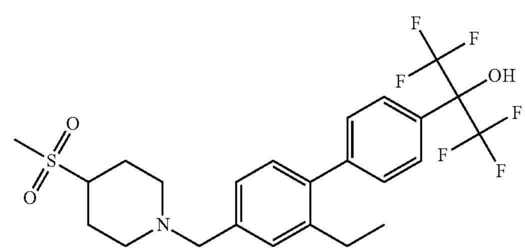 [SMILES: CCc1cc(CN2CCC(S(C)(=O)=O)CC2)ccc1-c1ccc(C(O)(C(F)(F)F)C(F)(F)F)cc1] | 2-(2'-ethyl-4'-((4-(methylsulfonyl)piperidin-1-yl)methyl)-[1,1'-biphenyl]-4-yl)-1,1,1,3,3,3-hexafluoropropan-2-ol | Aldehyde Int. 5 Amine Int. 21 | 524.4 |
| 11 | 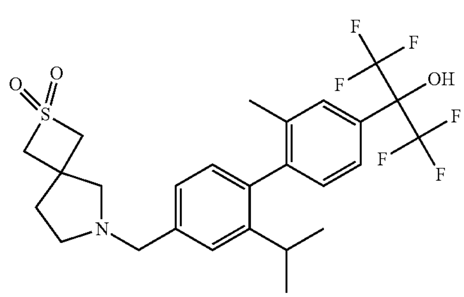 [SMILES: Cc1cc(C(O)(C(F)(F)F)C(F)(F)F)ccc1-c1ccc(CN2CCC3(C2)CS(=O)(=O)C3)cc1C(C)C] | 6-((4'-(1,1,1,3,3,3-hexafluoro-2-hydroxypropan-2-yl)-2-isopropyl-2'-methyl-[1,1'-biphenyl]-4-yl)methyl)-2-thia-6-azaspiro[3.4]octane 2,2-dioxide | Aldehyde Int. 20 Commercially available 2-thia-6-azaspiro[3.4] octane 2,2-dioxide | 550.5 |

TABLE 1-continued

| Ex. No. | Structure | Chemical Name | Intermediates used | LC-MS (ESI) m/z (M + H)+ |
|---|---|---|---|---|
| 12 | 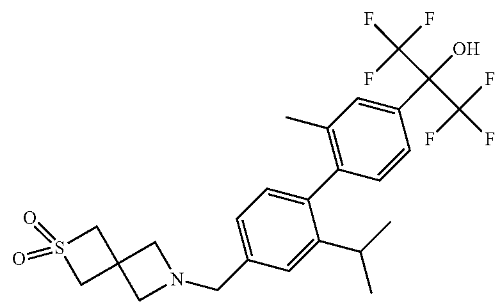 [SMILES: Cc1cc(C(O)(C(F)(F)F)C(F)(F)F)ccc1-c1ccc(CN2CC3(C2)CS(=O)(=O)C3)cc1C(C)C] | 6-((4'-(1,1,1,3,3,3-hexafluoro-2-hydroxypropan-2-yl)-2-isopropyl-2'-methyl-[1,1'-biphenyl]-4-yl)methyl)-2-thia-6-azaspiro[3.3]heptane 2,2-dioxide | Aldehyde Int. 20 Amine Int. 11 | 536.4 |
| 13 | 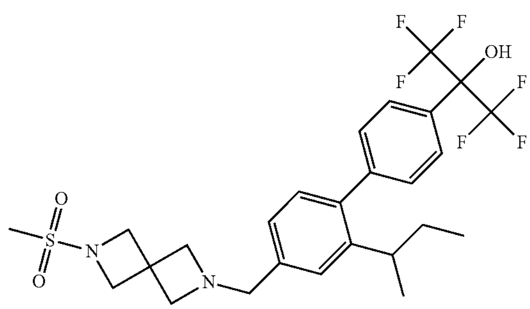 [SMILES: CCC(C)c1cc(CN2CC3(C2)CN(S(C)(=O)=O)C3)ccc1-c1ccc(C(O)(C(F)(F)F)C(F)(F)F)cc1] | 2-(2'-(sec-butyl)-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 10 Amine Int. 2 | 565.5 |
| 14 | 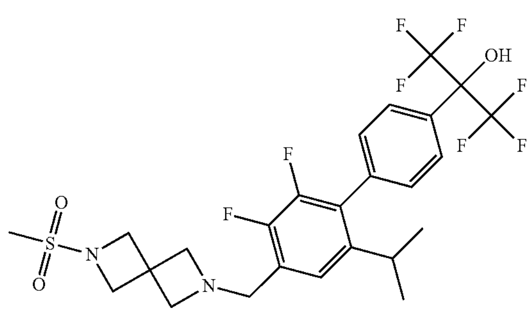 [SMILES: CC(C)c1cc(CN2CC3(C2)CN(S(C)(=O)=O)C3)c(F)c(F)c1-c1ccc(C(O)(C(F)(F)F)C(F)(F)F)cc1] | 2-(2',3'-difluoro-6'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 23 Amine Int. 2 | 587.3 |
| 15 | 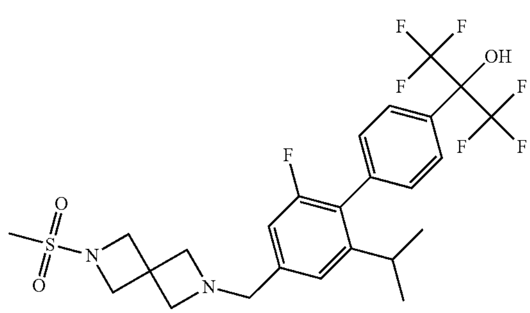 [SMILES: CC(C)c1cc(CN2CC3(C2)CN(S(C)(=O)=O)C3)cc(F)c1-c1ccc(C(O)(C(F)(F)F)C(F)(F)F)cc1] | 1,1,1,3,3,3-hexafluoro-2-(2'-fluoro-6'-isopropyl-4'-((6-(methylsulfonyl)-2,6-diazaspiro[3.3]heptan-2-yl)methyl)-[1,1'-biphenyl]-4-yl)propan-2-ol | Aldehyde Int. 24 Amine Int. 2 | 569.4 |

TABLE 1-continued

| Ex. No. | Structure | Chemical Name | Intermediates used | LC-MS (ESI) m/z (M + H)+ |
|---|---|---|---|---|
| 16 | 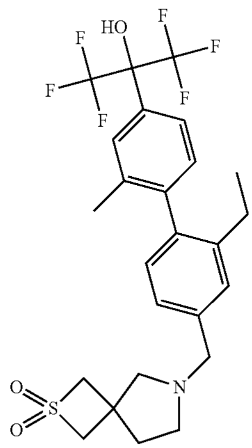 [SMILES: CCc1cc(CN2CCC3(C2)CS(=O)(=O)C3)ccc1-c1ccc(C(O)(C(F)(F)F)C(F)(F)F)cc1C] | 6-((2-ethyl-4'-(1,1,1,3,3,3-hexafluoro-2-hydroxypropan-2-yl)-2'-methyl-[1,1'-biphenyl]-4-yl)methyl)-2-thia-6-azaspiro[3.4]octane 2,2-dioxide | Aldehyde Int. 22 Commercially available 2-thia-6-azaspiro[3.4]octane 2,2-dioxide | 536.5 |
| 17 | 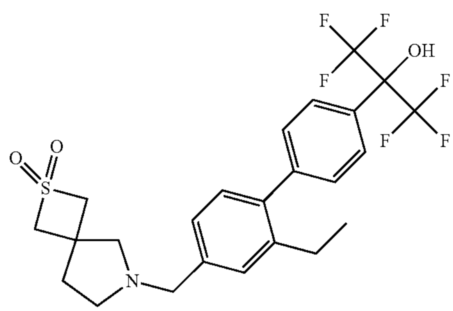 [SMILES: CCc1cc(CN2CCC3(C2)CS(=O)(=O)C3)ccc1-c1ccc(C(O)(C(F)(F)F)C(F)(F)F)cc1] | 6-((2-ethyl-4'-(1,1,1,3,3,3-hexafluoro-2-hydroxypropan-2-yl)-[1,1'-biphenyl]-4-yl)methyl)-2-thia-6-azaspiro[3.4]octane 2,2-dioxide | Aldehyde Int. 5 Commercially available 2-thia-6-azaspiro[3.4]octane 2,2-dioxide | 522.4 |
| 18 | 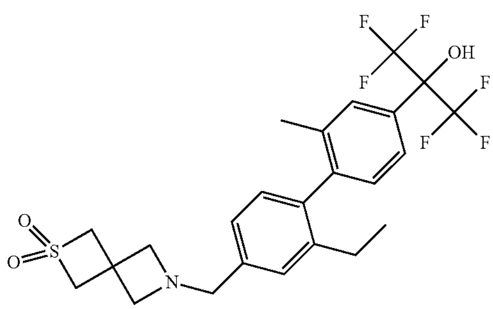 [SMILES: CCc1cc(CN2CC3(C2)CS(=O)(=O)C3)ccc1-c1ccc(C(O)(C(F)(F)F)C(F)(F)F)cc1C] | 6-((2-ethyl-4'-(1,1,1,3,3,3-hexafluoro-2-hydroxypropan-2-yl)-2'-methyl-[1,1'-biphenyl]-4-yl)methyl)-2-thia-6-azaspiro[3.3]heptane 2,2-dioxide | Aldehyde Int. 22 Amine Int. 11 | 522.5 |
| 19 | 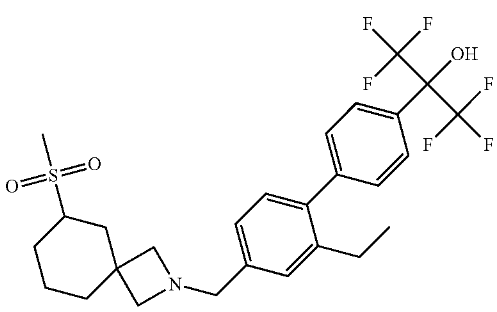 [SMILES: CCc1cc(CN2CC3(CCCC(S(C)(=O)=O)C3)C2)ccc1-c1ccc(C(O)(C(F)(F)F)C(F)(F)F)cc1] | 2-(2'-ethyl-4'-((6-(methylsulfonyl)-2,6-diazaspiro[3.5]nonan-2-yl)methyl)-[1,1'-biphenyl]-4-yl)-1,1,1,3,3,3-hexafluoropropan-2-ol | Aldehyde Int.5 Amine Int. 17 | 565.6 |

TABLE 1-continued

| Ex. No. | Structure | Chemical Name | Intermediates used | LC-MS (ESI) m/z (M + H)+ |
|---|---|---|---|---|
| 20 | 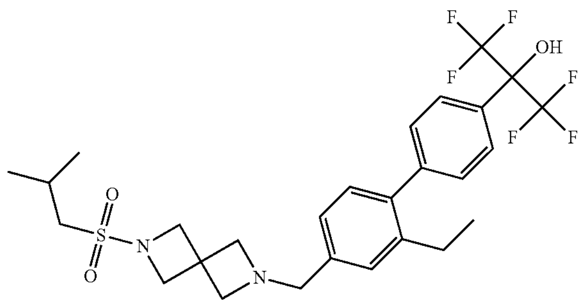 [SMILES: CCc1cc(CN2CC3(C2)CN(S(=O)(=O)CC(C)C)C3)ccc1-c1ccc(C(O)(C(F)(F)F)C(F)(F)F)cc1] | 2-(2'-ethyl-4'-((6-(isobutylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 5 Amine Int. 6 | 579.6 |
| 21 | 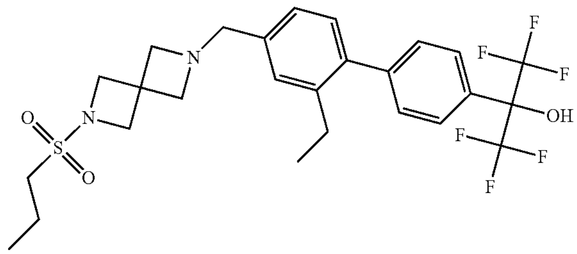 [SMILES: CCCS(=O)(=O)N1CC2(CN(Cc3ccc(-c4ccc(C(O)(C(F)(F)F)C(F)(F)F)cc4)c(CC)c3)C2)C1] | 2-(2'-ethyl-4'-((6-(propylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 5 Amine Int. 5 | 565.6 |
| 22 | 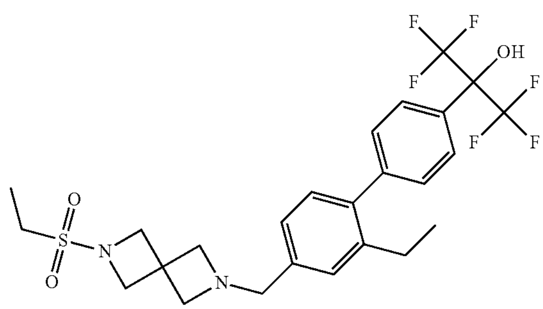 [SMILES: CCc1cc(CN2CC3(C2)CN(S(=O)(=O)CC)C3)ccc1-c1ccc(C(O)(C(F)(F)F)C(F)(F)F)cc1] | 2-(2'-ethyl-4'-((6-(ethylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 5 Amine Int. 3 | 551.5 |
| 23 | 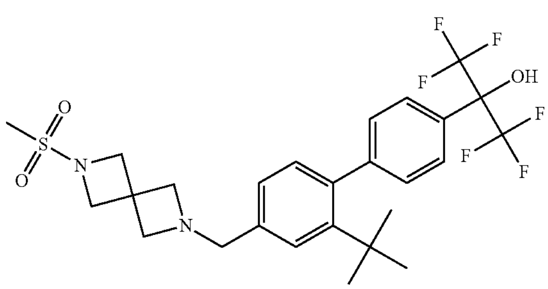 [SMILES: CC(C)(C)c1cc(CN2CC3(C2)CN(S(C)(=O)=O)C3)ccc1-c1ccc(C(O)(C(F)(F)F)C(F)(F)F)cc1] | 2-(2'-(tert-butyl)-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 13 Amine Int. 2 | 565.4 |
| 24 | 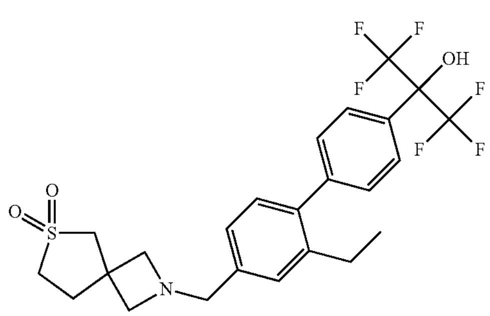 [SMILES: CCc1cc(CN2CC3(CCS(=O)(=O)C3)C2)ccc1-c1ccc(C(O)(C(F)(F)F)C(F)(F)F)cc1] | 2-((2-ethyl-4'-(1,1,1,3,3,3-hexafluoro-2-hydroxypropan-2-yl)-[1,1'-biphenyl]-4-yl)methyl)-6-thia-2-azaspiro[3.4]octane 6,6-dioxide | Aldehyde Int. 5 Amine Int. 12 | 522.5 |

TABLE 1-continued

| Ex. No. | Structure | Chemical Name | Intermediates used | LC-MS (ESI) m/z (M + H)+ |
|---|---|---|---|---|
| 25 | 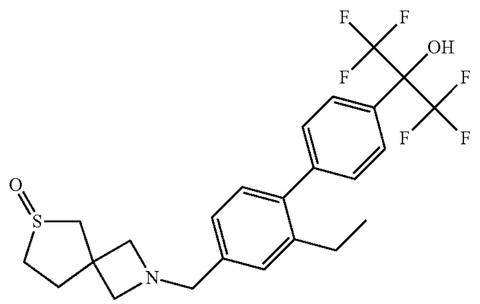 [SMILES: CCc1cc(CN2CC3(CCS(=O)C3)C2)ccc1-c1ccc(C(O)(C(F)(F)F)C(F)(F)F)cc1] | 2-((2-ethyl-4'-(1,1,1,3,3,3-hexafluoro-2-hydroxypropan-2-yl)-[1,1'-biphenyl]-4-yl)methyl)-6-thia-2-azaspiro[3.4]octane 6-oxide | Aldehyde Int. 5 Amine Int. 10 | 506.3 |
| 26 | 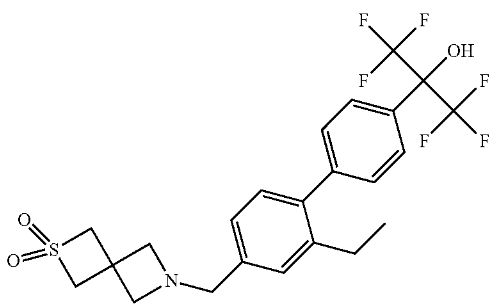 [SMILES: CCc1cc(CN2CC3(C2)CS(=O)(=O)C3)ccc1-c1ccc(C(O)(C(F)(F)F)C(F)(F)F)cc1] | 6-((2-ethyl-4'-(1,1,1,3,3,3-hexafluoro-2-hydroxypropan-2-yl)-[1,1'-biphenyl]-4-yl)methyl)-2-thia-6-azaspiro[3.3]heptane 2,2-dioxide | Aldehyde Int. 5 Amine Int. 11 | 508.2 |
| 27 | 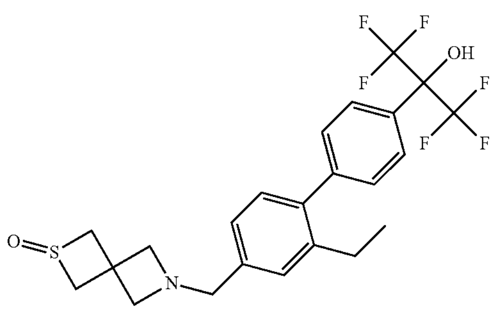 [SMILES: CCc1cc(CN2CC3(C2)CS(=O)C3)ccc1-c1ccc(C(O)(C(F)(F)F)C(F)(F)F)cc1] | 6-((2-ethyl-4'-(1,1,1,3,3,3-hexafluoro-2-hydroxypropan-2-yl)-[1,1'-biphenyl]-4-yl)methyl)-2-thia-6-azaspiro[3.3]heptane 2-oxide | Aldehyde Int. 5 Amine Int. 9 | 492.3 |
| 28 | 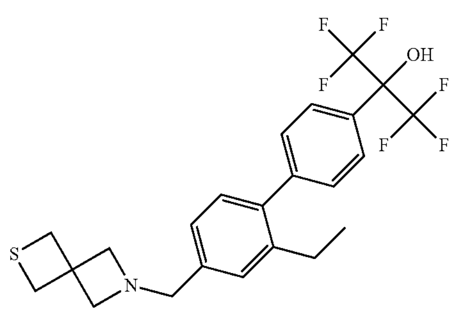 [SMILES: CCc1cc(CN2CC3(CSC3)C2)ccc1-c1ccc(C(O)(C(F)(F)F)C(F)(F)F)cc1] | 2-(4'-((2-thia-6-azaspiro[3.3]heptan-6-yl)methyl)-2'-ethyl-[1,1'-biphenyl]-4-yl)-1,1,1,3,3,3-hexafluoropropan-2-ol | Aldehyde Int. 5 Commercially available 2-thia-6-azaspiro[3.3]heptane | 476.3 |
| 29 | 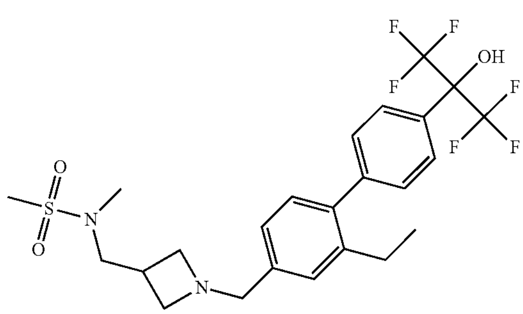 [SMILES: CCc1cc(CN2CC(CN(C)S(C)(=O)=O)C2)ccc1-c1ccc(C(O)(C(F)(F)F)C(F)(F)F)cc1] | N-((1-((2-ethyl-4'-(1,1,1,3,3,3-hexafluoro-2-hydroxypropan-2-yl)-[1,1'-biphenyl]-4-yl)methyl)azetidin-3-yl)methyl)-N-methylmethanesulfonamide | Aldehyde Int. 5 Amine Int. 14 | 539.6 |

TABLE 1-continued

| Ex. No. | Structure | Chemical Name | Intermediates used | LC-MS (ESI) m/z (M + H)+ |
|---|---|---|---|---|
| 30 | 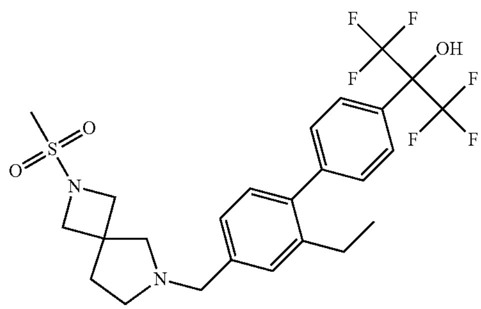 [SMILES: CCc1cc(CN2CCC3(C2)CN(S(C)(=O)=O)C3)ccc1-c1ccc(C(O)(C(F)(F)F)C(F)(F)F)cc1] | 2-(2'-ethyl-4'-((2-(methylsulfonyl)-2,6-diazaspiro[3.4]octan-6-yl)methyl)-[1,1'-biphenyl]-4-yl)-1,1,1,3,3,3-hexafluoropropan-2-ol | Aldehyde Int. 5 Amine Int. 15 | 551.6 |
| 31 | 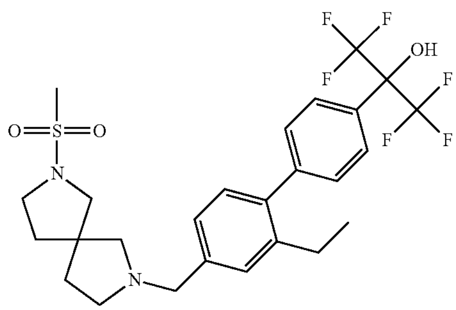 [SMILES: CCc1cc(CN2CCC3(CCN(S(C)(=O)=O)C3)C2)ccc1-c1ccc(C(O)(C(F)(F)F)C(F)(F)F)cc1] | 2-(2'-ethyl-4'-((7-(methylsulfonyl)-2,7-diazaspiro[4.4]nonan-2-yl)methyl)-[1,1'-biphenyl]-4-yl)-1,1,1,3,3,3-hexafluoropropan-2-ol | Aldehyde Int. 5 Amine Int. 19 | 565.6 |
| 32 | 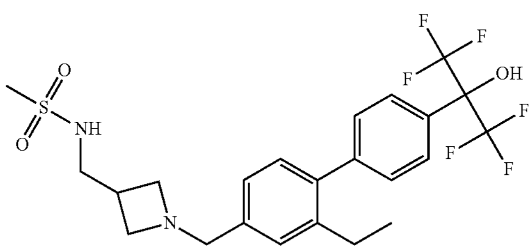 [SMILES: CCc1cc(CN2CC(CNS(C)(=O)=O)C2)ccc1-c1ccc(C(O)(C(F)(F)F)C(F)(F)F)cc1] | N-((1-((2-ethyl-4'-(1,1,1,3,3,3-hexafluoro-2-hydroxypropan-2-yl)-[1,1'-biphenyl]-4-yl)methyl)azetidin-3-yl)methyl)methanesulfonamide | Aldehyde Int. 5 Amine Int. 13 | 525.6 |
| 33 | 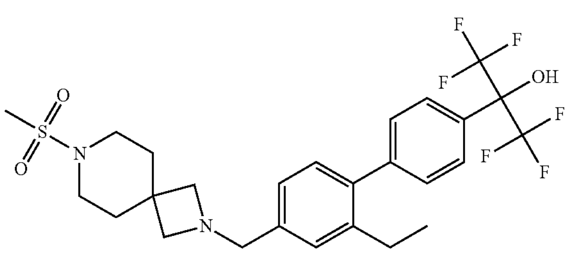 [SMILES: CCc1cc(CN2CC3(CCN(S(C)(=O)=O)CC3)C2)ccc1-c1ccc(C(O)(C(F)(F)F)C(F)(F)F)cc1] | 2-(2'-ethyl-4'-((7-(methylsulfonyl)-2,7-diazaspiro[3.5]nonan-2-yl)methyl)-[1,1'-biphenyl]-4-yl)-1,1,1,3,3,3-hexafluoropropan-2-ol | Aldehyde Int. 5 Amine Int. 16 | 565.7 |
| 34 | 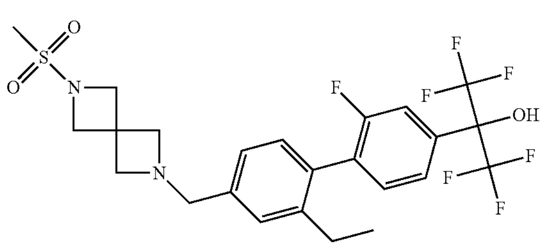 [SMILES: CCc1cc(CN2CC3(C2)CN(S(C)(=O)=O)C3)ccc1-c1ccc(C(O)(C(F)(F)F)C(F)(F)F)cc1F] | 2-(2'-ethyl-2-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 21 Amine Int. 2 | 555.2 |

TABLE 1-continued

| Ex. No. | Structure | Chemical Name | Intermediates used | LC-MS (ESI) m/z (M + H)+ |
|---|---|---|---|---|
| 35 | 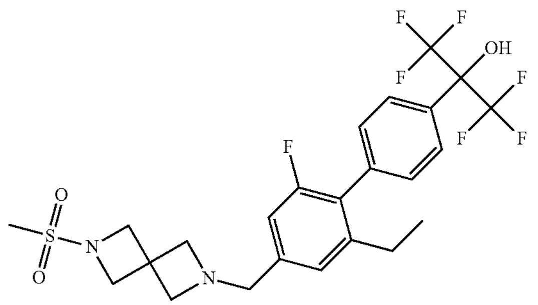 [SMILES: CCc1cc(CN2CC3(C2)CN(S(C)(=O)=O)C3)cc(F)c1-c1ccc(C(O)(C(F)(F)F)C(F)(F)F)cc1] | 2-(2'-ethyl-6'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 6 Amine Int. 2 | 555.3 |
| 36 | 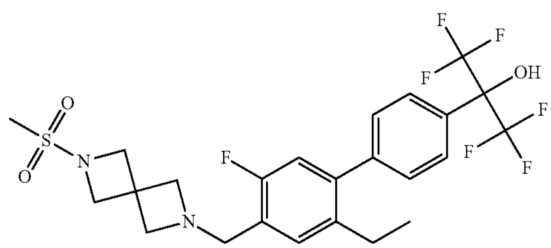 [SMILES: CCc1cc(CN2CC3(C2)CN(S(C)(=O)=O)C3)c(F)cc1-c1ccc(C(O)(C(F)(F)F)C(F)(F)F)cc1] | 2-(2'-ethyl-5'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 7 Amine Int. 2 | 555.3 |
| 37 | 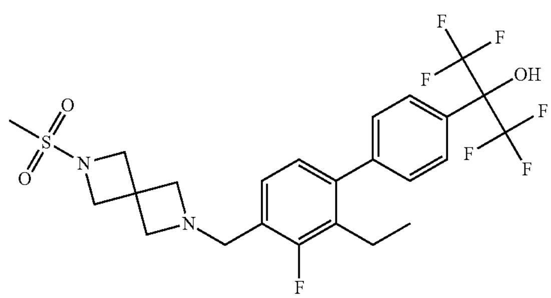 [SMILES: CCc1c(-c2ccc(C(O)(C(F)(F)F)C(F)(F)F)cc2)ccc(CN2CC3(C2)CN(S(C)(=O)=O)C3)c1F] | 2-(2'-ethyl-3'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 8 Amine Int. 2 | 555.3 |
| 38 | 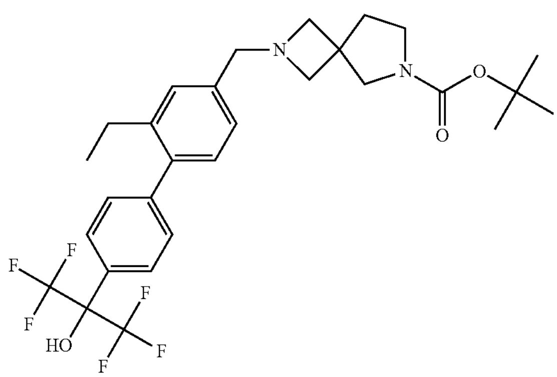 [SMILES: CCc1cc(CN2CC3(CCN(C(=O)OC(C)(C)C)C3)C2)ccc1-c1ccc(C(O)(C(F)(F)F)C(F)(F)F)cc1] | tert-butyl 2-((2-ethyl-4'-(1,1,1,3,3,3-hexafluoro-2-hydroxypropan-2-yl)-[1,1'-biphenyl]-4-yl)methyl)-2,6-diazaspiro[3.4]octane-6-carboxylate | Aldehyde Int. 5 Commercially available tert-butyl diazaspiro[3.4] octane-6-carboxylate | 573.4 |
| 39 | 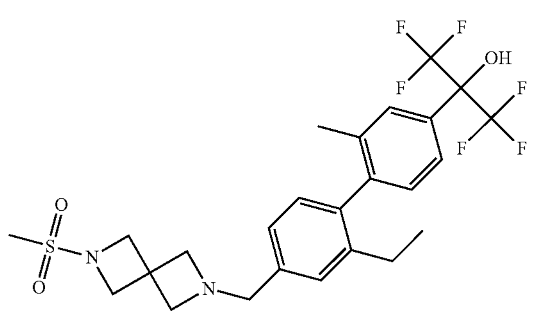 [SMILES: CCc1cc(CN2CC3(C2)CN(S(C)(=O)=O)C3)ccc1-c1ccc(C(O)(C(F)(F)F)C(F)(F)F)cc1C] | 2-(2'-ethyl-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 22 Amine Int. 2 | 551.3 |

TABLE 1-continued

| Ex. No. | Structure | Chemical Name | Intermediates used | LC-MS (ESI) m/z (M + H)+ |
|---|---|---|---|---|
| 40 | 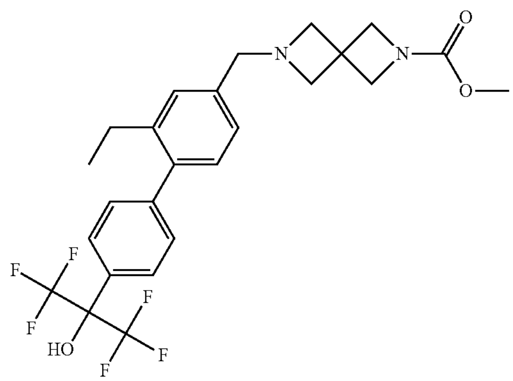 [SMILES: CCc1cc(CN2CC3(C2)CN(C(=O)OC)C3)ccc1-c1ccc(C(O)(C(F)(F)F)C(F)(F)F)cc1] | methyl 6-((2-ethyl-4'-(1,1,1,3,3,3-hexafluoro-2-hydroxypropan-2-yl)-[1,1'-biphenyl]-4-yl)methyl)-2,6-diazaspiro[3.3]heptane-2-carboxylate | Aldehyde Int. 5 Amine Int. 8 | 517.5 |
| 41 | 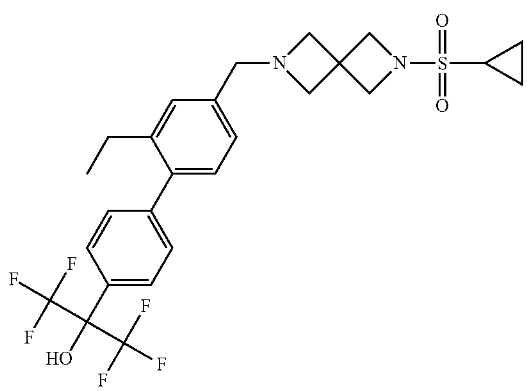 [SMILES: CCc1cc(CN2CC3(C2)CN(S(=O)(=O)C2CC2)C3)ccc1-c1ccc(C(O)(C(F)(F)F)C(F)(F)F)cc1] | 2-(4'-((6-(cyclopropylsulfonyl)-2,6-diazaspiro[3.3]heptan-2-yl)methyl)-2'-ethyl-[1,1'-biphenyl]-4-yl)-1,1,1,3,3,3-hexafluoropropan-2-ol | Aldehyde Int. 5 Amine Int. 4 | 563.6 |
| 42 | 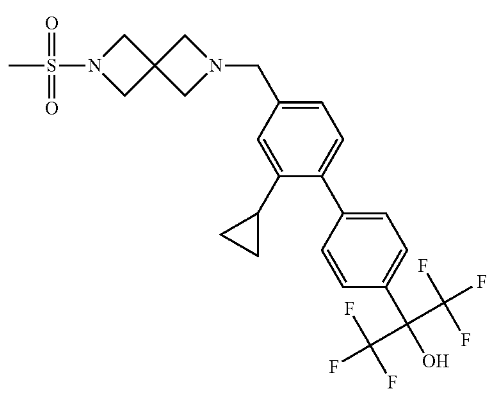 [SMILES: CS(=O)(=O)N1CC2(CN(Cc3ccc(-c4ccc(C(O)(C(F)(F)F)C(F)(F)F)cc4)c(C4CC4)c3)C2)C1] | 2-(2'-cyclopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 19 Amine Int. 2 | 549.2 |
| 43 | 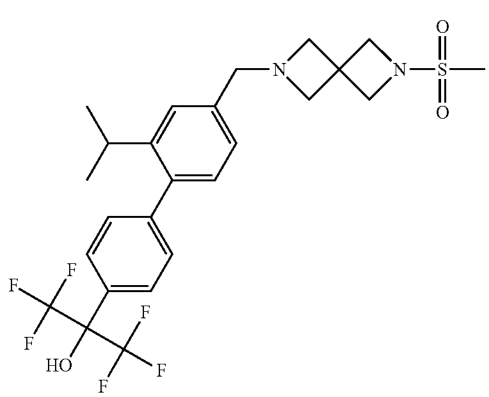 | 1,1,1,3,3,3-hexafluoro-2-(2'-isopropyl-4'-((6-(methylsulfonyl)-2,6-diazaspiro[3.3]heptan-2-yl)methyl)-[1,1'-biphenyl]-4-yl)propan-2-ol | Aldehyde Int. 20 Amine Int. 2 | 551.5 |

TABLE 1-continued

| Ex. No. | Structure | Chemical Name | Intermediates used | LC-MS (ESI) m/z (M + H)+ |
|---|---|---|---|---|
| 44 | 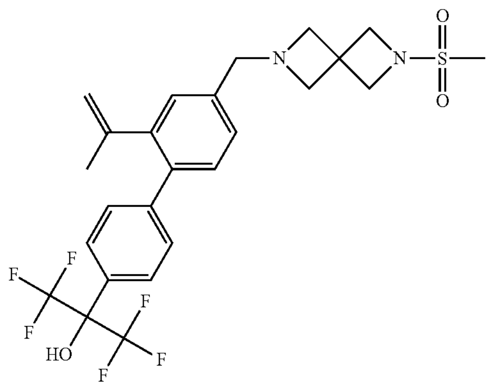 [SMILES: C=C(C)c1cc(CN2CC3(C2)CN(S(C)(=O)=O)C3)ccc1-c1ccc(C(O)(C(F)(F)F)C(F)(F)F)cc1] | 1,1,1,3,3,3-hexafluoro-2-(4'-((6-(methylsulfonyl)-2,6-diazaspiro[3.3]heptan-2-yl)methyl)-2'-(prop-1-en-2-yl)-[1,1'-biphenyl]-4-yl)propan-2-ol | Aldehyde Int. 18 Amine Int. 2 | 549.2 |
| 45 | 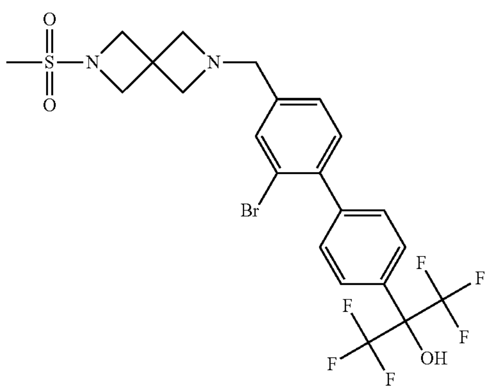 | 2-(2'-bromo-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 17 Amine Int. 2 | 587, 589 (1:1) |
| 46 | 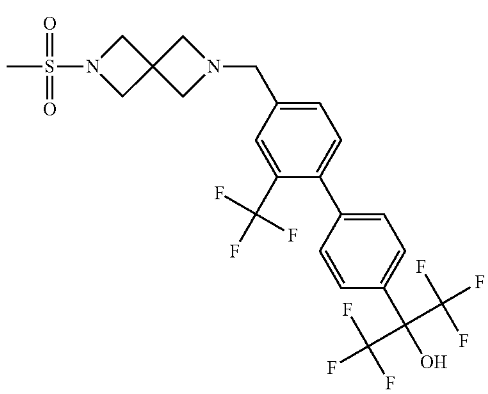 [SMILES: CS(=O)(=O)N1CC2(CN(Cc3ccc(-c4ccc(C(O)(C(F)(F)F)C(F)(F)F)cc4)c(C(F)(F)F)c3)C2)C1] | 1,1,1,3,3,3-hexafluoro-2-(4'-((6-(methylsulfonyl)-2,6-diazaspiro[3.3]heptan-2-yl)methyl)-2'-(trifluoromethyl)-[1,1'-biphenyl]-4-yl)propan-2-ol | Aldehyde Int. 16 Amine Int. 2 | 577.3 |
| 47 | 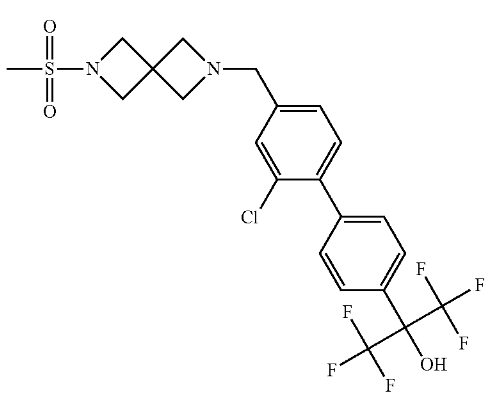 [SMILES: CS(=O)(=O)N1CC2(CN(Cc3ccc(-c4ccc(C(O)(C(F)(F)F)C(F)(F)F)cc4)c(Cl)c3)C2)C1] | 2-(2'-chloro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 15 Amine Int. 2 | 543, 545 (3:1) |

TABLE 1-continued

| Ex. No. | Structure | Chemical Name | Intermediates used | LC-MS (ESI) m/z (M + H)+ |
|---|---|---|---|---|
| 48 | 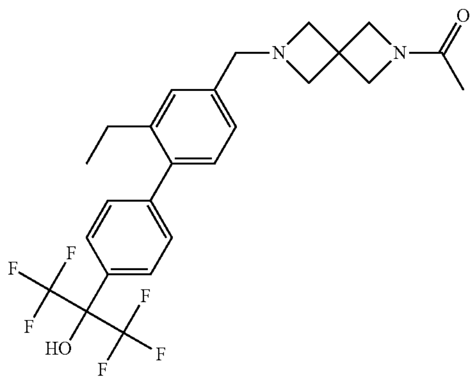 [SMILES: CCc1cc(CN2CC3(C2)CN(C(C)=O)C3)ccc1-c1ccc(C(O)(C(F)(F)F)C(F)(F)F)cc1] | 1-(6-((2-ethyl-4'-(1,1,1,3,3,3-hexafluoro-2-hydroxypropan-2-yl)-[1,1'-biphenyl]-4-yl)methyl)-2,6-diazaspiro[3.3]heptan-2-yl)ethan-1-one | Aldehyde Int. 5 Amine Int. 7 | 501.2 |
| 49 | 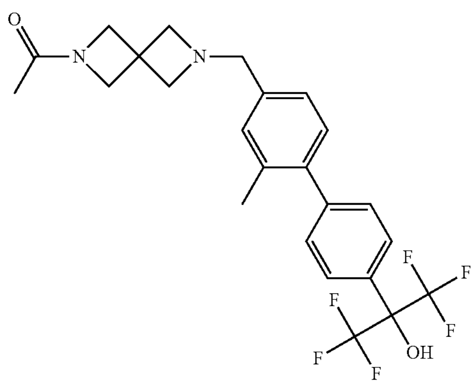 [SMILES: CC(=O)N1CC2(CN(Cc3ccc(-c4ccc(C(O)(C(F)(F)F)C(F)(F)F)cc4)c(C)c3)C2)C1] | 1-(6-((4'-(1,1,1,3,3,3-hexafluoro-2-hydroxypropan-2-yl)-2-methyl-[1,1'-biphenyl]-4-yl)methyl)-2,6-diazaspiro[3.3]heptan-2-yl)ethan-1-one | Aldehyde Int. 14 Amine Int. 7 | 487.3 |
| 50 | 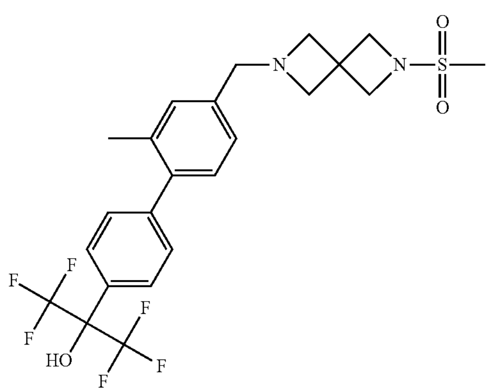 [SMILES: Cc1cc(CN2CC3(C2)CN(S(C)(=O)=O)C3)ccc1-c1ccc(C(O)(C(F)(F)F)C(F)(F)F)cc1] | 1,1,1,3,3,3-hexafluoro-2-(2'-methyl-4'-((6-(methylsulfonyl)-2,6-diazaspiro[3.3]heptan-2-yl)methyl)-[1,1'-biphenyl]-4-yl)propan-2-ol | Aldehyde Int. 14 Amine Int. 2 | 523.6 |
| 51 | 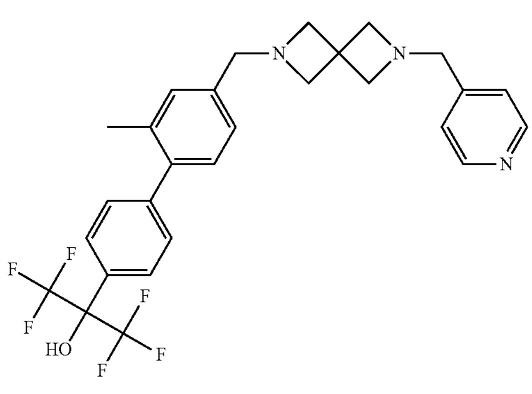 [SMILES: Cc1cc(CN2CC3(CN(Cc4ccncc4)C3)C2)ccc1-c1ccc(C(O)(C(F)(F)F)C(F)(F)F)cc1] | 1,1,1,3,3,3-hexafluoro-2-(2'-methyl-4'-((6-(pyridin-4-ylmethyl)-2,6-diazaspiro[3.3]heptan-2-yl)methyl)-[1,1'-biphenyl]-4-yl)propan-2-ol | Aldehyde Int. 14 Amine Int. 1 | 536.3 |

TABLE 1-continued

| Ex. No. | Structure | Chemical Name | Intermediates used | LC-MS (ESI) m/z (M + H)+ |
|---|---|---|---|---|
| 52 | 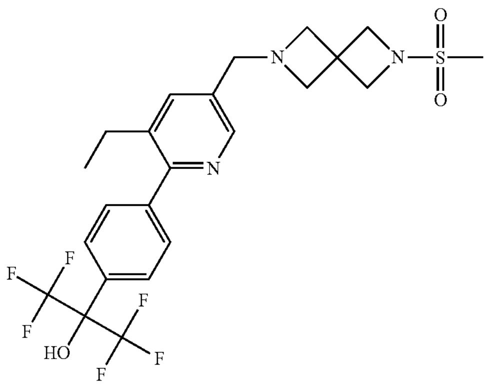 | 2-(4-(3-ethyl-5-(((6-(methylsulfonyl)-2,6-diazaspiro[3.3]heptan-2-yl)methyl)pyridin-2-yl)phenyl)-1,1,1,3,3,3-hexafluoropropan-2-ol | Aldehyde Int. 26 Amine Int. 2 | 538.3 |
| 53 | 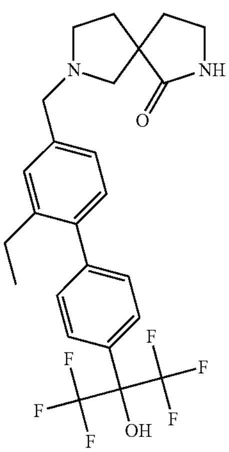 [SMILES: CCc1cc(CN2CCC3(CCNC3=O)C2)ccc1-c1ccc(C(O)(C(F)(F)F)C(F)(F)F)cc1] | 7-((2-ethyl-4'-(1,1,1,3,3,3-hexafluoro-2-hydroxypropan-2-yl)-[1,1'-biphenyl]-4-yl)methyl)-2,7-diazaspiro[4.4]nonan-1-one | Aldehyde Int. 5 Commercially available 2,7-diazaspiro[4.4]nonan-1-one | 501.3 |
| 54 | 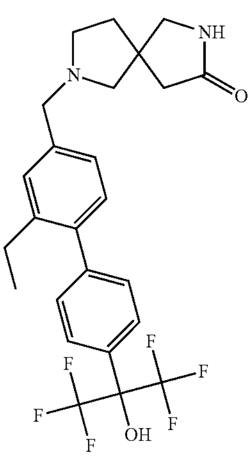 [SMILES: CCc1cc(CN2CCC3(CNC(=O)C3)C2)ccc1-c1ccc(C(O)(C(F)(F)F)C(F)(F)F)cc1] | 7-((2-ethyl-4'-(1,1,1,3,3,3-hexafluoro-2-hydroxypropan-2-yl)-[1,1'-biphenyl]-4-yl)methyl)-2,7-diazaspiro[4.4]nonan-3-one | Aldehyde Int. 5 Commercially available 2,7-diazaspiro[4.4]nonan-3-one | 501.3 |

TABLE 1-continued

| Ex. No. | Structure | Chemical Name | Intermediates used | LC-MS (ESI) m/z (M + H)+ |
|---|---|---|---|---|
| 55 | 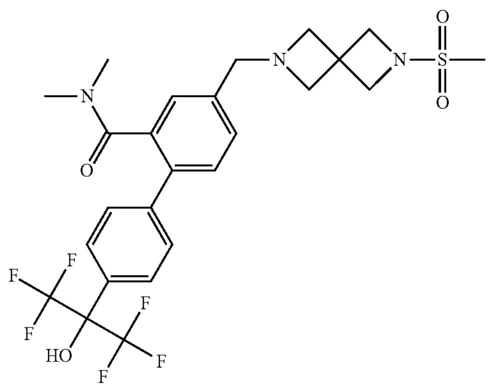 [SMILES: CN(C)C(=O)c1cc(CN2CC3(C2)CN(S(C)(=O)=O)C3)ccc1-c1ccc(C(O)(C(F)(F)F)C(F)(F)F)cc1] | 4'-(1,1,1,3,3,3-hexafluoro-2-hydroxypropan-2-yl)-N,N-dimethyl-4-((6-(methylsulfonyl)-2,6-diazaspiro[3.3]heptan-2-yl)methyl)-[1,1'-biphenyl]-2-carboxamide | Aldehyde Int. 30 Amine Int. 2 | 580.3 |
| 56 | 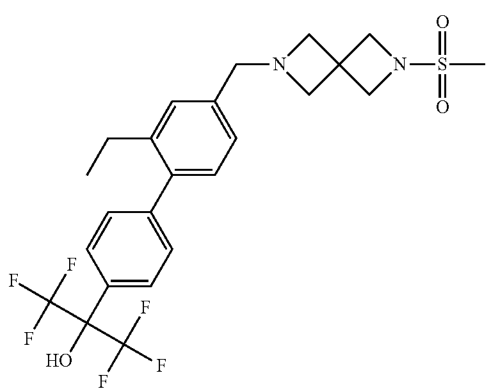 | 2-(2'-ethyl-2-methoxy-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol | Aldehyde Int. 27 Amine Int. 2 | 567.5 |
| 57 | 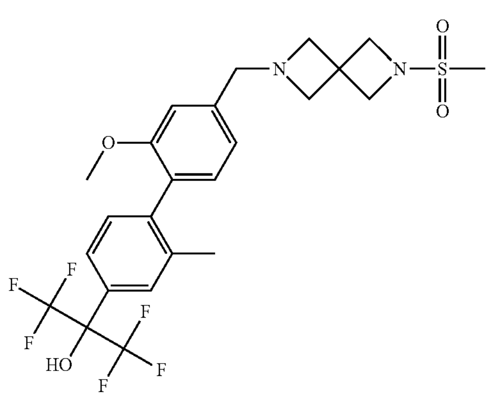 | 1,1,1,3,3,3-hexafluoro-2-(2'-methoxy-2-methyl-4'-((6-(methylsulfonyl)-2,6-diazaspiro[3.3]heptan-2-yl)methyl)-[1,1'-biphenyl]-4-yl)propan-2-ol | Aldehyde Int. 28 Amine Int. 2 | 553.5 |

TABLE 1-continued

| Ex. No. | Structure | Chemical Name | Intermediates used | LC-MS (ESI) m/z (M + H)+ |
|---|---|---|---|---|
| 58 | 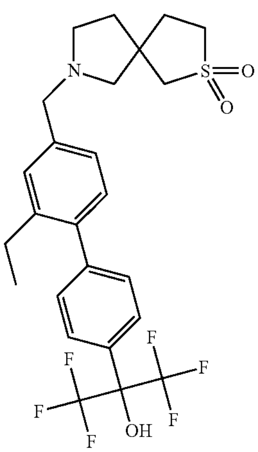 [SMILES: CCc1cc(CN2CCC3(CCS(=O)(=O)C3)C2)ccc1-c1ccc(C(O)(C(F)(F)F)C(F)(F)F)cc1] | 7-((2-ethyl-4'-(1,1,1,3,3,3-hexafluoro-2-hydroxypropan-2-yl)-[1,1'-biphenyl]-4-yl)methyl)-2-thia-7-azaspiro[4.4]nonane 2,2-dioxide | Aldehyde Int. 5 Commercially available 2-thia-7-azaspiro [4.4]nonane 2,2-dioxide | 536.3 |
| 59 | 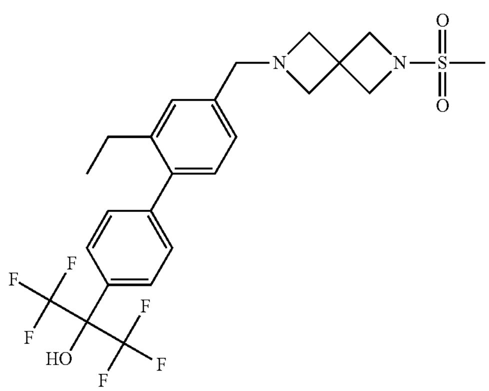 | 2-(5-(2-ethyl-4-((6-(methylsulfonyl)-2,6-diazaspiro[3.3]heptan-2-yl)methyl)phenyl)pyridin-2-yl)-1,1,1,3,3,3-hexafluoropropan-2-ol | Aldehyde Int. 29 Amine Int. 2 | 538.4 |
| 60 | 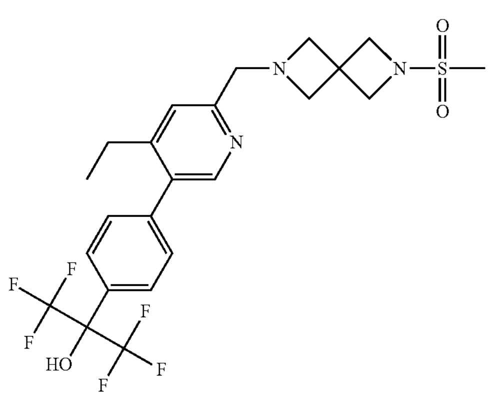 | 2-(4-(4-ethyl-6-((6-(methylsulfonyl)-2,6-diazaspiro[3.3]heptan-2-yl)methyl)pyridin-3-yl)phenyl)-1,1,1,3,3,3-hexafluoropropan-2-ol | Aldehyde Int. 25 Amine Int. 2 | 538.4 |

| Ex. No. | Structure | Chemical Name | Intermediates used | LC-MS (ESI) m/z $(M + H)^+$ |
|---|---|---|---|---|
| 61 | ![structure] | 4'-(1,1,1,3,3,3-hexafluoro-2-hydroxypropan-2-yl)-4-((6-(methylsulfonyl)-2,6-diazaspiro[3.3]heptan-2-yl)methyl)-[1,1'-biphenyl]-3-ol | Aldehyde Int. 31 Amine Int. 2 | 525.4 |

Example 62: Synthesis of 2-(4-(3-ethyl-5-((6-(methylsulfonyl)-2,6-diazaspiro[3.3]heptan-2-yl)methyl)pyridin-2-yl)-3-methylphenyl)-1,1,1,3,3,3-hexafluoropropan-2-ol

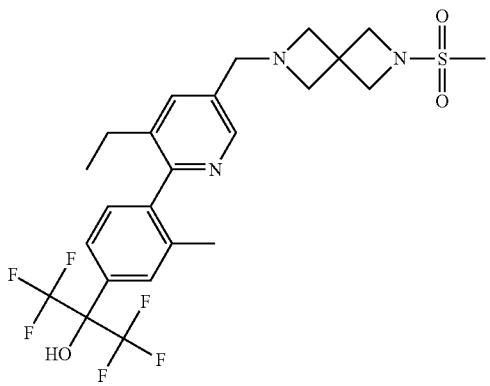 [SMILES: CCc1cc(CN2CC3(C2)CN(S(C)(=O)=O)C3)cnc1-c1ccc(C(O)(C(F)(F)F)C(F)(F)F)cc1C]

To a solution of 3-ethylpyridin-2-amine (1 g, 8.2 mmol, 1 equiv) in 1,4-dioxane (10 mL) and water (2 mL) at 0° C. was added NBS (1.45 g, 8.2 mmol, 1 equiv). The resulting mixture was stirred at 0° C. for 2 h. The reaction was diluted with water (50 mL) and extracted with DCM. The organic phase was separated and concentrated. The residue was purified on a silica gel column (hexane/ethyl acetate) to afford 5-bromo-3-ethylpyridin-2-amine (1.5 g) as a white solid.

5-Bromo-3-ethylpyridin-2-amine (1 g, 1 equiv), Zn(CN)$_2$ (1.5 equiv) and PdCl$_2$(dppf) (10%) were combined in dry DMF (18 mL). The resulting mixture was heated to 120° C. overnight. The reaction mixture was poured into DCM (100 mL) and washed with water and saturated NaHCO$_3$. The organic phase was dried over MgSO$_4$ and concentrated. The residue was purified on a silica gel column (hexane/ethyl acetate) to afford 6-amino-5-ethylnicotinonitrile (0.7 g) as a white solid.

To a solution of 6-amino-5-ethylnicotinonitrile (0.7 g, 1 equiv) in CH$_3$CN (15 mL) was added CuCl$_2$ (2 equiv) and CuCl (2 equiv). To the mixture was added n-butyl nitrite (1.3 equiv) at rt. The resulting mixture was stirred at rt for 1 h and then heated at reflux overnight. The reaction mixture was diluted with CH$_2$Cl$_2$ and washed with water, saturated NaHCO$_3$ solution, and water. The organic phase was dried over MgSO$_4$, concentrated, and purified on a silica gel column to afford 6-chloro-5-ethylnicotinonitrile (0.42 g) as a white solid.

6-Chloro-5-ethylnicotinonitrile (200 mg, 0.53 mmol, 1 equiv) was dissolved in 6 N HCl solution. The reaction was stirred at 100° C. for 3 h and then concentrated to give 6-chloro-5-ethylnicotinic acid which was used without purification.

To a mixture of 6-chloro-5-ethylnicotinic acid (220 mg, 1 equiv), triethylamine (150 mg, 3 equiv) and N,O-dimethylhydroxylamine hydrochloride (85 mg, 1.5 equiv) in DCM (10 mL) was added HBTU (280 mg, 1.4 equiv). The mixture was stirred at room temperature overnight. The reaction was washed with saturated NaHCO$_3$ solution, 2N HCl, and water. The organic phase was dried over MgSO$_4$, and concentrated in vacuo to afford 6-chloro-5-ethyl-N-methoxy-N-methylnicotinamide (150 mg) which was used without further purification.

6-Chloro-5-ethyl-N-methoxy-N-methylnicotinamide applied standard Suzuki coupling with 1,1,1,3,3,3-hexafluoro-2-(3-methyl-4-(4,4,5,5-tetramethyl-1,3,2-dioxaborolan-2-yl)phenyl)propan-2-ol to provide 5-ethyl-6-(4-(1,1,1,3,3,3-hexafluoro-2-hydroxypropan-2-yl)-2-methylphenyl)-N-methoxy-N-methylnicotinamide. 5-Ethyl-6-(4-(1,1,1,3,3,3-hexafluoro-2-hydroxypropan-2-yl)-2-methylphenyl)-N-methoxy-N-methylnicotinamide (Compound 7) was treated with 1 M LAH (1.2 equiv) at −78° C. to afford the aldehyde intermediate 5-ethyl-6-(4-(1,1,1,3,3,3-hexafluoro-2-hydroxypropan-2-yl)-2-methylphenyl)nicotinaldehyde.

The title compound was made using the reductive amination procedure described in the general procedure with the aldehyde intermediate from the previous step and Amine intermediate 2 from Example Q.

Example 63: Synthesis of 2-(6-(2-ethyl-4-((6-(methylsulfonyl)-2,6-diazaspiro[3.3]heptan-2-yl)methyl)phenyl)pyridin-3-yl)-1,1,1,3,3,3-hexafluoropropan-2-ol

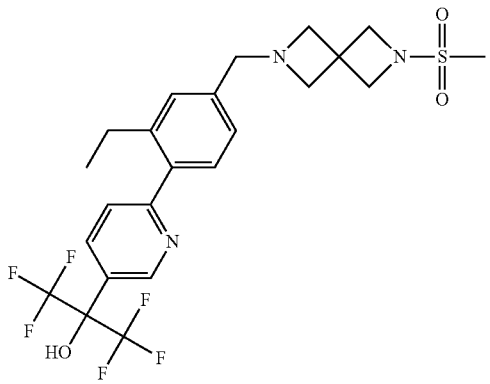 [SMILES: CCc1cc(CN2CC3(C2)CN(S(C)(=O)=O)C3)ccc1-c1ccc(C(O)(C(F)(F)F)C(F)(F)F)cn1]

To a solution of methyl 6-bromonicotinate (1.0 equiv) in THF (20 mL) was added TMSCF₃ (5.0 equiv). The mixture was cooled at −15° C. To the mixture was added 1 M TBAF in THF (3.0 equiv) dropwise for over 20 min. After addition of TMSCF₃, saturated NH₄Cl (50 mL) was added slowly. The mixture was stirred at rt for 15 min and extracted with 2×40 mL hexane. The organic phase was dried over MgSO₄ and concentrated in vacuum to afford 1-(6-bromopyridin-3-yl)-2,2,2-trifluoroethan-1-one which was used in the next step without purification.

1-(6-Bromopyridin-3-yl)-2,2,2-trifluoroethan-1-one and TMSCF₃ (5.0 equiv) was dissolved in THF (20 mL) and cooled to 0° C. TBAF (1 M, 5 mL) was added dropwise. The resulting mixture was stirred at 0° C. for 2 h. The reaction was quenched with saturated NH₄Cl (80 mL). The mixture was extracted with 2×40 mL hexane. The crude mixture was purified on a silica gel column to afford 2-(6-bromopyridin-3-yl)-1,1,1,3,3,3-hexafluoropropan-2-ol.

2-(6-Bromopyridin-3-yl)-1,1,1,3,3,3-hexafluoropropan-2-ol was substituted for Intermediate 1 in the Suzuki coupling reaction described in Step C of Example C to afford 3-ethyl-4-(5-(1,1,1,3,3,3-hexafluoro-2-hydroxypropan-2-yl)pyridin-2-yl)-N-methoxy-N-methylbenzamide. 3-Ethyl-4-(5-(1,1,1,3,3,3-hexafluoro-2-hydroxypropan-2-yl)pyridin-2-yl)-N-methoxy-N-methylbenzamide was reduced to 3-ethyl-4-(5-(1,1,1,3,3,3-hexafluoro-2-hydroxypropan-2-yl)pyridin-2-yl)benzaldehyde by LAH.

The title compound was made using the reductive amination procedure described in the general procedure with the aldehyde intermediate from the previous step and Amine Intermediate 2 from Example Q.

Example 64: Synthesis of 2-(4-(4-ethyl-6-((6-(methylsulfonyl)-2,6-diazaspiro[3.3]heptan-2-yl)methyl)pyridin-3-yl)-3-methylphenyl)-1,1,1,3,3,3-hexafluoropropan-2-ol

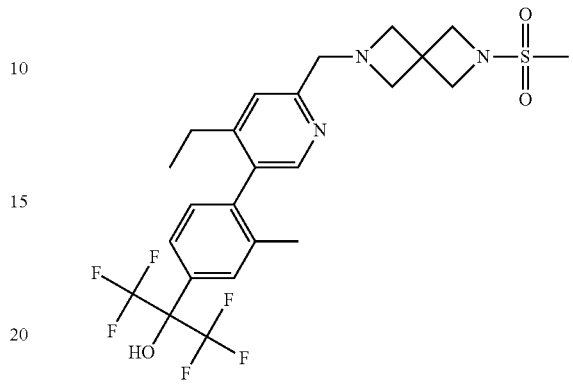

Commercially available 5-bromo-4-ethylpicolinaldehyde (1.0 equiv) and 2-(methylsulfonyl)-2,6-diazaspiro[3.3]heptane (Amine Intermediate 2) (1.2 equiv) were combined into 1,2-DCE (3 mL), the mixture was stirred at rt for 2 h, then NaBH(OAc)₃ (2.5 equiv) was added. The resulting mixture was stirred at rt overnight. Regular work up and purification on a silica gel column afforded 2-((5-bromo-4-ethylpyridin-2-yl)methyl)-6-(methylsulfonyl)-2,6-diazaspiro[3.3]heptane.

Standard Suzuki coupling between 2-((5-bromo-4-ethylpyridin-2-yl)methyl)-6-(methylsulfonyl)-2,6-diazaspiro[3.3]heptane and 1,1,1,3,3,3-hexafluoro-2-(3-methyl-4-(4,4,5,5-tetramethyl-1,3,2-dioxaborolan-2-yl)phenyl)propan-2-ol under the conditions described in Step A of Example K afforded the title compound.

Example 65: Synthesis of 2'-ethyl-4-(1,1,1,3,3,3-hexafluoro-2-hydroxypropan-2-yl)-4'-((6-(methylsulfonyl)-2,6-diazaspiro[3.3]heptan-2-yl)methyl)-[1,1'-biphenyl]-2-carbonitrile

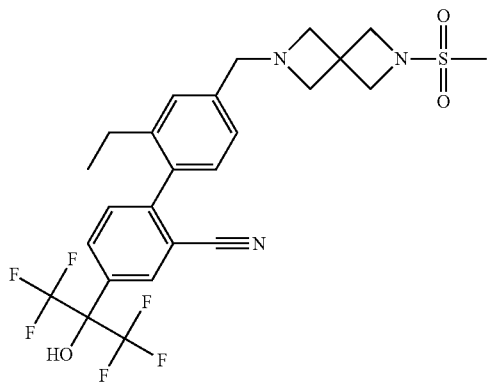 [SMILES: CCc1cc(CN2CC3(C2)CN(S(C)(=O)=O)C3)ccc1-c1ccc(C(O)(C(F)(F)F)C(F)(F)F)cc1C#N]

Step A. Synthesis of 3-ethyl-4-(4,4,5,5-tetramethyl-1,3,2-dioxaborolan-2-yl)benzaldehyde Intermediate. 4-Bromo-3-ethylbenzoic acid (5.0 g, 1.0 equiv), N,O-dimethylhydroxylamine hydrochloride (3.2 g, 1.5 equiv) and HBTU (9.6 g, 1.15 equiv) were combined in DMF (80 mL) at room temperature. To the reaction mixture was added TEA (11.2 g, 4.0 equiv) dropwise. The resulting mixture was stirred at rt overnight. The reaction was diluted with ethyl acetate (200 mL) and hexane (100 mL), then washed with 2×150 mL water, 2×100 mL 1N HCl, 2×100 mL saturated NaHCO$_3$, and brine. The organic phase was dried over MgSO$_4$ and concentrated in vacuum to provide 4-bromo-3-ethyl-N-methoxy-N-methylbenzamide (5.8 g, yield 98%) as a pale yellow oil which was used without further purification.

4-Bromo-3-ethyl-N-methoxy-N-methylbenzamide (1.0 equiv) was dissolved in dry THF and cooled to −50° C. To the solution was added 1 M LAH in THF (0.6 equiv). The reaction was stirred at −30° C. for 1 h and then quenched with 1N HCl at −10° C. to afford 4-bromo-3-ethylbenzaldehyde which was used without purification.

4-Bromo-3-ethylbenzaldehyde (1.0 equiv) and 4,4,4',4',5,5,5',5'-octamethyl-2,2'-bi(1,3,2-dioxaborolane) (1.15 equiv) were dissolved in dry toluene (25 mL). The mixture was degassed by bubbling N$_2$ for 5 min. PdCl$_2$(dppf) (0.1 equiv) and potassium acetate (1.5 equiv) were added to reaction mixture. The resulting mixture was heated at 100° C. in a sealed-tube for 15 h. The reaction mixture was dried in vacuum. The crude mixture was purified on a silica gel column to afford 3-ethyl-4-(4,4,5,5-tetramethyl-1,3,2-dioxaborolan-2-yl)benzaldehyde.

Step B. Synthesis of 2-bromo-5-(1,1,1,3,3,3-hexafluoro-2-hydroxypropan-2-yl)benzonitrile Intermediate: 2-Bromo-5-formylbenzonitrile (1.0 equiv) was dissolved in THF to which was added TMSCF$_3$ (2.0 equiv) and the mixture was cooled to 0° C. To the mixture was added CsF (0.3 equiv). The resulting mixture was stirred at 0° C. for 30 min and then at rt 1 h. To the mixture was added 1 M TBAF (2.0 equiv). The reaction was then quenched with saturated NH$_4$Cl (50 mL) and extracted with 2×40 mL hexane. The organic phase was dried over MgSO$_4$ and concentrated in vacuum to afford oil 2-bromo-5-(2,2,2-trifluoro-1-hydroxyethyl)benzonitrile which was used without purification.

2-Bromo-5-(2,2,2-trifluoro-1-hydroxyethyl)benzonitrile was dissolved in DCM, then DMP (1.5 equiv) was added at rt. The mixture was stirred at rt for 1 h and then quenched with saturated NaHCO$_3$. The crude mixture was purified on a silica gel column to afford 2-bromo-5-(2,2,2-trifluoroacetyl)benzonitrile.

2-Bromo-5-(2,2,2-trifluoroacetyl)benzonitrile and TMSCF$_3$ (2.0 equiv) was dissolved in anhydride THF (20 mL) and cooled to 0° C. 1 M TBAF in THF (1.0 equiv) was added dropwise. The resulting mixture was stirred at 0° C. for 2 h. The reaction was quenched with saturated NH$_4$Cl (80 mL). The mixture was extracted with 2×40 mL hexane. The crude mixture was purified on a silica gel column to afford 2-bromo-5-(1,1,1,3,3,3-hexafluoro-2-hydroxypropan-2-yl)benzonitrile.

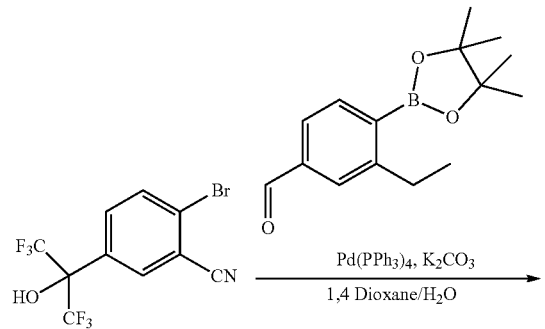

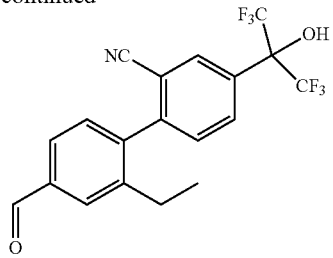

Step C: Synthesis of Aldehyde Intermediate. Suzuki coupling between 2-bromo-5-(1,1,1,3,3,3-hexafluoro-2-hydroxypropan-2-yl)benzonitrile from the previous step with 3-ethyl-4-(4,4,5,5-tetramethyl-1,3,2-dioxaborolan-2-yl)benzaldehyde from Step A under reaction conditions described in Step A of Example K, afforded the aldehyde intermediate 2'-ethyl-4'-formyl-4-(1,1,1,3,3,3-hexafluoro-2-hydroxypropan-2-yl)-[1,1'-biphenyl]-2-carbonitrile.

Step D: The title compound was made using the reductive amination procedure described in the general procedure with the aldehyde intermediate from Step C and Amine Intermediate 2 from Example Q.

Example 66: Synthesis of 2-(2,2'-dimethyl-3'-(6-(methylsulfonyl)-2,6-diazaspiro[3.3]heptan-2-yl)-[1,1'-biphenyl]-4-yl)-1,1,1,3,3,3-hexafluoropropan-2-ol

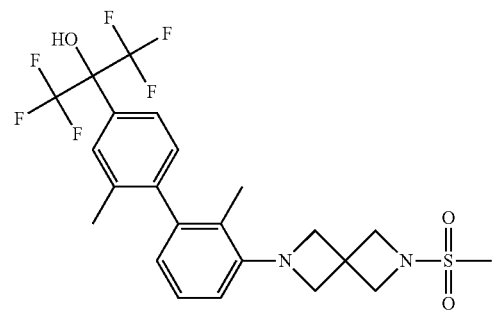 [SMILES: Cc1cc(C(O)(C(F)(F)F)C(F)(F)F)ccc1-c1cccc(N2CC3(C2)CN(S(C)(=O)=O)C3)c1C]

1,3-Dibromo-2-methylbenzene (1.2 equiv) and tert-butyl 2,6-diazaspiro[3.3]heptane-2-carboxylate oxalic acid (1.0 equiv) were suspended in 5 mL dry toluene, to which was added Pd$_2$(dba)$_3$ (0.05 equiv), RuPhos (0.1 equiv) and sodium t-butyloxide (2.5 equiv). The mixture was bubbled with N$_2$ for 5 min. The resulting mixture was heated at 100° C. for 5 h. The solvent was removed in high vacuum. The residue was purified on a silica gel column to afford tert-butyl 6-(3-bromo-2-methylphenyl)-2,6-diazaspiro[3.3]heptane-2-carboxylate.

tert-Butyl 6-(3-bromo-2-methylphenyl)-2,6-diazaspiro[3.3]heptane-2-carboxylate from the previous step was treated with 50% TFA in DCM to provide the corresponding amine as a TFA salt. The TFA salt amine was suspended into DCM and water, adjusted to pH >10 by adding 2 M K$_2$CO$_3$. The mixture was cooled to 0° C. and MsCl (2.0 equiv) was added. The mixture was stirred at rt for 2 h. The crude mixture was purified on a silica gel column to afford 2-(3-bromo-2-methylphenyl)-6-(methylsulfonyl)-2,6-diazaspiro[3.3]heptane.

Standard Suzuki coupling between 2-(3-bromo-2-methylphenyl)-6-(methylsulfonyl)-2,6-diazaspiro[3.3]heptane and Intermediate 2A under reaction conditions described in Step A of Example K afforded the title compound.

Example 67: Synthesis of 1,1,1,3,3,3-hexafluoro-2-(3-methyl-4-(6-(6-(methylsulfonyl)-2,6-diazaspiro[3.3]heptan-2-yl)pyridin-2-yl)phenyl)propan-2-ol

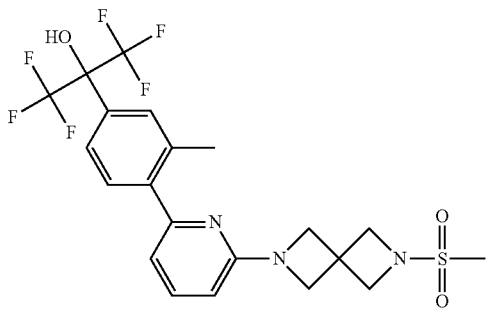 [SMILES: Cc1cc(C(O)(C(F)(F)F)C(F)(F)F)ccc1-c1cccc(N2CC3(C2)CN(S(C)(=O)=O)C3)n1]

The title compound was prepared using the procedure described in Example 66, but substituting 2,6-dibromopyridine for 1,3-dibromo-2-methylbenzene in the first step.

Example 68: Synthesis of 2-(2'-ethyl-3',6'-difluoro-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

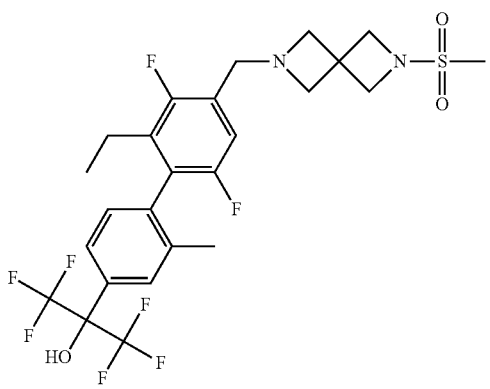

Step A. 2,5-difluoro-4-methoxybenzoic acid (500 mg) was treated with BBr$_3$ at room temperature for 24 h. The reaction was worked up with 2N HCl, and purified on a silica gel column to give 2,5-difluoro-4-hydroxybenzoic acid.

Step B. To a mixture of 2,5-difluoro-4-hydroxybenzoic acid (1 equiv), triethylamine (3 equiv) and N,O-dimethylhydroxylamine hydrochloride (10 equiv) in DCM (20 mL) was added HBTU (2.5 equiv). The mixture was stirred at room temperature overnight. The mixture was washed with 2N HCl and water. The organic phase was dried over MgSO$_4$, concentrated, and purified on a silica gel column to afford 2,5-difluoro-4-hydroxy-N-methoxy-N-methylbenzamide as a colorless oil.

Step C. To a solution of 2,5-difluoro-4-hydroxy-N-methoxy-N-methylbenzamide (1.0 equiv) in acetic acid (4 mL) was added NBS (1.1 equiv) at 0° C. The reaction mixture was warmed to room temperature and stirred for 2 h. The solvent was removed under reduced pressure. The residue was dissolved in EtOAc, washed with water, concentrated, and purified on a silica gel column to afford 3-bromo-2,5-difluoro-4-hydroxy-N-methoxy-N-methylbenzamide as a white solid.

Step D. To a solution of 3-bromo-2,5-difluoro-4-hydroxy-N-methoxy-N-methylbenzamide (1 equiv) in 1,4-dioxane (5 mL) was added 4,4,5,5-tetramethyl-2-vinyl-1,3,2-dioxaborolane (1.5 equiv), 2 M potassium carbonate solution (3 equiv), and Pd(PPh$_3$)$_4$ (0.05 equiv). The mixture was degassed and then bubbled with N$_2$ for 5 min, and then stirred at 90° C. overnight. Upon cooling to room temperature, the mixture was poured into NH$_4$Cl solution and extracted with DCM. The organic phase was dried over MgSO$_4$, concentrated, and purified on a silica gel column to afford 2,5-difluoro-4-hydroxy-N-methoxy-N-methyl-3-vinylbenzamide as a white solid.

Step E. To a mixture of 2,5-difluoro-4-hydroxy-N-methoxy-N-methyl-3-vinylbenzamide (1.0 equiv) and pyridine (0.5 mL) in DCM (10 mL) was added trifluoromethanesulfonic anhydride (1.5 equiv) dropwise at 0° C. The mixture was stirred at 0° C. for 1 h, and washed with saturated NaHCO$_3$ solution, and water. The organic phase was dried over MgSO$_4$, concentrated, and purified on a silica gel column to afford 3,6-difluoro-4-(methoxy(methyl)carbamoyl)-2-vinylphenyl trifluoromethanesulfonate as a pale yellow oil.

Step F. To a solution of 3,6-difluoro-4-(methoxy(methyl)carbamoyl)-2-vinylphenyl trifluoromethanesulfonate (1.0 equiv) in anhydrous 1,4-dioxane (10 mL) was added Intermediate 2A from Example A (1.5 equiv), 2 M potassium carbonate solution (3 equiv), and Pd(PPh$_3$)$_4$ (0.05 equiv). The mixture was degassed and then bubbled with N$_2$ for 5 min, and then stirred at 90° C. overnight. Upon cooling to room temperature, the mixture was poured into NH$_4$Cl solution and extracted with DCM. The organic phase was dried over MgSO$_4$, concentrated, and purified on a silica gel column to afford 3,6-difluoro-4'-(1,1,1,3,3,3-hexafluoro-2-hydroxypropan-2-yl)-N-methoxy-N-methyl-2-vinyl-[1,1'-biphenyl]-4-carboxamide as a white solid.

Step G. To a solution of 3,6-difluoro-4'-(1,1,1,3,3,3-hexafluoro-2-hydroxypropan-2-yl)-N-methoxy-N-methyl-2-vinyl-[1,1'-biphenyl]-4-carboxamide (1.0 equiv) in MeOH (10 mL) was added Pd/C (10% wt.). The reaction was shaken under H$_2$ (50 psi) environment for 4 h. The mixture was filtered to remove the catalyst and concentrated to afford 2-ethyl-3,6-difluoro-4'-(1,1,1,3,3,3-hexafluoro-2-hydroxypropan-2-yl)-N-methoxy-N-methyl-[1,1'-biphenyl]-4-carboxamide as a white solid.

Step H. To a solution of 2-ethyl-3,6-difluoro-4'-(1,1,1,3,3,3-hexafluoro-2-hydroxypropan-2-yl)-N-methoxy-N-methyl-[1,1'-biphenyl]-4-carboxamide (120 mg, 0.25 mmol, 1 equiv) in anhydrous THF (2 mL) was added 1.0 M LAH solution in THF (1.0 equiv) at −78° C. The reaction was stirred at −78° C. for 1 h and quenched by adding EtOAc before being warmed to room temperature. The mixture was poured into NH$_4$Cl solution and extracted with DCM. The organic phase was dried over MgSO$_4$, concentrated, and purified on a silica gel column to afford 2-ethyl-3,6-difluoro-4'-(1,1,1,3,3,3-hexafluoro-2-hydroxypropan-2-yl)-[1,1'-biphenyl]-4-carbaldehyde as a white solid.

Step I. The title compound was made using the reductive amination procedure described in the general procedure with the aldehyde intermediate from the previous step and Amine intermediate 2 from Example Q.

Example 69: Synthesis of 2-(2'-ethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

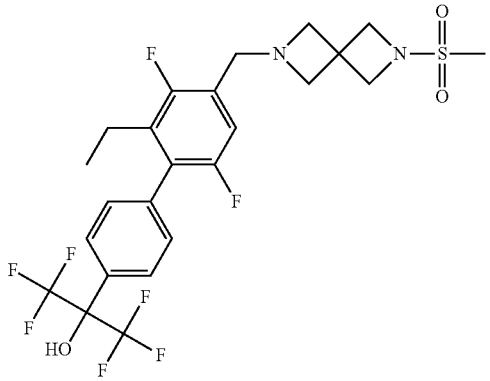 [SMILES: CCc1c(F)c(CN2CC3(C2)CN(S(C)(=O)=O)C3)cc(F)c1-c1ccc(C(O)(C(F)(F)F)C(F)(F)F)cc1]

The title compound was prepared as described in Example 68, substituting Intermediate 2 for Intermediate 2A in Step F.

Example 70: Synthesis of 2-(2'-ethyl-2,3',6'-trifluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

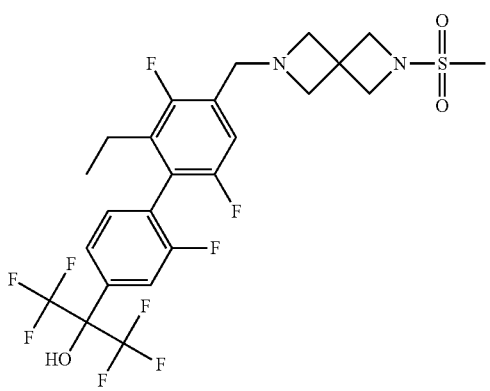 [SMILES: CCc1c(F)c(CN2CC3(C2)CN(S(C)(=O)=O)C3)cc(F)c1-c1ccc(C(O)(C(F)(F)F)C(F)(F)F)cc1F]

The title compound was prepared as described in Example 68, substituting Intermediate 2B for Intermediate 2A in Step F.

Example 71: Synthesis of 2-(2,2'-diethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

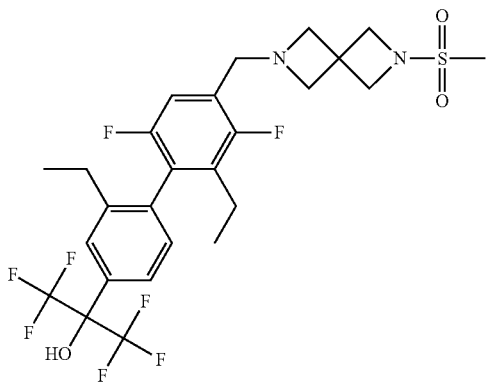 [SMILES: CCc1cc(C(O)(C(F)(F)F)C(F)(F)F)ccc1-c1c(F)cc(CN2CC3(C2)CN(S(C)(=O)=O)C3)c(F)c1CC]

The title compound was prepared as described in Example 68 substituting Intermediate 2C for Intermediate 2A in Step F.

Example 72: Synthesis of 2-(2-chloro-2'-ethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

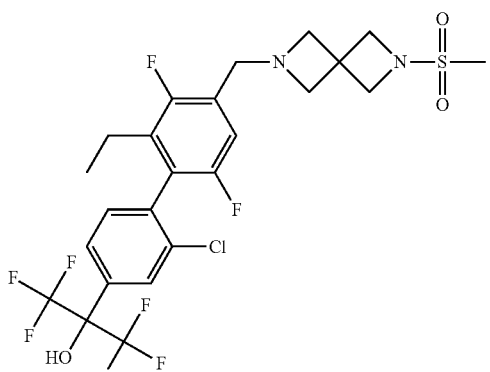

The title compound was prepared as described in Example 68, substituting Intermediate 2D for Intermediate 2A in Step F.

Example 73: Synthesis of 2-(4-(2-ethyl-6-((6-(methylsulfonyl)-2,6-diazaspiro[3.3]heptan-2-yl)methyl)pyridin-3-yl)-3-methylphenyl)-1,1,1,3,3,3-hexafluoropropan-2-ol

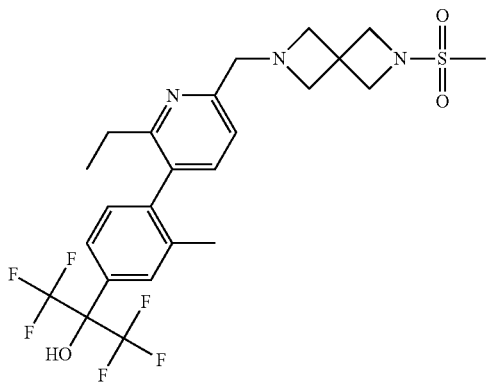

5-bromo-6-ethylpicolinaldehyde (1.0 equiv) and Amine Intermediate 2 from Example Q 1.2 equiv) were combined into 1,2-DCE (3 mL). The mixture was stirred at rt for 2 h and then NaBH(OAc)$_3$ (2.5 equiv) was added. The resulting mixture was stirred at rt overnight. Regular work up and purification on a silica gel column afforded 2-((5-bromo-6-ethylpyridin-2-yl)methyl)-6-(methylsulfonyl)-2,6-diazaspiro[3.3]heptane.

Standard Suzuki coupling between 2-((5-bromo-6-ethylpyridin-2-yl)methyl)-6-(methylsulfonyl)-2,6-diazaspiro[3.3]heptane and Intermediate 2A from Example A under conditions described in Step A of Example K afforded 2-(4-(2-ethyl-6-((6-(methylsulfonyl)-2,6-diazaspiro[3.3]heptan-2-yl)methyl)pyridin-3-yl)-3-methylphenyl)-1,1,1,3,3,3-hexafluoropropan-2-ol.

Example 74: Synthesis of 2-(3',6'-difluoro-2'-isopropyl-4'-((2-(methylsulfonyl)-2,6-diazaspiro[3.4]octan-6-yl)methyl)-[1,1'-biphenyl]-4-yl)-1,1,1,3,3,3-hexafluoropropan-2-ol

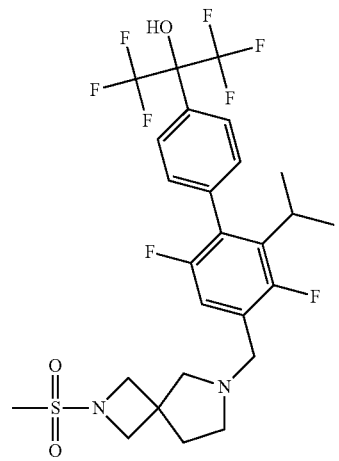 [SMILES: CC(C)c1c(F)c(CN2CCC3(C2)CN(S(C)(=O)=O)C3)cc(F)c1-c1ccc(C(O)(C(F)(F)F)C(F)(F)F)cc1]

The title compound was made using the reductive amination procedure described in the general procedure with Aldehyde Intermediate 11 from Example H and Amine Intermediate 15 from Example W.

Example 75: Synthesis of 2-(2-chloro-2'-ethyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

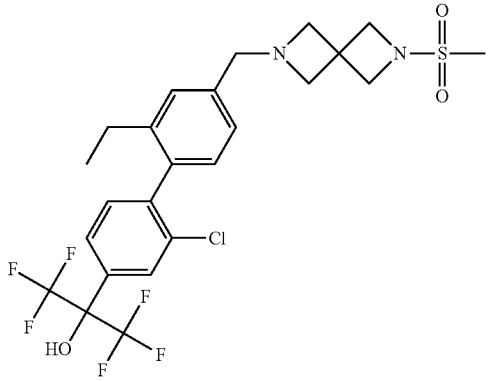 [SMILES: CCc1cc(CN2CC3(C2)CN(S(C)(=O)=O)C3)ccc1-c1ccc(C(O)(C(F)(F)F)C(F)(F)F)cc1CC]

The title compound was made using the procedure described in Example 65 but substituting 4-bromo-3-chlorobenzaldehyde for 2-bromo-5-formylbenzonitrile in Step A.

Example 76: Synthesis of 2-(2-ethyl-2'-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

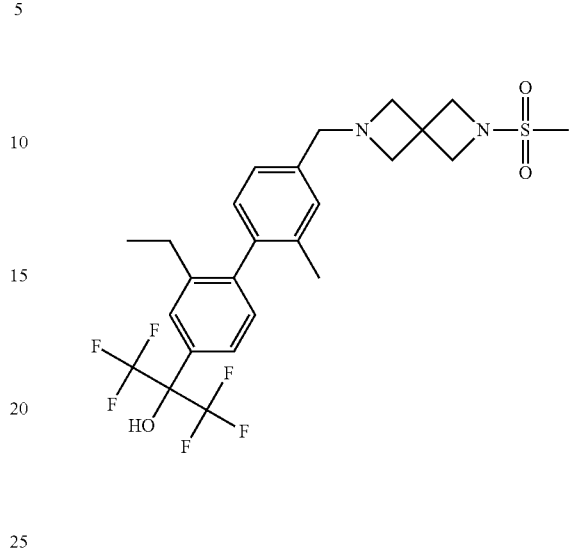

The title compound was prepared using the procedure described in Steps B and C of Example 65, but substituting 4-bromo-3-ethylbenzaldehyde for 2-bromo-5-formylbenzonitrile in Step B and substituting (4-formyl-2-methylphenyl)boronic acid for 3-ethyl-4-(4,4,5,5-tetramethyl-1,3,2-dioxaborolan-2-yl)benzaldehyde in Step C.

Example 77: Synthesis of 2-(2,2'-diethyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

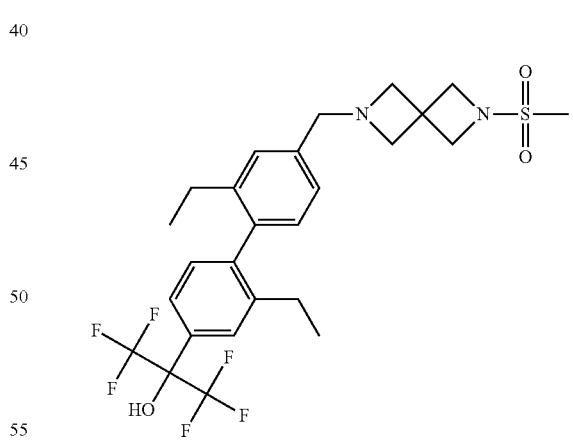

The aldehyde intermediate 2,2'-diethyl-4'-(1,1,1,3,3,3-hexafluoro-2-hydroxypropan-2-yl)-[1,1'-biphenyl]-4-carbaldehyde was prepared using the procedure described in Step C of Example C, but substituting 2-(4-bromo-3-ethylphenyl)-1,1,1,3,3,3-hexafluoropropan-2-ol for Intermediate 1 and substituting 3-ethyl-4-(4,4,5,5-tetramethyl-1,3,2-dioxaborolan-2-yl)benzaldehyde for compound 9.

The title compound was prepared using the general procedure using the aldehyde from the previous step and Amine Intermediate 2 from Example Q.

Example 78: Synthesis of 1,1,1,3,3,3-hexafluoro-2-(5'-fluoro-2'-isopropyl-4'-((6-(methylsulfonyl)-2,6-diazaspiro[3.3]heptan-2-yl)methyl)-[1,1'-biphenyl]-4-yl)propan-2-ol

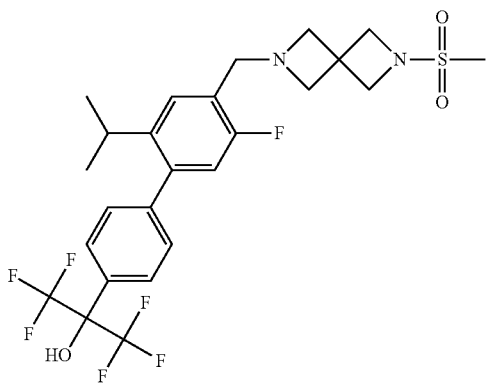 [SMILES: CC(C)c1cc(CN2CC3(C2)CN(S(C)(=O)=O)C3)c(F)cc1-c1ccc(C(O)(C(F)(F)F)C(F)(F)F)cc1]

Step A. To a mixture of 2-fluoro-4-hydroxybenzoic acid (1.0 equiv), triethylamine (3.0 equiv) and N,O-dimethylhydroxylamine hydrochloride (10.0 equiv) in DMF (10 mL) was added HBTU (2.5 equiv). The mixture was stirred at room temperature overnight. The reaction mixture was diluted with 40 mL EtOAc and 20 mL hexane and washed with 2N HCl, water, and brine. The organic phase was dried over MgSO$_4$, concentrated, and purified on a silica gel column to afford 2-fluoro-4-hydroxy-N-methoxy-N-methylbenzamide.

Step B. To a solution of 2-fluoro-4-hydroxy-N-methoxy-N-methylbenzamide (1.0 equiv) in AcOH (10 mL) was added NBS (1.0 g) at 0° C. The reaction mixture was stirred at 0° C. to rt for 1 h, diluted with EtOAc, and washed with water. The organic layer was concentrated and purified on a silica gel column to give 5-bromo-2-fluoro-4-hydroxy-N-methoxy-N-methylbenzamide.

Step C. 5-Bromo-2-fluoro-4-hydroxy-N-methoxy-N-methylbenzamide was dissolved in DMF, to which was added K$_2$CO$_3$ (3.0 equiv) and benzyl bromide (1.2 equiv). The resulting mixture was heated at 50° C. for 1 h. The reaction was diluted with ethyl acetate and washed with water. The crude mixture was purified on a silica gel column to afford 4-(benzyloxy)-5-bromo-2-fluoro-N-methoxy-N-methylbenzamide.

Step D. Standard Suzuki coupling between 4-(benzyloxy)-5-bromo-2-fluoro-N-methoxy-N-methylbenzamide and 4,4,5,5-tetramethyl-2-(prop-1-en-2-yl)-1,3,2-dioxaborolane afforded 4-(benzyloxy)-2-fluoro-N-methoxy-N-methyl-5-(prop-1-en-2-yl)benzamide.

Step E. 4-(Benzyloxy)-2-fluoro-N-methoxy-N-methyl-5-(prop-1-en-2-yl)benzamide in MeOH was hydrogenated at 50 PSI in presence of Pd/C (10% by weight) for 5 h to afford 2-fluoro-4-hydroxy-5-isopropyl-N-methoxy-N-methylbenzamide.

Step F. To a mixture of 2-fluoro-4-hydroxy-5-isopropyl-N-methoxy-N-methylbenzamide (1.0 equiv) and pyridine (3.0 equiv) in DCM (10 mL) was added trifluoromethanesulfonic anhydride (1.5 equiv) dropwise at 0° C. The mixture was stirred at 0° C. for 1 h, and washed with saturated NaHCO$_3$ solution and water. The organic phase was dried over MgSO$_4$, concentrated, and purified on a silica gel column to afford 5-fluoro-2-isopropyl-4-(methoxy(methyl)carbamoyl)phenyl trifluoromethanesulfonate as a white solid.

Step G. To a solution of 5-fluoro-2-isopropyl-4-(methoxy(methyl)carbamoyl)phenyl trifluoromethanesulfonate (1.0 equiv) in anhydrous 1,4-dioxane (2 mL) was added boronic ester Intermediate 2 (1.3 equiv), 2 M potassium carbonate solution (3.0 equiv), and Pd(PPh$_3$)$_4$ (0.05 equiv). The mixture was bubbled N$_2$ for 5 min, and then stirred at 90° C. in a sealed tube for 3 h. Upon cooling to room temperature, the mixture was poured into NH$_4$Cl solution and extracted with DCM. The organic phase was dried over MgSO$_4$, concentrated, and purified on a silica gel column to afford 5-fluoro-4'-(1,1,1,3,3,3-hexafluoro-2-hydroxypropan-2-yl)-2-isopropyl-N-methoxy-N-methyl-[1,1'-biphenyl]-4-carboxamide as a white solid.

Step H. To a solution of 5-fluoro-4'-(1,1,1,3,3,3-hexafluoro-2-hydroxypropan-2-yl)-2-isopropyl-N-methoxy-N-methyl-[1,1'-biphenyl]-4-carboxamide (1 equiv) in anhydrous THF (2 mL) was added 1.0 M LAH solution in THF (1.0 equiv) at −78° C. The reaction was stirred at −78° C. for 1 h and quenched by adding EtOAc before being warmed to room temperature. The mixture was poured into NH$_4$Cl solution and extracted with DCM. The organic phase was dried over MgSO$_4$, concentrated, and purified on a silica gel column to afford 5-fluoro-4'-(1,1,1,3,3,3-hexafluoro-2-hydroxypropan-2-yl)-2-isopropyl-[1,1'-biphenyl]-4-carbaldehyde as a white solid.

Step I. The title compound was prepared using the general procedure using the aldehyde intermediate from the previous step and Amine Intermediate 2.

Example 79: Synthesis of 1,1,1,3,3,3-hexafluoro-2-(5'-fluoro-2'-isopropyl-2-methyl-4'-((6-(methylsulfonyl)-2,6-diazaspiro[3.3]heptan-2-yl)methyl)-[1,1'-biphenyl]-4-yl)propan-2-ol

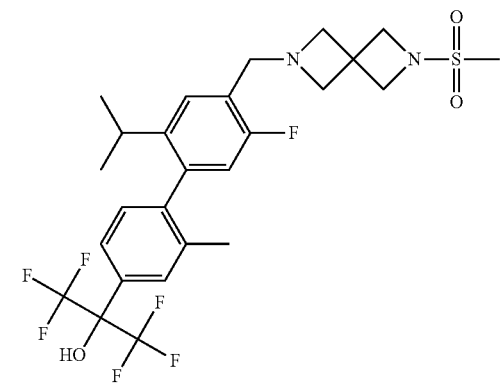 [SMILES: Cc1cc(C(O)(C(F)(F)F)C(F)(F)F)ccc1-c1cc(F)c(CN2CC3(C2)CN(S(C)(=O)=O)C3)cc1C(C)C]

The title compound was made using the procedure described in Example 78, but substituting Intermediate 2A for Intermediate 2 in Step G.

Example 80: Synthesis of 2-(2,5'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

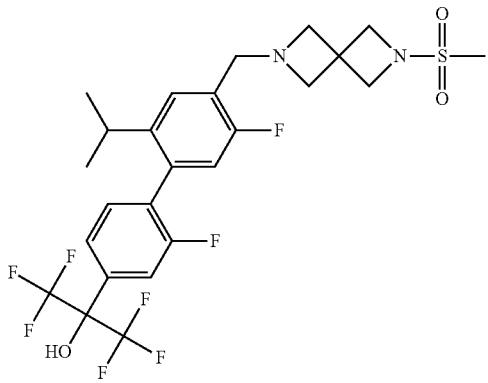 [SMILES: CC(C)c1cc(CN2CC3(C2)CN(S(C)(=O)=O)C3)c(F)cc1-c1ccc(C(O)(C(F)(F)F)C(F)(F)F)cc1F]

The title compound was made using the procedure described in Example 78, but substituting Intermediate 2C for Intermediate 2 in Step G.

Example 81: Synthesis of 2-(2-chloro-5'-fluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

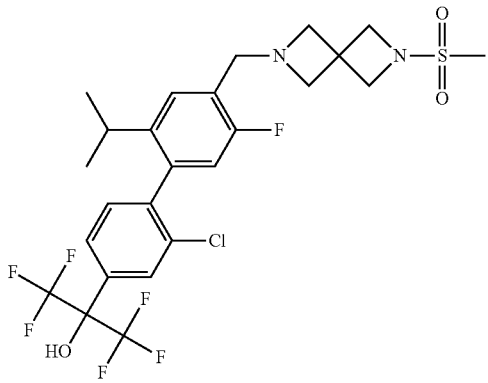 [SMILES: CC(C)c1cc(CN2CC3(C2)CN(S(C)(=O)=O)C3)c(F)cc1-c1ccc(C(O)(C(F)(F)F)C(F)(F)F)cc1Cl]

The title compound was made using the procedure described in Example 78, but substituting Intermediate 2D for Intermediate 2 in Step G.

Example 82: Synthesis of 2-(2'-ethyl-2,5'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

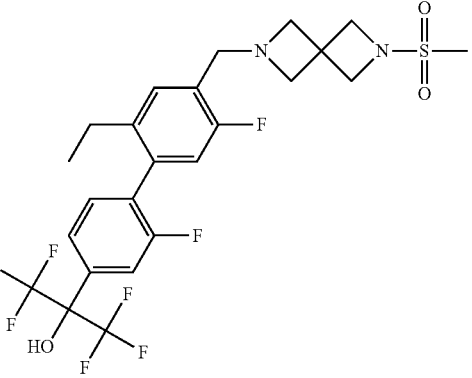

The title compound was synthesized using the procedures described in Steps D through I of Example 78, but substituting 4,4,5,5-tetramethyl-2-vinyl-1,3,2-dioxaborolane for 4,4,5,5-tetramethyl-2-(prop-1-en-2-yl)-1,3,2-dioxaborolane and substituting Intermediate 2C for Intermediate 2 in Step G.

Example 83: Synthesis of 2-(2-chloro-2'-ethyl-5'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

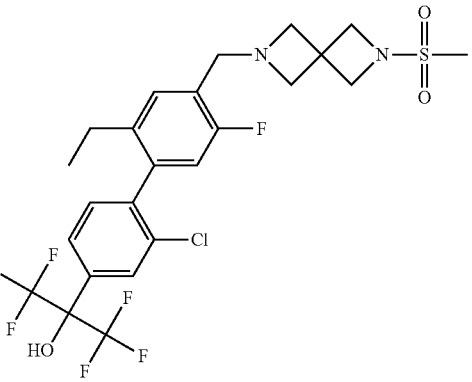

The title compound was synthesized using the procedures described in Steps D through I of Example 78, but substituting 4,4,5,5-tetramethyl-2-vinyl-1,3,2-dioxaborolane for 4,4,5,5-tetramethyl-2-(prop-1-en-2-yl)-1,3,2-dioxaborolane and substituting Intermediate 2D for Intermediate 2 in Step G.

Example 84: Synthesis of 2-(3',6'-difluoro-2'-iso-propyl-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

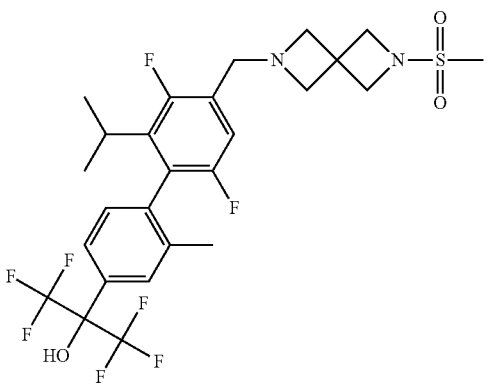 [SMILES: Cc1cc(C(O)(C(F)(F)F)C(F)(F)F)ccc1-c1c(F)cc(CN2CC3(C2)CN(S(C)(=O)=O)C3)c(F)c1C(C)C]

The aldehyde intermediate 3,6-difluoro-4'-(1,1,1,3,3,3-hexafluoro-2-hydroxypropan-2-yl)-2-isopropyl-2'-methyl-[1,1'-biphenyl]-4-carbaldehyde was prepared using the procedure described in Example H, but substituting 1,1,1,3,3,3-hexafluoro-2-(3-methyl-4-(4,4,5,5-tetramethyl-1,3,2-dioxaborolan-2-yl)phenyl)propan-2-ol for 1,1,1,3,3,3-hexafluoro-2-(4-(4,4,5,5-tetramethyl-1,3,2-dioxaborolan-2-yl)phenyl)propan-2-ol in Step F.

The title compound was prepared using the general procedure using the aldehyde intermediate from the previous step and Amine Intermediate 2.

Example 85: Synthesis of 2-(2-ethyl-3',6'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

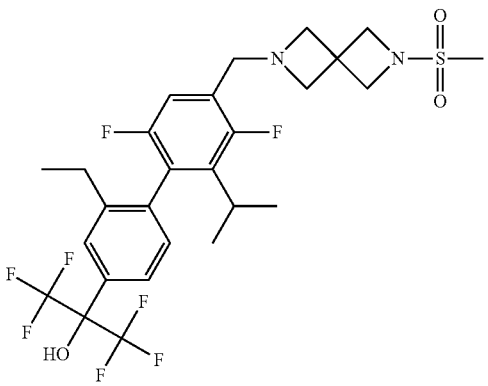 [SMILES: CCc1cc(C(O)(C(F)(F)F)C(F)(F)F)ccc1-c1c(F)cc(CN2CC3(C2)CN(S(C)(=O)=O)C3)c(F)c1C(C)C]

The aldehyde intermediate 2'-ethyl-3,6-difluoro-4'-(1,1,1,3,3,3-hexafluoro-2-hydroxypropan-2-yl)-2-isopropyl-[1,1'-biphenyl]-4-carbaldehyde was prepared using the procedure described in Example H, but substituting 2-(3-ethyl-4-(4,4,5,5-tetramethyl-1,3,2-dioxaborolan-2-yl)phenyl)-1,1,1,3,3,3-hexafluoropropan-2-ol for 1,1,1,3,3,3-hexafluoro-2-(4-(4,4,5,5-tetramethyl-1,3,2-dioxaborolan-2-yl)phenyl)propan-2-ol in Step F.

The title compound was prepared using the general procedure using the aldehyde intermediate from the previous step and Amine Intermediate 2.

Example 86: Synthesis of 1,1,1,3,3,3-hexafluoro-2-(2,3',6'-trifluoro-2'-isopropyl-4'-((6-(methylsulfonyl)-2,6-diazaspiro[3.3]heptan-2-yl)methyl)-[1,1'-biphenyl]-4-yl)propan-2-ol

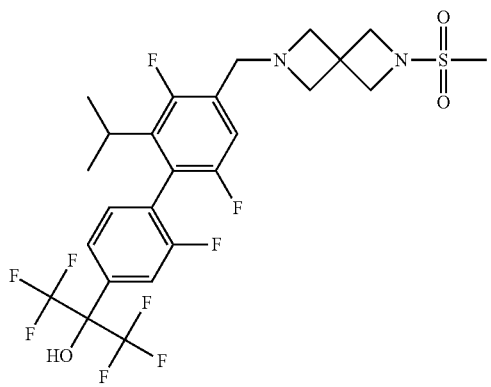 [SMILES: CC(C)c1c(F)c(CN2CC3(C2)CN(S(C)(=O)=O)C3)cc(F)c1-c1ccc(C(O)(C(F)(F)F)C(F)(F)F)cc1F]

The aldehyde intermediate 2',3,6-trifluoro-4'-(1,1,1,3,3,3-hexafluoro-2-hydroxypropan-2-yl)-2-isopropyl-[1,1'-biphenyl]-4-carbaldehyde was prepared using the procedure described in Example H, but substituting 1,1,1,3,3,3-hexafluoro-2-(3-fluoro-4-(4,4,5,5-tetramethyl-1,3,2-dioxaborolan-2-yl)phenyl)propan-2-ol for 1,1,1,3,3,3-hexafluoro-2-(4-(4,4,5,5-tetramethyl-1,3,2-dioxaborolan-2-yl)phenyl)propan-2-ol in Step F.

The title compound was prepared using the general procedure using the aldehyde intermediate from the previous step and Amine Intermediate 2.

Example 87: Synthesis of 2-(2-chloro-3',6'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

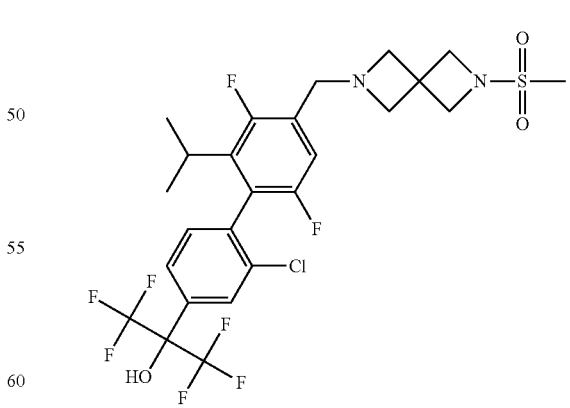

The aldehyde intermediate 2'-chloro-3,6-difluoro-4'-(1,1,1,3,3,3-hexafluoro-2-hydroxypropan-2-yl)-2-isopropyl-[1,1'-biphenyl]-4-carbaldehyde was prepared using the procedure described in Example H, but substituting 2-(3-chloro-4-(4,4,5,5-tetramethyl-1,3,2-dioxaborolan-2-yl)phenyl)-1,1, 1,3,3,3-hexafluoropropan-2-ol for 1,1,1,3,3,3-hexafluoro-2-(4-(4,4,5,5-tetramethyl-1,3,2-dioxaborolan-2-yl)phenyl)propan-2-ol in Step F.

The title compound was prepared using the general procedure using the aldehyde intermediate from the previous step and Amine Intermediate 2.

Example 88: Synthesis of 2-(2'-cyclopropyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

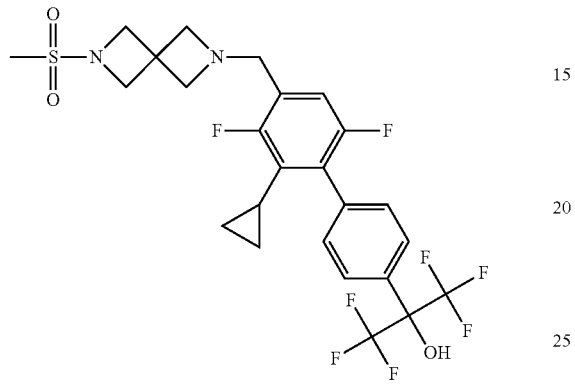

Step A. 2,5-difluoro-4-methoxybenzoic acid (500 mg) was treated with BBr$_3$ at room temperature for 24 h. The reaction was worked up with 2N HCl, and purified on a silica gel column to give the corresponding 2,5-difluoro-4-hydroxybenzoic acid.

Step B. To a mixture of 2,5-difluoro-4-hydroxybenzoic acid (380 mg, 2.18 mmol, 1.0 equiv), triethylamine (660 mg, 6.6 mmol, 3.0 equiv) and N,O-dimethylhydroxylamine hydrochloride (2.14 g, 21.8 mmol, 10.0 equiv) in DCM (20 mL) was added HBTU (1.25 g, 3.27 mmol, 1.5 equiv). The mixture was stirred at room temperature overnight. The mixture was washed with saturated NaHCO$_3$ solution, 2N HCl, and water. The organic phase was dried over MgSO$_4$, concentrated, and purified on a silica gel column to afford 2,5-difluoro-4-hydroxy-N-methoxy-N-methylbenzamide (190 mg) as a colorless oil.

Step C. To a solution of 2,5-difluoro-4-hydroxy-N-methoxy-N-methylbenzamide (190 mg, 0.87 mmol, 1.0 equiv) in acetic acid (4 mL) was added NBS (190 mg, 1.05 mmol, 1.2 equiv) at 0° C. The reaction was warmed to room temperature and stirred for 2 h. The solvent was removed under reduced pressure. The residue was dissolved in EtOAc, washed with water, concentrated, and purified on a silica gel column to afford 3-bromo-2,5-difluoro-4-hydroxy-N-methoxy-N-methylbenzamide (240 mg) as a white solid.

Step D. 3-Bromo-2,5-difluoro-4-hydroxy-N-methoxy-N-methylbenzamide (1.0 equiv) and potassium cyclopropyltrifluoroborate (2.5 equiv) were combined in dioxane (5 mL) and water (2 mL), then added K$_2$CO$_3$ (3.0 equiv) and Pd(PPh$_3$)$_4$ (0.08 equiv). The resulting mixture was bubbled N$_2$ for 5 min, then heated at 90° C. in sealed tube for 14 h. The reaction mixture was diluted with ethyl acetate and washed with saturated NH$_4$Cl and water. The crude mixture was purified on a silica gel column to provide 3-cyclopropyl-2,5-difluoro-4-hydroxy-N-methoxy-N-methylbenzamide.

Step E. 3-Cyclopropyl-2,5-difluoro-4-hydroxy-N-methoxy-N-methylbenzamide was treated with trifluoromethanesulfonic anhydride (1.5 equiv) in presence of pyridine (1.5 equiv) as base at 0° C. to afford 2-cyclopropyl-3,6-difluoro-4-(methoxy(methyl)carbamoyl)phenyl trifluoromethanesulfonate.

Step F. Suzuki coupling between 2-cyclopropyl-3,6-difluoro-4-(methoxy(methyl)carbamoyl)phenyl trifluoromethanesulfonate and Intermediate 2 under conditions described in Step A of Example K except with heating to 90° C. overnight, afforded 2-cyclopropyl-3,6-difluoro-4'-(1,1,1,3,3,3-hexafluoro-2-hydroxypropan-2-yl)-N-methoxy-N-methyl-[1,1'-biphenyl]-4-carboxamide.

Step G. 2-Cyclopropyl-3,6-difluoro-4'-(1,1,1,3,3,3-hexafluoro-2-hydroxypropan-2-yl)-N-methoxy-N-methyl-[1,1'-biphenyl]-4-carboxamide from the previous step was reduced to the aldehyde intermediate 2-cyclopropyl-3,6-difluoro-4'-(1,1,1,3,3,3-hexafluoro-2-hydroxypropan-2-yl)-[1,1'-biphenyl]-4-carbaldehyde by LAH at −78° C.

Step H. The title compound was prepared using the general procedure using the aldehyde intermediate from the previous step and Amine Intermediate 2.

Example 89: Synthesis of 2-(2'-cyclopropyl-3',6'-difluoro-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

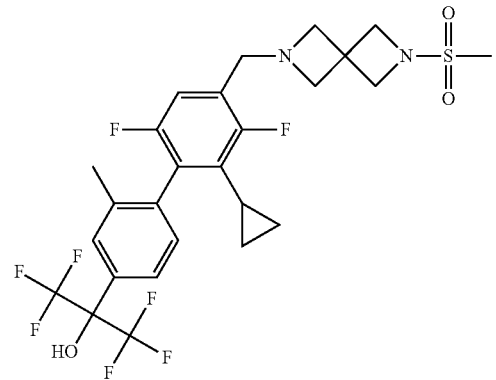 [SMILES: Cc1cc(C(O)(C(F)(F)F)C(F)(F)F)ccc1-c1c(F)cc(CN2CC3(C2)CN(S(C)(=O)=O)C3)c(F)c1C1CC1]

The title compound was made using the procedure described in Example 88, but substituting Intermediate 2A for Intermediate 2 in Step F.

Example 90: Synthesis of 2-(2'-cyclopropyl-2-ethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

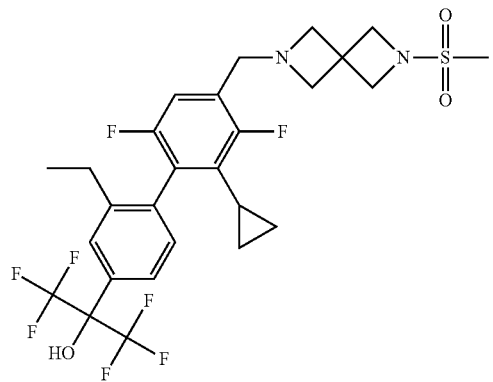 [SMILES: CCc1cc(C(O)(C(F)(F)F)C(F)(F)F)ccc1-c1c(F)cc(CN2CC3(C2)CN(S(C)(=O)=O)C3)c(F)c1C1CC1]

The title compound was made using the procedure described in Example 88, but substituting Intermediate 2B for Intermediate 2 in Step F.

Example 91: Synthesis of 2-(2'-cyclopropyl-2,3',6'-trifluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

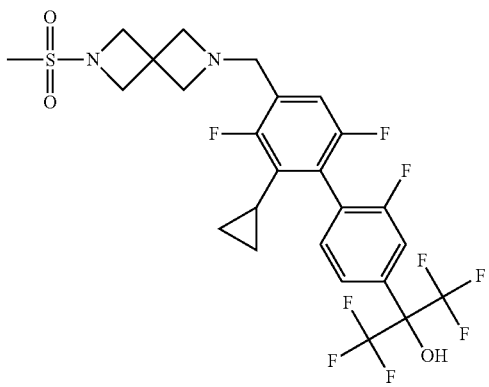 [SMILES: CS(=O)(=O)N1CC2(CN(Cc3cc(F)c(-c4ccc(C(O)(C(F)(F)F)C(F)(F)F)cc4F)c(C4CC4)c3F)C2)C1]

The title compound was made using the procedure described in Example 88, but substituting Intermediate 2C for Intermediate 2 in Step F.

Example 92: Synthesis of 2-(2-chloro-2'-cyclopropyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol

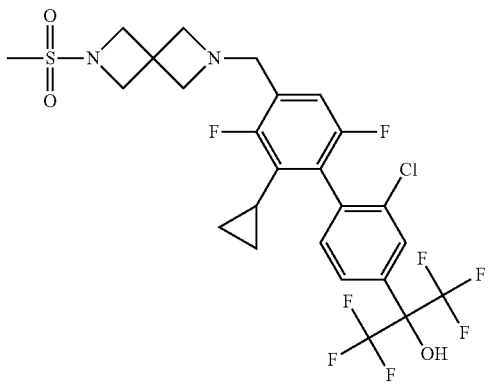 [SMILES: CS(=O)(=O)N1CC2(CN(Cc3cc(F)c(-c4ccc(C(O)(C(F)(F)F)C(F)(F)F)cc4Cl)c(C4CC4)c3F)C2)C1]

The title compound was made using the procedure described in Example 88, but substituting Intermediate 2D for Intermediate 2 in Step F.

Example 93: Gal4 Ligand Binding Assay

Compounds of the present invention were tested in a human RORγ ligand binding assay using a commercially available cell based ligand binding reporter assay in 96-well format (Cat #1304001, INDIGO Biosciences, State College, Pa.). The N-terminal DNA binding domains (DBD) of the native RORγ and RORγt receptors have been substituted with that of the yeast GAL4-DBD and stably transfected in HEK293T cells that also stably express luciferase under the regulation by upstream activation sequence of yeast Gal4. These cells constitutively express high level RORγ activity due to binding of endogenous co-factors. Both agonist and inverse agonist activity can be detected. The assay was performed according to kit manufacturer's instructions as follows. 10 mM compound stocks were diluted serially 1:3 with DMSO and further diluted with provided media to generate 10 titration points from 60 μM to 3 nM. These treatment conditions were added to the plates as 2× media in 100 μL volume. Each plate includes a positive control with 10 titration points as well as 6 negative control wells with vehicle only, with final DMSO concentration of 0.2%. RORγ reporter cells were rapidly thawed and added to the plates in 100 μL volume. The plates were incubated for 24 h in a 37° C. humidified 5% $CO_2$ incubator. Media was removed before the addition of room temperature luciferous detection substrate. After 5 minute incubation, relative light units (RLUs) were quantified using a plate reading luminometer. Data was normalized to positive control wells with only 0.2%0DMSO. Before establishing internal controls, ursolic acid was used as control.

TABLE 2

$IC_{50}$ values for RORγt inverse agonists in RORγt Gal fusion assay.

| Example No. | RORγt ($IC_{50}$) | Example No. | RORγt ($IC_{50}$) | Example No. | RORγt ($IC_{50}$) | Example No. | RORγt ($IC_{50}$) |
|---|---|---|---|---|---|---|---|
| 1 | B | 2 | A | 3 | A | 4 | A |
| 5 | A | 6 | B | 7 | A | 8 | A |
| 9 | B | 10 | A | 11 | A | 12 | B |
| 13 | A | 14 | A | 15 | A | 16 | A |
| 17 | B | 18 | A | 19 | B | 20 | B |
| 21 | B | 22 | B | 23 | A | 24 | B |
| 25 | C | 26 | B | 27 | B | 28 | C |
| 29 | C | 30 | A | 31 | A | 32 | C |
| 33 | B | 34 | A | 35 | A | 36 | A |
| 37 | A | 38 | B | 39 | A | 40 | B |
| 41 | B | 42 | A | 43 | A | 44 | A |
| 45 | B | 46 | B | 47 | C | 48 | C |
| 49 | C | 50 | B | 51 | C | 52 | B |
| 53 | B | 54 | B | 55 | C | 56 | B |
| 57 | A | 58 | A | 59 | B | 60 | A |
| 61 | B | 62 | B | 63 | B | 64 | A |
| 65 | A | 66 | B | 67 | C | 68 | A |
| 69 | A | 70 | A | 71 | A | 72 | A |
| 73 | C | 74 | B | 75 | A | 76 | A |
| 77 | A | 78 | A | 79 | A | 80 | A |
| 81 | A | 82 | A | 83 | A | 84 | A |
| 85 | A | 86 | A | 87 | A | 88 | A |
| 89 | A | 90 | A | 91 | A | 92 | A |

A: $IC_{50}$ < 50 nM;
B: $IC_{50}$ = 50 nM – 250 nM;
C: $IC_{50}$ > 250 nM

Example 94: Human PBMC $T_H17$ Differentiation Assay

This assay tests compounds for their modulatory effect on RORγt as measured by IL-17 production by CD4+ T cells under conditions which favor $T_H17$ differentiation. Fresh healthy donor peripheral blood mononuclear cells (PBMC) were isolated using a Ficoll gradient. CD4+ T cells were purified using a negative selection kit and magnetic separation from Stemcell Technologies according to manufacturer's instruction (Cat #17952, Vancouver, Canada). 2.5× $10^4$ CD4+ T cells were incubated per well in a 96-well plate with 1:1 ratio of anti-CD3/CD28 stimulation beads (Cat #11131D, Gibco DYNAL, Waltham, Mass.) in the presence of rhIL-6 (50 ng/mL), rhIL-1b (10 ng/mL), rhTGF-b1 (1 ng/mL), rhIL-23 (5 ng/mL), anti-IL-4 (10 ug/mL) and anti-IFNg (10 ug/mL). Compounds were added 1 h before the start of the differentiation at various concentrations, with a final concentration of 0.1% DMSO. Cells were incubated at 37° C. 5% $CO_2$ for 3 days before harvesting of the supernatant for U-plex human IL-17A ELISA (Cat #K151ATA-4, Meso Scale Discovery, Rockville, Md.). Data was normalized to DMSO control wells. Cell viability was also measured after the supernatant removal, using MTT assay kit (CAT #11465007001, Sigma-Aldrich, St. Louis, Mo.).

In one embodiment, the compounds provided herein were found to have $IC_{50}$s of less than about 500 nM. In another embodiment, the compounds provided herein were found to have $IC_{50}$s of less than about 250 nM. In another embodiment, the compounds provided herein were found to have $IC_{50}$s of less than about 200 nM. In another embodiment, the compounds provided herein were found to have $IC_{50}$s of less than about 150 nM. In another embodiment, the compounds provided herein were found to have $IC_{50}$s of less than about 100 nM.

Example 95: Patient PBMC IL-17A Inhibition Assay

This assay is designed to screen compounds for their inhibitory effect on the release of IL-17 from isolated human $T_H17$ cells. Peripheral blood mononuclear cells (PBMC) from psoriasis, systemic lupus erythematosus, Crohn's disease and rheumatoid arthritis patients were purchased from Precision For Medicine (Frederick, Md.). $4 \times 10^5$ cells were incubated per well in a 96-well plate with Cytostim, human (Cat #130-092-172, Miltenyi Biotec, Bergisch Gladbach, Germany) according to manufacturer's instructions. Cells were incubated in the presence or absence of various concentrations of compounds, with a final concentration of 0.1% DMSO and starting at the time of stimulation. After 48 hours of incubation at 37° C. and 5% $CO_2$, supernatant was removed to measure IL-17A by ELISA (Cat #BMS2017, ThermoFisher Scientific, Waltham, Mass.). Data was normalized to DMSO control wells. Cell viability was also measured after the supernatant removal, using CellTiter-Glo Luminescent Cell Viability Assay Kit (Cat #G7570, Promega, Madison, Wis.).

In one embodiment, the compounds provided herein were found to have $IC_{50}$s of less than about 5 µM. In one embodiment, the compounds provided herein were found to have $IC_{50}$s of less than about 2.5 µM. In one embodiment, the compounds provided herein were found to have $IC_{50}$s of less than about 2 µM. In one embodiment, the compounds provided herein were found to have $IC_{50}$s of less than about 1 µM. In another embodiment, the compounds provided herein were found to have $IC_{50}$s of less than about 1500 nM. In another embodiment, the compounds provided herein were found to have $IC_{50}$s of less than about 500 nM. In another embodiment, the compounds provided herein were found to have $IC_{50}$s of less than about 250 nM. In another embodiment, the compounds provided herein were found to have $IC_{50}$s of less than about 300 nM. In another embodiment, the compounds provided herein were found to have $IC_{50}$s of less than about 200 nM. In another embodiment, the compounds provided herein were found to have $IC_{50}$s of less than about 150 nM. In another embodiment, the compounds provided herein were found to have $IC_{50}$s of less than about 100 nM. In another embodiment, the compounds provided herein were found to have $IC_{50}$s of less than about 50 nM.

The examples and embodiments described herein are for illustrative purposes only and in some embodiments, various modifications or changes are to be included within the purview of disclosure and scope of the appended claims.

What is claimed is:

1. A compound having the Formula (I):

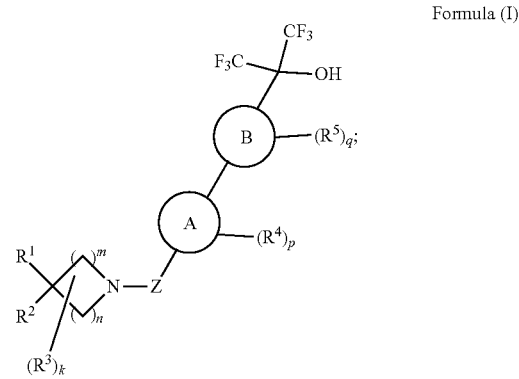

Formula (I)

or a pharmaceutically acceptable salt, solvate, or stereoisomer thereof, wherein:

is phenyl, or a 5-membered or 6-membered heteroaryl ring;

is phenyl, or a 5-membered or 6-membered heteroaryl ring;

Z is —$(C(R^6)(R^7))_t$—;

$R^1$ and $R^2$ are selected from (i) and (ii):
(i) $R^1$ and $R^2$, together with the carbon atom to which they are attached, form a 4-, 5-, or 6-membered heterocyclyl ring wherein the 4-, 5-, or 6-membered heterocyclyl ring is optionally substituted with 1 to 4 $R^{3a}$ groups; and
(ii) $R^1$ is hydrogen and $R^2$ is —$S(O)_2R^{10}$, —$C_1$-$C_6$alkyl-$S(O)_2R^{10}$, —$N(R^{11})S(O)_2R^{10}$, or —$C_1$-$C_6$alkyl-$N(R^{11})S(O)_2R^{10}$;

each $R^3$ is independently selected from halo and $C_1$-$C_6$alkyl;

each $R^{3a}$ is independently selected from $C_1$-$C_6$alkyl, $C_1$-$C_6$haloalkyl, $C_2$-$C_9$heteroaryl, $(C_2$-$C_9$heteroaryl)-$C_1$-$C_6$alkylene-, oxo, —$S(O)_2R^{10}$, —$C(O)R^{10}$, —$C(O)OR^{11}$, and —$C(O)N(R^{11})_2$, wherein $C_2$-$C_9$heteroaryl and $(C_2$-$C_9$heteroaryl)-$C_1$-$C_6$alkylene- are optionally substituted with 1 to 3 groups independently selected from halo, $C_1$-$C_6$alkyl, $C_1$-$C_6$haloalkyl, and hydroxyl;

each $R^4$ and each $R^5$ are each independently selected from halo, cyano, —OH, $C_1$-$C_6$alkyl, $C_2$-$C_6$alkenyl, $C_1$-$C_6$haloalkyl, $C_1$-$C_6$alkoxy, $C_3$-$C_8$cycloalkyl, —$N(R^9)_2$, —$C(O)R^8$, —$C(O)OR^9$, —$C(O)N(R^9)_2$, —$N(R^9)C(O)R^8$, —$N(R^9)SO_2R^8$, —$SO_2R^8$, and —$SO_2N(R^8)_2$;

each $R^6$ and each $R^7$ are each independently hydrogen, halo, or $C_1$-$C_6$alkyl;

each $R^8$ is independently $C_1$-$C_6$alkyl or $C_1$-$C_6$haloalkyl;

each $R^9$ is independently hydrogen, $C_1$-$C_6$alkyl, or $C_1$-$C_6$haloalkyl;

each $R^{10}$ is independently $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene- is optionally substituted with 1 to 3 groups selected from halo, $C_1$-$C_6$alkyl, $C_1$-$C_6$haloalkyl, and hydroxyl;

each $R^{11}$ is independently hydrogen, $C_1$-$C_6$alkyl, or $C_1$-$C_6$haloalkyl;

m is 1, 2, or 3;
n is 1, 2, or 3;
k is 0, 1, 2, 3, or 4;
p is 0, 1, 2, 3, or 4;
q is 0, 1, 2, 3 or 4; and
t is 0, 1, 2, or 3.

2. The compound of claim 1, or a pharmaceutically acceptable salt, solvate, or stereoisomer thereof, wherein (B)

is phenyl.

3. The compound of claim 2, or a pharmaceutically acceptable salt, solvate, or stereoisomer thereof, wherein (B)

is phenyl.

4. The compound of claim 3, or a pharmaceutically acceptable salt, solvate, or stereoisomer thereof, wherein $R^1$ and $R^2$, together with the carbon atom to which they are attached, form a 4-, 5-, or 6-membered heterocyclyl ring wherein the 4-, 5-, or 6-membered heterocyclyl ring is optionally substituted with 1 to 2 $R^{3a}$ groups.

5. The compound of claim 4 having the Formula (II), or a pharmaceutically acceptable salt, solvate, or stereoisomer thereof:

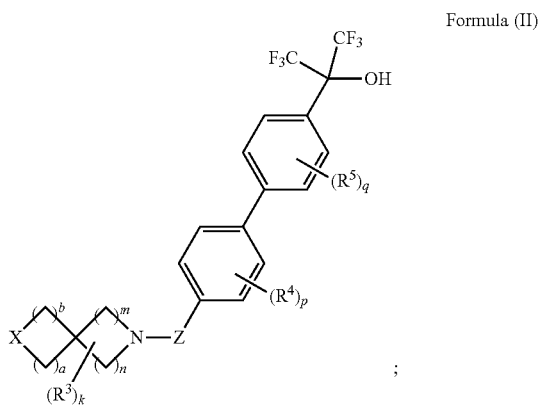

Formula (II)

wherein:
X is —O—, —NH—, —N($R^{3a}$)—, —S—, —S(O)—, or —S(O)$_2$—;

a is 1 or 2; and
b is 1 or 2.

6. The compound of claim 5 having the Formula (IIa):

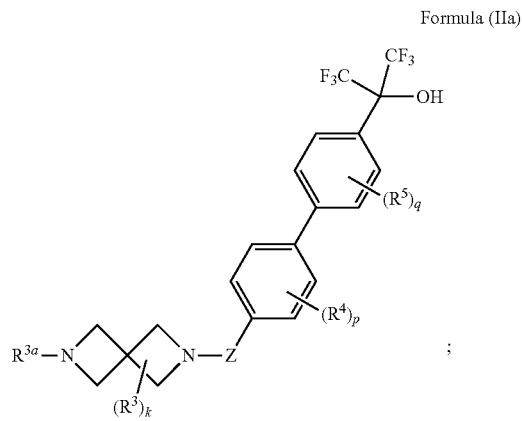

Formula (IIa)

or a pharmaceutically acceptable salt, solvate, or stereoisomer thereof.

7. The compound of claim 6, or a pharmaceutically acceptable salt, solvate, or stereoisomer thereof, wherein $R^{3a}$ is —S(O)$_2$R$^{10}$, —C(O)R$^{10}$, or —C(O)OR$^{11}$.

8. The compound of claim 7, or a pharmaceutically acceptable salt, solvate, or stereoisomer thereof, wherein $R^{3a}$ is —S(O)$_2$R$^{10}$ and $R^{10}$ is $C_1$-$C_6$alkyl.

9. The compound of claim 3, or a pharmaceutically acceptable salt, solvate, or stereoisomer thereof, wherein $R^1$ is hydrogen and $R^2$ is —S(O)$_2$R$^{10}$, —$C_1$-$C_6$alkyl-S(O)$_2$R$^{10}$, —N(R$^{11}$)S(O)$_2$R$^{10}$, or —$C_1$-$C_6$alkyl-N(R$^{11}$)S(O)$_2$R$^{10}$.

10. The compound of claim 9, or a pharmaceutically acceptable salt, solvate, or stereoisomer thereof, wherein $R^{10}$ is $C_1$-$C_6$alkyl.

11. The compound of claim 8, or a pharmaceutically acceptable salt, solvate, or stereoisomer thereof, wherein each $R^6$ and each $R^7$ are hydrogen.

12. The compound of claim 11, or a pharmaceutically acceptable salt, solvate, or stereoisomer thereof, wherein t is 1.

13. The compound of claim 12, or a pharmaceutically acceptable salt, solvate, or stereoisomer thereof, wherein p is 0, 1, 2, or 3.

14. The compound of claim 13, or a pharmaceutically acceptable salt, solvate, or stereoisomer thereof, wherein each $R^4$ is independently halo, $C_1$-$C_6$alkyl, $C_2$-$C_6$alkenyl, $C_1$-$C_6$haloalkyl, $C_1$-$C_6$alkoxy, or $C_3$-$C_8$cycloalkyl.

15. The compound of claim 14, or a pharmaceutically acceptable salt, solvate, or stereoisomer thereof, wherein q is 0, 1, or 2.

16. The compound of claim 15, or a pharmaceutically acceptable salt, solvate, or stereoisomer thereof, wherein each $R^5$ is independently halo, cyano, $C_1$-$C_6$alkyl, $C_1$-$C_6$haloalkyl, or $C_1$-$C_6$alkoxy.

17. The compound of claim 16, or a pharmaceutically acceptable salt, solvate, or stereoisomer thereof, wherein k is 0.

18. The compound of claim 1, or a pharmaceutically acceptable salt or solvate thereof, selected from:

2-(2'-ethyl-4'-((4-((methylsulfonyl)methyl)piperidin-1-yl)methyl)-[1,1'-biphenyl]-4-yl)-1,1,1,3,3,3-hexafluoropropan-2-ol;

2-(2'-ethyl-4'-((4-(methylsulfonyl)piperidin-1-yl)methyl)-[1,1'-biphenyl]-4-yl)-1,1,1,3,3,3-hexafluoropropan-2-ol;

N-((1-((2-ethyl-4'-(1,1,1,3,3,3-hexafluoro-2-hydroxypropan-2-yl)-[1,1'-biphenyl]-4-yl)methyl)azetidin-3-yl)methyl)-N-methylmethanesulfonamide;

N-((1-((2-ethyl-4'-(1,1,1,3,3,3-hexafluoro-2-hydroxypropan-2-yl)-[1,1'-biphenyl]-4-yl)methyl)azetidin-3-yl)methyl)methanesulfonamide;

2-(3',6'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(3',5'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

6-((4'-(1,1,1,3,3,3-hexafluoro-2-hydroxypropan-2-yl)-2-isopropyl-2'-methyl-[1,1'-biphenyl]-4-yl)methyl)-2-thia-6-azaspiro[3.4]octane 2,2-dioxide;

6-((4'-(1,1,1,3,3,3-hexafluoro-2-hydroxypropan-2-yl)-2-isopropyl-2'-methyl-[1,1'-biphenyl]-4-yl)methyl)-2-thia-6-azaspiro[3.3]heptane 2,2-dioxide;

2-(2'-ethyl-4'-((6-(methylsulfonyl)-2-azaspiro[3.3]heptan-2-yl)methyl)-[1,1'-biphenyl]-4-yl)-1,1,1,3,3,3-hexafluoropropan-2-ol;

2-(2'-(sec-butyl)-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2',3'-difluoro-6'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(2'-fluoro-6'-isopropyl-4'-((6-(methylsulfonyl)-2,6-diazaspiro[3.3]heptan-2-yl)methyl)-[1,1'-biphenyl]-4-yl)propan-2-ol;

6-((2-ethyl-4'-(1,1,1,3,3,3-hexafluoro-2-hydroxypropan-2-yl)-2'-methyl-[1,1'-biphenyl]-4-yl)methyl)-2-thia-6-azaspiro[3.4]octane 2,2-dioxide;

6-((2-ethyl-4'-(1,1,1,3,3,3-hexafluoro-2-hydroxypropan-2-yl)-[1,1'-biphenyl]-4-yl)methyl)-2-thia-6-azaspiro[3.4]octane 2,2-dioxide;

6-((2-ethyl-4'-(1,1,1,3,3,3-hexafluoro-2-hydroxypropan-2-yl)-2'-methyl-[1,1'-biphenyl]-4-yl)methyl)-2-thia-6-azaspiro[3.3]heptane 2,2-dioxide;

2-(2'-ethyl-4'-((6-(methylsulfonyl)-2,6-diazaspiro[3.5]nonan-2-yl)methyl)-[1,1'-biphenyl]-4-yl)-1,1,1,3,3,3-hexafluoropropan-2-ol;

2-(2'-ethyl-4'-((2-(methylsulfonyl)-2,6-diazaspiro[3.5]nonan-6-yl)methyl)-[1,1'-biphenyl]-4-yl)-1,1,1,3,3,3-hexafluoropropan-2-ol;

2-(2'-ethyl-4'-((6-(isobutylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-4'-((6-(propylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-4'-((6-(ethylsulfonyl)-2,6-diazaspiro[3.3]heptan-2-yl)methyl)-[1,1'-biphenyl]-4-yl)-1,1,1,3,3,3-hexafluoropropan-2-ol;

2-((2-ethyl-4'-(1,1,1,3,3,3-hexafluoro-2-hydroxypropan-2-yl)-[1,1'-biphenyl]-4-yl)methyl)-7-thia-2-azaspiro[3.5]nonane 7,7-dioxide;

2-(2'-(tert-butyl)-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-((2-ethyl-4'-(1,1,1,3,3,3-hexafluoro-2-hydroxypropan-2-yl)-[1,1'-biphenyl]-4-yl)methyl)-6-thia-2-azaspiro[3.4]octane 6,6-dioxide;

2-((2-ethyl-4'-(1,1,1,3,3,3-hexafluoro-2-hydroxypropan-2-yl)-[1,1'-biphenyl]-4-yl)methyl)-6-thia-2-azaspiro[3.4]octane 6-oxide;

6-((2-ethyl-4'-(1,1,1,3,3,3-hexafluoro-2-hydroxypropan-2-yl)-[1,1'-biphenyl]-4-yl)methyl)-2-thia-6-azaspiro[3.3]heptane 2,2-dioxide;

6-((2-ethyl-4'-(1,1,1,3,3,3-hexafluoro-2-hydroxypropan-2-yl)-[1,1'-biphenyl]-4-yl)methyl)-2-thia-6-azaspiro[3.3]heptane 2-oxide;

2-(4'-((2-thia-6-azaspiro[3.3]heptan-6-yl)methyl)-2'-ethyl-[1,1'-biphenyl]-4-yl)-1,1,1,3,3,3-hexafluoropropan-2-ol;

2-(2'-ethyl-4'-((2-(methylsulfonyl)-2,6-diazaspiro[3.4]octan-6-yl)methyl)-[1,1'-biphenyl]-4-yl)-1,1,1,3,3,3-hexafluoropropan-2-ol;

2-(2'-ethyl-4'-((7-(methylsulfonyl)-2,7-diazaspiro[4.4]nonan-2-yl)methyl)-[1,1'-biphenyl]-4-yl)-1,1,1,3,3,3-hexafluoropropan-2-ol;

2-(2'-ethyl-4'-((7-(methylsulfonyl)-2,7-diazaspiro[3.5]nonan-2-yl)methyl)-[1,1'-biphenyl]-4-yl)-1,1,1,3,3,3-hexafluoropropan-2-ol;

2-(2'-ethyl-4'-((2-(methylsulfonyl)-2,7-diazaspiro[3.5]nonan-7-yl)methyl)-[1,1'-biphenyl]-4-yl)-1,1,1,3,3,3-hexafluoropropan-2-ol;

2-(2'-ethyl-2-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-4'-((6-(methylsulfonyl)-2,6-diazaspiro[3.4]octan-2-yl)methyl)-[1,1'-biphenyl]-4-yl)-1,1,1,3,3,3-hexafluoropropan-2-ol;

2-(2'-ethyl-6'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-5'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-3'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

tert-butyl 2-((2-ethyl-4'-(1,1,1,3,3,3-hexafluoro-2-hydroxypropan-2-yl)-[1,1'-biphenyl]-4-yl)methyl)-2,6-diazaspiro[3.4]octane-6-carboxylate;

2-(2'-ethyl-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

methyl 6-((2-ethyl-4'-(1,1,1,3,3,3-hexafluoro-2-hydroxypropan-2-yl)-[1,1'-biphenyl]-4-yl)methyl)-2,6-diazaspiro[3.3]heptane-2-carboxylate;

2-(4'-((6-(cyclopropylsulfonyl)-2,6-diazaspiro[3.3]heptan-2-yl)methyl)-2'-ethyl-[1,1'-biphenyl]-4-yl)-1,1,1,3,3-hexafluoropropan-2-ol;

2-(2'-cyclopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(2'-isopropyl-4'-((6-(methylsulfonyl)-2,6-diazaspiro[3.3]heptan-2-yl)methyl)-[1,1'-biphenyl]-4-yl)propan-2-ol;

tert-butyl 6-((2-ethyl-4'-(1,1,1,3,3,3-hexafluoro-2-hydroxypropan-2-yl)-[1,1'-biphenyl]-4-yl)methyl)-2,6-diazaspiro[3.3]heptane-2-carboxylate;

1,1,1,3,3,3-hexafluoro-2-(4'-((6-(methylsulfonyl)-2,6-diazaspiro[3.3]heptan-2-yl)methyl)-2'-(prop-1-en-2-yl)-[1,1'-biphenyl]-4-yl)propan-2-ol;

2-(2'-bromo-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(4'-((6-(methylsulfonyl)-2,6-diazaspiro[3.3]heptan-2-yl)methyl)-2'-(trifluoromethyl)-[1,1'-biphenyl]-4-yl)propan-2-ol;

2-(2'-chloro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1-(6-((2-ethyl-4'-(1,1,1,3,3,3-hexafluoro-2-hydroxypropan-2-yl)-[1,1'-biphenyl]-4-yl)methyl)-2,6-diazaspiro[3.3]heptan-2-yl)ethan-1-one;

2-(2'-ethyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1-(6-((4'-(1,1,1,3,3,3-hexafluoro-2-hydroxypropan-2-yl)-2-methyl-[1,1'-biphenyl]-4-yl)methyl)-2,6-diazaspiro[3.3]heptan-2-yl)ethan-1-one;

1,1,1,3,3,3-hexafluoro-2-(2'-methyl-4'-((6-(methylsulfonyl)-2,6-diazaspiro[3.3]heptan-2-yl)methyl)-[1,1'-biphenyl]-4-yl)propan-2-ol;

1,1,1,3,3,3-hexafluoro-2-(2'-methyl-4'-((6-(pyridin-4-ylmethyl)-2,6-diazaspiro[3.3]heptan-2-yl)methyl)-[1,1'-biphenyl]-4-yl)propan-2-ol;

2-(4-(3-ethyl-5-((6-(methylsulfonyl)-2,6-diazaspiro[3.3]heptan-2-yl)methyl)pyridin-2-yl)phenyl)-1,1,1,3,3,3-hexafluoropropan-2-ol;

7-((2-ethyl-4'-(1,1,1,3,3,3-hexafluoro-2-hydroxypropan-2-yl)-[1,1'-biphenyl]-4-yl)methyl)-2,7-diazaspiro[4.4]nonan-1-one;

7-((2-ethyl-4'-(1,1,1,3,3,3-hexafluoro-2-hydroxypropan-2-yl)-[1,1'-biphenyl]-4-yl)methyl)-2,7-diazaspiro[4.4]nonan-3-one;

4'-(1,1,1,3,3,3-hexafluoro-2-hydroxypropan-2-yl)-N,N-dimethyl-4-((6-(methylsulfonyl)-2,6-diazaspiro[3.3]heptan-2-yl)methyl)-[1,1'-biphenyl]-2-carboxamide;

2-(2'-ethyl-2-methoxy-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(2'-methoxy-2-methyl-4'-((6-(methylsulfonyl)-2,6-diazaspiro[3.3]heptan-2-yl)methyl)-[1,1'-biphenyl]-4-yl)propan-2-ol;

7-((2-ethyl-4'-(1,1,1,3,3,3-hexafluoro-2-hydroxypropan-2-yl)-[1,1'-biphenyl]-4-yl)methyl)-2-thia-7-azaspiro[4.4]nonane 2,2-dioxide;

2-(5-(2-ethyl-4-((6-(methylsulfonyl)-2,6-diazaspiro[3.3]heptan-2-yl)methyl)phenyl)pyridin-2-yl)-1,1,1,3,3,3-hexafluoropropan-2-ol;

2-(4-(4-ethyl-6-((6-(methylsulfonyl)-2,6-diazaspiro[3.3]heptan-2-yl)methyl)pyridin-3-yl)phenyl)-1,1,1,3,3,3-hexafluoropropan-2-ol;

4'-(1,1,1,3,3,3-hexafluoro-2-hydroxypropan-2-yl)-4-((6-(methylsulfonyl)-2,6-diazaspiro[3.3]heptan-2-yl)methyl)-[1,1'-biphenyl]-3-ol;

2-(2'-cyclopropyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-cyclopropyl-2,3',6'-trifluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-2'-cyclopropyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(2,3',6'-trifluoro-2'-isopropyl-4'-((6-(methylsulfonyl)-2,6-diazaspiro[3.3]heptan-2-yl)methyl)-[1,1'-biphenyl]-4-yl)propan-2-ol;

2-(2'-cyclopropyl-2-ethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-cyclopropyl-3',6'-difluoro-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-5'-fluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(5'-fluoro-2'-isopropyl-2-methyl-4'-((6-(methylsulfonyl)-2,6-diazaspiro[3.3]heptan-2-yl)methyl)-[1,1'-biphenyl]-4-yl)propan-2-ol;

2-(2,5'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-3',6'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-ethyl-3',6'-difluoro-2'-isopropyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(3',6'-difluoro-2'-isopropyl-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2,2'-diethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-2'-ethyl-3',6'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-2'-ethyl-5'-fluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-2,5'-difluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

1,1,1,3,3,3-hexafluoro-2-(5'-fluoro-2'-isopropyl-4'-((6-(methylsulfonyl)-2,6-diazaspiro[3.3]heptan-2-yl)methyl)-[1,1'-biphenyl]-4-yl)propan-2-ol;

2-(2,2'-diethyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2'-ethyl-2,3',6'-trifluoro-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-ethyl-2'-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(2-chloro-2'-ethyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2-(3',6'-difluoro-2'-isopropyl-4'-((2-(methylsulfonyl)-2,6-diazaspiro[3.4]octan-6-yl)methyl)-[1,1'-biphenyl]-4-yl)-1,1,1,3,3,3-hexafluoropropan-2-ol;

2-(4-(2-ethyl-6-((6-(methylsulfonyl)-2,6-diazaspiro[3.3]heptan-2-yl)methyl)pyridin-3-yl)-3-methylphenyl)-1,1,1,3,3,3-hexafluoropropan-2-ol;

2-(2'-ethyl-3',6'-difluoro-2-methyl-4'-((6-(methylsulfonyl)-2,6-diazaspiro[3.3]heptan-2-yl)methyl)-[1,1'-biphenyl]-4-yl)-1,1,1,3,3,3-hexafluoropropan-2-ol;

2'-ethyl-4-(1,1,1,3,3,3-hexafluoro-2-hydroxypropan-2-yl)-4'-((6-(methylsulfonyl)-2,6-diazaspiro[3.3]heptan-2-yl)methyl)-[1,1'-biphenyl]-2-carbonitrile;

2-(4-(4-ethyl-6-((6-(methylsulfonyl)-2,6-diazaspiro[3.3]heptan-2-yl)methyl)pyridin-3-yl)-3-methylphenyl)-1,1,1,3,3,3-hexafluoropropan-2-ol;

2-(6-(2-ethyl-4-((6-(methylsulfonyl)-2,6-diazaspiro[3.3]heptan-2-yl)methyl)phenyl)pyridin-3-yl)-1,1,1,3,3,3-hexafluoropropan-2-ol;

2-(4-(3-ethyl-5-((6-(methylsulfonyl)-2,6-diazaspiro[3.3]heptan-2-yl)methyl)pyridin-2-yl)-3-methylphenyl)-1,1,1,3,3,3-hexafluoropropan-2-ol;

1,1,1,3,3,3-hexafluoro-2-(3-methyl-4-(6-(6-(methylsulfonyl)-2,6-diazaspiro[3.3]heptan-2-yl)pyridin-2-yl)phenyl)propan-2-ol; and 2-(2,2'-dimethyl-3'-(6-(methylsulfonyl)-2,6-diazaspiro[3.3]heptan-2-yl)-[1,1'-biphenyl]-4-yl)-1,1,1,3,3,3-hexafluoropropan-2-ol; or a pharmaceutically acceptable salt or solvate thereof.

19. A pharmaceutical composition comprising a compound of claim 1, or a pharmaceutically acceptable salt or solvate thereof, and a pharmaceutically acceptable carrier.

20. A method of treating a disease, disorder or condition in an individual in need thereof comprising administering to the individual a therapeutically effective amount of a compound of claim 1, or a pharmaceutically acceptable salt, solvate, or stereoisomer thereof, wherein the disease, disorder or condition is selected from psoriasis, psoriatic arthritis, uveitis, ulcerative colitis, asthma, allergic rhinitis, chronic obstructive pulmonary disease (COPD), atopic dermatitis, vitiligo, vesiculobullous dermatosis, rheumatoid arthritis, ankylosing spondylitis, reactive arthritis, arthritis associated with inflammatory bowel disease, juvenile rheumatoid arthritis, Crohn's disease, inflammatory bowel disease, lupus, lupus nephritis, multiple sclerosis, axial spodyloarthritides, hidraenitis suppurativa, Sjögren's syndrome, regional enteritis, Tolosa-Hunt syndrome, undifferentiated connective tissue disease, obesity, obesity-induced insulin resistance, atherosclerosis, and type II diabetes.

* * * * *